US012667573B2

(12) United States Patent
Iyer et al.

(10) Patent No.: US 12,667,573 B2
(45) Date of Patent: Jun. 30, 2026

(54) COMPOUNDS, COMPOSITIONS, AND METHODS FOR THE TREATMENT OF DISEASE

(71) Applicant: invoX Pharma Limited, Cambridge (GB)

(72) Inventors: Radhakrishnan P. Iyer, Shrewsbury, MA (US); Seetharamaiyer Padmanabhan, Lexington, MA (US); Subramanian Baskaran, Shrewsbury, MA (US); Anjaneyulu Sheri, Shrewsbury, MA (US); Dillon Cleary, Norton, MA (US); Ron Mastrolia, Raynham, MA (US); Shenghua Zhou, Shrewsbury, MA (US); Sreerupa Challa, Shrewsbury, MA (US); Rayomand H. Gimi, Chelmsford, MA (US); Vishal Nair, Norwood, MA (US); Leena Praba Suppiah, Edmond, OK (US)

(73) Assignee: invoX Pharma Limited, Cambridge (GB)

( * ) Notice: Subject to any disclaimer, the term of this patent is extended or adjusted under 35 U.S.C. 154(b) by 1214 days.

(21) Appl. No.: 17/435,830

(22) PCT Filed: Mar. 5, 2020

(86) PCT No.: PCT/US2020/021120

§ 371 (c)(1),
(2) Date: Sep. 2, 2021

(87) PCT Pub. No.: WO2020/181050

PCT Pub. Date: Sep. 10, 2020

(65) Prior Publication Data

US 2022/0168309 A1 Jun. 2, 2022

Related U.S. Application Data

(60) Provisional application No. 62/879,178, filed on Jul. 26, 2019, provisional application No. 62/814,025, filed on Mar. 5, 2019.

(51) Int. Cl.

| | |
|---|---|
| ***C07D 473/00*** | (2006.01) |
| ***A61K 31/437*** | (2006.01) |
| ***A61K 31/519*** | (2006.01) |
| ***A61K 31/52*** | (2006.01) |
| ***A61K 31/5377*** | (2006.01) |
| ***A61K 31/675*** | (2006.01) |
| ***A61P 37/06*** | (2006.01) |
| ***C07D 471/04*** | (2006.01) |
| ***C07D 473/40*** | (2006.01) |
| ***C07D 487/04*** | (2006.01) |
| ***C07D 519/00*** | (2006.01) |
| ***C07F 9/6561*** | (2006.01) |

(52) U.S. Cl.

CPC ............ *A61K 31/52* (2013.01); *A61K 31/437* (2013.01); *A61K 31/519* (2013.01); *A61K 31/5377* (2013.01); *A61K 31/675* (2013.01); *A61P 37/06* (2018.01); *C07D 471/04* (2013.01); *C07D 473/00* (2013.01); *C07D 473/40* (2013.01); *C07D 487/04* (2013.01); *C07D 519/00* (2013.01); *C07F 9/65616* (2013.01)

(58) Field of Classification Search

CPC ............................ C07D 473/40; C07D 473/34
See application file for complete search history.

(56) References Cited

U.S. PATENT DOCUMENTS

| | | | |
|---|---|---|---|
| 5,994,361 | A | 11/1999 | Penney et al. |
| 6,110,923 | A | 8/2000 | Ely |
| 7,238,700 | B2 | 7/2007 | Palle et al. |
| 2013/0039933 | A1 | 2/2013 | Barber |

FOREIGN PATENT DOCUMENTS

| | | | |
|---|---|---|---|
| WO | WO-2008/130581 | A1 | 10/2008 |
| WO | WO-2010/019392 | A1 | 2/2010 |
| WO | WO-2012/167053 | A1 | 12/2012 |
| WO | WO-2013/157562 | A1 | 10/2013 |
| WO | WO-2015/075598 | A1 | 5/2015 |
| WO | WO-2015/137887 | A1 | 9/2015 |
| WO | 2016/120305 | A1 | 8/2016 |
| WO | WO-2019/165032 | A1 | 8/2019 |
| WO | WO-2019/195063 | A1 | 10/2019 |
| WO | WO-2019/195124 | A1 | 10/2019 |
| WO | WO-2020/010092 | A1 | 1/2020 |
| WO | WO-2020/181050 | A1 | 9/2020 |

OTHER PUBLICATIONS

Quy et al. (Medicines, (2019), 6(1), 20, pp. 1-13).*
PubChem-CID: 86302595 Create Date: Dec. 31, 2014, pp. 1-9.
PubChem-CID: 13247039 Create Date Feb. 8, 2007, pp. 1-7.
PubChem-CID: 91623209 Create Date Mar. 19, 2015, pp. 1-11.
PubChem-CID: 57642832 Create Date Aug. 19, 2012, pp. 1-10.
Haag et al., "Targeting STING with covalent small-molecule inhibitors" Nature, Jul. 4, 2018, pp. 269-273, vol. 559, No. 7713.
Quy et al., "Xanthine oxidase inhibitory potential", Medicines, Jan. 29, 2019, p. 1.
Singh et al., "Studies on nucleosides Part XIII. Synthesis and antiviral activity of acyclic analogues of spongosine", Indian Journal of Chemistry, 258: 823-827 (1986).
Haag et al., "Targeting STING with covalent small-molecule inhibitors." Nature 559.7713 (2018): 269-273.
International Search Report and Written Opinion for International Application No. PCT/US2020/021120 mailed May 20, 2020.
PubChem Database CID=13247039, <https://pubchem.ncbi.nlm.nih.gov/compound/13247039> Create Date: Feb. 8, 2007 (Feb. 8, 2007) pp. 1-7; p. 2, structure.

(Continued)

*Primary Examiner* — Susanna Moore

(74) *Attorney, Agent, or Firm* — Foley Hoag LLP; Dana M. Gordon; Alexander J. Chatterley

(57) ABSTRACT

Disclosed are compounds and compositions for inhibiting the expression of a pattern recognition receptor (e.g., STING), and methods of use thereof.

11 Claims, 8 Drawing Sheets

(56) References Cited

OTHER PUBLICATIONS

PubChem Database CID=57642832, <https://pubchem.ncbi.nlm.nih.gov/compound/57642832> Create Date: Aug. 19, 2012 (Aug. 19, 2012) pp. 1-11; p. 2, structure.
PubChem Database CID=86302595, <https://pubchem.ncbi.nlm.nih.gov/compound/86302595> Create Date: Dec. 31, 2014 (Dec. 31, 2014) pp. 1-8; p. 2, structure.
PubChem Database CID=91623209, <https://pubchem.ncbi.nlm.nih.gov/compound/91623209> Create Date: Mar. 19, 2015 (Mar. 19, 2015) pp. 1-12; p. 2, structure.

* cited by examiner

COMPOUNDS, COMPOSITIONS, AND METHODS FOR THE TREATMENT OF DISEASE

CROSS-REFERENCE TO RELATED APPLICATIONS

This application is a U.S. National Stage application of International Application No. PCT/US2020/021120 filed on Mar. 5, 2020, said International Application No. PCT/US2020/021120 claims benefit under 35 U.S.C. § 119(e) of the U.S. Provisional Application Nos. 62/879,178 filed Jul. 26, 2019; and 62/814,025 filed Mar. 5, 2019.

BACKGROUND

Mammalian cells have evolved several intracellular sensors that recognize anomalous species (e.g., DNA) in the cytosol and trigger innate immune reaction in response. Examples of these sensors include: endosomal Toll-like receptors, expressed in plasmacytoid dendritic cells (pDCs) and B cells; absent in melanoma 2 (AIM2) which recognizes double-stranded DNA (dsDNA) and induces the activation of pro-inflammatory IL1b and IL18 cytokines; and stimulator of Interferon Genes (STING), which binds to cyclic dinucleotides (CDNs) and results in the induction of Interferon and NF-kβ signaling pathways.

Another example of a dsDNS sensor is cyclic GMP-AMP synthase (cGAS), which utilizes cellular ATP and GTP to produce CDN 2'3'-cGAMP (i.e., a natural STING agonist) in response to being activated. Said CDNs bind to STING and trigger the movement of STING from the endoplasmic reticulum (ER) to the Golgi apparatus which in turn activates transcription factors, such as IRF3 and NF-kβ, to induce gene expression and cytokine production.

Furthermore, although type I IFNs are essential for host defense against microbial infections, IFN production by aberrant innate immune signaling can occur through the failure to distinguish between self- and foreign-nucleotides. In turn, this may result in inflammatory disorders, such as systemic lupus erythematosus (SLE) or rheumatoid arthritis. Thus, the inability to appropriately degrade or process self-DNA present in the cytoplasm can lead to inflammation through a cGAS-STING-IFN signaling cascade. Indeed, genetic defects in the exonucleases that degrade cytoplasmic DNA have been demonstrated to occur in humans, resulting in a variety of auto-immune conditions. For example, Trex1, a nuclear 3'-5' DNA exonuclease, degrades both ssDNA and dsDNA present in the cytoplasm. Patients suffering from Aicardi-Goutieres Syndrome (AGS) and severe forms of SLE have been found to exhibit mutations in Trex1, and such diseases are characterized by high cytokine levels and inflammation of the central nervous system (e.g., encephalopathy). As evidence of the severity of these diseases, many individuals suffering from AGS do not survive childhood. However, while Trex1−/− mice that exhibit high levels of cytokines, such as TNF-α and IL1-P, generally die within 10 weeks of birth, Trex1−/− STING−/− mice are completely viable, exhibiting dramatically reduced cytokine activity, negligible anti-nuclear antibodies (ANA), and do not show significant inflammation of organs.

Trex1 may also be required to eliminate unused DNA arising from the cell division process, which may otherwise antagonize the innate immune pathways by triggering cGAS generated CDNs—which augment STING function. Thus, the loss of Trex1 facilitates STING activity and cytokine production, predominantly in cells of hematopoietic lineage, to cause several inflammatory disorders.

Moreover, damage-associated DNA modification, such as that resulting from the oxidation of DNA (e.g., 8-hydroxyguanosine (8-OH-G)) by UV-irradiation or pathogen elicited ROS, has been demonstrated to trigger STING-dependent signaling. This modified DNA can evade efficient Trex1 degradation, which results in STING signaling to trigger host immune responses to eliminate the modified DNA. Elimination of the modified DNA is important as it has been linked to certain types of lupus, for example by avoiding nuclease degradation and activating certain cytosolic DNA sensors.

Furthermore, it has been reported that mutations in STING can result in auto-inflammatory disorders. For example, patients suffering from vascular and pulmonary syndrome (VAPS), a systemic inflammatory disorders that can cause lesions of the ears, nose and cheeks were found to exhibit point mutations in exon 5 of STING (e.g., N154S, V155M, and V147L). Such STING variants represent a gain of function phenotype, which stimulates the production of type I IFNs thereby causing STING to become active without robust ligand activation. This role for STING in VAPS is now referred to as STING-associated vasculopathy with onset in infancy (SAVI).

SUMMARY OF THE INVENTION

Therapeutic agents that antagonize aberrant IFN and NF-KB signaling are needed as such therapeutics may be useful in the treatment of a variety of diseases such as arthritis, SLE, SAVI and AGS, Familial chilblain lupus (CHBL), Retinal vasculopathy with cerebral leukodystrophy (RVCL), Sjögren's syndrome, Adult onset Still Syndrome (AOSS/Wissler-Fanconi syndrome), CANDLE, Singleton-Merten syndrome (SGMRT), X-linked reticulate pigmentary disorder (XLPDR), Spondyloenchrondrodysplasia (SPENCD), NASH (a subset of NAFLD with inflammation that leads to cirrhosis leukodystrophy (RVCL)), Pulmonary fibrosis, Idiopathic pulmonary fibrosis, and Geographic atrophy (GA) (also known as atrophic age-related macular degeneration (AMD) or advanced dry AMD). In addition, in certain types of cancer where inflammation plays a tumor-promoting role, such antagonists may have a therapeutic benefit.

In certain aspects, the present disclosure provides compounds of formula I, II, III, IV, or V:

I

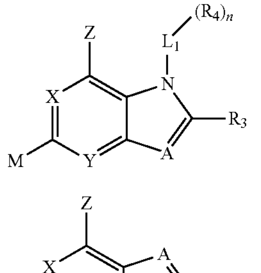

II

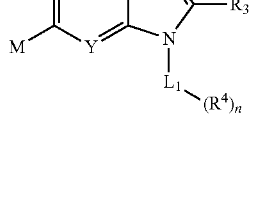

-continued

III

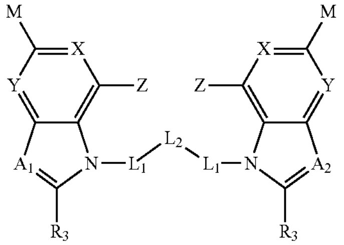

IV

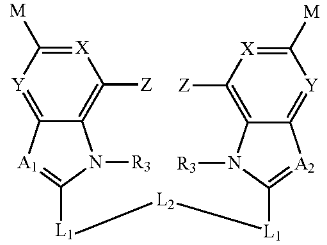

V

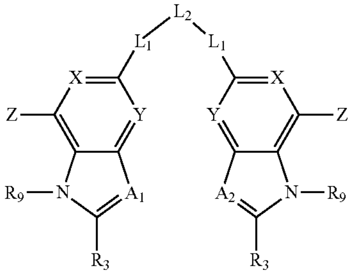

or a pharmaceutically acceptable salt thereof;

wherein

- A, $A_1$, and $A_2$ are each independently N or CH;
- X is N or CH;
- Y is N or CH;
- M and Z are each independently selected from the group consisting of hydrogen, halo, CN, $CF_3$, alkyloxy, $SR^1$, $SOR^1$, $SO_2R^1$, $SO_2N(R^1)(R^2)$, $OR^1$, $NHCOR^1$, $NHSO_2R^1$, $NHCONHR^1$, $NHSO_2NHR^1$, $N(R^1)(R^2)$, $COR^1$, $CO_2R^1$, $CON(R^1)(R^2)$, alkyl, alkenyl, alkynyl, cycloalkyl, cycloalkenyl, aryl, heteroaryl, and heterocyclyl;
- $L^1$ and $L^2$ are each independently selected from the group consisting of a bond, O, S, $N(R^{10})$, alkylenyl, alkenylenyl, alkynylenyl, acyl, heteroaryl, amido, sulfonamido, and heteroalkylenyl; or $L^1$ or $L^2$ is linked to $R^3$ or Z to form a cycloalkyl, aryl, amido, sulfonamido, or heteroaryl;
- $R^1$, $R^2$, $R^5$, $R^6$, $R^7$ $R^8$, $R^9$, and $R^{10}$ are each independently selected from the group consisting of hydrogen, alkyl, heteroalkyl, alkenyl, alkynyl, acyl, cycloalkyl, heterocyclyl, aryl, aralkyl, heteroaryl, amino acid, and amino ester; or $R^1$ and $R^2$ combine to form a heterocyclyl;
- $R^3$ is hydrogen, alkyl, haloalkyl, hydroxyalkyl, alkyloxyalkyl, aminoalkyl, alkenyl, alkynyl, cycloalkyl, aryl, heteroaryl, $SOR^5$, $SO_2R^5$, $SO_2N(R^5)(R^6)$, $COR^5$, CON (RS)($R^6$), halo, CN, $CF_3$, $SR^5$, $OR^5$, $NHCOR^5$, $NHCONHR^5$, $NHSO_2NHR^5$, or $N(R^5)(R^6)$
- each $R^4$ is independently halo, CN, $CF_3$, $SR^7$, $SOR^7$, $SO_2R^7$, $SO_2N(R^7)(R^8)$, $OR^7$, $NHCOR^7$, $NHSO_2R^7$, $NHCONHR^7$, $NHSO_2NHR^7$, $N(R^7)(R^8)$, $COR^7$, $CO_2R^7$, $OC(O)R^7$, $CON(R^7)(R^8)$, $OP(O)(OR^7)_2$ or $OP(S)(OR^7)_2$, alkyl, alkenyl, alkynyl, cycloalkyl, cycloalkenyl, aryl, heteroaryl, or heterocyclyl; and
- n is an integer from 0-18.

In certain aspects, the present disclosure provides pharmaceutical compositions comprising a compound of the discourse and at least one pharmaceutically acceptable excipient.

In certain aspects, the present disclosure provides methods of treating certain diseases (e.g., cancer, neurodegenerative disorders, or inflammatory disorders) with a compound or composition of the disclosure.

DETAILED DESCRIPTION OF THE INVENTION

Pattern Recognition Receptors

Figure 1:
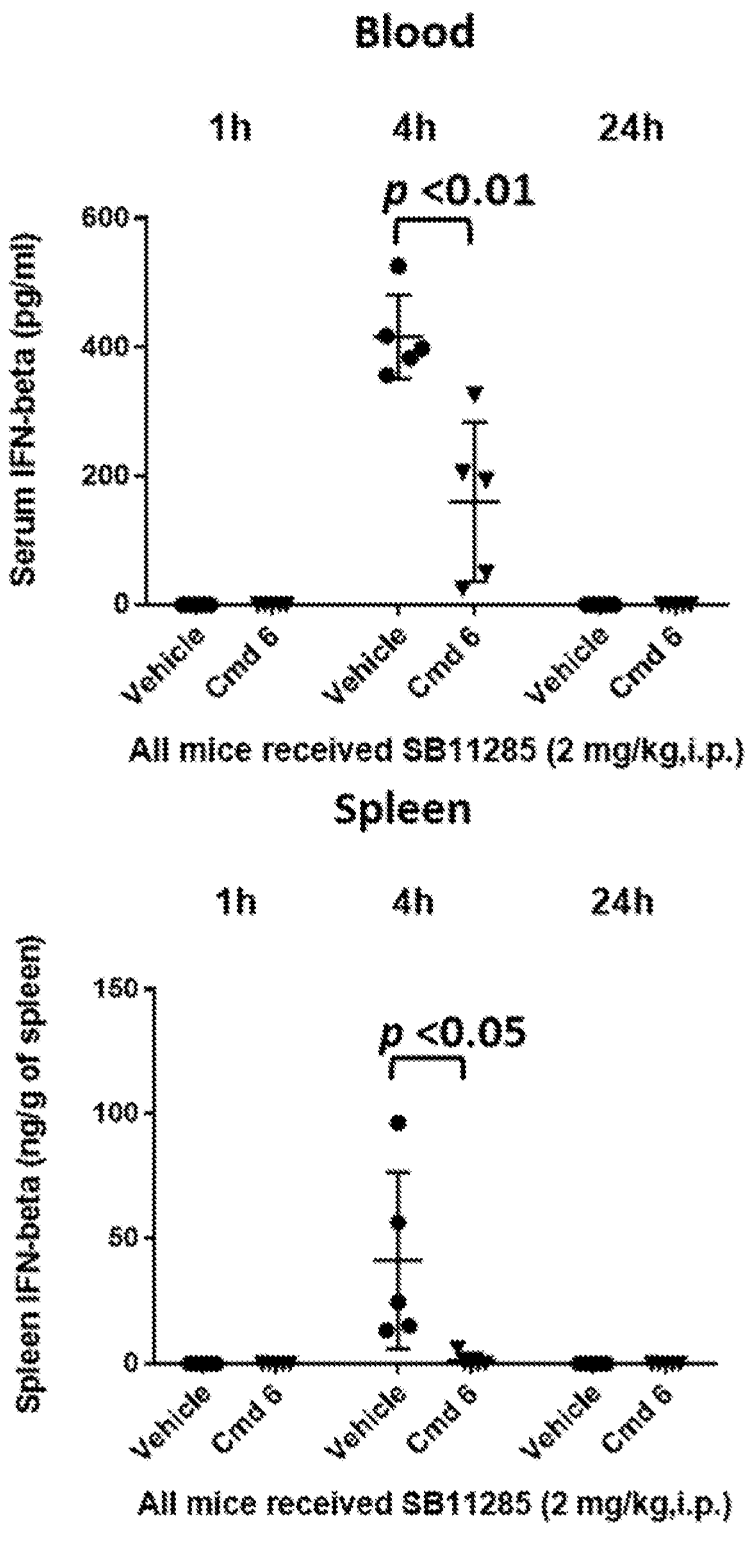
FIG. 1 shows the results of a study where mice treated with either vehicle or compound 6 (10 mg/kg) via i.p. injection for 1 hour followed by treatment with SB 11285 (2 mg/kg i.p.). Blood, spleen, and liver samples were collected at 1 hour, 4 hours, and 24 hours post treatment with SB 11285. The production of IFN-β was monitored using ELISA. The basal level of IFN-β in untreated mice (n=2) was undetectable in all tested tissues.
Figure 1:
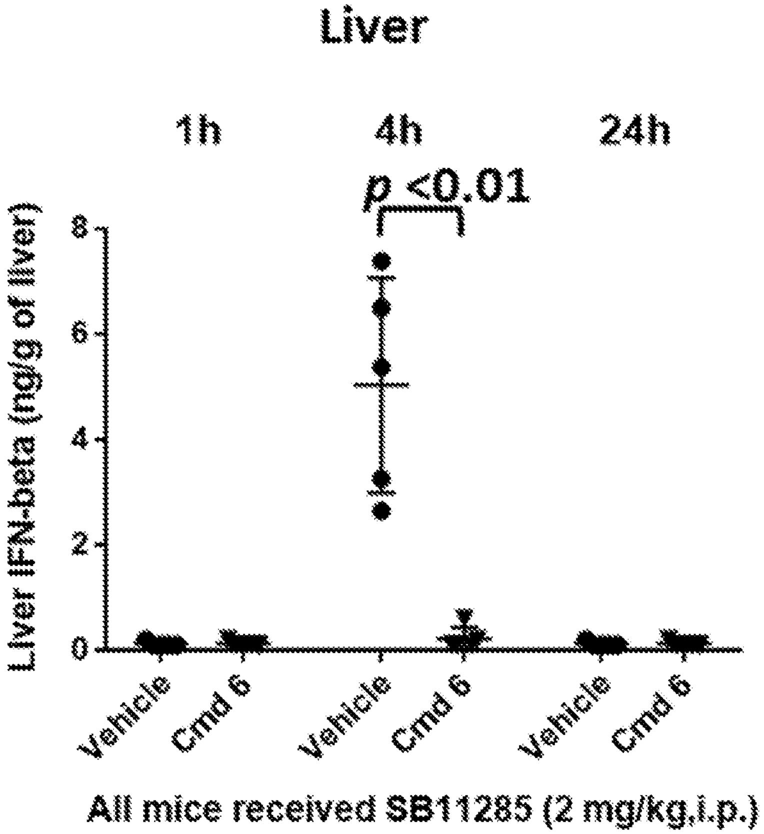

Pattern recognition receptors (PRRs) are a broad class of proteins which recognize pathogen-associated molecular patterns (PAMPs) conserved within pathogenic invaders. PAMPs are typically products of biosynthetic pathways that are essential to the survival and/or infectivity of the pathogen, e.g., lipopolysaccharides, glycoproteins, and nucleic acids. Recognition of PAMPs by their cognate PRRs activates signaling pathways that result in the production of immune defense factors such as pro-inflammatory and anti-inflammatory cytokines, type I interferons (IFN-α, IFN-β), and/or interferon stimulated genes (ISGs).

The stimulator of interferon genes (STING) is a cytosolic microbial-derived DNA sensor that has been shown to be particularly sensitive to double-stranded DNA and cyclic dinucleotides (e.g., cyclic di-GMP) (Burdette, D. L. and Vance, R. E. (2013) *Nat Immunol* 14:19-26). Two molecules of STING form a homodimer mediated by an α-helix present in the C-terminal dimerization domain, and molecular binding studies have revealed that each STING dimer binds one molecule of microbial nucleic acids, e.g., DNA or a cyclic dinucleotide. Upon ligand binding, STING activates the innate immune response through interaction with RIG-I and IPS-1, resulting in interferon production (e.g., IFN-α and IFN-β) and other downstream signaling events.

Another class of PRRs includes RIG-I, which is the founding member of a family of PRRs termed RIG-I-like receptors (RLRs) that primarily detect RNA derived from foreign sources. It is a critical sensor of microbial infection (e.g., viral infection) in most cells and is constitutively expressed at low levels in the cytosol. After ligand binding, the expression of RIG-I is rapidly enhanced, leading to increased RIG-I concentrations in the cell (Jensen, S. and Thomsen, A. R. *J Virol* (2012) 86:2900-2910; Yoneyama M. et al. *Nat Immunol* (2004) 5:730-737). RIG-I is an ATP-dependent helicase containing a central DExD/H box ATPase domain and tandem N-terminal caspase-recruiting domains (CARDs) that mediate downstream signaling. The C-terminus of RIG-I comprises an ssRNA/dsRNA-binding domain that when unbound acts to silence CARD function at the N-terminus. Without wishing to be bound by theory, it is believed that upon recognition of target RNA structures, two N-terminal CARDs are exposed, allowing for interaction with the CARD of a downstream binding partner, IFN-β promoter stimulator 1 (IPS-1), also known as mitochondrial antiviral signaling molecule (MAVS) and CARDIF. This interaction in turn triggers further downstream signaling, such as induction of IRF3, IRF7, NF-κB, IFNs, and cytokine production.

Another class of PRRs encompasses the nucleotide-binding and oligomerization domain (NOD)-like receptors, or NLR family (Caruso, R. et al, Immunity (2014) 41:898-908), which includes the microbial sensor NOD2. NOD2 is composed of an N-terminal CARD, a centrally-located nucleotide-binding oligomerization domain, and a C-terminal leucine rich repeat domain that is responsible for binding microbial PAMPs. Ligand binding activates NOD2 and is believed to drive interaction with the CARD-containing kinase RIPK2, which in turn activates a number of downstream proteins including NF-κB, MAPK, IRF7, and IRF3, the latter of which results in the induction of type 1 interferons. NOD2 is expressed in a diverse set of cell types, including macrophages, dendritic cells, paneth cells, epithelial cells (e.g., lung epithelial cells, intestinal epithelia), and osteoblasts. Recent work has also shown that mutation of NOD2 may contribute to inflammatory disorders such as Crohn's disease, resulting in an aberrant inflammatory response upon stimulation.

Without wishing to be bound by theory, the mechanism of action of a compound of a formula of the disclosure entails its host immune modulating activity, which may inhibit endogenous IFNs via the inhibition of a PRR, e.g., RIG-I, NOD2, and STING. Inhibition may occur by binding of a compound of the disclosure to the nucleotide binding domain of a PRR (e.g., STING), as described previously, and may further result in the inhibition of PRR expression (e.g., STING expression). The inhibition of signaling may occur by directly competing with the natural ligand for the binding site of the PRR or alternatively by interacting with a different domain outside of the ligand binding domain of the PRR.

Exemplary Compounds of the Disclosure

In certain aspects, the present disclosure provides compounds of formula I, II, III, IV, or V:

I

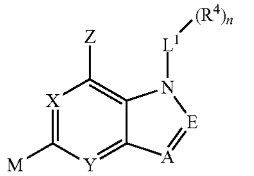

II

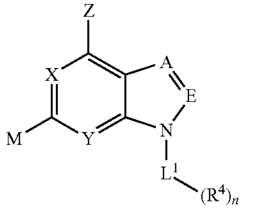

III

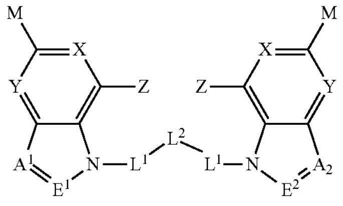

IV

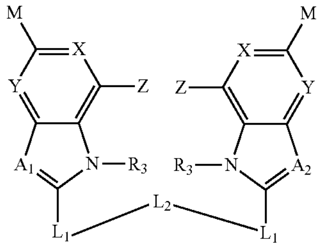

V

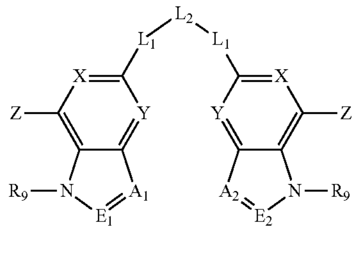

or a pharmaceutically acceptable salt thereof;

wherein

A, $A_1$, and $A_2$ are each independently N or CH;

E, $E_1$, and $E_2$ are each independently N or $CR^3$;

X is N or CH;

Y is N or CH;

M and Z are each independently selected from the group consisting of hydrogen, halo, CN, $CF_3$, alkyloxy, $SR^1$, $SOR^1$, $SO_2R^1$, $SO_2N(R^1)(R^2)$, $OR^1$, $NHCOR^1$, $NHSO_2R^1$, $NHCONHR^1$, $NHSO_2NHR^1$, $N(R^1)(R^2)$, $COR^1$, $CO_2R^1$, $CON(R^1)(R^2)$, alkyl, alkenyl, alkynyl, cycloalkyl, cycloalkenyl, aryl, heteroaryl, and heterocyclyl;

$L^1$ and $L^2$ are each independently selected from the group consisting of a bond, O, S, $N(R^{10})$, alkylenyl, alkenylenyl, alkynylenyl, acyl, heteroaryl, amido, sulfonamido, and heteroalkylenyl; or $L^1$ or $L^2$ is linked to $R^3$ or Z to form a cycloalkyl, aryl, amido, sulfonamido, or heteroaryl;

$R^1$, $R^2$, $R^5$, $R^6$, $R^7$ $R^8$, $R^9$, and $R^{10}$ are each independently selected from the group consisting of hydrogen, alkyl, heteroalkyl, alkenyl, alkynyl, acyl, cycloalkyl, heterocyclyl, aryl, aralkyl, heteroaryl, amino acid, and amino ester; or $R^1$ and $R^2$ combine to form a heterocyclyl;

$R^3$ is hydrogen, alkyl, haloalkyl, hydroxyalkyl, alkyloxyalkyl, aminoalkyl, alkenyl, alkynyl, cycloalkyl, aryl, heteroaryl, $SOR^5$, $SO_2R^5$, $SO_2N(R^5)(R^6)$, $COR^5$, $CON(R^5)(R^6)$, halo, CN, $CF_3$, $SR^5$, $OR^5$, $NHCOR^5$, $NHCONHR^5$, $NHSO_2NHR^5$, or $N(R^5)(R^6)$;

each $R^4$ is independently halo, CN, $CF_3$, $SR^7$, $SOR^7$, $SO_2R^7$, $SO_2N(R^7)(R^8)$, $OR^7$, $NHCOR^7$, $NHSO_2R^7$, $NHCONHR^7$, $NHSO_2NHR^7$, $N(R^7)(R^8)$, $COR^7$, $CO_2R^7$, $OC(O)R^7$, $CON(R^7)(R^8)$, $OP(O)(OR^7)_2$ or $OP(S)(OR^7)_2$, alkyl, alkenyl, alkynyl, cycloalkyl, cycloalkenyl, aryl, heteroaryl, or heterocyclyl; and n is an integer from 0-18.

In certain embodiments, E is $CR^3$. In certain embodiments, $E^1$ is $CR^3$. In certain embodiments, $E^2$ is $CR^3$.

In other aspects, the present disclosure provides compounds of formula I', II', III', IV', or V':

I'

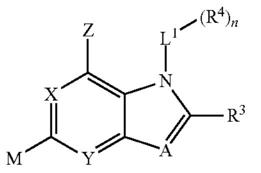

II'

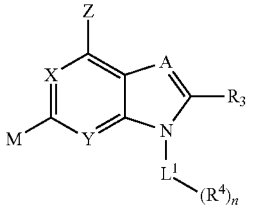

III'

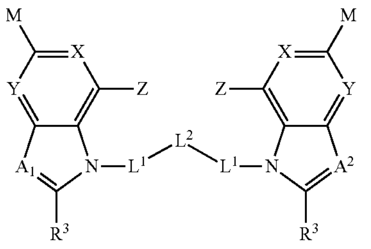

IV'

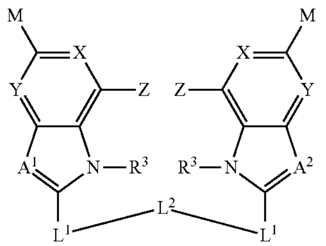

-continued

V'

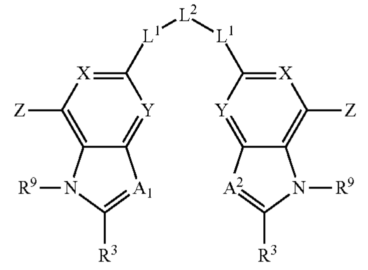

or a pharmaceutically acceptable salt thereof, wherein

A, $A_1$, and $A_2$ are each independently N or CH;

X is N or CH;

Y is N or CH;

M and Z are each independently selected from the group consisting of hydrogen, halo, CN, $CF_3$, $SR^1$, $SOR^1$, $SO_2R^1$, $SO_2N(R^1)(R^2)$, $OR^1$, $NHCOR^1$, $NHSO_2R^1$, $NHCONHR^1$, $NHSO_2NHR^1$, $N(R^1)(R^2)$, $COR^1$, $CO_2R^1$, $CON(R^1)(R^2)$, alkyl, alkenyl, alkynyl, cycloalkyl, cycloalkenyl, aryl, heteroaryl, and heterocyclyl;

$L^1$ and $L^2$ are each independently selected from the group consisting of a bond, O, S, $N(R^{10})$, alkylenyl, alkenylenyl, alkynylenyl, heteroaryl, amido, sulfonamido, and heteroalkylenyl; or $L^1$ or $L^2$ is linked to $R^3$ or Z to form a cycloalkyl, aryl, amido, sulfonamido, or heteroaryl;

$R^1$, $R^2$, $R^5$, $R^6$, $R^7$ $R^8$, $R^9$, and $R^{10}$ are each independently selected from the group consisting of hydrogen, alkyl, alkenyl, hydroxyalkyl, alkynyl, acyl, cycloalkyl, heterocyclyl, heterocyclylalkyl, aryl, aralkyl, and heteroaryl;

$R^3$ is hydrogen, alkyl, alkenyl, alkynyl, cycloalkyl, aryl, heteroaryl, $SOR^5$, $SO_2R^5$, $SO_2N(R^5)(R^6)$, $COR^5$, $CON(R^5)(R^6)$, halo, CN, $CF_3$, $SR^5$, $OR^5$, $NHCOR^5$, $NHCONHR^5$, $NHSO_2NHR^5$, or $N(R^5)(R^6)$;

each $R^4$ is independently halo, CN, $CF_3$, $SR^7$, $SOR^7$, $SO_2R^7$, $SO_2N(R^7)(R^8)$, $OR^7$, $NHCOR^7$, $NHSO_2R^7$, $NHCONHR^7$, $NHSO_2NHR^7$, $N(R^7)(R^8)$, $COR^7$, $CO_2R^7$, $CON(R^7)(R^8)$, alkyl, alkenyl, alkynyl, cycloalkyl, cycloalkenyl, aryl, heteroaryl, or heterocyclyl; and n is an integer from 0-18.

In other aspects, the present disclosure provides compounds represented by formula I'', II', III', IV'', or V'':

I''

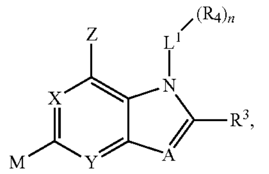

II''

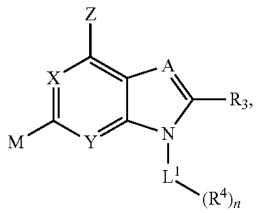

-continued

III″

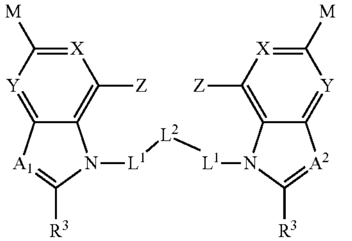

IV″

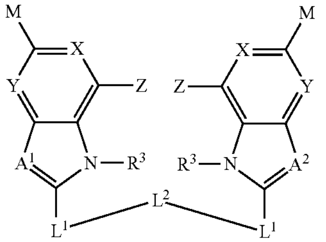

V″

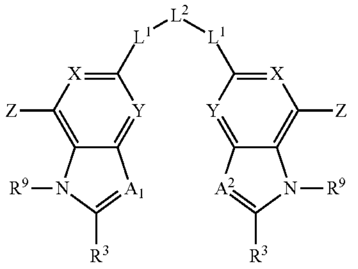

or a pharmaceutically acceptable salt thereof, wherein

A, $A_1$, and $A_2$ are each independently N or CH;

X is N or CH;

Y is N or CH;

M and Z are each independently selected from the group consisting of hydrogen, halo, CN, $CF_3$, $SR^1$, $SOR^1$, $SO_2R^1$, $SO_2N(R^1)(R^2)$, $OR^1$, $NHCOR^1$, $NHSO_2R^1$, $NHCONHR^1$, $NHSO_2NHR^1$, $N(R^1)(R^2)$, $COR^1$, $CO_2R^1$, $CON(R^1)(R^2)$, alkyl, alkenyl, alkynyl, cycloalkyl, cycloalkenyl, aryl, heteroaryl, and heterocyclyl;

$L^1$ and $L^2$ are each independently selected from the group consisting of a bond, O, S, $N(R^{10})$, alkylenyl, alkenylenyl, and alkynylenyl; or $L^1$ or $L^2$ is linked to $R^3$ or Z to form a cycloalkyl, aryl, or heteroaryl;

$R^1$, $R^2$, $R^5$, $R^6$, $R^7$ $R^1$, $R^9$, and $R^{10}$ are each independently selected from the group consisting of hydrogen, alkyl, alkenyl, alkynyl, cycloalkyl, heterocyclyl, aryl, aralkyl, and heteroaryl;

$R^3$ is hydrogen, alkyl, alkenyl, alkynyl, cycloalkyl, aryl, heteroaryl, $SOR^5$, $SO_2R^5$, $SO_2N(R^5)(R^5)$, $COR^5$, or $CON(R^5)(R^6)$;

each $R^4$ is independently halo, CN, $CF_3$, $SR^7$, $SOR^7$, $SO_2R^7$, $SO_2N(R^7)(R^8)$, $OR^7$, $NHCOR^7$, $NHSO_2R^7$, $NHCONHR^7$, $NHSO_2NHR^7$, $N(R^7)(R^8)$, $COR^7$, $CO_2R^7$, $CON(R^7)(R^8)$, alkyl, alkenyl, alkynyl, cycloalkyl, cycloalkenyl, aryl, heteroaryl, or heterocyclyl; and n is an integer from 0-10.

In certain embodiments, the compound is represented by formula I:

I

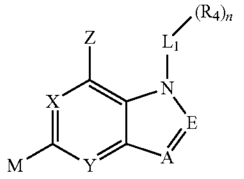

or a pharmaceutically acceptable salt thereof.

In certain embodiments, the compound is represented by formula II:

II

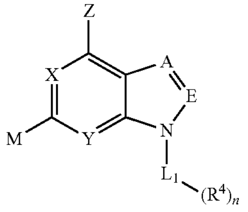

or a pharmaceutically acceptable salt thereof.

In certain embodiments, the compound is represented by formula I:

I′

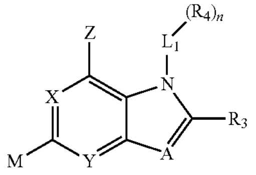

or a pharmaceutically acceptable salt thereof.

In certain embodiments, the compound is represented by formula II:

II′

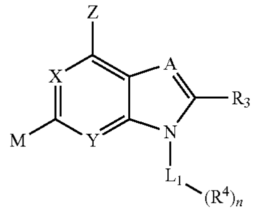

or a pharmaceutically acceptable salt thereof.

In certain embodiments of Formula I or II, A is CH. In other embodiments, A is N.

In certain embodiments of formula I or II, $L^1$ is $C_1$alkylenyl, $C_1$-$C_6$alkylenyl, $C_1$-$C_7$alkylenyl, $C_1$-$C_9$alkylenyl, $C_1$-$C_{10}$alkylenyl, $C_1$-$C_{15}$alkylenyl, or $C_1$-$C_{16}$alkylenyl. In certain embodiments, $L^1$ is $C_1$-$C_{15}$alkylenyl or $C_1$-$C_{15}$heteroalkylenyl (e.g., triethylene glycolyl). In certain embodiments, $L^1$ is $C_1$alkylenyl, $C_1$-$C_6$alkylenyl, $C_1$-$C_7$alkylenyl, $C_1$-$C_9$alkylenyl, $C_1$-$C_{10}$alkylenyl, or $C_1$-$C_{15}$alkylenyl. In certain embodiments, $C_1$alkylenyl, $C_2$alkylenyl, $C_3$alkylenyl, $C_4$alkylenyl, $C_5$alkylenyl, $C_6$alkylenyl, $C_7$alkylenyl, $C_9$alkylenyl, $C_{10}$alkylenyl, or Cisalkylenyl. In certain embodiments, $L^1$ is $C_1$alkylenyl, $C_2$alkylenyl, $C_3$alkylenyl, $C_4$alkylenyl, $C_5$alkylenyl, $C_6$alkylenyl, $C_7$alkylenyl, $C_9$alkylenyl, $C_{10}$alkylenyl, $C_{15}$alkylenyl, or $C_{1-6}$alkylenyl. In other embodiments, $L_1$ is $C_{11}$heteroalkylenyl (e.g., triethylene glycolyl). In yet other embodiments, $L_1$ is acyl (e.g., $C_4$Acyl). In certain embodiments, a carbon of $L^1$ is replaced by heterocyclyl (e.g., pyrrolidinyl, piperidinyl, or piperazinyl). In certain embodiments, a carbon of $L^1$ is replaced by oxygen. In certain embodiments, a carbon of $L^1$ is replaced by nitrogen (e.g., —NH— or —N(alkyl)-). In certain embodiments of formula I or II, $R^4$ is $CO_2R^7$, $COR^7$, aryl (e.g., methoxyphenyl), heterocyclyl (e.g., piperazinonyl), $OR^7$, heterocyclyl (e.g., morpholinyl), heteroaryl (e.g., tetrazolyl or methyltetrazolyl), $CON(R^7)(R^8)$, $OP(O)(OR^7)_2$, or $OP(S)(OR^7)_2$. In certain embodiments, $R^7$ and $R^8$ combine to form a heterocyclyl (e.g., piperidinyl or morpholinyl). In certain embodiments, $R^4$ is $CO_2R^7$, aryl (e.g., methoxyphenyl), heterocyclyl (e.g., piperazinonyl) or $OR^7$. In certain embodiments, the heterocyclyl comprises a nitrogen (e.g., piperidinyl). In certain embodiments, the heterocyclyl comprises a nitrogen (e.g., piperidinyl, or methylpiperidinyl). In certain embodiments, the nitrogen is substituted with oxygen (e.g., an oxide). In other embodiments, the nitrogen is substituted with acyl.

In other embodiments, $R^4$ is $OC(O)R^7$. In yet other embodiments, $R^4$ is $COR^7$. In certain embodiments, $R^7$ is alkyl (e.g., methyl, ethyl, isopropyl, or tertiary butyl), heteroalkyl, aralkyl (e.g., methoxyphenylmethylenyl), hydroxyalkyl (e.g., hydroxyethyl, hydroxypropyl, or dihydroxypropyl), or heterocyclylalkyl (e.g., dimethyldioxolanmethyl). In certain embodiments, $R^7$ is an amino acid or amino ester. In certain embodiments, the amino acid or amino ester is naturally occurring. In certain embodiments, the amino ester is valine methyl ester. In certain embodiments, $R^7$ is alkyl (e.g., methyl or ethyl) or aralkyl (e.g., methoxyphenylmethylenyl). In certain embodiments, $R^7$ is alkyl (e.g., methyl, ethyl, or isopropyl). In certain embodiments, $R^7$ is heteroalkyl (e.g., diethylene glycolyl, hydroxyethyl, hydroxypropyl, or dihydroxypropyl). In certain embodiments, wherein $R^7$ is cycloalkylalkyl (e.g., cyclopropylalkyl). In certain embodiments, $R^7$ is deutroalkyl (e.g., deutromethyl). In certain embodiments, the carbon of $R^7$ that is bonded to $R^4$ is in the S configuration. In other embodiments, the carbon of $R^7$ that is bonded to $R^4$ is in the R configuration. In certain embodiments, $R^7$ is substituted with hydroxyl. In certain embodiments, $R^7$ is H.

In yet other embodiments, $R^4$ is $OP(O)(OR^7)_2$, or $OP(S)(OR^7)_2$. In certain embodiments, each $R^7$ is H. In other embodiments, one $R^7$ is H and the other $R^7$ is alkyl (e.g., cyanoethyl). In yet other embodiments, $R^4$ is $CON(R^7)(R^8)$. In certain embodiments, $R^7$ and $R^8$ are both H. In other embodiments, $R^7$ is H and $R^8$ is alkyl (e.g., methyl). In yet other embodiments, $R^7$ and $R^8$ are both alkyl (e.g., methyl). In certain embodiments, one or more hydrogens of $R^7$ is replaced with a deuterium. In other embodiments, $R^1$ is acyl (e.g., $C(O)CH_3$). In yet other embodiments, $R^1$ is H. In further embodiments, $R^4$ is halo (e.g., chloro).

In certain embodiments of Formulas I or II, n is 0, 1, or 2.

In certain embodiments, the compound is represented by formula III:

III

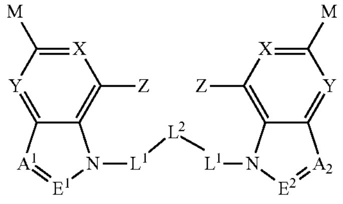

or a pharmaceutically acceptable salt thereof.

In certain embodiments, the compound is represented by formula IV:

IV

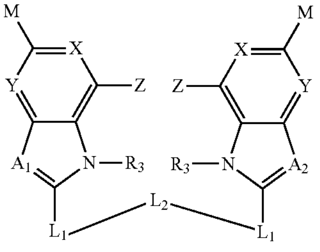

or a pharmaceutically acceptable salt thereof.

In certain embodiments, the compound is represented by formula V:

V

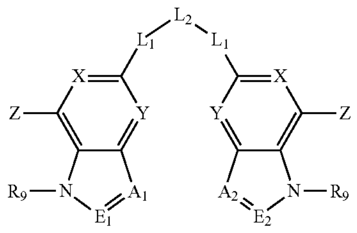

or a pharmaceutically acceptable salt thereof.

In certain embodiments, the compound is represented by formula III':

III'

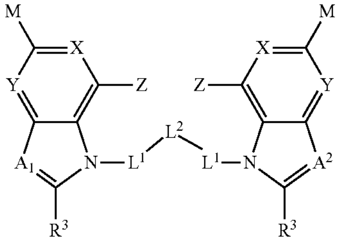

or a pharmaceutically acceptable salt thereof.

In certain embodiments, the compound is represented by formula IV:

IV'

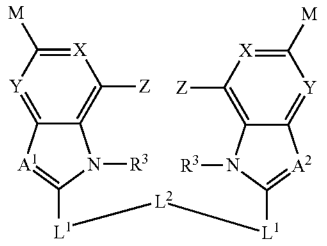

or a pharmaceutically acceptable salt thereof.

In certain embodiments, the compound is represented by formula V':

V'

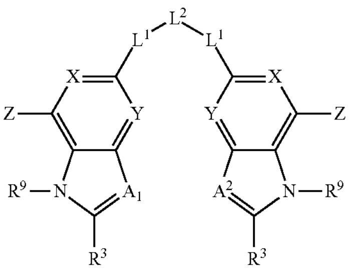

or a pharmaceutically acceptable salt thereof.

In certain embodiments of Formulas III, IV, and V, $A_1$ is N.

In certain embodiments of Formulas III, IV, and V, $A_2$ is N.

In certain embodiments of Formulas III, IV, and V, $L^1$ is $C_1$-$C_{17}$alkylenyl, $C_1$-$C_{17}$alkenylenyl, or $C_1$-$C_{17}$alkynylenyl. In certain embodiments, $L^1$ is $C_4$alkylenyl, $C_8$alkylenyl, $C_{10}$alkylenyl or $C_{12}$alkylenyl. In other embodiments of Formulas III, IV, and V, each $L^1$ is oxygen. In yet other embodiments of Formulas III, IV, and V, each $L^1$ is a bond.

In certain embodiments of Formulas III, IV, and V, $L^2$ is $C_1$-$C_{17}$alkylenyl, $C_1$-$C_{17}$alkenylenyl, or $C_1$-$C_{17}$alkynylenyl. In certain embodiments, $L^2$ is $C_1$-$C_{17}$alkylenyl. In certain embodiments, $L^2$ is $C_2$alkylenyl or $C_4$alkylenyl. In other embodiments, $L^2$ is $C_4$alkenylenyl. In certain embodiments, the stereochemistry of the alkene is cis. In other embodiments, the stereochemistry of the alkene is trans.

In certain embodiments of Formulas III, IV, and V, a carbon of $L^1$ or $L^2$ is replaced by acyl or amido. In certain embodiments, a carbon of $L^1$ or $L^2$ is replaced by sulfonamido.

In certain embodiments of Formulas III, IV, and V, a carbon of $L^1$ or $L^2$ is substituted with an oxo (i.e., =O). In certain embodiments, a carbon of $L^1$ or $L^2$ is substituted with $CO_2R^1$.

In certain embodiments, $L^2$ is $C_1$-$C_7$alkylenyl (e.g., $C_1$-$C_2$alkylenyl).

In certain embodiments of Formulas III, IV, and V, $R^1$ is alkyl (e.g., methyl).

In certain embodiments of Formulas I, II, III, IV, and V, X is N. In other embodiments, X is CH.

In certain embodiments of Formulas I, II, III, IV, and V, Y is N. In other embodiments, Y is CH.

In certain embodiments of Formulas I, II, III, IV, and V, $R^3$ is hydrogen. In other embodiments, $R^3$ is alkyl (e.g., methyl). In yet other embodiments, $R^3$ is haloalkyl (e.g., chloromethyl). In yet other embodiments, $R^3$ is alkyloxyalkyl (e.g., methoxymethyl). In yet other embodiments, $R^3$ is hydroxyalkyl (e.g., hydroxymethyl). In yet other embodiments, $R^3$ is aminoalkyl (e.g., diethylamino). In other embodiments, $R^3$ is hydroxyl. In yet other embodiments, $R^3$ is aryl (e.g., phenyl). In yet other embodiments, $R^3$ is alkynyl (e.g., ethynyl). In certain embodiments, the alkyne is substituted with cycloalkyl (e.g., cyclopropyl). In certain embodiments, $R^3$ is heterocyclylalkyl (e.g., morpholinylalkyl).

In certain embodiments of Formulas I, II, III, IV, and V, Z is hydrogen. In other embodiments, Z is alkyloxy (e.g., ethyloxy). In yet other embodiments, Z is hydroxyl or halo (e.g., Cl). In certain embodiments, Z is chloro. In yet other embodiments, Z is CN. In yet other embodiments, Z is amino (e.g., $NH_2$). In yet other embodiments, Z is $SR^1$, $SO_2R^1$, or $N(R^1)(R^2)$. In certain embodiments, $R^1$ is hydrogen or alkyl (e.g., methyl, ethyl, or hexyl). In certain embodiments, $R^1$ is alkyl (e.g., methyl, ethyl, isopropyl, or hexyl). In certain embodiments, the alkyl is substituted with sulfonamido (e.g., $SO_2NH_2$) or carboxyl (e.g., $CO_2H$). In certain embodiments, the alkyl is substituted with amino or alkylamino (e.g., dimethylamino). In other embodiments, the alkyl is substituted with hydroxyl. In yet other embodiments, the alkyl is substituted with heterocyclyl (e.g., morpholinyl). In certain embodiments, $R^2$ is hydrogen or alkyl. In certain embodiments, $R^2$ is alkyl (e.g., methyl).

In certain embodiments of Formulas I, II, III, IV, and V, M is hydrogen, halo (e.g., Cl), or $NH_2$. In certain embodiments, M is halo (e.g., Cl or F). In other embodiments, M is CN. In yet other embodiments, M is $N(R^1)(R^2)$. In certain embodiments, $R^1$ is H and $R^2$ is acyl.

In certain embodiments of formula I or II, the compound is represented by formula Ia or IIa:

Ia

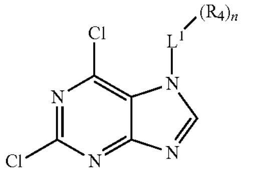

IIa

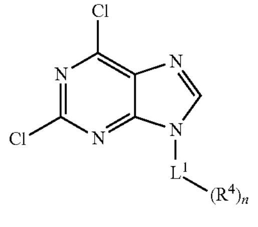

or a pharmaceutically acceptable salt thereof.

In certain embodiments of formula Ia or IIa, $L^1$ is $C_1$alkylenyl, $C_1$-$C_6$alkylenyl, $C_1$-$C_7$alkylenyl, $C_1$-$C_9$alkylenyl, $C_1$-$C_{10}$alkylenyl, or $C_1$-$C_{15}$alkylenyl. In certain embodiments, $L^1$ is $C_1$alkylenyl, $C_6$alkylenyl, $C_7$alkylenyl, $C_9$alkylenyl, $C_{10}$alkylenyl, or $C_{15}$alkylenyl.

In certain embodiments of formula Ia or IIa, $R^4$ is $CO_2R$, aryl (e.g., methoxyphenyl), heterocyclyl (e.g., piperazinonyl) or $OR^1$. In certain embodiments, $R^1$ is alkyl (e.g., methyl or ethyl) or aralkyl (e.g., methoxyphenylmethylenyl).

In certain embodiments of formula Ia or IIa, n is 0, 1, or 2.

In certain embodiments, the compound is selected from the group consisting of:
| Compound Number | Structure |
|---|---|
| 1 | 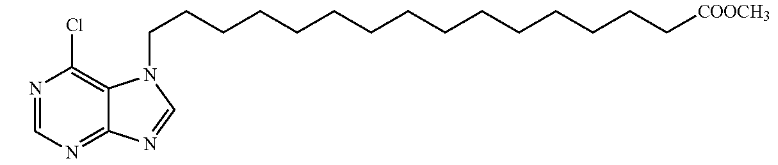 [SMILES: COC(=O)CCCCCCCCCCCCCCCn1cnc2ncnc(Cl)c21] |
| 2 | 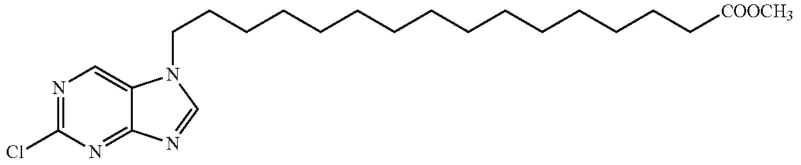 [SMILES: COC(=O)CCCCCCCCCCCCCCCn1cnc2nc(Cl)ncc21] |
| 3 | 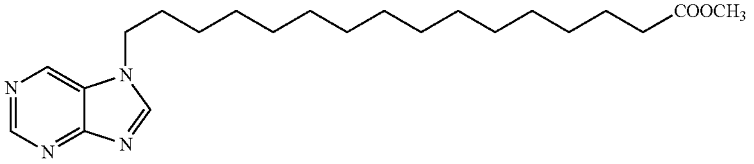 [SMILES: COC(=O)CCCCCCCCCCCCCCCn1cnc2ncncc21] |
| 4 | 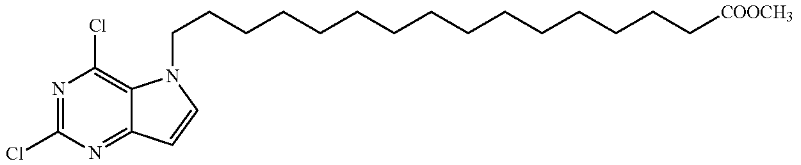 [SMILES: COC(=O)CCCCCCCCCCCCCCCn1ccc2nc(Cl)nc(Cl)c21] |
| 5 | 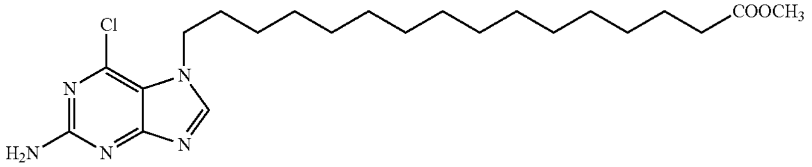 [SMILES: COC(=O)CCCCCCCCCCCCCCCn1cnc2nc(N)nc(Cl)c21] |
| 6 | 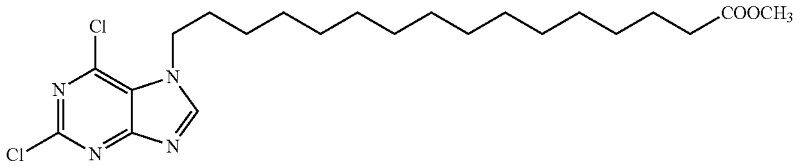 [SMILES: COC(=O)CCCCCCCCCCCCCCCn1cnc2nc(Cl)nc(Cl)c21] |
| 7 | 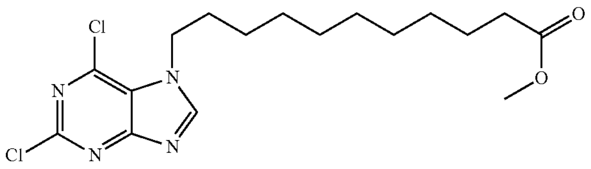 [SMILES: COC(=O)CCCCCCCCCCn1cnc2nc(Cl)nc(Cl)c21] |
| 8 | 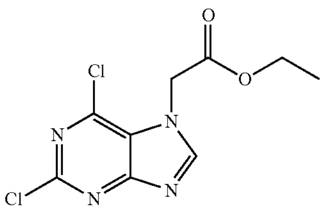 [SMILES: CCOC(=O)Cn1cnc2nc(Cl)nc(Cl)c21] |

-continued
| Compound Number | Structure |
|---|---|
| 9 | 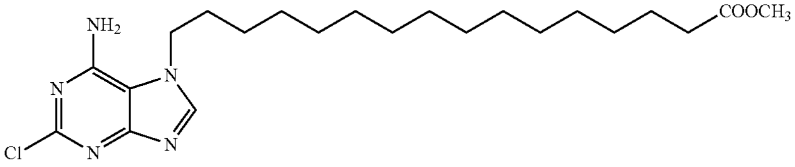 |
| 10 | 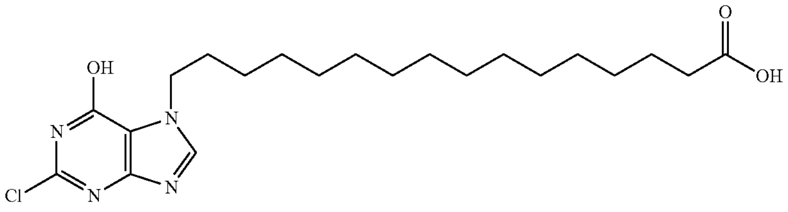 [SMILES: O=C(O)CCCCCCCCCCCCCCCn1cnc2nc(Cl)nc(O)c21] |
| 11 | 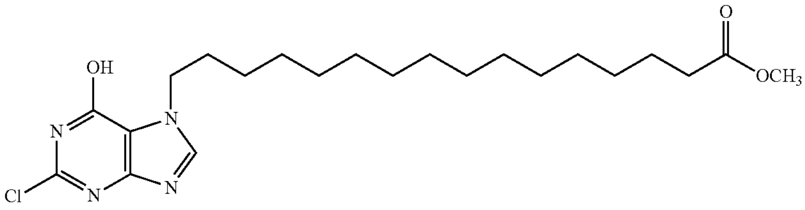 [SMILES: COC(=O)CCCCCCCCCCCCCCCn1cnc2nc(Cl)nc(O)c21] |
| 12 | 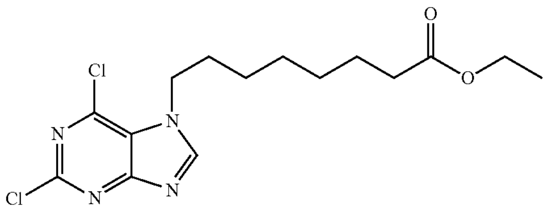 [SMILES: CCOC(=O)CCCCCCCn1cnc2nc(Cl)nc(Cl)c21] |
| 13 | 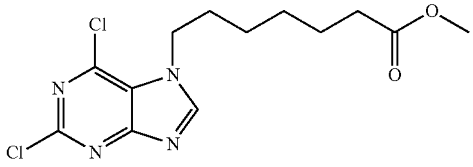 [SMILES: COC(=O)CCCCCCn1cnc2nc(Cl)nc(Cl)c21] |
| 14 | 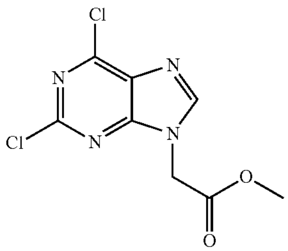 [SMILES: COC(=O)Cn1cnc2c(Cl)nc(Cl)nc21] |
| 15 | 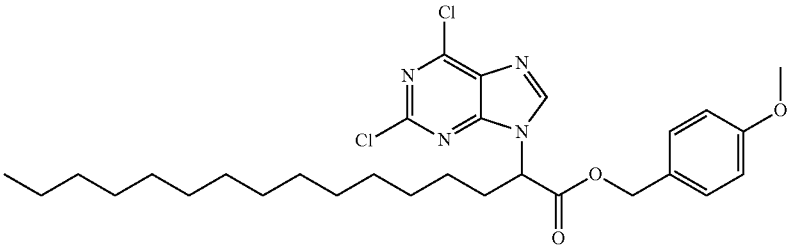 [SMILES: CCCCCCCCCCCCCCC(C(=O)OCc1ccc(OC)cc1)n1cnc2c(Cl)nc(Cl)nc21] |

-continued
| Compound Number | Structure |
|---|---|
| 16 | 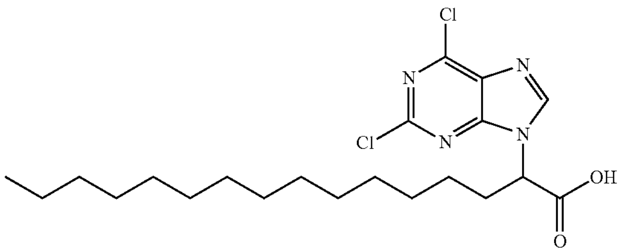 [SMILES: CCCCCCCCCCCCCCC(C(=O)O)n1cnc2c(Cl)nc(Cl)nc21] |
| 17 | 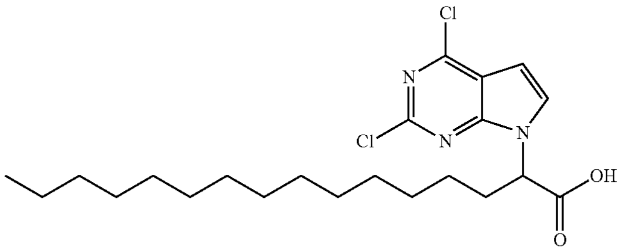 [SMILES: CCCCCCCCCCCCCCC(C(=O)O)n1ccc2c(Cl)nc(Cl)nc21] |
| 18 | 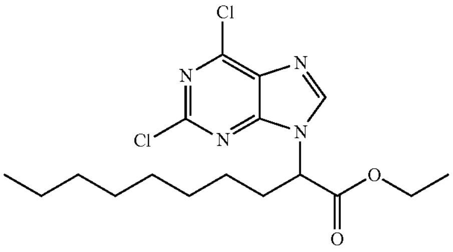 [SMILES: CCCCCCCCC(C(=O)OCC)n1cnc2c(Cl)nc(Cl)nc21] |
| 19 | 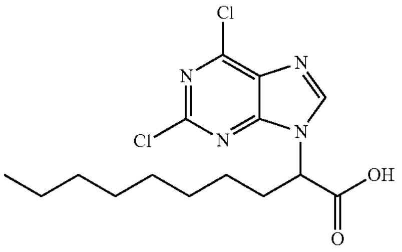 [SMILES: CCCCCCCCC(C(=O)O)n1cnc2c(Cl)nc(Cl)nc21] |
| 20 | 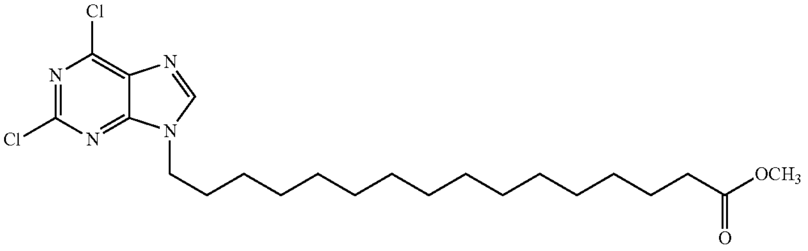 [SMILES: COC(=O)CCCCCCCCCCCCCCCn1cnc2c(Cl)nc(Cl)nc21] |

-continued
| Compound Number | Structure |
|---|---|
| 21 | 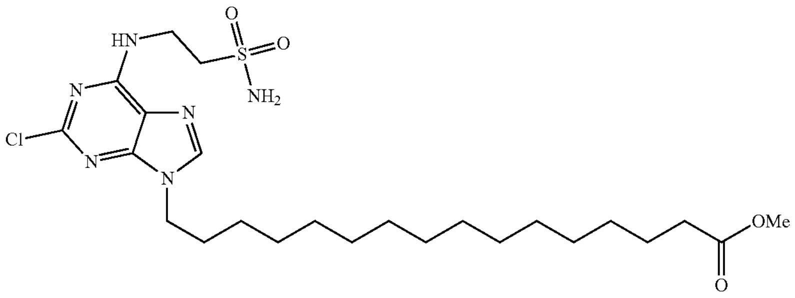 [SMILES: COC(=O)CCCCCCCCCCCCCCCn1cnc2c(NCCS(N)(=O)=O)nc(Cl)nc21] |
| 22 | 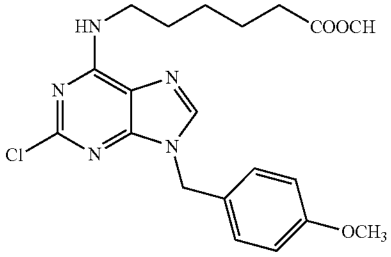 |
| 23 | 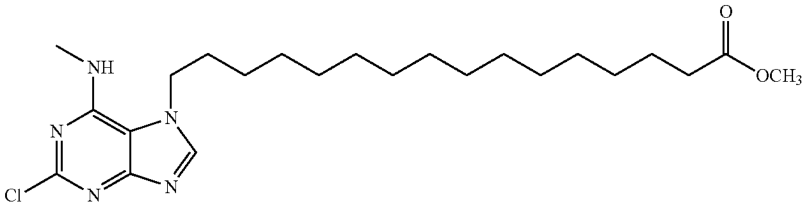 [SMILES: CNc1nc(Cl)nc2ncn(CCCCCCCCCCCCCCCC(=O)OC)c12] |
| 24 | 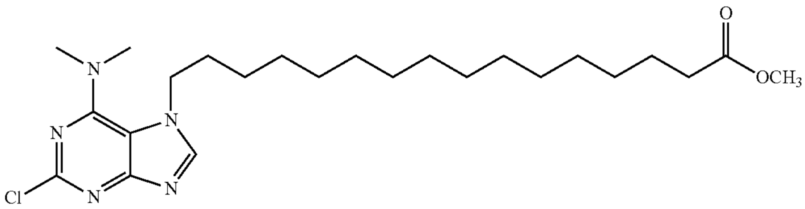 [SMILES: COC(=O)CCCCCCCCCCCCCCCn1cnc2nc(Cl)nc(N(C)C)c21] |
| 25 | 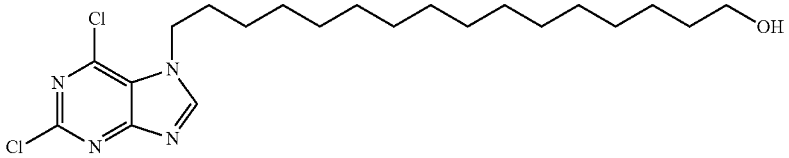 [SMILES: OCCCCCCCCCCCCCCCCn1cnc2nc(Cl)nc(Cl)c21] |
| 26 | 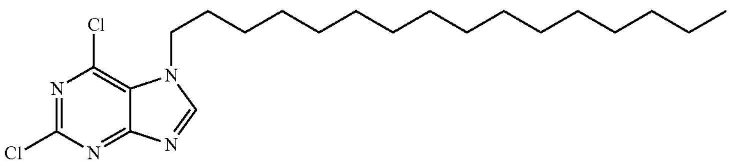 [SMILES: CCCCCCCCCCCCCCCCn1cnc2nc(Cl)nc(Cl)c21] |
| 27 | 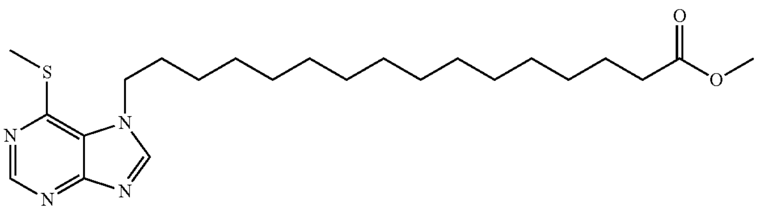 [SMILES: COC(=O)CCCCCCCCCCCCCCCn1cnc2ncnc(SC)c21] |

-continued
| Compound Number | Structure |
| --- | --- |
| 28 | 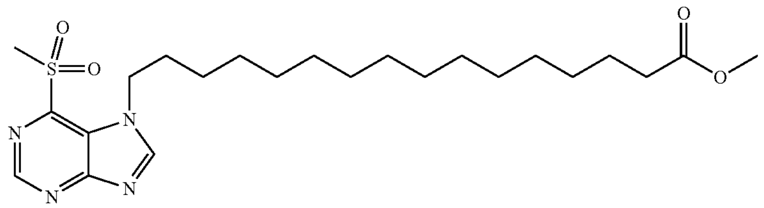 [SMILES: COC(=O)CCCCCCCCCCCCCCCn1cnc2ncnc(S(C)(=O)=O)c21] |
| 29 | 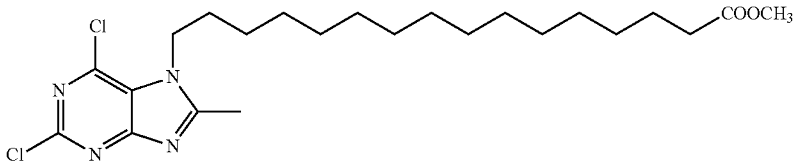 [SMILES: COC(=O)CCCCCCCCCCCCCCCn1c(C)nc2nc(Cl)nc(Cl)c21] |
| 30 | 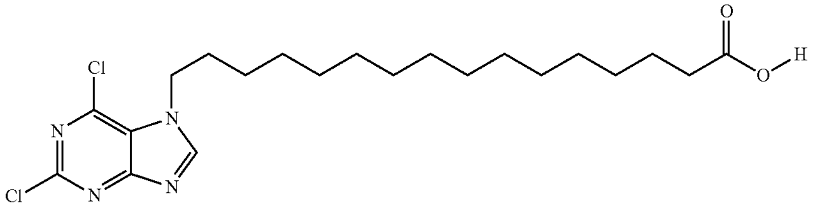 [SMILES: O=C(O)CCCCCCCCCCCCCCCn1cnc2nc(Cl)nc(Cl)c21] |
| 31 | 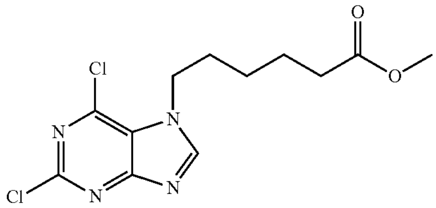 [SMILES: COC(=O)CCCCCn1cnc2nc(Cl)nc(Cl)c21] |
| 32 | 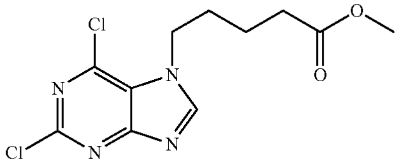 [SMILES: COC(=O)CCCCn1cnc2nc(Cl)nc(Cl)c21] |
| 33 | 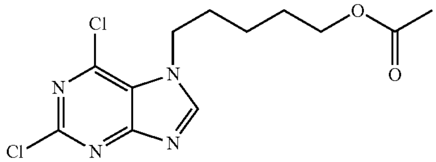 [SMILES: CC(=O)OCCCCCn1cnc2nc(Cl)nc(Cl)c21] |
| 34 | 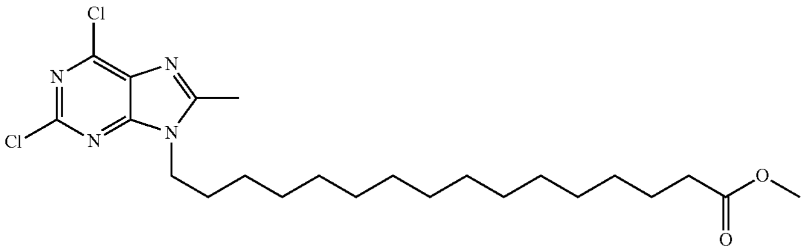 [SMILES: COC(=O)CCCCCCCCCCCCCCCn1c(C)nc2c(Cl)nc(Cl)nc21] |

-continued
| Compound Number | Structure |
|---|---|
| 35 | 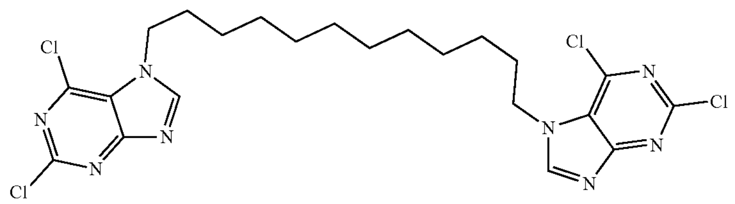 [SMILES: Clc1nc(Cl)c2c(ncn2CCCCCCCCCCCCn2cnc3nc(Cl)nc(Cl)c32)n1] |
| 36 | 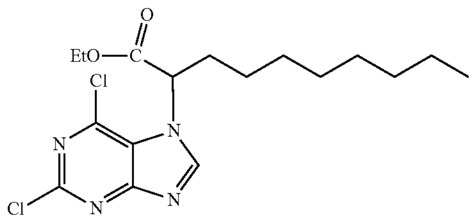 [SMILES: CCCCCCCCC(C(=O)OCC)n1cnc2nc(Cl)nc(Cl)c21] |
| 37 | 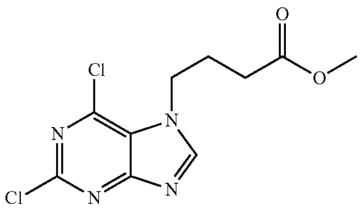 [SMILES: COC(=O)CCCn1cnc2nc(Cl)nc(Cl)c21] |
| 38 | 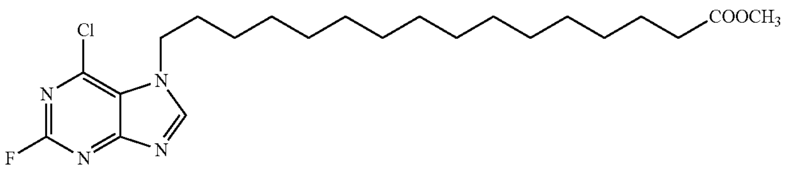 [SMILES: COC(=O)CCCCCCCCCCCCCCCn1cnc2nc(F)nc(Cl)c21] |
| 39 | 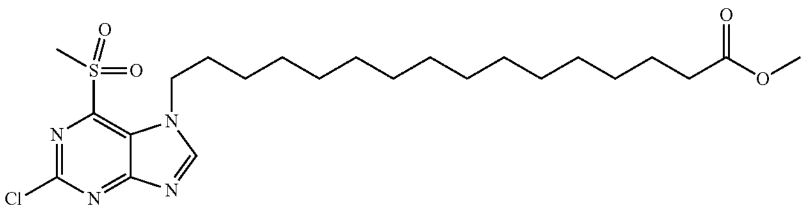 [SMILES: COC(=O)CCCCCCCCCCCCCCCn1cnc2nc(Cl)nc(S(C)(=O)=O)c21] |
| 40 | 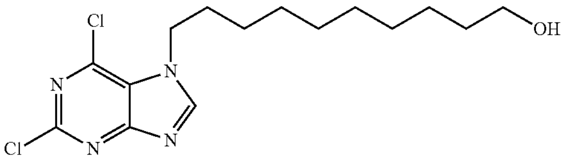 [SMILES: OCCCCCCCCCCn1cnc2nc(Cl)nc(Cl)c21] |
| 41 | 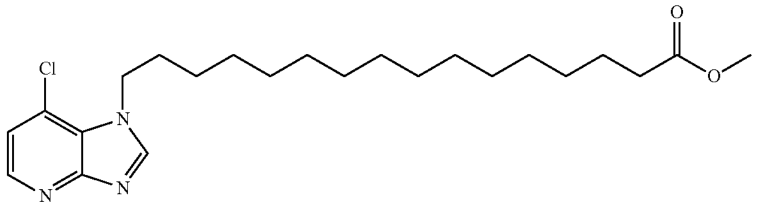 [SMILES: COC(=O)CCCCCCCCCCCCCCCn1cnc2nccc(Cl)c21] |

-continued
| Compound Number | Structure |
|---|---|
| 42 | 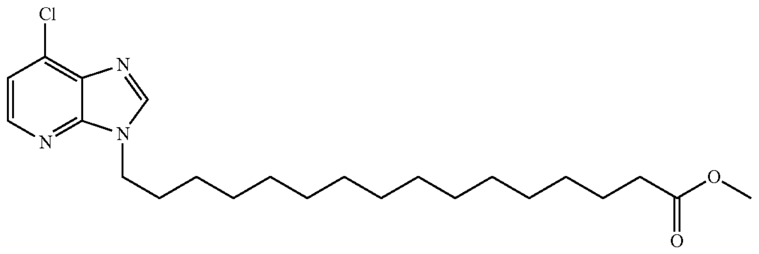 [SMILES: COC(=O)CCCCCCCCCCCCCCCn1cnc2c(Cl)ccnc21] |
| 43 | 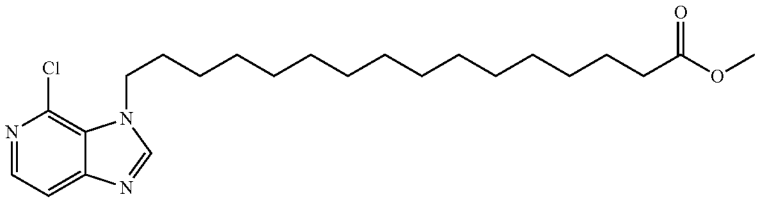 [SMILES: COC(=O)CCCCCCCCCCCCCCCn1cnc2ccnc(Cl)c21] |
| 44 | 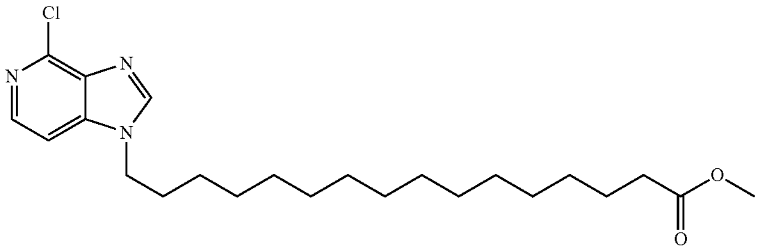 [SMILES: COC(=O)CCCCCCCCCCCCCCCn1cnc2c(Cl)nccc21] |
| 45 | 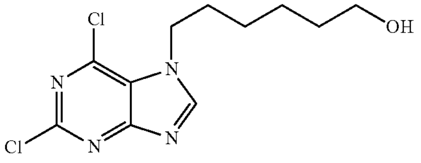 [SMILES: OCCCCCCn1cnc2nc(Cl)nc(Cl)c21] |
| 46 | 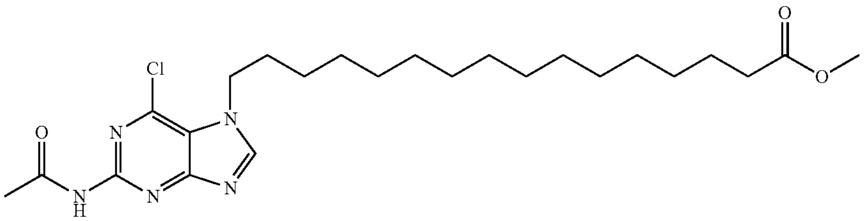 [SMILES: COC(=O)CCCCCCCCCCCCCCCn1cnc2nc(NC(C)=O)nc(Cl)c21] |
| 47 | 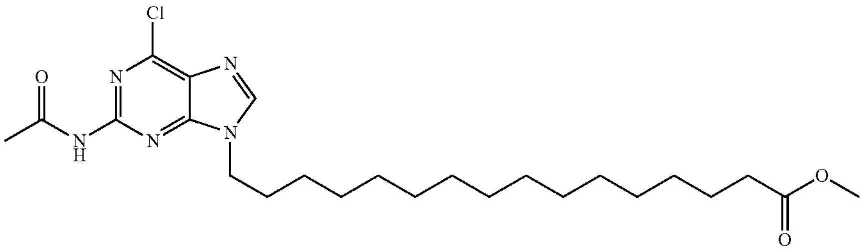 [SMILES: COC(=O)CCCCCCCCCCCCCCCn1cnc2c(Cl)nc(NC(C)=O)nc21] |
| 48 | 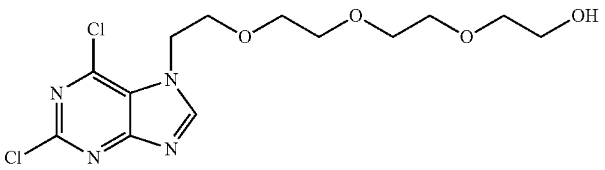 [SMILES: OCCOCCOCCOCCn1cnc2nc(Cl)nc(Cl)c21] |

-continued
| Compound Number | Structure |
|---|---|
| 49 | 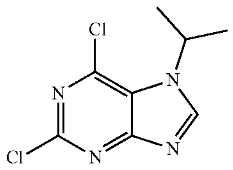 |
| 50 | 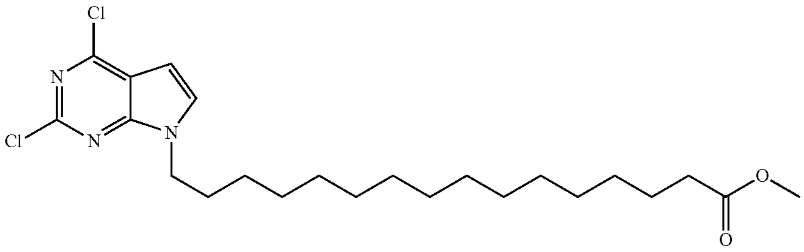 [SMILES: COC(=O)CCCCCCCCCCCCCCCn1ccc2c(Cl)nc(Cl)nc21] |
| 51 | 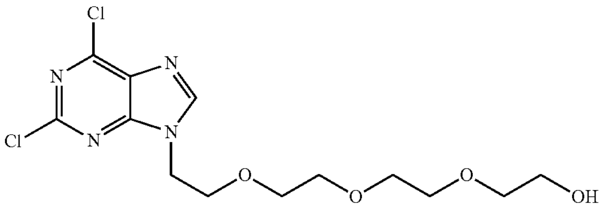 [SMILES: OCCOCCOCCOCCn1cnc2c(Cl)nc(Cl)nc21] |
| 52 | 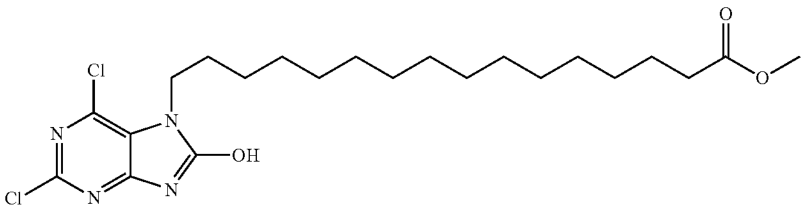 [SMILES: COC(=O)CCCCCCCCCCCCCCCn1c(O)nc2nc(Cl)nc(Cl)c21] |
| 53 | 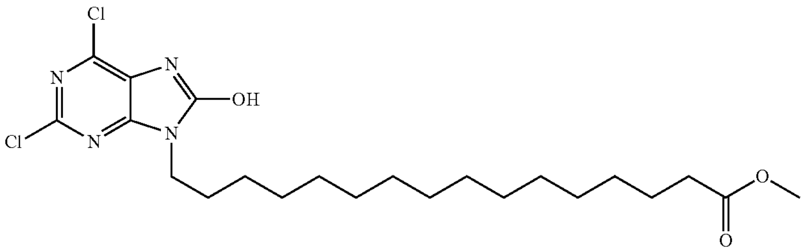 [SMILES: COC(=O)CCCCCCCCCCCCCCCn1c(O)nc2c(Cl)nc(Cl)nc21] |
| 54 | 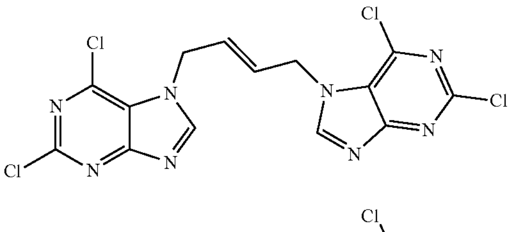 |
| 55 | 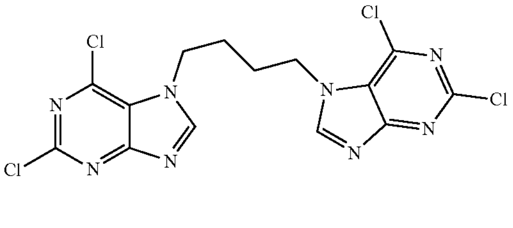 [SMILES: Clc1nc(Cl)c2c(ncn2CCCCn2cnc3nc(Cl)nc(Cl)c32)n1] |

-continued
| Compound Number | Structure |
| --- | --- |
| 56 | 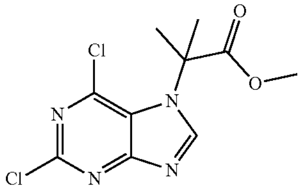 [SMILES: COC(=O)C(C)(C)n1cnc2nc(Cl)nc(Cl)c21] |
| 57 | 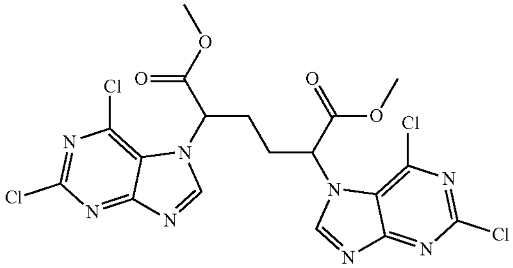 [SMILES: COC(=O)C(CCC(C(=O)OC)n1cnc2nc(Cl)nc(Cl)c21)n1cnc2nc(Cl)nc(Cl)c21] |
| 58 | 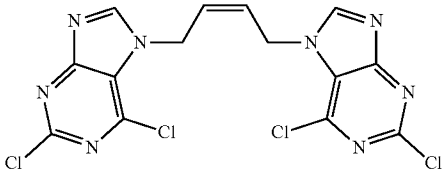 [SMILES: Clc1nc(Cl)c2c(ncn2C/C=C\Cn2cnc3nc(Cl)nc(Cl)c32)n1] |
| 59 | 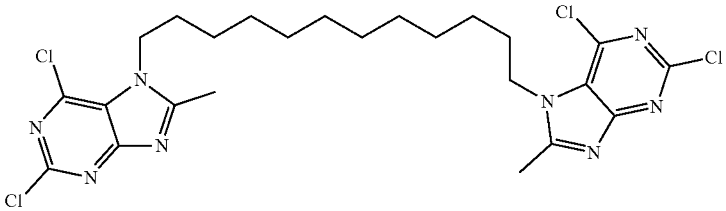 [SMILES: Cc1nc2nc(Cl)nc(Cl)c2n1CCCCCCCCCCCCn1c(C)nc2nc(Cl)nc(Cl)c21] |
| 60 | 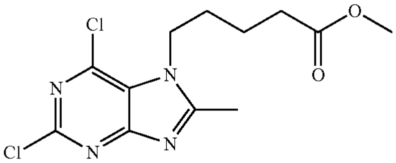 [SMILES: COC(=O)CCCCn1c(C)nc2nc(Cl)nc(Cl)c21] |
| 61 | 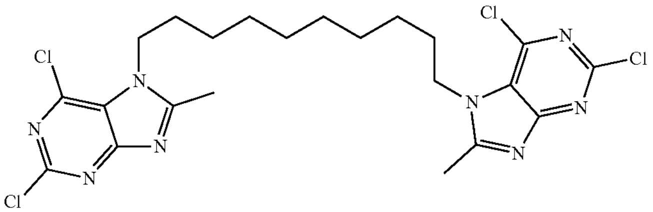 [SMILES: Cc1nc2nc(Cl)nc(Cl)c2n1CCCCCCCCCCn1c(C)nc2nc(Cl)nc(Cl)c21] |
| 62 | 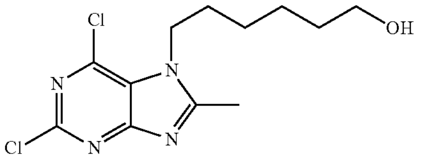 [SMILES: Cc1nc2nc(Cl)nc(Cl)c2n1CCCCCCO] |

-continued
| Compound Number | Structure |
| --- | --- |
| 63 | 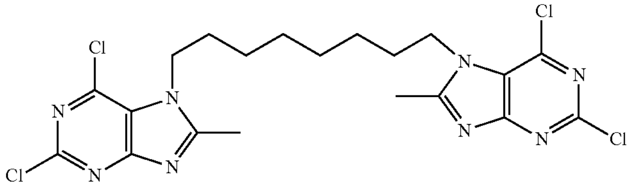 [SMILES: Cc1nc2nc(Cl)nc(Cl)c2n1CCCCCCCCn1c(C)nc2nc(Cl)nc(Cl)c21] |
| 64 | 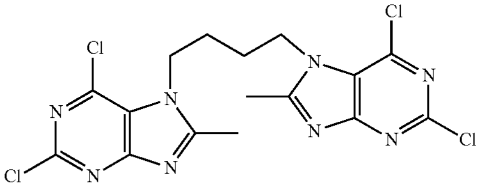 [SMILES: Cc1nc2nc(Cl)nc(Cl)c2n1CCCCn1c(C)nc2nc(Cl)nc(Cl)c21] |
| 65 | 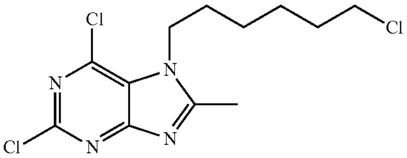 [SMILES: Cc1nc2nc(Cl)nc(Cl)c2n1CCCCCCCl] |
| 66 | 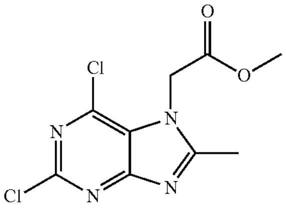 [SMILES: COC(=O)Cn1c(C)nc2nc(Cl)nc(Cl)c21] |
| 67 | 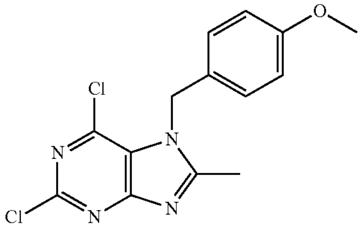 [SMILES: COc1ccc(Cn2c(C)nc3nc(Cl)nc(Cl)c32)cc1] |
| 68 | 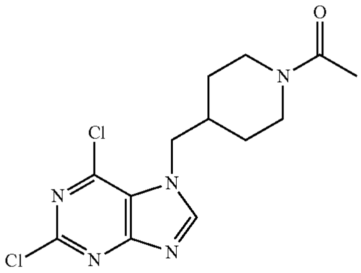 [SMILES: CC(=O)N1CCC(Cn2cnc3nc(Cl)nc(Cl)c32)CC1] |
| 69 | 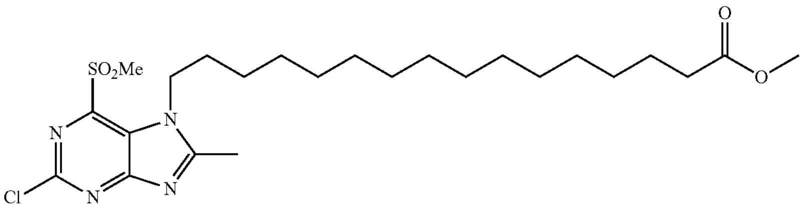 [SMILES: COC(=O)CCCCCCCCCCCCCCCn1c(C)nc2nc(Cl)nc(S(C)(=O)=O)c21] |

-continued
| Compound Number | Structure |
|---|---|
| 70 | 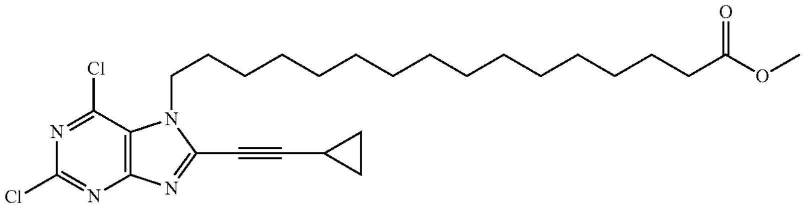 [SMILES: COC(=O)CCCCCCCCCCCCCCCn1c(C#CC2CC2)nc2nc(Cl)nc(Cl)c21] |
| 71 | 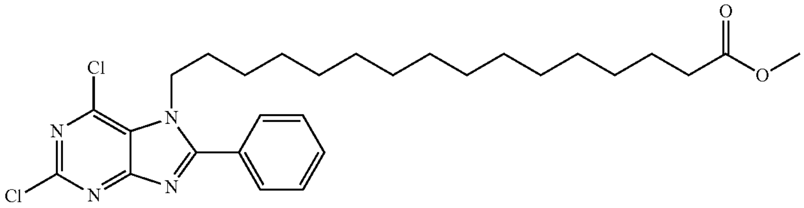 [SMILES: COC(=O)CCCCCCCCCCCCCCCn1c(-c2ccccc2)nc2nc(Cl)nc(Cl)c21] |
| 72 | 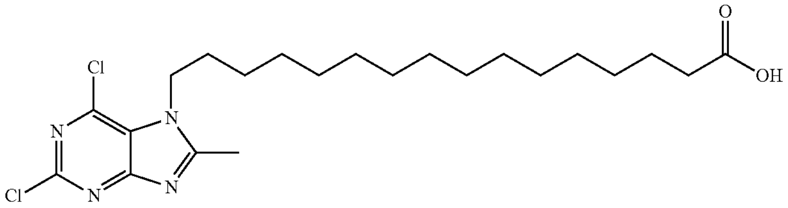 [SMILES: Cc1nc2nc(Cl)nc(Cl)c2n1CCCCCCCCCCCCCCCC(=O)O] |
| 73 | 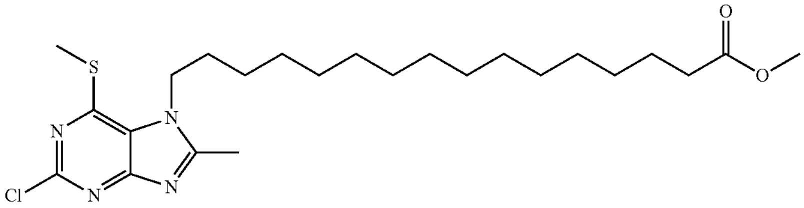 [SMILES: COC(=O)CCCCCCCCCCCCCCCn1c(C)nc2nc(Cl)nc(SC)c21] |
| 74 | 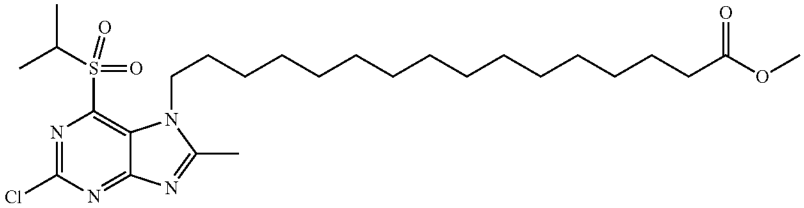 [SMILES: COC(=O)CCCCCCCCCCCCCCCn1c(C)nc2nc(Cl)nc(S(=O)(=O)C(C)C)c21] |
| 75 | 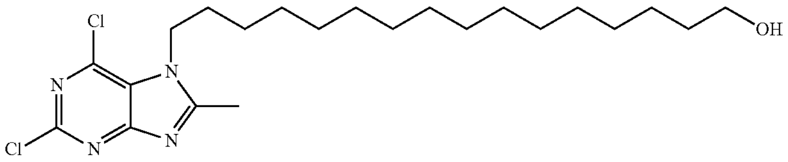 [SMILES: Cc1nc2nc(Cl)nc(Cl)c2n1CCCCCCCCCCCCCCCCO] |
| 76 | 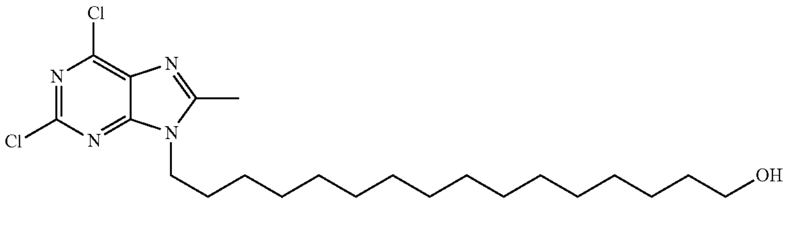 [SMILES: Cc1nc2c(Cl)nc(Cl)nc2n1CCCCCCCCCCCCCCCCO] |

-continued
| Compound Number | Structure |
|---|---|
| 77 | 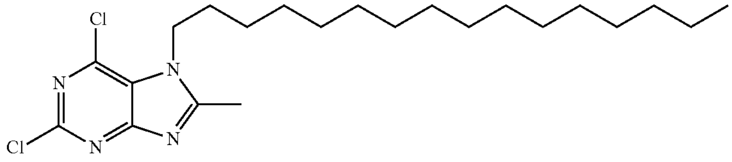 [SMILES: CCCCCCCCCCCCCCCCn1c(C)nc2nc(Cl)nc(Cl)c21] |
| 78 | 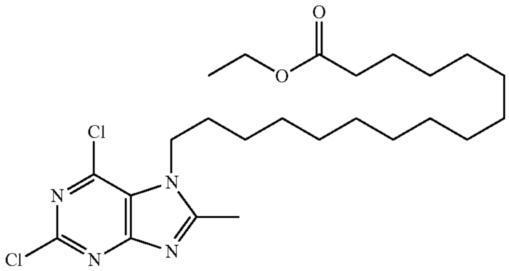 [SMILES: CCOC(=O)CCCCCCCCCCCCCCCn1c(C)nc2nc(Cl)nc(Cl)c21] |
| 79 | 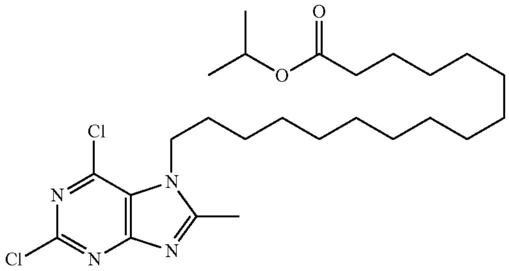 [SMILES: Cc1nc2nc(Cl)nc(Cl)c2n1CCCCCCCCCCCCCCCC(=O)OC(C)C] |
| 80 | 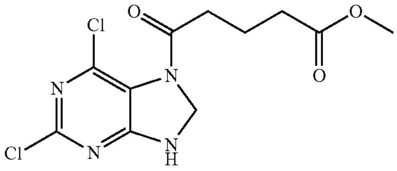 [SMILES: COC(=O)CCCC(=O)N1CNc2nc(Cl)nc(Cl)c21] |
| 81 | 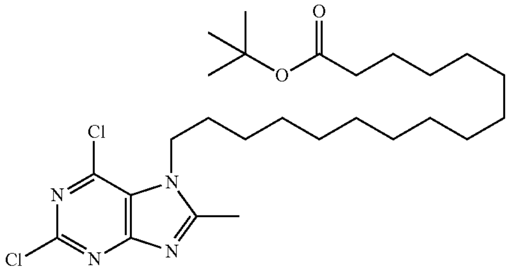 [SMILES: Cc1nc2nc(Cl)nc(Cl)c2n1CCCCCCCCCCCCCCCC(=O)OC(C)(C)C] |
| 82 | 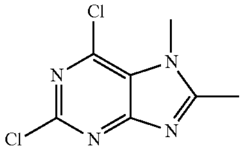 |
| 83 | 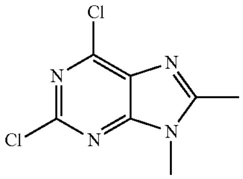 |

-continued
| Compound Number | Structure |
| --- | --- |
| 84 | 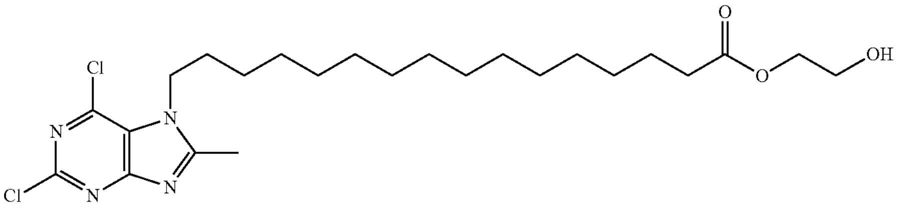 |
| 85 | 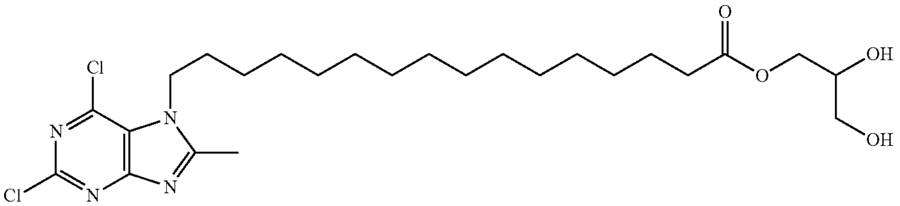 |
| 86 | 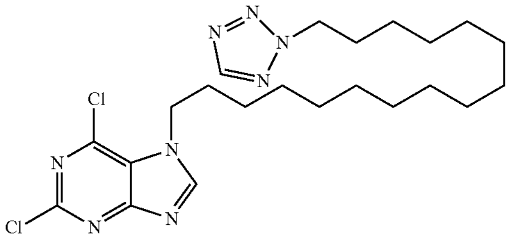 [SMILES: Clc1nc(Cl)c2c(ncn2CCCCCCCCCCCCCCCCn2ncnn2)n1] |
| 87 | 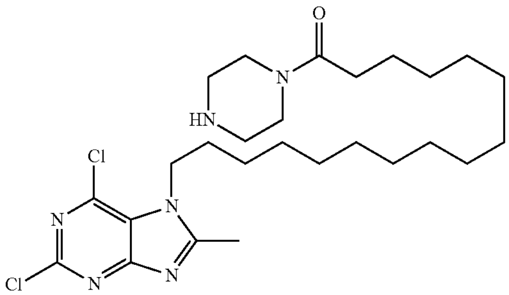 [SMILES: Cc1nc2nc(Cl)nc(Cl)c2n1CCCCCCCCCCCCCCCC(=O)N1CCNCC1] |
| 88 | 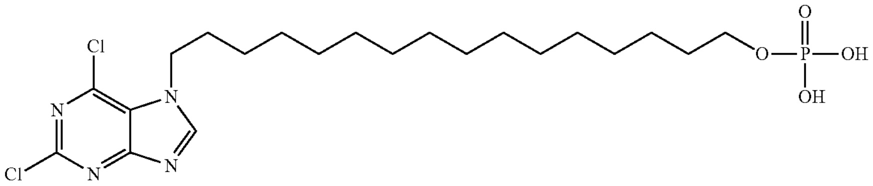 [SMILES: O=P(O)(O)OCCCCCCCCCCCCCCCCn1cnc2nc(Cl)nc(Cl)c21] |
| 89 | 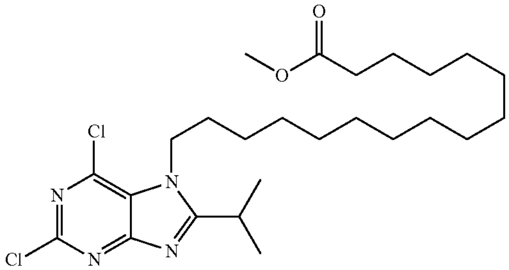 [SMILES: COC(=O)CCCCCCCCCCCCCCCn1c(C(C)C)nc2nc(Cl)nc(Cl)c21] |

-continued
| Compound Number | Structure |
|---|---|
| 90 | 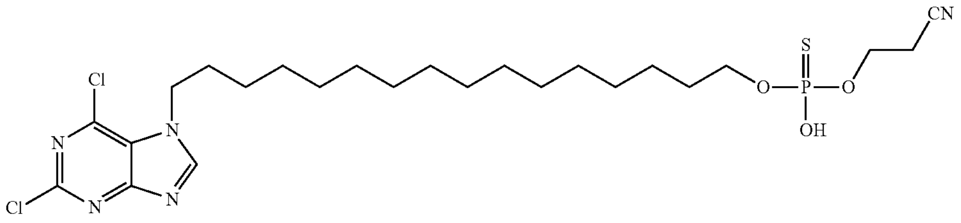 [SMILES: N#CCCOP(O)(=S)OCCCCCCCCCCCCCCCCn1cnc2nc(Cl)nc(Cl)c21] |
| 91 | 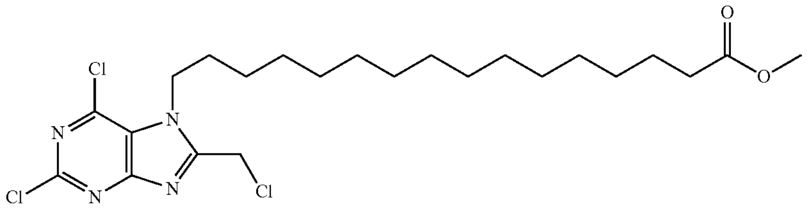 [SMILES: COC(=O)CCCCCCCCCCCCCCCn1c(CCl)nc2nc(Cl)nc(Cl)c21] |
| 92 | 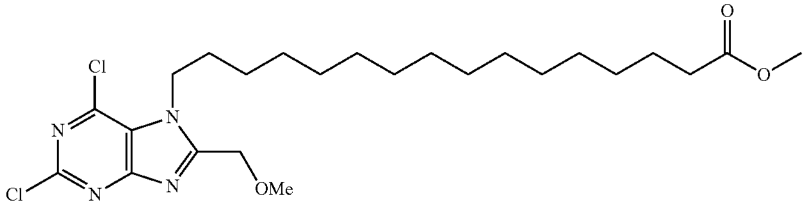 [SMILES: COCc1nc2nc(Cl)nc(Cl)c2n1CCCCCCCCCCCCCCCC(=O)OC] |
| 93 | 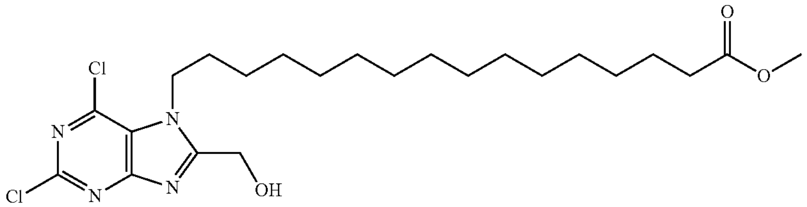 |
| 94 | 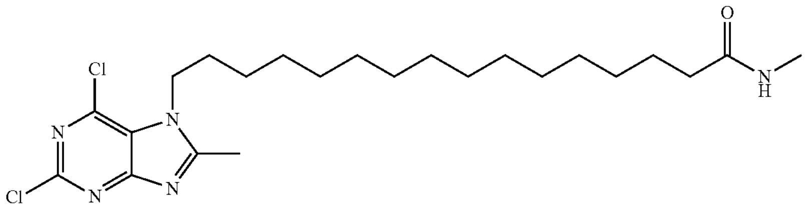 [SMILES: CNC(=O)CCCCCCCCCCCCCCCn1c(C)nc2nc(Cl)nc(Cl)c21] |
| 95 | 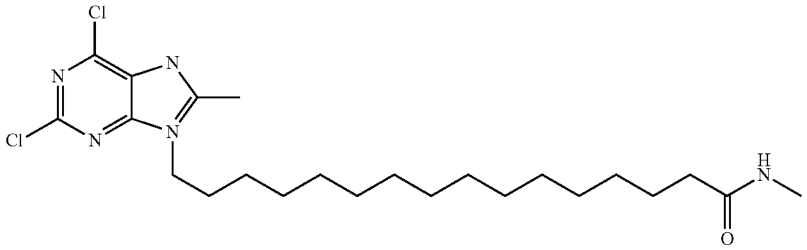 |
| 96 | 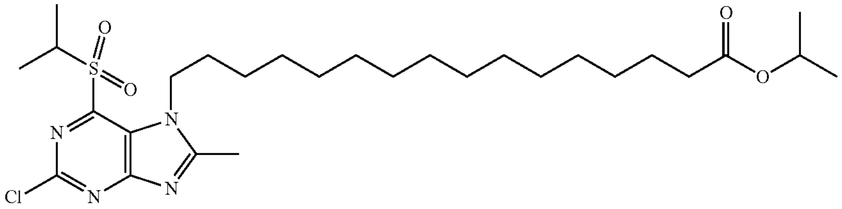 [SMILES: Cc1nc2nc(Cl)nc(S(=O)(=O)C(C)C)c2n1CCCCCCCCCCCCCCCC(=O)OC(C)C] |

-continued
| Compound Number | Structure |
|---|---|
| 97 | 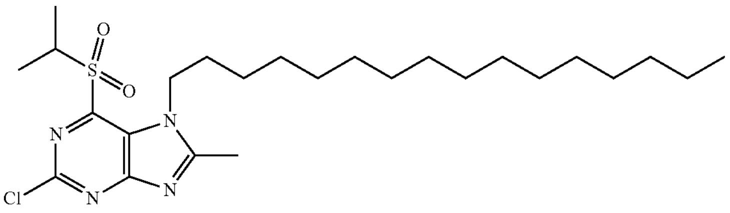 [SMILES: CCCCCCCCCCCCCCCCn1c(C)nc2nc(Cl)nc(S(=O)(=O)C(C)C)c21] |
| 98 | 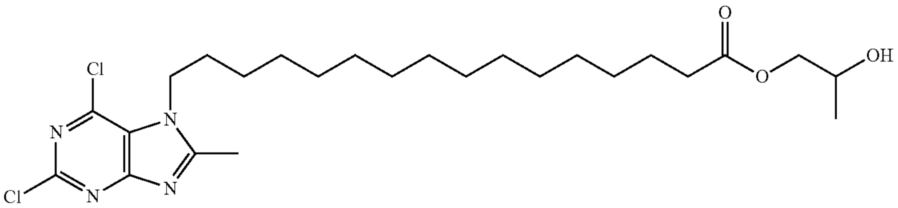 [SMILES: Cc1nc2nc(Cl)nc(Cl)c2n1CCCCCCCCCCCCCCCC(=O)OCC(C)O] |
| 99 | 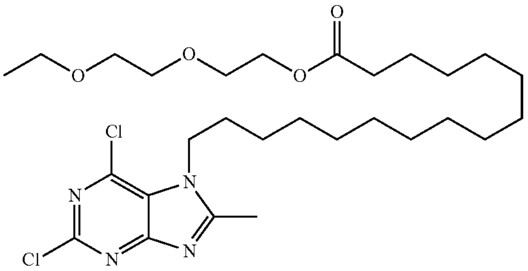 [SMILES: CCOCCOCCOC(=O)CCCCCCCCCCCCCCCn1c(C)nc2nc(Cl)nc(Cl)c21] |
| 100 | 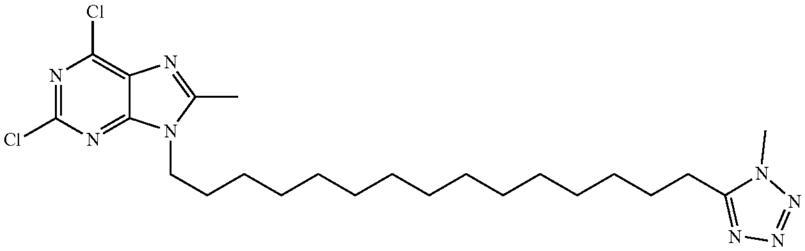 [SMILES: Cc1nc2c(Cl)nc(Cl)nc2n1CCCCCCCCCCCCCCCc1nnnn1C] |
| 101 | 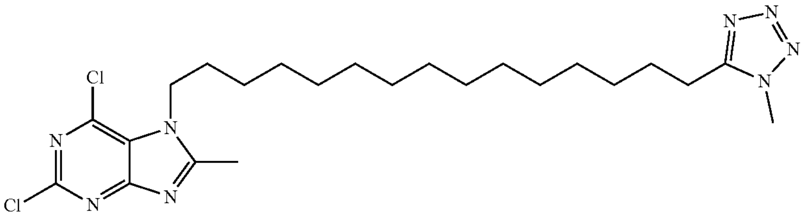 [SMILES: Cc1nc2nc(Cl)nc(Cl)c2n1CCCCCCCCCCCCCCCc1nnnn1C] |
| 102 | 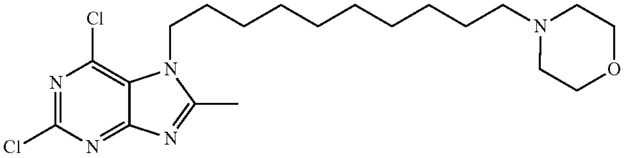 [SMILES: Cc1nc2nc(Cl)nc(Cl)c2n1CCCCCCCCCCN1CCOCC1] |

-continued
| Compound Number | Structure |
|---|---|
| 103 | 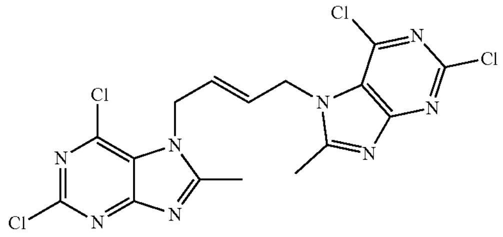 [SMILES: Cc1nc2nc(Cl)nc(Cl)c2n1C/C=C/Cn1c(C)nc2nc(Cl)nc(Cl)c21] |
| 104 | 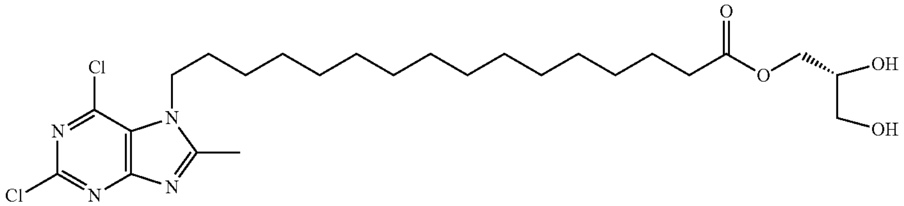 [SMILES: Cc1nc2nc(Cl)nc(Cl)c2n1CCCCCCCCCCCCCCCC(=O)OC[C@H](O)CO] |
| 105 | 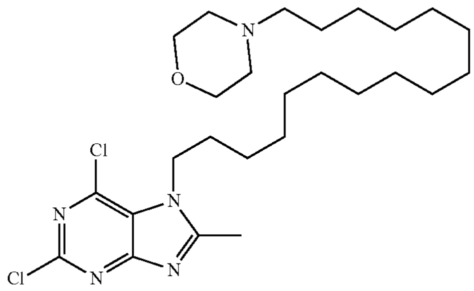 [SMILES: Cc1nc2nc(Cl)nc(Cl)c2n1CCCCCCCCCCCCCCCCN1CCOCC1] |
| 106 | 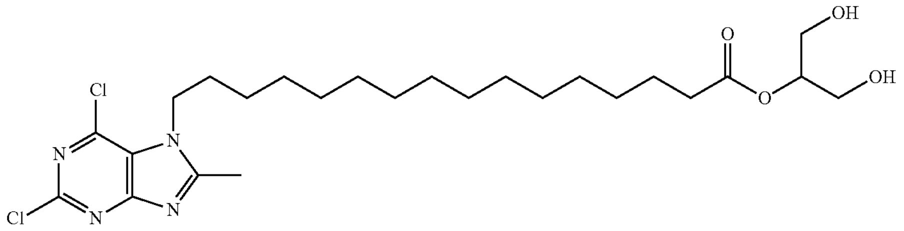 [SMILES: Cc1nc2nc(Cl)nc(Cl)c2n1CCCCCCCCCCCCCCCC(=O)OC(CO)CO] |
| 107 | 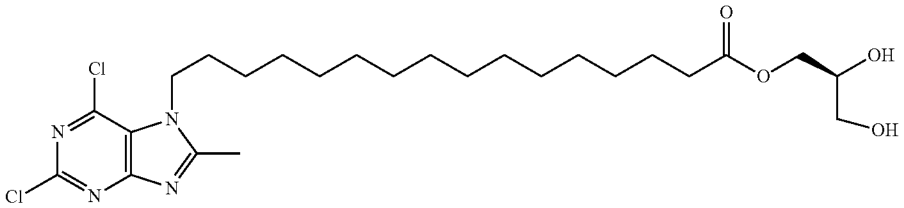 [SMILES: Cc1nc2nc(Cl)nc(Cl)c2n1CCCCCCCCCCCCCCCC(=O)OC[C@@H](O)CO] |
| 108 | 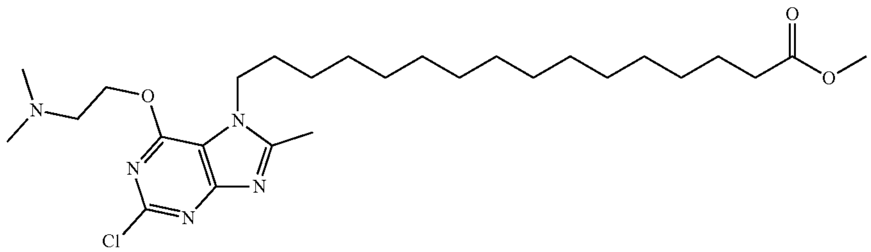 |

-continued
| Compound Number | Structure |
|---|---|
| 109 | 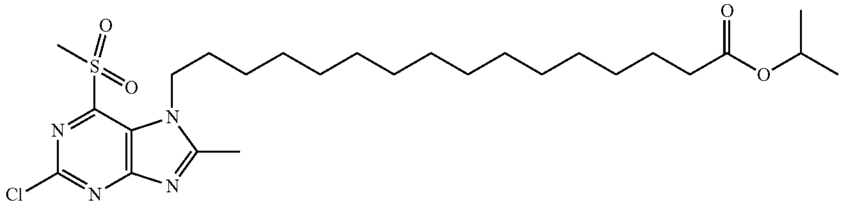 [SMILES: Cc1nc2nc(Cl)nc(S(C)(=O)=O)c2n1CCCCCCCCCCCCCCCC(=O)OC(C)C] |
| 110 | 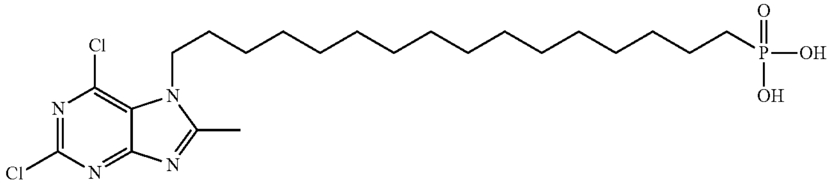 [SMILES: Cc1nc2nc(Cl)nc(Cl)c2n1CCCCCCCCCCCCCCCCP(=O)(O)O] |
| 111 | 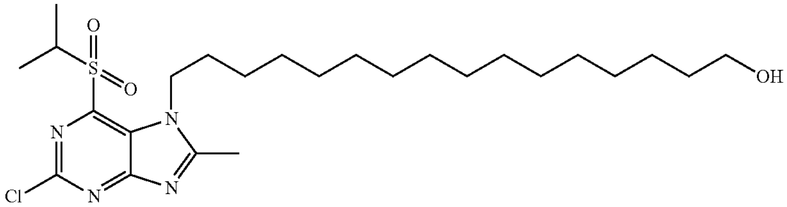 [SMILES: Cc1nc2nc(Cl)nc(S(=O)(=O)C(C)C)c2n1CCCCCCCCCCCCCCCCO] |
| 112 | 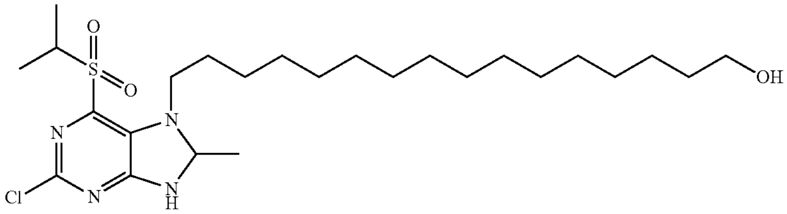 [SMILES: CC1Nc2nc(Cl)nc(S(=O)(=O)C(C)C)c2N1CCCCCCCCCCCCCCCCO] |
| 113 | 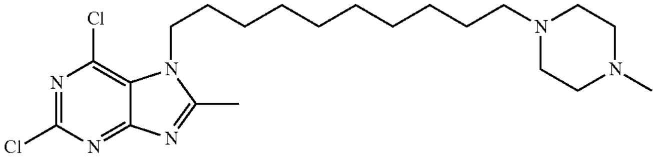 [SMILES: Cc1nc2nc(Cl)nc(Cl)c2n1CCCCCCCCCCN1CCN(C)CC1] |
| 114 | 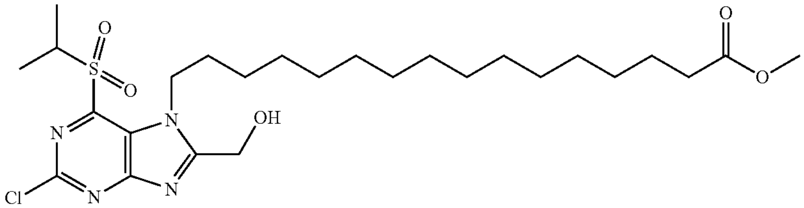 [SMILES: COC(=O)CCCCCCCCCCCCCCCn1c(CO)nc2nc(Cl)nc(S(=O)(=O)C(C)C)c21] |
| 115 | 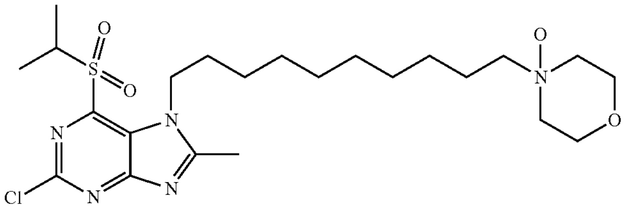 |

-continued
| Compound Number | Structure |
|---|---|
| 116 | 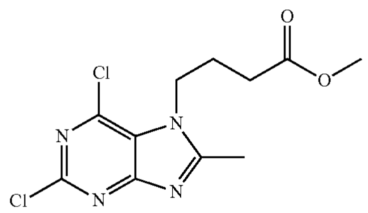 [SMILES: COC(=O)CCCn1c(C)nc2nc(Cl)nc(Cl)c21] |
| 117 | 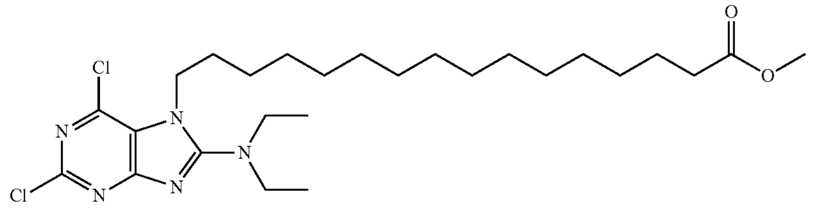 [SMILES: CCN(CC)c1nc2nc(Cl)nc(Cl)c2n1CCCCCCCCCCCCCCCC(=O)OC] |
| 118 | 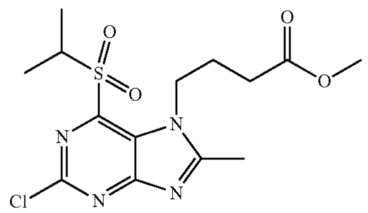 [SMILES: COC(=O)CCCn1c(C)nc2nc(Cl)nc(S(=O)(=O)C(C)C)c21] |
| 119 | 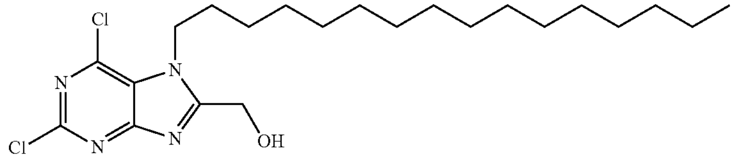 [SMILES: CCCCCCCCCCCCCCCCn1c(CO)nc2nc(Cl)nc(Cl)c21] |
| 120 | 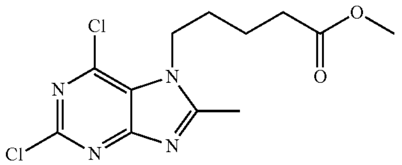 [SMILES: COC(=O)CCCCn1c(C)nc2nc(Cl)nc(Cl)c21] |
| 121 | 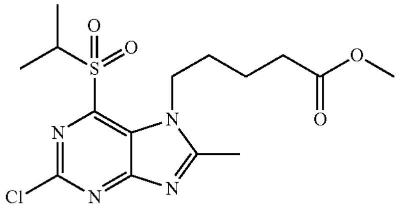 [SMILES: COC(=O)CCCCn1c(C)nc2nc(Cl)nc(S(=O)(=O)C(C)C)c21] |
| 122 | 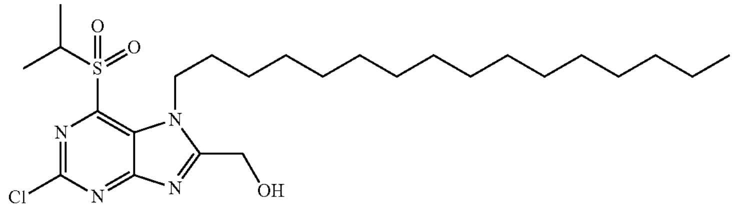 [SMILES: CCCCCCCCCCCCCCCCn1c(CO)nc2nc(Cl)nc(S(=O)(=O)C(C)C)c21] |

-continued
| Compound Number | Structure |
|---|---|
| 123 | 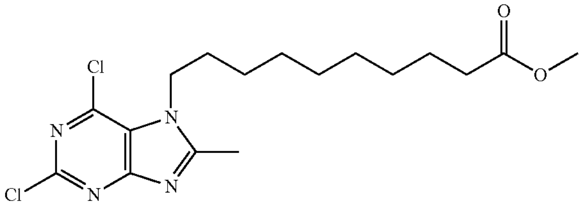 [SMILES: COC(=O)CCCCCCCCCn1c(C)nc2nc(Cl)nc(Cl)c21] |
| 124 | 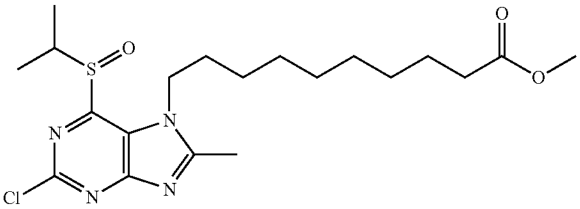 [SMILES: COC(=O)CCCCCCCCCn1c(C)nc2nc(Cl)nc(S(=O)C(C)C)c21] |
| 125 | 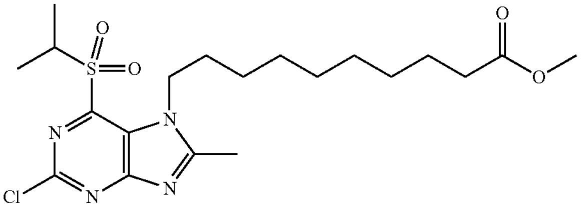 [SMILES: COC(=O)CCCCCCCCCn1c(C)nc2nc(Cl)nc(S(=O)(=O)C(C)C)c21] |
| 126 | 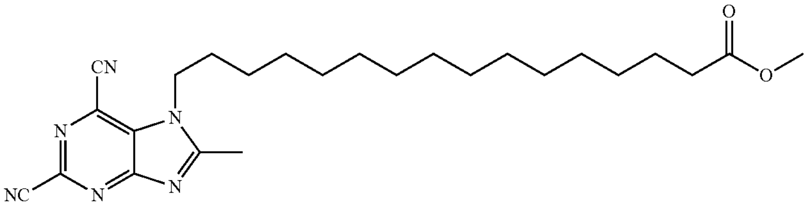 [SMILES: COC(=O)CCCCCCCCCCCCCCCn1c(C)nc2nc(C#N)nc(C#N)c21] |
| 127 | 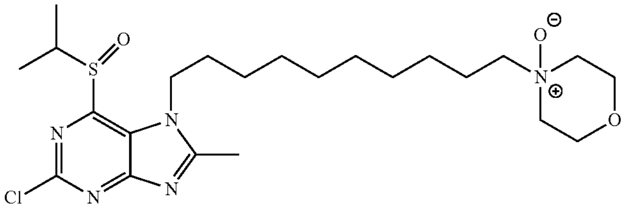 [SMILES: Cc1nc2nc(Cl)nc(S(=O)C(C)C)c2n1CCCCCCCCCC[N+]1([O-])CCOCC1] |
| 128 | 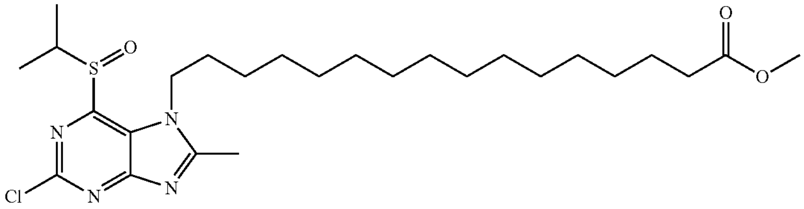 [SMILES: COC(=O)CCCCCCCCCCCCCCCn1c(C)nc2nc(Cl)nc(S(=O)C(C)C)c21] |
| 129 | 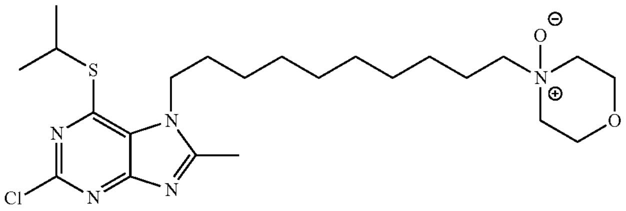 [SMILES: Cc1nc2nc(Cl)nc(SC(C)C)c2n1CCCCCCCCCC[N+]1([O-])CCOCC1] |

-continued
| Compound Number | Structure |
|---|---|
| 130 | 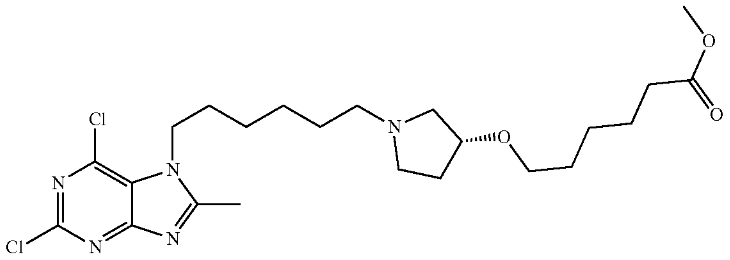 [SMILES: COC(=O)CCCCCO[C@@H]1CCN(CCCCCCn2c(C)nc3nc(Cl)nc(Cl)c32)C1] |
| 131 | 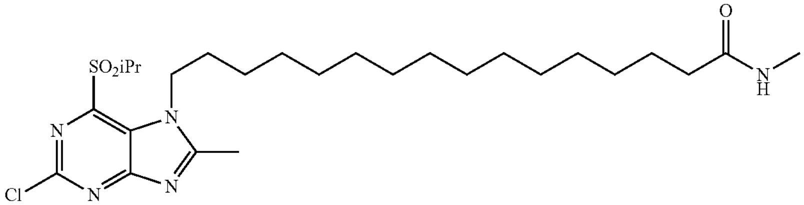 |
| 132 | 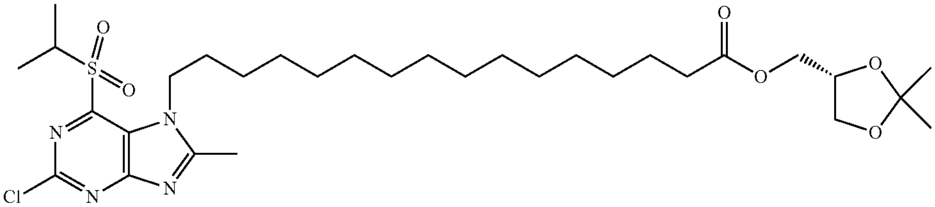 [SMILES: Cc1nc2nc(Cl)nc(S(=O)(=O)C(C)C)c2n1CCCCCCCCCCCCCCCC(=O)OC[C@H]1COC(C)(C)O1] |
| 133 | 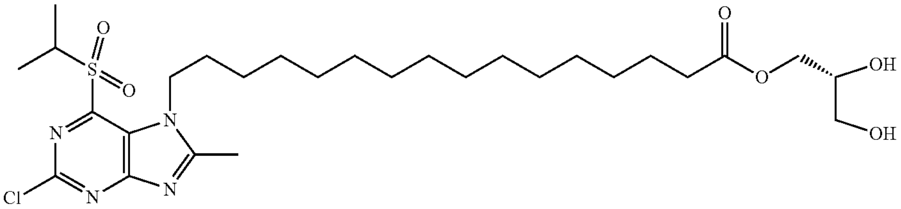 [SMILES: Cc1nc2nc(Cl)nc(S(=O)(=O)C(C)C)c2n1CCCCCCCCCCCCCCCC(=O)OC[C@H](O)CO] |
| 134 | 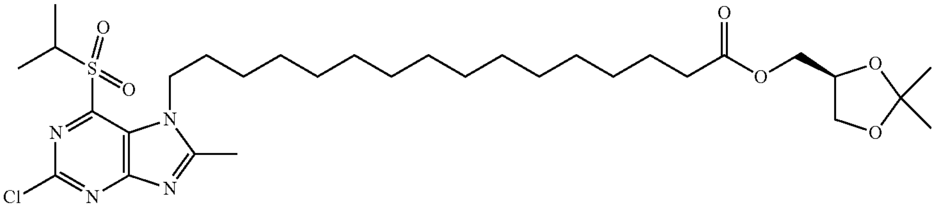 [SMILES: Cc1nc2nc(Cl)nc(S(=O)(=O)C(C)C)c2n1CCCCCCCCCCCCCCCC(=O)OC[C@@H]1COC(C)(C)O1] |
| 135 | 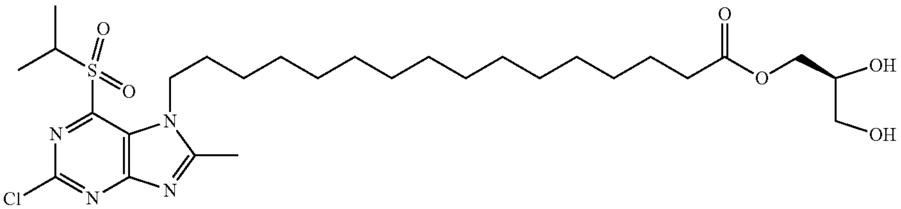 [SMILES: Cc1nc2nc(Cl)nc(S(=O)(=O)C(C)C)c2n1CCCCCCCCCCCCCCCC(=O)OC[C@@H](O)CO] |
| 136 | 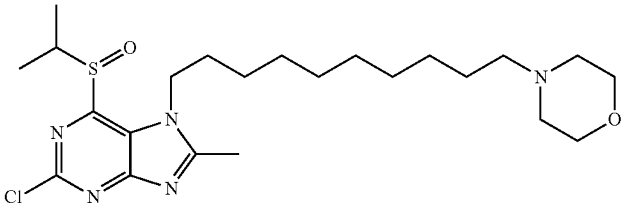 [SMILES: Cc1nc2nc(Cl)nc(S(=O)C(C)C)c2n1CCCCCCCCCCN1CCOCC1] |

-continued
| Compound Number | Structure |
|---|---|
| 137 | 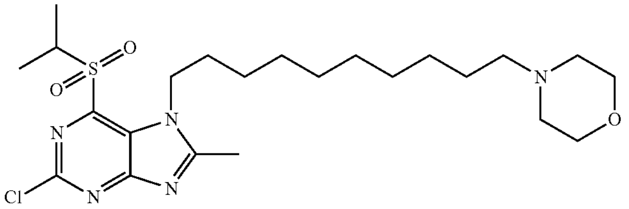 [SMILES: Cc1nc2nc(Cl)nc(S(=O)(=O)C(C)C)c2n1CCCCCCCCCCN1CCOCC1] |
| 138 | 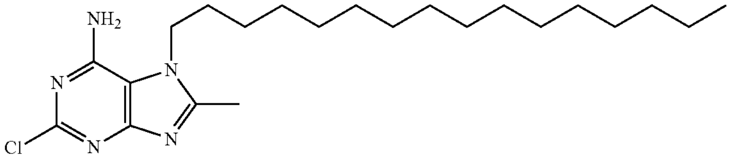 [SMILES: CCCCCCCCCCCCCCCCn1c(C)nc2nc(Cl)nc(N)c21] |
| 139 | 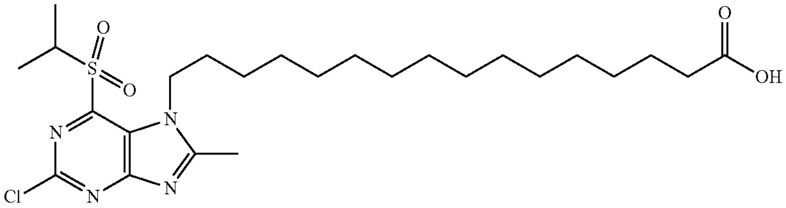 [SMILES: Cc1nc2nc(Cl)nc(S(=O)(=O)C(C)C)c2n1CCCCCCCCCCCCCCCC(=O)O] |
| 140 | 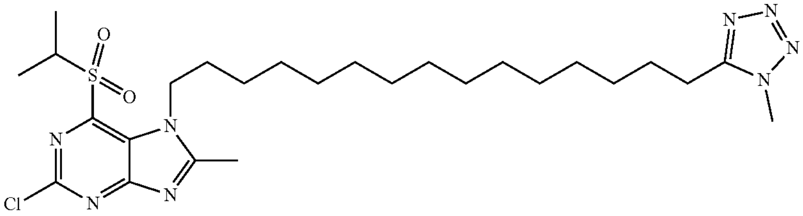 [SMILES: Cc1nc2nc(Cl)nc(S(=O)(=O)C(C)C)c2n1CCCCCCCCCCCCCCCc1nnnn1C] |
| 141 | 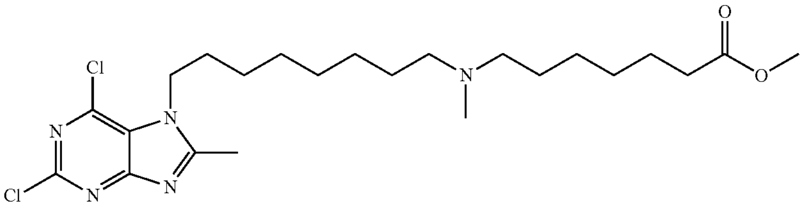 [SMILES: COC(=O)CCCCCCN(C)CCCCCCCCn1c(C)nc2nc(Cl)nc(Cl)c21] |
| 142 | 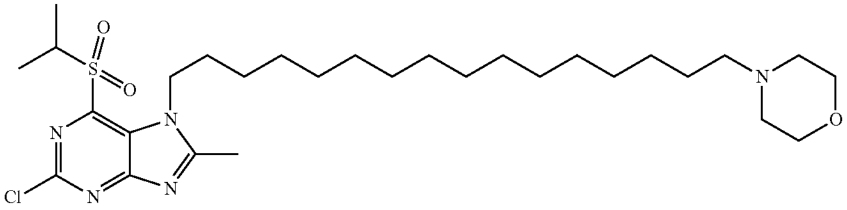 [SMILES: Cc1nc2nc(Cl)nc(S(=O)(=O)C(C)C)c2n1CCCCCCCCCCCCCCCCN1CCOCC1] |
| 143 | 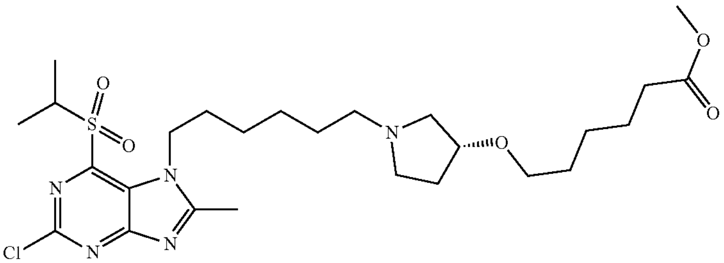 [SMILES: COC(=O)CCCCCO[C@@H]1CCN(CCCCCCn2c(C)nc3nc(Cl)nc(S(=O)(=O)C(C)C)c32)C1] |

-continued
| Compound Number | Structure |
|---|---|
| 144 | 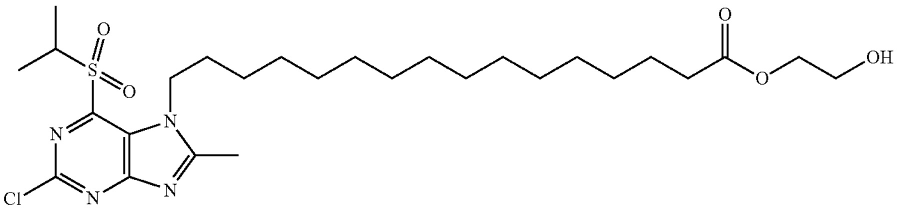 [SMILES: Cc1nc2nc(Cl)nc(S(=O)(=O)C(C)C)c2n1CCCCCCCCCCCCCCCC(=O)OCCO] |
| 145 | 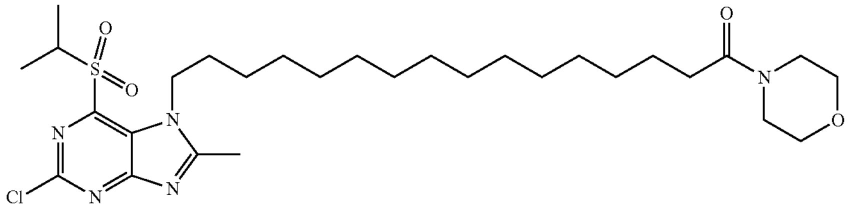 [SMILES: Cc1nc2nc(Cl)nc(S(=O)(=O)C(C)C)c2n1CCCCCCCCCCCCCCCC(=O)N1CCOCC1] |
| 146 | 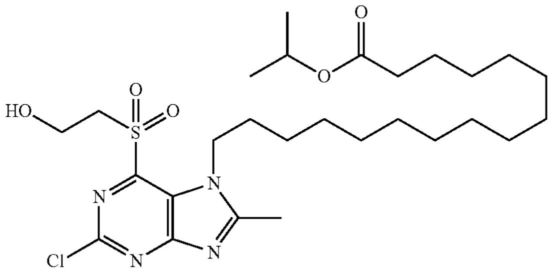 [SMILES: Cc1nc2nc(Cl)nc(S(=O)(=O)CCO)c2n1CCCCCCCCCCCCCCCC(=O)OC(C)C] |
| 147 | 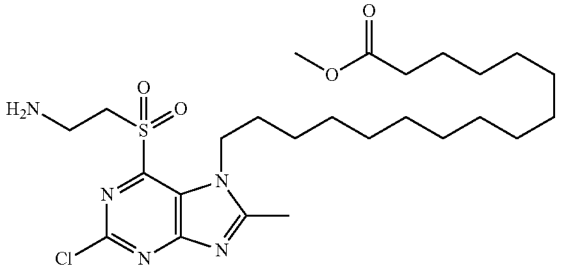 [SMILES: COC(=O)CCCCCCCCCCCCCCCn1c(C)nc2nc(Cl)nc(S(=O)(=O)CCN)c21] |
| 148 | 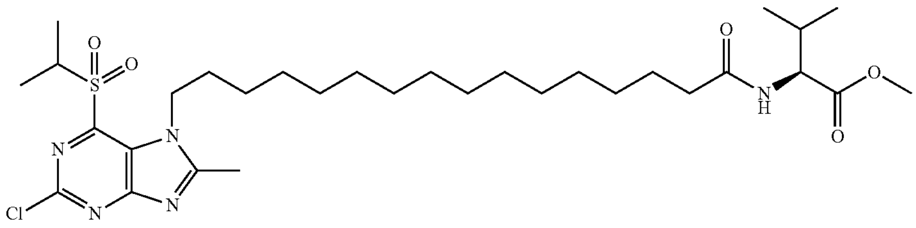 [SMILES: COC(=O)[C@@H](NC(=O)CCCCCCCCCCCCCCCn1c(C)nc2nc(Cl)nc(S(=O)(=O)C(C)C)c21)C(C)C] |
| 149 | 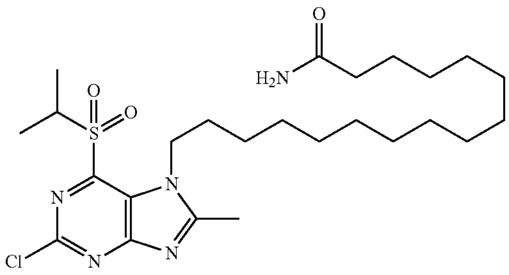 [SMILES: Cc1nc2nc(Cl)nc(S(=O)(=O)C(C)C)c2n1CCCCCCCCCCCCCCCC(N)=O] |

-continued
| Compound Number | Structure |
|---|---|
| 150 | 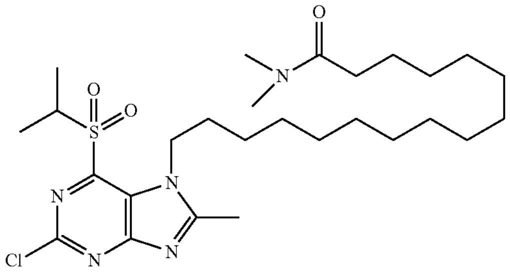 [SMILES: Cc1nc2nc(Cl)nc(S(=O)(=O)C(C)C)c2n1CCCCCCCCCCCCCCCC(=O)N(C)C] |
| 151 | 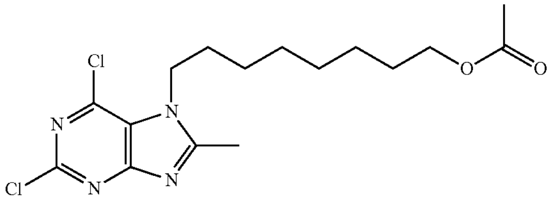 [SMILES: CC(=O)OCCCCCCCCn1c(C)nc2nc(Cl)nc(Cl)c21] |
| 152 | 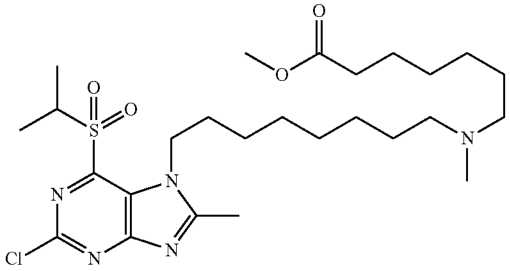 [SMILES: COC(=O)CCCCCCN(C)CCCCCCCCn1c(C)nc2nc(Cl)nc(S(=O)(=O)C(C)C)c21] |
| 153 | 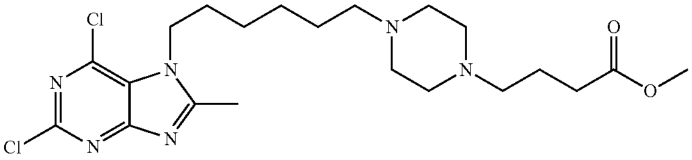 [SMILES: COC(=O)CCCN1CCN(CCCCCCn2c(C)nc3nc(Cl)nc(Cl)c32)CC1] |
| 154 | 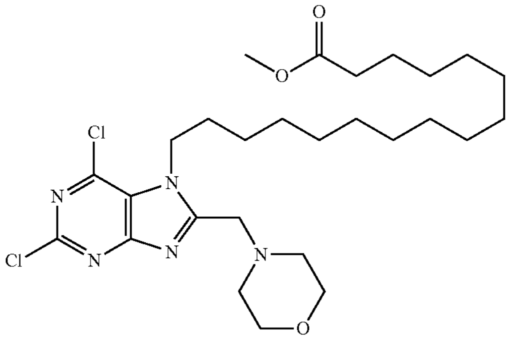 [SMILES: COC(=O)CCCCCCCCCCCCCCCn1c(CN2CCOCC2)nc2nc(Cl)nc(Cl)c21] |
| 155 | 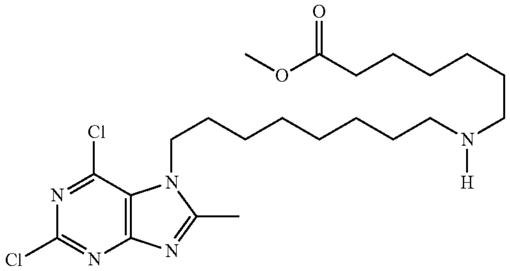 [SMILES: COC(=O)CCCCCCNCCCCCCCCn1c(C)nc2nc(Cl)nc(Cl)c21] |

-continued
| Compound Number | Structure |
|---|---|
| 156 | 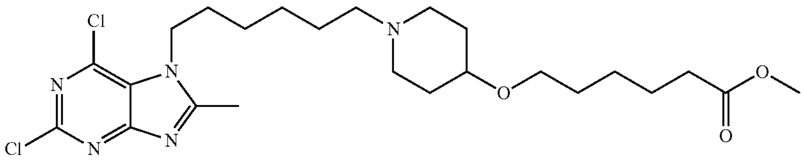 [SMILES: COC(=O)CCCCCOC1CCN(CCCCCCn2c(C)nc3nc(Cl)nc(Cl)c32)CC1] |
| 157 | 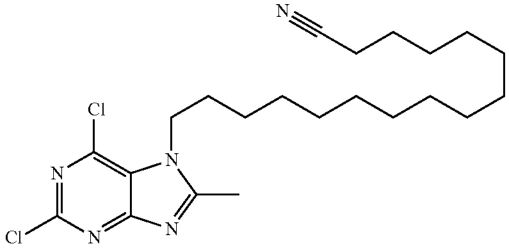 [SMILES: Cc1nc2nc(Cl)nc(Cl)c2n1CCCCCCCCCCCCCCCC#N] |
| 158 | 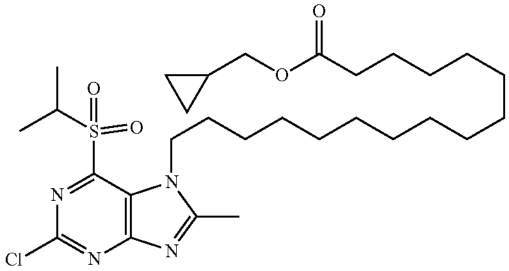 [SMILES: Cc1nc2nc(Cl)nc(S(=O)(=O)C(C)C)c2n1CCCCCCCCCCCCCCCC(=O)OCC1CC1] |
| 159 | 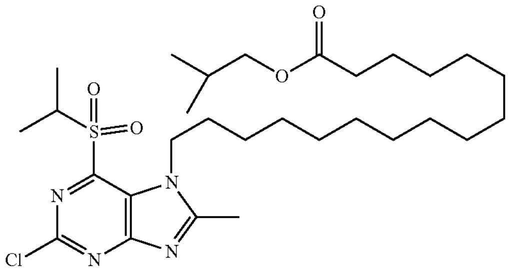 [SMILES: Cc1nc2nc(Cl)nc(S(=O)(=O)C(C)C)c2n1CCCCCCCCCCCCCCCC(=O)OCC(C)C] |
| 160 | 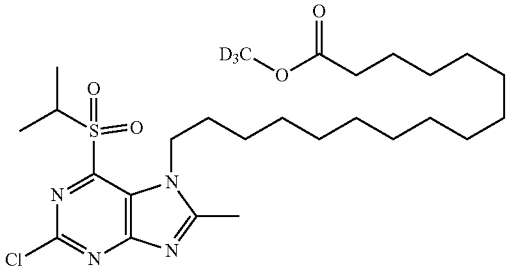 [SMILES: [2H]C([2H])([2H])OC(=O)CCCCCCCCCCCCCCCn1c(C)nc2nc(Cl)nc(S(=O)(=O)C(C)C)c21] |
| 161 | 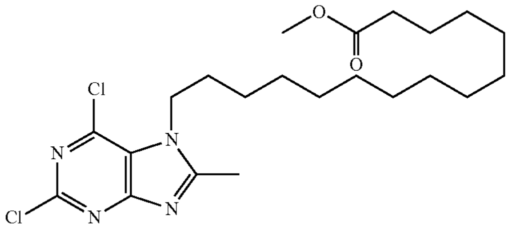 [SMILES: COC(=O)CCCCCCCCCCCCCCn1c(C)nc2nc(Cl)nc(Cl)c21] |

-continued
| Compound Number | Structure |
| --- | --- |
| 162 | 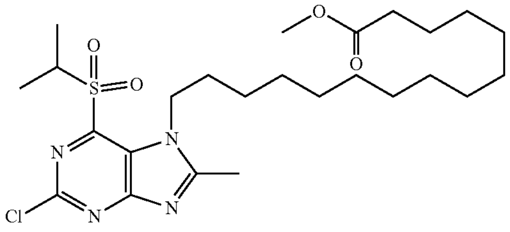 [SMILES: COC(=O)CCCCCCCCCCCCCCn1c(C)nc2nc(Cl)nc(S(=O)(=O)C(C)C)c21] |
| 163 | 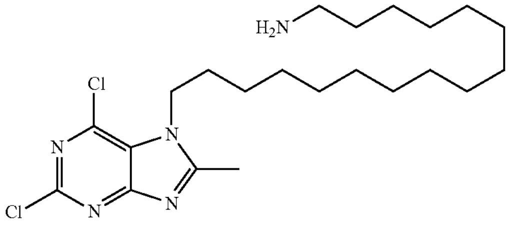 [SMILES: Cc1nc2nc(Cl)nc(Cl)c2n1CCCCCCCCCCCCCCCCN] |
| 164 | 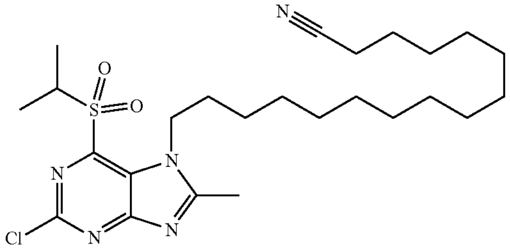 [SMILES: Cc1nc2nc(Cl)nc(S(=O)(=O)C(C)C)c2n1CCCCCCCCCCCCCCCC#N] |
| 165 | 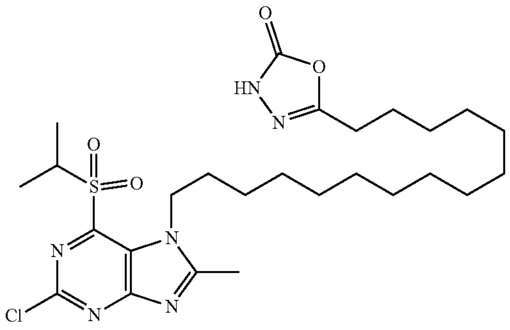 [SMILES: Cc1nc2nc(Cl)nc(S(=O)(=O)C(C)C)c2n1CCCCCCCCCCCCCCCc1n[nH]c(=O)o1] |
| 166 | 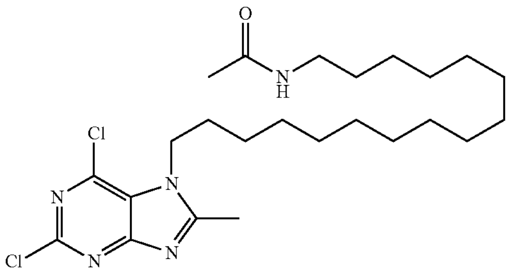 [SMILES: CC(=O)NCCCCCCCCCCCCCCCCn1c(C)nc2nc(Cl)nc(Cl)c21] |

-continued

| Compound Number | Structure |
|---|---|
| 167 | 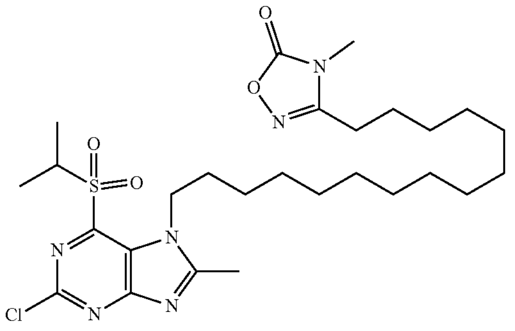 [SMILES: Cc1nc2nc(Cl)nc(S(=O)(=O)C(C)C)c2n1CCCCCCCCCCCCCCCc1noc(=O)n1C] |
| 168 | 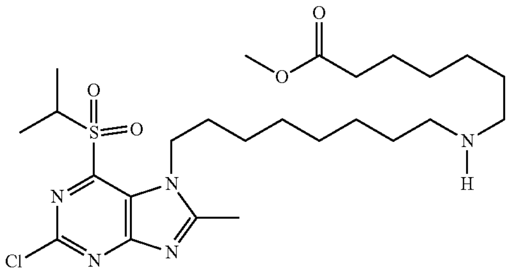 [SMILES: COC(=O)CCCCCCNCCCCCCCCn1c(C)nc2nc(Cl)nc(S(=O)(=O)C(C)C)c21] |

or a pharmaceutically acceptable salt thereof.

The compounds provided herein may contain one or more asymmetric centers and thus occur as racemates and racemic mixtures, single enantiomers, individual diastereomers, and diastereomeric mixtures. All such isomeric forms of these compounds are expressly included within the scope. Unless otherwise indicated when a compound is named or depicted by a structure without specifying the stereochemistry and has one or more chiral centers, it is understood to represent all possible stereoisomers of the compound. The compounds provided herewith may also contain linkages (e.g., carbon-carbon bonds, carbon-nitrogen bonds, phosphorus-oxygen bonds, or phosphorus-sulfur bonds) or substituents that can restrict bond rotation, e.g., restriction resulting from the presence of a ring or double bond. In some embodiments, the compound of a formula of the disclosure comprises an isomer (e.g., an R-isomer or S-isomer) or a mixture of isomers (e.g., R-isomers or S-isomers) of a formula of the disclosure.

This disclosure also includes all suitable isotopic variations of a compound of the disclosure. An isotopic variation of a compound of the invention is defined as one in which at least one atom is replaced by an atom having the same atomic number but an atomic mass different from the atomic mass usually or predominantly found in nature. Examples of isotopes that can be incorporated into a compound of the invention include isotopes of hydrogen, carbon, nitrogen, oxygen, phosphorus, sulphur, fluorine, chlorine, bromine and iodine, such as $^{2}H$ (deuterium), $^{3}H$ (tritium), $^{11}C$, $^{13}C$, $^{14}C$, $^{15}N$, $^{17}O$, $^{18}O$, $^{32}P$, $^{33}P$, $^{33}S$, $^{34}S$, $^{35}S$, $^{36}S$, $^{18}F$, $^{36}Cl$, $^{82}Br$, $^{123}I$, $^{124}I$, $^{129}I$ and $^{131}I$, respectively. Accordingly, recitation of "hydrogen" or "H" should be understood to encompass $^{1}H$ (protium), $^{2}H$ (deuterium), and $^{3}H$ (tritium) unless otherwise specified. Certain isotopic variations of a compound of the invention, for example, those in which one or more radioactive isotopes such as $^{3}H$ or $^{14}C$ are incorporated, are useful in drug and/or substrate tissue distribution studies. Tritiated and carbon-14, i.e., $^{14}C$, isotopes are particularly preferred for their ease of preparation and detectability. Further, substitution with isotopes such as deuterium may afford certain therapeutic advantages resulting from greater metabolic stability, for example, increased in vivo half-life or reduced dosage requirements and hence may be preferred in some circumstances. Such variants may also have advantageous optical properties arising, for example, from changes to vibrational modes due to the heavier isotope. Isotopic variations of a compound of the invention can generally be prepared by conventional procedures known by a person skilled in the art such as by the illustrative methods or by the preparations described in the examples hereafter using appropriate isotopic variations of suitable reagents.

Exemplary Methods of Use

The present disclosure relates to methods of inhibiting the expression of PRRs (e.g., STING) in a subject, in particular for the treatment of an inflammatory disorder or a proliferative disease (e.g., cancer). In some embodiments, the method comprises administration of a compound of the disclosure or pharmaceutically acceptable salt thereof. It is to be noted that the suppression of any PRR with these compounds can depress interferon and/or NF-KB production which can reduce the expression of a variety of PRRs which are reducible genes by feedback mechanisms.

Treatment of Inteiferonopathies

In some embodiments, the present disclosure provides a method of treating a type I interferonopathy (e.g., STING-associated vasculopathy with onset in infancy (SAVI)) in a subject, comprising administering to the subject a therapeutically effective amount of a compound or composition of the disclosure. In certain embodiments, the interferonopathy is Aicardi-Goutieres Syndrome (AGS). In other embodiments, the interferonopathy is lupus (e.g., a genetic form of lupus).

Treatment of Inflammatory Disorders

In some embodiments, the methods of reducing the expression of a PRR (e.g., STING) disclosed herein comprise administration of an effective amount of a compound of the disclosure or a pharmaceutically acceptable salt thereof to a subject suffering from an inflammatory disorder.

In some embodiments, the present disclosure provides a method of treating an inflammatory disorder in a subject, comprising administering to the subject a therapeutically effective amount of a compound or composition of the disclosure.

In some embodiments, the inflammatory disorder is arthritis, SLE, SAVI, AGS, Familial chilblain lupus (CHBL), Retinal vasculopathy with cerebral leukodystrophy (RVCL), Sjögren's syndrome, Adult onset Still Syndrome (AOSS/Wissler-Fanconi syndrome), CANDLE, Singleton-Merten syndrome (SGMRT), X-linked reticulate pigmentary disorder (XLPDR), Spondyloenchrondrodysplasia (SPENCD), vascular and pulmonary syndrome, NASH, Pulmonary fibrosis, Idiopathic pulmonary fibrosis, or Geographic atrophy (GA).

In some embodiments, the inflammatory disorder is the inflammatory disorder is an ocular allergy, conjunctivitis, keratoconjunctivitis sicca, vernal conjunctivitis, allergic rhinitis, autoimmune hematological disorders (e.g., hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g., ulcerative colitis and Crohn's disease), irritable bowel syndrome, celiac disease, periodontitis, hyaline membrane disease, kidney disease, glomerular disease, alcoholic liver disease, multiple sclerosis, endocrine ophthalmopathy, Grave's disease, sarcoidosis, alveolitis, chronic hypersensitivity pneumonitis, primary biliary cirrhosis, uveitis (anterior and posterior), Sjögren's syndrome, interstitial lung fibrosis, psoriatic arthritis, systemic juvenile idiopathic arthritis, nephritis, vasculitis, diverticulitis, interstitial cystitis, glomerulonephritis (e.g., including idiopathic nephrotic syndrome or minimal change nephropathy), chronic granulomatous disease, endometriosis, leptospirosis renal disease, glaucoma, retinal disease, headache, pain, complex regional pain syndrome, cardiac hypertrophy, muscle wasting, catabolic disorders, obesity, fetal growth retardation, hypercholesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma, acute lung injury, acute respiratory distress syndrome, eosinophilia, hypersensitivities, anaphylaxis, fibrositis, gastritis, gastroenteritis, nasal sinusitis, silica induced diseases, chronic obstructive pulmonary disease (COPD), cystic fibrosis, acid-induced lung injury, pulmonary hypertension, polyneuropathy, cataracts, muscle inflammation in conjunction with systemic sclerosis, inclusion body myositis, thyroiditis, Addison's disease, lichen planus, appendicitis, atopic dermatitis, allergy, blepharitis, bronchiolitis, bronchitis, bursitis, cervicitis, cholangitis, cholecystitis, chronic graft rejection, colitis, cystitis, dacryoadenitis, dermatitis, juvenile rheumatoid arthritis, encephalitis, endocarditis, endometritis, enteritis, enterocolitis, epicondylitis, epididymitis, fasciitis, Henoch-Schonlein purpura, hepatitis, hidradenitis suppurativa, immunoglobulin A nephropathy, interstitial lung disease, laryngitis, mastitis, meningitis, myelitis, myocarditis, myositis, oophoritis, orchitis, osteitis, otitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, vulvitis, alopecia areata, erythema multiforma, dermatitis herpetiformis, vitiligo, hypersensitivity angiitis, urticaria, bullous pemphigoid, pemphigus vulgaris, pemphigus *foliaceus*, paraneoplastic pemphigus, epidermolysis bullosa acquisita, acute and chronic gout, chronic gouty arthritis, psoriasis, Cryopyrin Associated Periodic Syndrome (CAPS) or osteoarthritis.

In some embodiments, the condition, disease or disorder is selected from the group consisting of type I interferonopathies (e.g., STING-associated vasculopathy with onset in infancy (SAVI)), Aicardi-Goutieres Syndrome (AGS), genetic forms of lupus, and inflammation-associated disorders such as systemic lupus erythematosus, and rheumatoid arthritis. In certain embodiments, the condition, disease or disorder is an autoimmune disease (e.g., a cytosolic DNA-triggered autoinflammatory disease). Non-limiting examples include rheumatoid arthritis, systemic lupus erythematosus, multiple sclerosis, inflammatory bowel diseases (IBDs) comprising Crohn disease (CD) and ulcerative colitis (UC), which are chronic inflammatory conditions with polygenic susceptibility. In certain embodiments, the condition is an inflammatory bowel disease. In certain embodiments, the condition is Crohn's disease, autoimmune colitis, iatrogenic autoimmune colitis, ulcerative colitis, colitis induced by one or more chemotherapeutic agents, colitis induced by treatment with adoptive cell therapy, colitis associated by one or more alloimmune diseases (such as graft-vs-host disease, e.g., acute graft vs. host disease and chronic graft vs. host disease), radiation enteritis, collagenous colitis, lymphocytic colitis, microscopic colitis, and radiation enteritis. In certain of these embodiments, the condition is alloimmune disease (such as graft-vs-host disease, e.g., acute graft vs. host disease and chronic graft vs. host disease), celiac disease, irritable bowel syndrome, rheumatoid arthritis, lupus, scleroderma, psoriasis, cutaneous T-cell lymphoma, uveitis, and mucositis (e.g., oral mucositis, esophageal mucositis or intestinal mucositis)

Treatment of Cancer

In some embodiments, the methods of reducing the expression of a PRR (e.g., a PR formula of the disclosure or a pharmaceutically acceptable salt thereof to a subject suffering from cancer. In some embodiments, the methods of reducing expression of STING disclosed herein comprise administration of a compound of the disclosure or a pharmaceutically acceptable salt thereof to a subject suffering from cancer. In some embodiments, the methods of reducing expression of RIG-I disclosed herein comprise administration of a compound of the disclosure or a pharmaceutically acceptable salt thereof to a subject suffering from cancer. In some embodiments, the methods of reducing expression of NOD2 disclosed herein comprise administration of a compound of the disclosure or a pharmaceutically acceptable salt thereof to a subject suffering from cancer. In some embodiments, the cancer is selected from a cancer of the breast, bone, brain, cervix, colon, gastrointestinal tract, eye, gall bladder, lymph nodes, blood, lung, liver, skin, mouth, prostate, ovary, penis, pancreas, uterus, testicles, stomach, thymus, thyroid, or other part of the body. In some embodiments, the cancer comprises a solid tumor (e.g., a carcinoma, a sarcoma, or a lymphoma). In some embodiments, the cancer is a hepatocellular carcinoma or other cancer of the liver. In some embodiments, the cancer is a leukemia or other cancer of the blood. In some embodiments, the cancer comprises breast cancer, renal cell carcinoma, colon cancer, melanoma, ovarian cancer, head and neck squamous cell carcinoma, pancreatic cancer, prostate cancer, lung cancer, brain cancer, thyroid cancer, renal cancer, testis cancer, stomach cancer, urothelial cancer, skin cancer, cervical cancer, endometrial cancer, liver cancer, lung cancer, lymphoma or gastrointestinal stromal cancer and solid tumors. In certain embodiments, cancer is selected from the group consisting of melanoma, cervical cancer, breast cancer, ovarian cancer, prostate cancer, testicular cancer, urothelial carcinoma, bladder cancer, non-small cell lung cancer, small cell lung cancer, sarcoma, colorectal adenocarcinoma, gastrointestinal stromal tumors, gastroesophageal carcinoma, colorectal cancer, pancreatic cancer, kidney cancer, hepatocellular cancer, malignant mesothelioma, leukemia, lymphoma, myelodysplasia syndrome, multiple myeloma, transitional cell carcinoma, neuroblastoma, plasma cell neoplasms, Wilm's tumor, or hepatocellular carcinoma. In some embodiments, the cancer cells (e.g., tumor cells) comprise specific cancer-associated antigens that induce a T-cell-mediated anti-tumor response. In some embodiments, the cancer is selected from the group consisting of melanoma, carcinoma, lymphoma, blastoma, sarcoma, and leukemia or lymphoid malignancies. In some embodiments, the cancer is selected from the group consisting of breast cancer, colon cancer, rectal cancer, colorectal cancer, kidney or renal cancer, clear cell cancer lung cancer including small-cell lung cancer, non-small cell lung cancer, adenocarcinoma of the lung and squamous carcinoma of the lung, squamous cell cancer (e.g. epithelial squamous cell cancer), cervical cancer, ovarian cancer, prostate cancer, prostatic neoplasms, liver cancer, bladder cancer, cancer of the peritoneum, hepatocellular cancer, gastric or stomach cancer including gastrointestinal cancer, gastrointestinal stromal tumor, pancreatic cancer, head and neck cancer, glioblastoma, retinoblastoma, astrocytoma, thecomas, arrhenoblastomas, hepatoma, hematologic malignancies including non-Hodgkins lymphoma (NHL), multiple myeloma, myelodysplasia disorders, myeloproliferative disorders, chronic myelogenous leukemia, and acute hematologic malignancies, endometrial or uterine carcinoma, endometriosis, endometrial stromal sarcoma, fibrosarcomas, choriocarcinoma, salivary gland carcinoma, vulval cancer, thyroid cancer, esophageal carcinomas, hepatic carcinoma, anal carcinoma, penile carcinoma, nasopharyngeal carcinoma, laryngeal carcinomas, Kaposi's sarcoma, mast cell sarcoma, ovarian sarcoma, uterine sarcoma, melanoma, malignant mesothelioma, skin carcinomas, Schwannoma, oligodendroglioma, neuroblastomas, neuroectodermal tumor, rhabdomyosarcoma, osteogenic sarcoma, leiomyosarcomas, Ewing Sarcoma, peripheral primitive neuroectodermal tumor, urinary tract carcinomas, thyroid carcinomas, Wilm's tumor, as well as abnormal vascular proliferation associated with phakomatoses, edema (such as that associated with brain tumors), and Meigs' syndrome. In some embodiments, the cancer is melanoma In certain embodiments, the cancer is refractory. In certain embodiments, the cancer is relapsed.

In some embodiments, the methods of reducing expression of a PRR (e.g., STING, RIG-I, MDA5, LGP2) in a subject suffering from a cancer disclosed herein result in a decrease in PRR expression (e.g., STING expression). In some embodiments, expression of a PRR (e.g., STING) is reduced by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, reduction of expression of a PRRs (e.g., STING) occurs within about 5 minutes of administration of a compound of the disclosure or a pharmaceutically acceptable salt thereof. In some embodiments, reduction of expression of a PRRs (e.g., STING) occurs within about 5 minutes of administration of a compound of the disclosure or a pharmaceutically acceptable salt thereof. In some embodiments, reduction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of the disclosure or a pharmaceutically acceptable salt thereof. It is recognized that deactivation of STING by compounds may lead to reduction of expression of other PRRs, such as RIG-I, MDA5, NOD2 etc.

In some embodiments, the methods of reducing expression of a PRR (e.g., STING) in a subject suffering from a cancer disclosed herein results in an decrease in PRR expression (e.g., STING expression). In some embodiments, expression of a PRR (e.g., STING) is reducted by a factor of about 1.1, about 1.2, about 1.3, about 1.4, about 1.5, about 1.6, about 1.7, about 1.8, about 1.9, about 2, about 2.5, about 3, about 4, about 5, about 7.5, about 10, about 15, about 20, about 25, about 30, about 40, about 50, about 75, about 100, about 150, about 200, about 250, about 500, about 1000, about 1500, about 2500, about 5000, about 10,000, or more. In some embodiments, reduction of expression of a PRR (e.g., STING) occurs within about 5 minutes of administration of a compound of the disclosure or a pharmaceutically acceptable salt thereof. In some embodiments, reduction of expression of a PRR (e.g., STING) occurs within about 10 minutes, about 15 minutes, about 20 minutes, about 25 minutes, about 30 minutes, about 45 minutes, about 1 hour, about 1.5 hours, about 2 hours, about 3 hours, about 4 hours, about 5 hours, about 6 hours, about 7 hours, about 8 hours, about 10 hours, about 12 hours or more following administration of a compound of the disclosure or a pharmaceutically acceptable salt thereof.

Treatment of Neurodegenerative Disorders

In another aspect, the present disclosure provides methods of treating a neurodegenerative disorder in a subject, comprising administering to the subject a therapeutically effective amount of a compound of the disclosure. In some embodiments, the neurodegenerative disease is mediated by an inflammatory response (e.g., multiple sclerosis).

In some embodiments, the neurodegenerative disease is selected from the group consisting of Alzheimer's disease, Parkinson's disease, multiple sclerosis, stroke, amyotrophic lateral sclerosis, cerebellar ataxia, dementia, frontotemporal dementia, prion disease, Huntington's disease, cerebral ischemia, cerebral dementia syndrome, infection-induced neurodegeneration disorders, AIDS-encephalopathy, Creutzfeldt-Jakob disease, encephalopathies induced by solvents, trauma-induced brain damage, and spinal cord injury.

In some embodiments, the neurodegenerative disease is selected from the group consisting of disorders that involve the central nervous system (brain, brainstem and cerebellum), the peripheral nervous system (including cranial nerves), and the autonomic nervous system (parts of which are located in both central and peripheral nervous system).

Non-limiting examples of neurological disorders include acquired epileptiform aphasia, acute disseminated encephalomyelitis, adrenoleukodystrophy, age-related macular degeneration, agenesis of the corpus callosum, agnosia, Aicardi syndrome, Alexander disease, Alpers' disease, alternating hemiplegia, Alzheimer's disease, Vascular dementia, amyotrophic lateral sclerosis, anencephaly, Angelman syndrome, angiomatosis, anoxia, aphasia, apraxia, arachnoid cysts, arachnoiditis, Anronl-Chiari malformation, arteriovenous malformation, Asperger syndrome, ataxia telegiectasia, attention deficit hyperactivity disorder, autism, autonomic dysfunction, back pain, Batten disease, Behcet's disease, Bell's palsy, benign essential blepharospasm, benign focal, amyotrophy, benign intracranial hypertension, Binswanger's disease, blepharospasm, Bloch Sulzberger syndrome, brachial plexus injury, brain abscess, brain injury, brain tumors (including glioblastoma multiforme), spinal tumor, Brown-Sequard syndrome, Canavan disease, carpal tunnel syndrome, causalgia, central pain syndrome, central pontine myelinolysis, cephalic disorder, cerebral aneurysm, cerebral arteriosclerosis, cerebral atrophy, cerebral gigantism, cerebral palsy, Charcot-Marie-Tooth disease, chemotherapy-induced neuropathy and neuropathic pain, Chiari malformation, chorea, chronic inflammatory demyelinating polyneuropathy, chronic pain, chronic regional pain syndrome, Coffin Lowry syndrome, coma, including persistent vegetative state, congenital facial diplegia, corticobasal degeneration, cranial arteritis, craniosynostosis, Creutzfeldt-Jakob disease, cumulative trauma disorders, Cushing's syndrome, cytomegalic inclusion body disease, cytomegalovirus infection, dancing eyesdancing feet syndrome, Dandy-Walker syndrome, Dawson disease, De Morsier's syndrome, Dejerine-Klumke palsy, dementia, dermatomyositis, diabetic neuropathy, diffuse sclerosis, dysautonomia, dysgraphia, dyslexia, dystonias, early infantile epileptic encephalopathy, empty sella syndrome, encephalitis, encephaloceles, encephalotrigeminal angiomatosis, epilepsy, Erb's palsy, essential tremor, Fabry's disease, Fahr's syndrome, fainting, familial spastic paralysis, febrile seizures, Fisher syndrome, Friedreich's ataxia, fronto-temporal dementia and other "tauopathies", Gaucher's disease, Gerstmann's syndrome, giant cell arteritis, giant cell inclusion disease, globoid cell leukodystrophy, Guillain-Barre syndrome, HTLV-1-associated myelopathy, Hallervorden-Spatz disease, head injury, headache, hemifacial spasm, hereditary spastic paraplegia, heredopathia atactica polyneuritiformis, herpes zoster oticus, herpes zoster, Hirayama syndrome, HIV-associated dementia and neuropathy (also neurological manifestations of AIDS), holoprosencephaly, Huntington's disease and other polyglutamine repeat diseases, hydranencephaly, hydrocephalus, hypercortisolism, hypoxia, immune-mediated encephalomyelitis, inclusion body myositis, incontinentia pigmenti, infantile phytanic acid storage disease, infantile refsum disease, infantile spasms, inflammatory myopathy, intracranial cyst, intracranial hypertension, Joubert syndrome, Kearns-Sayre syndrome, Kennedy disease Kinsboume syndrome, Klippel Feil syndrome, Krabbe disease, Kugelberg-Welander disease, kuru, Lafora disease, Lambert-Eaton myasthenic syndrome, Landau-Kleffner syndrome, lateral medullary (Wallenberg) syndrome, learning disabilities, Leigh's disease, Lennox-Gustaut syndrome, Lesch-Nyhan syndrome, leukodystrophy, Lewy body dementia, Lissencephaly, locked—in syndrome, Lou Gehrig's disease (i.e., motor neuron disease or amyotrophic lateral sclerosis), lumbar disc disease, Lyme disease-neurological sequelae, Machado-Joseph disease, macrencephaly, megalencephaly, Melkersson-Rosenthal syndrome, Menieres disease, meningitis, Menkes disease, metachromatic leukodystrophy, microcephaly, migraine, Miller Fisher syndrome, mini-strokes, mitochondrial myopathies, Mobius syndrome, monomelic amyotrophy, motor neuron disease, Moyamoya disease, mucopolysaccharidoses, milti-infarct dementia, multifocal motor neuropathy, multiple sclerosis and other demyelinating disorders, multiple system atrophy with postural hypotension, p muscular dystrophy, myasthenia gravis, myelinoclastic diffuse sclerosis, myoclonic encephalopathy of infants, myoclonus, myopathy, myotonia congenital, narcolepsy, neurofibromatosis, neuroleptic malignant syndrome, neurological manifestations of AIDS, neurological sequelae of lupus, neuromyotonia, neuronal ceroid lipofuscinosis, neuronal migration disorders, Niemann-Pick disease, O'Sullivan-McLeod syndrome, occipital neuralgia, occult spinal dysraphism sequence, Ohtahara syndrome, olivopontocerebellar atrophy, opsoclonus myoclonus, optic neuritis, orthostatic hypotension, overuse syndrome, paresthesia, Parkinson's disease, paramyotonia congenital, paraneoplastic diseases, paroxysmal attacks, Parry Romberg syndrome, PelizaeusMerzbacher disease, periodic paralyses, peripheral neuropathy, painful neuropathy and neuropathic pain, persistent vegetative state, pervasive developmental disorders, photic sneeze reflex, phytanic acid storage disease, Pick's disease, pinched nerve, pituitary tumors, polymyositis, porencephaly, post-polio syndrome, postherpetic neuralgia, postinfectious encephalomyelitis, postural hypotension, Prader-Willi syndrome, primary lateral sclerosis, prion diseases, progressive hemifacial atrophy, progressive multifocal leukoencephalopathy, progressive sclerosing poliodystrophy, progressive supranuclear palsy, pseudotumor cerebri, Ramsay-Hunt syndrome (types I and II), Rasmussen's encephalitis, reflex sympathetic dystrophy syndrome, Refsum disease, repetitive motion disorders, repetitive stress injuries, restless legs syndrome, retrovirus-associated myelopathy, Rett syndrome, Reye's syndrome, Saint Vitus dance, Sandhoff disease, Schilder's disease, schizencephaly, septo-optic dysplasia, shaken baby syndrome, shingles, Shy-Drager syndrome, Sjögren's syndrome, sleep apnea, Soto's syndrome, spasticity, spinabifida, spinal cord injury, spinal cord tumors, spinal muscular atrophy, Stiff-Person syndrome, stroke, Sturge-Weber syndrome, subacute sclerosing panencephalitis, subcortical arteriosclerotic encephalopathy, Sydenham chorea, syncope, syringomyelia, tardive dyskinesia, Tay-Sachs disease, temporal arteritis, tethered spinal cord syndrome, Thomsen disease, thoracic outlet syndrome, Tic Douloureux, Todd's paralysis, Tourette syndrome, transient ischemic attack, transmissible spongiform encephalopathies, transverse myelitis, traumatic brain injury, tremor, trigeminal neuralgia, tropical spastic paraparesis, tuberous sclerosis, vascular dementia (multi-infarct dementia), vasculitis including temporal arteritis, Von Hippel-Lindau disease, Wallenberg's syndrome, Werdnig-Hoffman disease, West syndrome, whiplash, Williams syndrome, Wildon's disease, amyotrophe lateral sclerosis and Zellweger syndrome.

Treatment of Infectious Diseases

Modulation of the immune system by STING provides for the treatment of diseases, including diseases caused by foreign agents. In another aspect, the present disclosure provides methods of treating an infectious disease in a subject, comprising administering to the subject a therapeutically effective amount of a compound of the disclosure. Exemplary infectious disease that may be treated and/or prevented by the method of the present invention include an infection by a bacterium (e.g., a Gram-positive or Gram-negative bacterium), an infection by a fungus, an infection by a parasite, and an infection by a virus. In one embodiment of the present invention, the infection is a bacterial infection (e.g., infection by *E. coli, Klebsiella pneumoniae, Pseudomonas aeruginosa, Salmonella* spp., *Staphylococcus aureus, Streptococcus* spp., or vancomycin-resistant *enterococcus*), or sepsis. In another embodiment, the infection is a fungal infection (e.g. infection by a mould, a yeast, or a higher fungus). In still another embodiment, the infection is a parasitic infection (e.g., infection by a single-celled or multicellular parasite, including Giardia duodenalis, *Cryptosporidium parvum, Cyclospora cayetanensis*, and *Toxoplasma* gondiz). In yet another embodiment, the infection is a viral infection (e.g., infection by a virus associated with AIDS, avian flu, chickenpox, cold sores, common cold, gastroenteritis, glandular fever, influenza, measles, mumps, pharyngitis, pneumonia, rubella, SARS, and lower or upper respiratory tract infection (e.g., respiratory syncytial virus). In certain embodiments, the viral infection is corona virus (e.g., COVID-19). In certain embodiments, the condition, disease or disorder is hepatits B (see, e.g., WO 2015/061294, the contents of which is hereby fully incorporated by reference).

Treatment of Other Diseases, Disorders, and Conditions

The compounds of the disclosure may also be used to treat other diseases or disorders, such as those recited in PCT/US2019/040317, the contents of which is hereby incorporated by reference by its entirety In some embodiments, the condition, disease or disorder is selected from cardiovascular diseases (including e.g., myocardial infarction). In some embodiments, the condition, disease or disorder is age-related macular degeneration. In some embodiments, the condition, disease or disorder is mucositis, also known as stomatitits, which can occur as a result of chemotherapy or radiation therapy, either alone or in combination as well as damage caused by exposure to radiation outside of the context of radiation therapy. In some embodiments, the condition, disease or disorder is uveitis, which is inflammation of the uvea (e.g., anterior uveitis, e.g., iridocyclitis or iritis, intermediate uveitis (also known as pars planitis), posterior uveitis, or chorioretinitis, e.g., pan-uveitis). In some embodiments, the condition, disease or disorder is selected from the group consisting of a cancer, a neurological disorder, an autoimmune disease, uvetitis, a cardiovascular disease, age-related macular degeneration, and mucositis. Still other examples can include those indications discussed herein and below in contemplated combination therapy regimens

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

A "therapeutically effective amount" or a "therapeutically effective dose" of a drug or agent is an amount of a drug or an agent that, when administered to a subject will have the intended therapeutic effect. The full therapeutic effect does not necessarily occur by administration of one dose, and may occur only after administration of a series of doses. Thus, a therapeutically effective amount may be administered in one or more administrations. The precise effective amount needed for a subject will depend upon, for example, the subject's size, health and age, and the nature and extent of the condition being treated, such as cancer or MDS. The skilled worker can readily determine the effective amount for a given situation by routine experimentation.

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted. As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "alkylene" and "alkylenyl" refers to the diradical of an alkyl group.

The terms "alkenylene" and "alkenylenyl" refer to the diradicals of an alkenyl group.

The terms "alkynylene" and "alkynylenyl" refer to the diradicals of an alkynyl group.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_x$-$C_y$", when used in conjunction with. a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

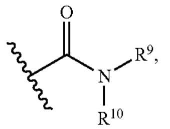

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

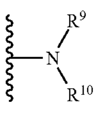

or

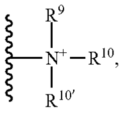

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

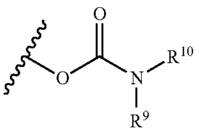

or

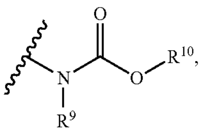

wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The term "heteroalkyl" refers to saturated aliphatic groups, including but not limited to $C_1$-$C_{10}$ straight-chain alkyl groups or $C_1$-$C_{10}$ branched-chain alkyl groups, wherein one or more of the carbon atoms has been replaced with a heteroatom (e.g., O, NH, or S). Examples of "heteroalkyl" groups include, but are not limited to, ethylene glycols, such as diethylene glycol, triethylene glycol, or an oligoethylene glycol.

The term "heteroalkylene" and "heteroalkylenyl" refers to the diradical of an heteroalkyl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group —$OSO_3H$, or a pharmaceutically acceptable salt thereof.

The term "sulfonamide" is art-recognized and refers to the group represented by the general formulae

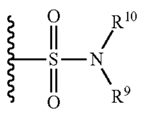 or 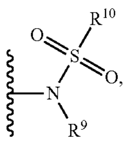, wherein $R^9$ and $R^{10}$ independently represents hydrogen or hydrocarbyl.

The term "sulfoxide" is art-recognized and refers to the group-S(O)—.

The term "sulfonate" is art-recognized and refers to the group $SO_3H$, or a pharmaceutically acceptable salt thereof.

The term "sulfone" is art-recognized and refers to the group —$S(O)_2$—.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —$C(O)SR^9$ or —$SC(O)R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

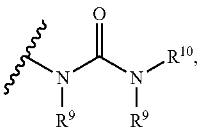, wherein $R^9$ and $R^{10}$ independently represent hydrogen or a hydrocarbyl.

The term "modulate" as used herein includes the inhibition or suppression of a function or activity. (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds represented by a formula of the disclosure. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Mono or di-acid salts can be formed, and such salts may exist in either a hydrated, solvated or substantially anhydrous form. In general, the acid addition salts of compounds of a formula of the disclosure are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of a compound of formula of the disclosure for laboratory use, or for subsequent conversion to a pharmaceutically acceptable acid addition salt.

The term "pharmaceutically acceptable basic addition salt" as used herein means any non-toxic organic or inorganic base addition salt of any acid compounds represented by a compound of a formula of the disclosure or any of their intermediates. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form the compound of the present disclosure (e.g., compounds of a formula of the disclosure). Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The prodrugs of this disclosure are metabolized to produce a compound of a formula of the disclosure. The present disclosure includes within its scope, prodrugs of the compounds described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filter, diluent, excipient, solvent or encapsulating material useful for formulating a drug for medicinal or therapeutic use.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

As used herein, the term "Antagonist," refers to an agent (e.g., a small molecule) that blocks, dampens or otherwise downregulates a biological response by binding to and blocking a receptor.

As used herein, the term "antagonism" refers to the process of blocking, dampening or otherwise downregulating a biological response by the binding of an agent (e.g., a small molecule) to a receptor.

As used herein, the phrase "inhibitor of signals" refers to an agent (e.g., a small molecule) that blocks signals passed from one biological agent (e.g., a protein or cell) to another biological agent (e.g., a second protein or cell).

Blocking these signals can affect many functions of the cell, including cell division and cell death, and may kill cancer cells.

As used herein, the terms "suppress" and "suppression" refer to the decrease or reduction of a function, e.g., the decrease or enhancement of the reduction of a pattern recognition receptor (e.g., STING). In some embodiments, "reduction of PRR expression" refers to reduction the of transcription of PRR RNA, e.g., STING RNA (e.g., mRNA, e.g., an reduction or suppression of), or the translation of a PRR protein, e.g., the STING protein (e.g., an reduction or suppression of). In some embodiments, suppression of PRR expression (e.g., STING expression) refers to the reduction or suppression of the concentration of a PRR RNA, e.g., or STING RNA (e.g., mRNA) or the STING protein, e.g., in a cell. In some embodiments, reduction of PRR expression (e.g., STING expression) refers to the reduction of the number of copies of PRR RNA, e.g., STING RNA (e.g., mRNA) or PRR protein, e.g., the STING protein, e.g., in a cell. In some embodiments, to suppress expression of a PRR (e.g., STING) may refer to the initiation of PRR RNA (e.g., STING RNA (e.g., mRNA)) or transcription or PRR protein (e.g., STING protein) translation. In some embodiments, to reduce expression of a PRR (e.g., STING) may refer to an increase in the rate of PRR RNA (e.g., STING RNA (e.g., mRNA)) transcription or an increase in the rate of PRR protein (e.g., STING protein) expression.

As used herein, the terms "deactivate" or "deactivation" refer to the suppression or reduction of a function, e.g., of a downstream pathway, e.g., a downstream signaling pathway. In some embodiments, deactivation of a pattern recognition receptor (PRR) (e.g., STING) refers to the suppression of a specific protein or pathway, e.g., through interaction with a downstream signaling partner (e.g., IFN-β promoter stimulator 1 (IPS-1), IRF3, IRF7, NF-κB, interferons (e.g., IFN-α or IFN-β) and/or cytokines). In some embodiments, deactivation of a PRR may suppress the induction of expression of a PRR (e.g., STING) by about 0.1%, about 0.5%, about 1%, about 5%, about 10%, about 15%, about 20%, about 25%, about 30%, about 40%, about 50%, about 60%, about 70%, about 80%, about 90%, about 95%, or more compared to a reference standard (e.g., basal expression levels of a PRR (e.g., STING)).

As used herein, the terms "reference treatment" or "reference standard" refer to a standardized level or standardized treatment that is used as basis for comparison. In some embodiments, the reference standard or reference treatment is an accepted, well known, or well characterized standard or treatment in the art. In some embodiments, the reference standard describes an outcome of a method described herein. In some embodiments, the reference standard describes a level of a marker (e.g., a level of induction of a PRR, e.g., STING) in a subject or a sample, e.g., prior to initiation of treatment, e.g., with a compound or composition described herein. In some embodiments, the reference standard describes a measure of the presence of, progression of, or severity of a disease or the symptoms thereof, e.g., prior to initiation of treatment, e.g., with a compound or composition described herein.

As used herein, the term "Cmd" refers to the word "compound" or "Compound", and all of the terms are used interchangeably.

The term "nucleobase" as used herein, is a nitrogen-containing biological compound found linked to a sugar within a nucleoside—the basic building blocks of deoxyribonucleic acid (DNA) and ribonucleic acid (RNA). The primary, or naturally occurring, nucleobases are cytosine (DNA and RNA), guanine (DNA and RNA), adenine (DNA and RNA), thymine (DNA) and uracil (RNA), abbreviated as C, G, A, T, and U, respectively. Because A, G, C, and T appear in the DNA, these molecules are called DNA-bases; A, G, C, and U are called RNA-bases. Adenine and guanine belong to the double-ringed class of molecules called purines (abbreviated as R). Cytosine, thymine, and uracil are all pyrimidines. Other nucleobases that do not function as normal parts of the genetic code are termed non-naturally occurring.

The selective incorporation of one or more deuterium atom(s) into a compound of general formula I, II, III, IV, or V may alter the physicochemical properties (such as for example acidity [C. L. Perrin, et al., J. Am. Chem. Soc., 2007, 129, 4490; A. Streitwieser et al., J. Am. Chem. Soc., 1963, 85, 2759;], basicity [C. L. Perrin et al., J. Am. Chem. Soc., 2005, 127, 9641; C. L. Perrin, et al., J. Am. Chem. Soc., 2003, 125, 15008; C. L. Perrin in Advances in Physical Organic Chemistry, 44, 144], lipophilicity [B. Testa et al., Int. J. Pharm., 1984, 19(3), 271]), and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102; D. J. Kushner et al., Can. J. Physiol. Pharmacol., 1999, 77, 79). These changes in the exposure to parent drug and metabolites can have important consequences with respect to the pharmacodynamics, tolerability and efficacy of a deuterium-containing compound of general formula I, II, III, IV, or V. In some cases deuterium substitution reduces or eliminates the formation of an undesired or toxic metabolite and enhances the formation of a desired metabolite (e.g., Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g., Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g., lower number of doses or lower dosage to achieve the desired effect) and/or may produce lower metabolite loads.

Patient Selection and Monitoring

The methods of the present disclosure described herein entail administration of a compounds or a pharmaceutically acceptable salt thereof to a subject to deactivate the PRR for IFNs, ISGs and cytokines production or additionally induce the expression of PRRs (e.g., RIG-I, STING etc.). In some embodiments, the subject is suffering from or is diagnosed with a condition, e.g., a proliferative disease or an inflammatory disorder. Accordingly, a patient and/or subject can be selected for treatment using a compounds or a pharmaceutically acceptable salt thereof by first evaluating the patient and/or subject to determine whether the subject is suffering from a proliferative disease or an inflammatory disorder. A subject can be evaluated suffering from a proliferative disease or an inflammatory disorder using methods known in the art. The subject can also be monitored, for example, subsequent to administration of a compounds described herein or a pharmaceutically acceptable salt thereof.

In some embodiments, the subject is a mammal. In some embodiments, the subject is a human. In some embodiments, the subject is an adult. In some embodiments, the subject has a proliferative disease, (e.g., cancer) or an inflammatory disorder.

In some embodiments, the subject is treatment naïve. In some embodiments, the subject has been previously treated for a proliferative disease (e.g., a cancer) an inflammatory disorder. In some embodiments, the subject has relapsed.

Combination Therapies

A compound described herein may be used in combination with other known therapies. Administered "in combination", as used herein, means that two (or more) different treatments are delivered to the subject during the course of the subject's affliction with the disorder, e.g., the two or more treatments are delivered after the subject has been diagnosed with the disorder and before the disorder has been cured or eliminated or treatment has ceased for other reasons. In some embodiments, the delivery of one treatment is still occurring when the delivery of the second begins, so that there is overlap in terms of administration. This is sometimes referred to herein as "simultaneous" or "concurrent delivery". In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

A compound described herein and the at least one additional therapeutic agent can be administered simultaneously, in the same or in separate compositions, or sequentially. For sequential administration, the compounds described herein can be administered first, and the additional agent can be administered second, or the order of administration can be reversed.

In some embodiments, the combination of a compound disclosed herein or a pharmaceutically acceptable salt thereof and the additional agent has a synergistic or additive effect. In some embodiments, the term "additive" refers to an outcome wherein when two agents are used in combination, the combination of the agents acts in a manner equal to but not greater than the sum of the individual activity of each agent.

In some embodiments, the term "additive" refers to an outcome wherein when two agents are used in combination, the combination of the agents acts in a manner equal to but not greater than the sum of the individual activity of each agent. In some embodiments, the terms "synergy" or "synergistic" refer to an outcome wherein when two agents are used in combination, the combination of the agents acts so as to require a lower concentration of each individual agent than the concentration required to be efficacious in the absence of the other agent. In some embodiments, a synergistic effect results in a reduced in a reduced minimum inhibitory concentration of one or both agents, such that the effect is greater than the sum of the effects. A synergistic effect is greater than an additive effect. In some embodiments, the agents in the composition herein may exhibit a synergistic effect, wherein the activity at a particular concentration is greater than at least about 1.25, 1.5, 1.75, 2, 2.5, 3, 4, 5, 10, 12, 15, 20, 25, 50, or 100 times the activity of either agent alone.

For example, any of the methods described herein may further comprise the administration of a therapeutically effective amount of an additional agent. Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells. In some embodiments, the additional agent is an anti-cancer agent, e.g., an alkylating agent (e.g., cyclophosphamide).

In an embodiment, the additional agent is an immunooncology agent, for example, an agent that deactivates the immune system, e.g., making it able to recognize cancer cells and destroy them. Exemplary immunooncology compounds are compounds that inhibit the immune checkpoint blockade pathway. In an embodiment, the compound is an antibody such as a PD-1 or PD-$L_1$ antibody or a co-stimulatory antibody. In some embodiments, the compound is an anti-CTLA4 antibody. In another embodiment, the agent is a cell-based agent, such as CAR-t therapy.

In another embodiment, the additional agent is an anti-inflammatory agent (e.g., a steroid).

Dosages

The compositions of the present disclosure are formulated into acceptable dosage forms by conventional methods known to those of skill in the art. Actual dosage levels of the active ingredients in the compositions of the present disclosure (e.g., a compound of the present disclosure) may be varied so as to obtain an amount of the active ingredient which is effective to achieve the desired therapeutic response for a particular subject, composition, and mode of administration, without being toxic to the subject. The selected dosage level will depend upon a variety of pharmacokinetic factors including the activity of the particular compositions of the present disclosure employed, the route of administration, the time of administration, the rate of absorption of the particular agent being employed, the duration of the treatment, other drugs, substances, and/or materials used in combination with the particular compositions employed, the age, sex, weight, condition, general health and prior medical history of the subject being treated, and like factors well known in the medical arts. A physician or veterinarian having ordinary skill in the art can readily determine and prescribe the effective amount of the composition required. For example, the physician or veterinarian can start doses of the substances of the disclosure employed in the composition at levels lower than that required in order to achieve the desired therapeutic effect and gradually increase the dosage until the desired effect is achieved. In general, a suitable daily dose of a composition of the disclosure will be that amount of the substance which is the lowest dose effective to produce a therapeutic effect. Such an effective dose will generally depend upon the factors described above. Preferably, the effective daily dose of a therapeutic composition may be administered as two, three, four, five, six or more sub-doses administered separately at appropriate intervals throughout the day, optionally, in unit dosage forms.

In some embodiments, therapeutic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject afflicted with the disorders described herein (e.g., HBV infection). Preferred prophylactic dosage levels are between about 0.1 mg/kg to about 1000 mg/kg (e.g., about 0.2 mg/kg, 0.5 mg/kg, 1.0 mg/kg, 1.5 mg/kg, 2 mg/kg, 3 mg/kg, 4 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, 200 mg/kg, 250 mg/kg, 300 mg/kg, 350 mg/kg, 400 mg/kg, 450 mg/kg, 500 mg/kg, 600 mg/kg, 700 mg/kg, 800 mg/kg, 900 mg/kg, or 1000 mg/kg) of the composition per day administered (e.g., orally or intraperitoneally) to a subject. The dose may also be titrated (e.g., the dose may be escalated gradually until signs of toxicity appear, such as headache, diarrhea, or nausea).

The frequency of treatment may also vary. The subject can be treated one or more times per day (e.g., once, twice, three, four or more times) or every so-many hours (e.g., about every 2, 4, 6, 8, 12, or 24 hours). The composition can be administered 1 or 2 times per 24 hours. The time course of treatment may be of varying duration, e.g., for two, three, four, five, six, seven, eight, nine, ten, or more days, two weeks, 1 month, 2 months, 4 months, 6 months, 8 months, 10 months, or more than one year. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Pharmaceutical Compositions

The compositions and methods of the present invention may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a self-emulsifying drug delivery system or a self-microemulsifying drug delivery system. The pharmaceutical composition (preparation) also can be a liposome or other polymer matrix, which can have incorporated therein, for example, a compound of the invention. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896 (all of which are incorporated by reference).

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules. and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

For use in the methods of this invention, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the invention may be used alone or conjointly administered with another type of therapeutic agent.

The present disclosure includes the use of pharmaceutically acceptable salts of compounds of the invention in the compositions and methods of the present invention. In certain embodiments, contemplated salts of the invention include, but are not limited to, alkyl, dialkyl, trialkyl or tetra-alkyl ammonium salts. In certain embodiments, contemplated salts of the invention include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the invention include, but are not limited to, Na, Ca, K, Mg, Zn or other metal salts. In certain embodiments, contemplated salts of the invention include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-l0-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Routes of Administration

The compounds and compositions used in the methods described herein may be administered to a subject in a variety of forms depending on the selected route of administration, as will be understood by those skilled in the art. Exemplary routes of administration of the compositions used in the methods described herein include oral, topical, enteral, or parenteral applications. Topical applications include but are not limited to epicutaneous, inhalation, enema, eye drops, ear drops, and applications through mucous membranes in the body. Enteral applications include oral administration, rectal administration, vaginal administration, and gastric feeding tubes. Parenteral administration includes intravenous, intraarterial, intracapsular, intraorbital, intracardiac, intradermal, transtracheal, subcuticular, intraarticular, subcapsular, subarachnoid, intraspinal, epidural, intrastemal, intraperitoneal, subcutaneous, intramuscular, transepithelial, nasal, intrapulmonary, intrathecal, rectal, and topical modes of administration. Parenteral administration may be by continuous infusion over a selected period of time. In certain embodiments of the disclosure, a composition described herein comprising a compounds is administered orally. In other embodiments of the disclosure, a composition described herein comprising a compounds is administered parenterally (e.g., intraperitoneally). It is recognized that for treatment of solid tumors, direct injection of the compounds into the tumor may also be carried out (e.g., intratumoral administration). It is recognized that for treatment of solid tumors, direct injection of the compounds into the tumor may also be carried out (e.g., intratumoral administration).

The choice of the route of administration will depend on whether a local or systemic effect is to be achieved. For example, for local effects, the composition can be formulated for topical administration and applied directly where its action is desired. For systemic, long term effects, the composition can be formulated for enteral administration and given via the digestive tract. For systemic, immediate and/or short, term effects, the composition can be formulated for parenteral administration and given by routes other than through the digestive tract.

EXAMPLES

The invention now being generally described, it will be more readily understood by reference to the following examples which are included merely for purposes of illustration of certain aspects and embodiments of the present invention, and are not intended to limit the invention.

Example 1: Preparation of Exemplary Compounds of the Disclosure

Method 1:

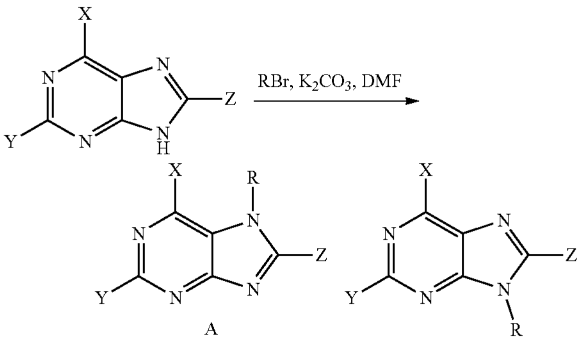

A
7-Regiomer

B
9-Regiomer

To a solution of suitably substituted purine (2 mmol) and RBr/RCl/RI (2.5 mmol) in anhyd. DMF (5 mL) anhyd. potassium carbonate (3 mmol) and a few crystals of NaI were added. The suspension was slowly heated in an oil-bath at 65-70° C. for 3 h under argon. Progress of the reaction was monitored on TLC using DCM-MeOH (2.5%). After the completion of the reaction, the reaction mixture was cooled to rt and concentrated at 50° C. to remove most of DMF. Hexane (10 mL) was added and remaining DMF was removed. The residue was partitioned between EtOAc (50 mL) and water (15 mL). Organic layer was separated, and aq. layer was re-extracted in EtOAc (25 mL). Combined organic layer was washed with water (15 ml), sodium bicarbonate (5%, 2× 15 mL) and later with satd. NaCl solution (10 mL). Organic layer was dried over anhyd. $Na_2SO_4$, filtered and concentrated. Residue was mixed with silica gel and purified by CombiFlash using hexanes and EtOAc as eluent. Fractions with same Rf values were collected and appropriate tubes were mixed, concentrated, to give the both regiomers A and B which were confirmed by $^1$H-NMR and LCMS.

Method 2A:

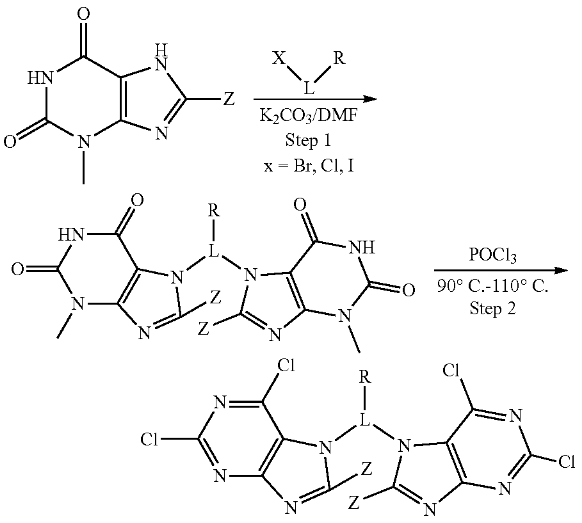

Step 1: Used similar method as described for method 1.

Step 2: To a solution of compound (0.1 mmol) in POCl3 (1 mL) was added DBU(0.2 mmol)mmol). The reaction mixture was stirred at 80° C. for 12 h. The solution was cooled and was added to ice cold solution of dilute $NaHCO_3$ (1 mL). DCM (5 mL) was added and extracted two times. After layer separation and drying, solvent was evaporated. The crude was taken in DMSO and purified by combi flash reverse phase C18 silica gel column chromatography using 0-100% $CH_3CN—H_2O$ as gradient to provide products as solids.

Method 2B:

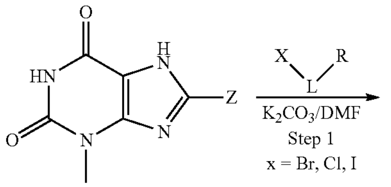

-continued

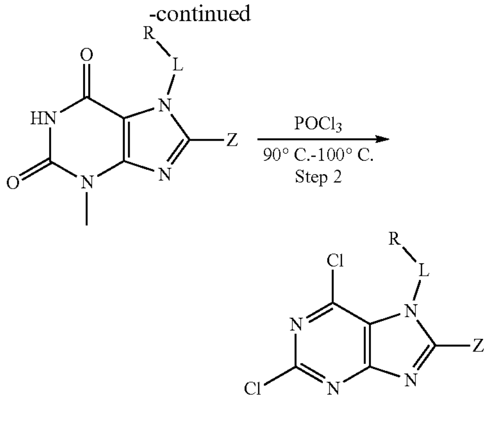

Step 1: Used similar method as described for method 1.

Step 2: To a solution of compound (0.1 mmol) in POCl3 (1 mL) was added DBU(0.2 mmol)mmol). The reaction mixture was stirred at 80° C. for 12 h. The solution was cooled and was added to ice cold solution of dil.NaHC03 (1 mL). DCM (5 mL) was added and extracted two times. After layer separation and drying, solvent was evaporated. The crude was taken in DMSO and purified by combi flash reverse phase C18 silica gel column chromatography using 0-100% $CH_3CN—H_2O$ as gradient to provide products as solids.

Compound 1: 6-chloro-7-(16-carbomethoxyhexadecyl)purine

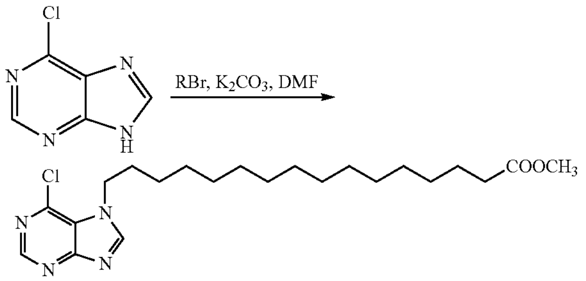

1

To a solution of 6-dichloropurine (0.31 g, 2 mmol) and methyl 16-bromohexadecanoate (0.84g g, 2.40 mmol) in anhyd. DMF (5 mL) anhyd. potassium carbonate (0.41 g, 2.97 mmol, oven dried) and a few crystals of NaI were added. The suspension was slowly heated in an oil-bath at 65-70° C. for 3 h under argon. Progress of the reaction was monitored on TLC using DCM-MeOH (2.5%). After the completion of the reaction, the reaction mixture was cooled to rt and concentrated at 50° c. to remove most of DMF. Hexane (10 mL) was added and remaining DMF was removed. The residue was partitioned between EtOAc (50 mL) and water (15 mL). Organic layer was separated, and aq. layer was reextracted in EtOAc (25 mL). Combined organic layer was washed with water (15 ml), sodium bicarbonate (5%, 2× 15 mL) and later with satd. NaCl solution (10 mL). Organic layer was dried over anhyd. $Na_2SO_4$, filtered and concentrated. Residue was mixed with silica gel and purified by CombiFlash using hexanes and EtOAc as eluent. Fractions with same Rf values were collected and appropriate tubes were mixed, concentrated, to give the both regiomers which were confirmed by 1H-NMR and LCMS. LCMS (m/z) 445.32 [M+Na]; $^1$H-NMR ($CDCl_3$) δ 8.88 (s, 1H), 8.21 (s, 1H), 4.46 (t, 2H), 3.66 (s, 3H), 2.28 (t, 2H), 1.86 (m, 2H), 1.65 (m, 2H), 1.25 (m, 22H).

Compound 2: 2-chloro-7-(16-Carbomethoxyhexadecyl)purine

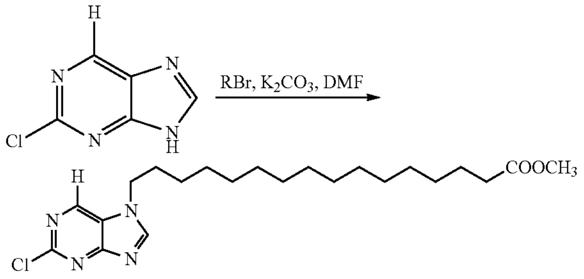

2

Compound 2 was prepared by following a procedure similar to that described for compound 1 using 2-chloropurine. LCMS: 445 (M+Na); $^1$H-NMR ($CDCl_3$) δ 8.56 (s, 1H), 7.98 (s, 1H), 3.99 (t, 2H), 3.4 (s, 3H), 2.04 (t, 2H), 1.67 (m, 2H), 1.33 (m, 2H), 0.97 (m, 22H).

Compound 3: 7-(16-Carbomethoxyhexadecyl)purine

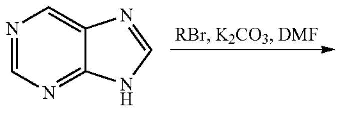

-continued

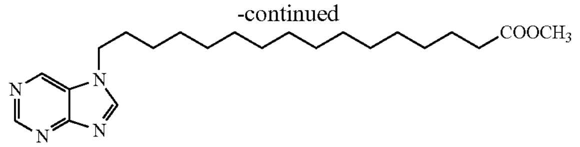

9

Compound 3 was prepared by following a procedure similar to that described for compound 1 using purine. LCMS: m/z 441.13 (M+Na); $^1$H-NMR ($CDCl_3$) δ 9.16 (s, 1H), 8.97 (s, 1H), 8.21 (s, 1H), 4.28 (t, 2H), 3.66 (s, 3H), 2.29 (t, 2H), 1.95 (m, 2H), 1.61 (m, 2H), 1.27 (m, 22H).

Compound 4: 5-(16-Carbomethoxyhexdecyl)-2,4-dichloropyrrolo[3,2-d]pyrimidine

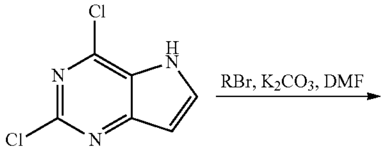

1

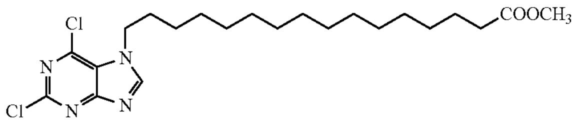

10

Compound 4 was prepared by following a procedure similar to that described for compound 1 using 2,4-dichloropyrrolo[3,2-d]pyrimidine to get a white solid. LCMS: m/z 456.44 (M+1); $^1$H-NMR ($CDCl_3$) δ 7.51 (s, 1H), 6.63 (s, 1H), 4.43 (t, 2H), 3.66 (s, 3H), 2.29 (t, 2H), 1.85 (m, 2H), 1.61 (m, 2H), 1.40 (m, 22H).

Compound 5: 2-Amino-6-chloro-7-(16-carbomethoxyhexadecyl)purine

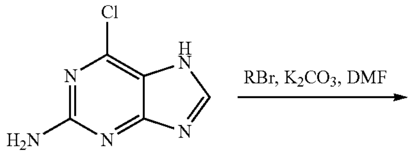

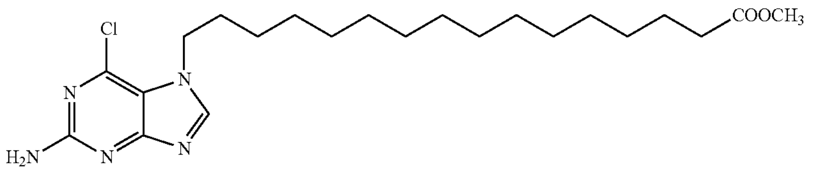

11

Compound 5 was prepared by following a procedure similar to that described for compound 1 using 2-Amino-6-chloropurine and methyl 16-bromohexadecanoate. $^1$H NMR ($CDCl_3$) δ 7.94 (s, 1H), 5.06 (s, 2H), 4.31 (t, J=6.9 MHz, 2H), 3.67 (s, 3H), 2.30 (t, J=7.2 MHz, 2H), 1.86 (m, 2H), 1.63 (m, 2H), 1.26 (m, 22H).

Compound 6: 2,6-Dichloro-9-(16-carbomethoxy-hexadecyl)purine and 2,6-Dichloro-7-(16-carbomethoxyhexadecyl)purine

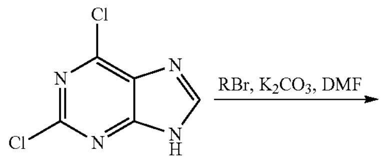

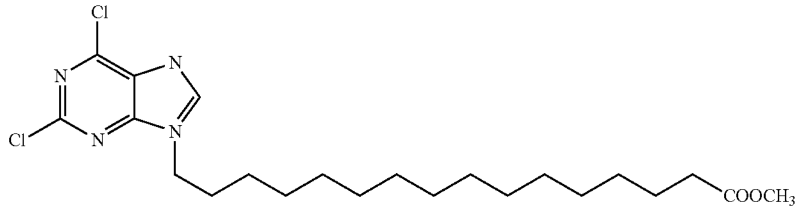

20

+

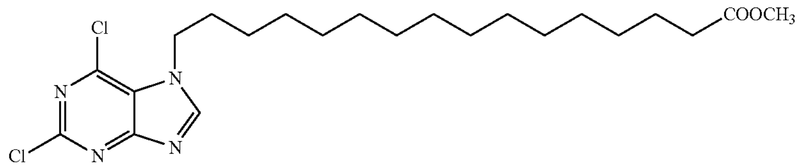

6

Compounds 6 and 20 were prepared by following a procedure similar to that described for compound 1 using 2-6-dichloropurine. Compound 20, H-NMR ($CDCl_3$) δ 8.09 (s, 1H), 4.24 (t, 211), 3.64 (s, 3H), 2.28 (t, 2H), 1.89 (m, 2H), 1.63 (m, 2H), 1.40 (m, 22H); Compound 6, LCMS: m/z 479.31 (M+Na); $^1$H-NMR ($CDCl_3$) δ 8.22 (s, 1H), 4.44 (t, 2H), 3.66 (s, 3H), 2.28 (t, 2H), 1.92 (m, 2H), 1.62 (m, 2H), 1.34 (m, 22H).

Compound 7: 2,6-Dichloro-7-(11-carbomethoxyundecyl)purine

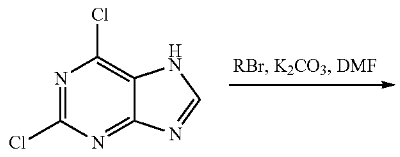

-continued

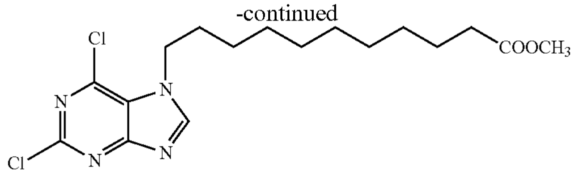

7

Compound 7 was prepared by following a procedure similar to that described for compound 1 using 2-6-dichloropurine, and methyl 11-bromoundecanoate. $^1$H NMR ($CDCl_3$) δ 8.22 (s, 1H), 4.44 (t, 2H), 3.66 (s, 3H), 2.30 (t, 2H), 1.91 (m, 2H), 1.59 (m, 211), 1.29 (m, 12H). Compound 8 was prepared by following a procedure analogous to that described for compound 1 and was obtained as a viscous liquid. $^1$H-NMR ($CDCl_3$) δ 8.07 (s, 111), 5.01 (s, 2H), 4.13 (q, 2H), 1.12 (t, 3H).

Compound 9: methyl (6-amino-2-chloro-7H-purin-7-yl)hexadecanoate

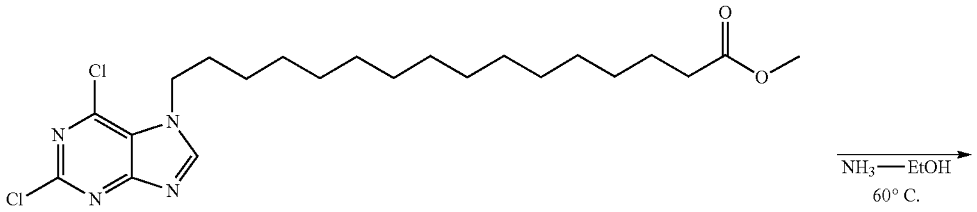

6

-continued

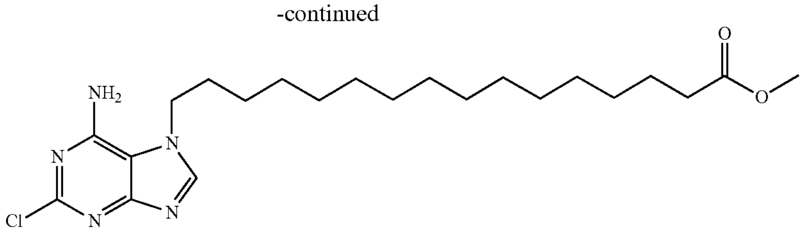

9

To a solution of compound 6 (15 mg, 0.03 mmol) in EtOH (1 mL) was added NH3-EtOH (2M, 0.18 mmol). The reaction mixture was stirred at 60° C. for 12h. Sat $NH_4Cl$ (0.5 mL) was added, stirred for 5 min. Solvent was evaporated. The crude was purified by combi flash reverse phase C18 silica gel column chromatography using 0-100% $CH_3CN$—$H_2O$ as gradient to provide compound 9 as a white solid. LCMS (m/z) 437.2 [M−H]; $^1$H-NMR (DMSO) δ 9.15 (s, 1H), 4.69 (bs, 2H, $D_2O$ exchangeable), 3.83 (m, 2H), 3.54 (s, 3H) 2.54 (m, 2H), 2.07 (m, 2H), 1.75 (m, 2H), 1.47 (m, 22H).

Compound 10: 16-(2-chloro-6-hydroxy-7H-purin-7-yl)hexadecanoic acid

Compound 11: methyl 16-(2-chloro-6-hydroxy-7H-purin-7-yl)hexadecanoate

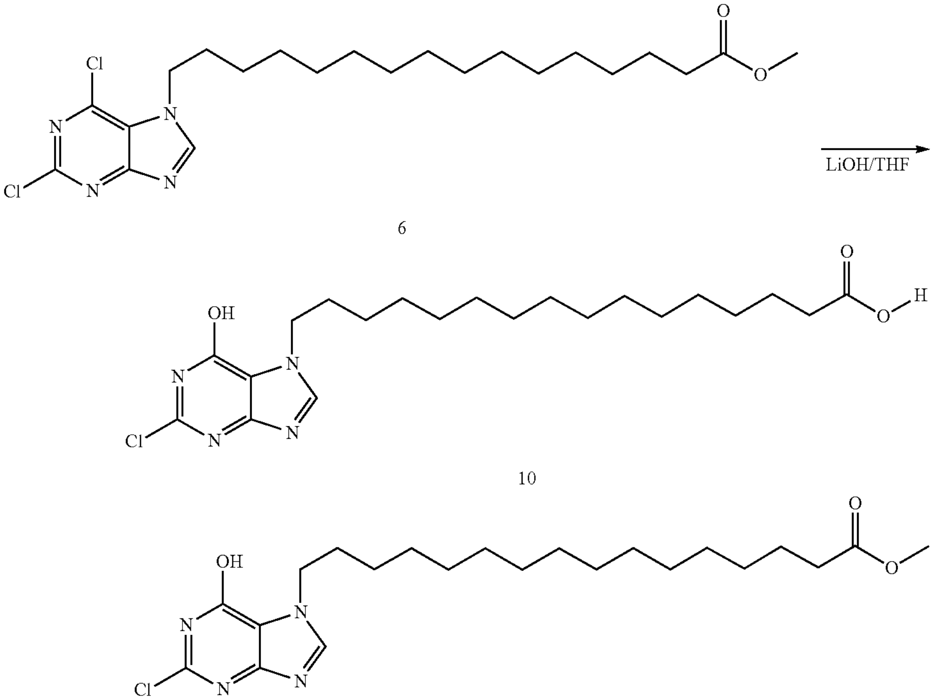

6

10

11

To a solution of compound 6 (60 mg, 0.1 mmol) in THF (1 mL) was added LiOH (1 M in water, 0.3 mmol). The reaction mixture was stirred at rt for 24 h. Sat $NH_4Cl$ (0.5 mL) was added, stirred for 5 min. Solvent was evaporated. The crude was taken in DMSO and purified by combi flash reverse phase C18 silica gel column chromatography using 0-100% $CH_3CN$—$H_2O$ as gradient to provide compound 10 and 11 as white solids. Compound 10: 12 mg (Yield 21%); LCMS (m/z) 425.2 [M+H]; $^1$H-NMR (DMSO) δ 8.57 (s, 1H, $D_2O$ exchangeable), 7.74 (s, 111), 4.35 (m, 2H), 4.19 (m, 2H), 4.11 (s, 1H), 3.39 (m, 2H), 1.86 (m, 6H), 1.41 (m, 4H), 1.21 (m, 14H). Compound 11: 14 mg (Yield 24%); LCMS (m/z) 439.2 [M+H]; $^1$H-NMR (DMSO) δ 8.14 (s, 1H), 4.39 (m, 2H), 4.29 (s, 3H), 3.77 (m, 1H), 2.48 (m, 3H), 1.94 (m, 2H), 1.72 (m, 2H), 1.34 (m, 19H).

Compound 12: 6-chloro-7-(8-carboethoxyoctyl)purine

Compound 12 was prepared by following a procedure similar to that described for compound 1 from corresponding starting materials: LCMS (m/z) 359.05 [M+H]. $^1$H-NMR ($CDCl_3$) δ 8.106 (s, 1H), 4.324 (t, 2H), 4.015 (q, 2H), 2.168 (t, 2H), 1.804 (d, 2H), 1.488 (d, 2H), 1.248 (s, 6H), 1.140 (t, 3H).

Compound 13: 6-chloro-7-(7-carbomethoxyheptyl)purine

Compound 13 was prepared by following a procedure similar to that described for compound 1 from corresponding starting materials: LCMS (m/z) 331.07 [M+H]; $^{1}$H-NMR ($CDCl_3$) $\delta$ 8.490 (s, 1H), 4.709 (t, 2H), 3.920 (s, 3H), 2.578 (m, 2H), 2.201 (d, 2H), 1.898 (d, 2H), 1.654 (m, 4H).

Compound 14: Ethyl 2-(2,6-dichloro-9H-purin-9-yl)acetate

Compound 14 was prepared by following a procedure similar to that described for compound 1 from corresponding starting materials: 1H-NMR ($CDCl_3$) $\delta$ 8.24 (s, 1H), 5.17 (s, 2H), 4.29 (q, 2H), 1.28 (t, 3H).

Compound 16: 2-(2,6-dichloro-9H-purin-9-yl)hexadecenoic acid

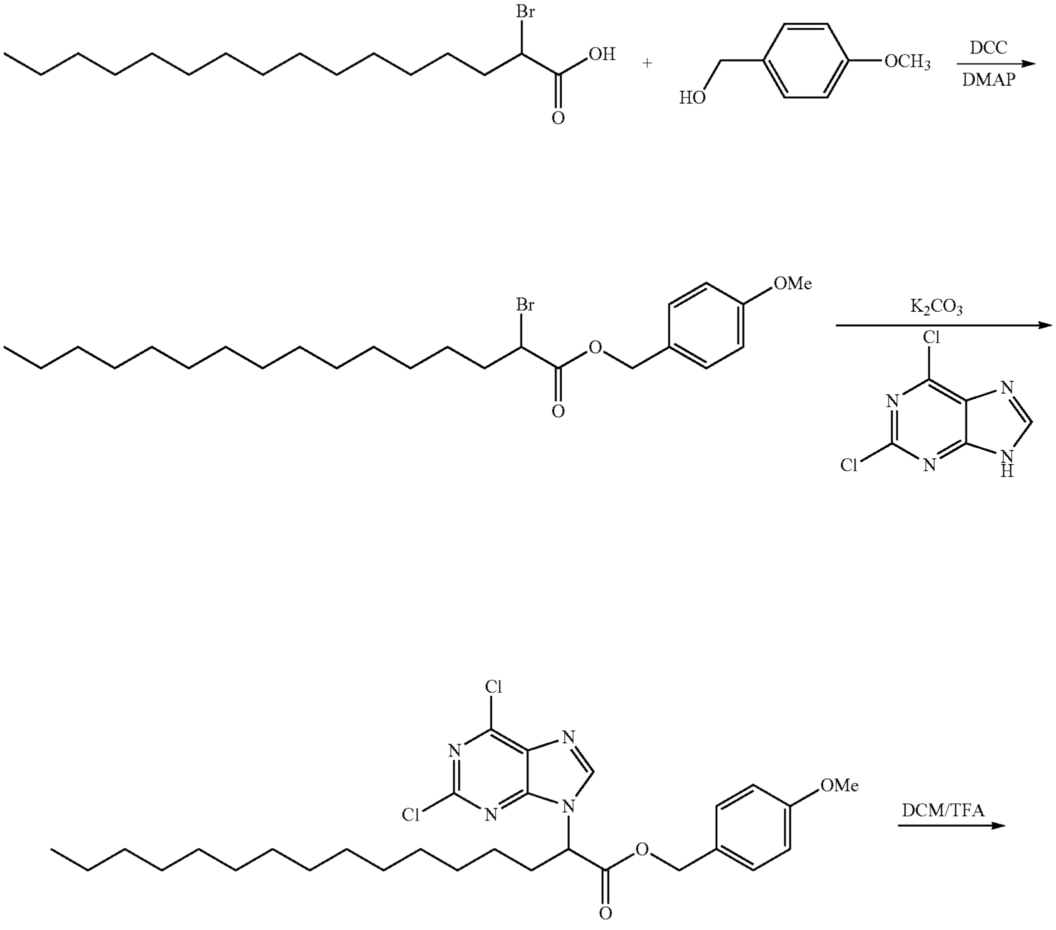

15

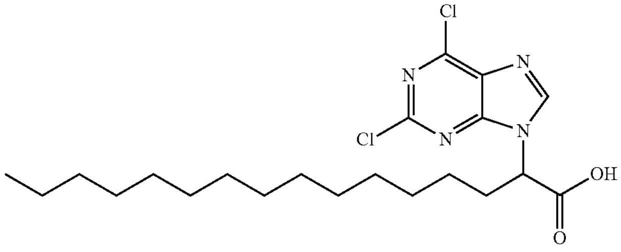

16

Step 1: To a mixture of 2-bromohexadecanoic acid (1.0 g, 2.98 mmol) and p-methoxybenzyl alcohol (0.61 g, 4.47 mmol) in dichloromethane (10 mL) was added N,N'-dicyclohexylcarbodiimide (615 mg, 2.98 mmol) in one portion. Catalytic 4-dimethylaminopyridine (50 mg) was added, reaction mixture was stirred at room temperature for overnight. TLC analysis showed formation of product, reaction mixture was diluted with dichloromethane (50 mL) and filtered through Buchner funnel to remove cyclohexyl urea. Dichloromethane layer was washed with water (50 mL), dried over $Na_2SO_4$ and concentrated under reduced pressure to give crude product. Crude product 4-methoxybenzyl 2-bromohexadecanoate was purified on combi flash silica gel column chromatography using 0-10% ethyl acetate in hexane to get 950 mg of intermediate bromo compound as a viscous liquid.

Step 2: To a solution of a 2,6-dicholoropurine (332 mg, 1.75 mmol) in DMF (10 mL) was added $K_2CO_3$ (486 mg, 3.51 mmol) and 4-methoxybenzyl 2-bromohexadecanoate (800 mg, 1.75 mmol). Reaction mixture was stirred at room temperature for two days under argon atm. TLC analysis showed completion of the reaction. Reaction mixture was diluted with DCM (50 mL) and washed with water (2×25 mL). Organic layers were dried over $Na_2SO_4$, concentrated under reduced pressure and dried under high vacuum for 1 h to get crude product. Crude product was purified on combi flash silica gel column chromatography using 0-20% ethyl acetate gradient in hexane to get 500 mg of pure compound 15.

Step 3: To a solution of a 4-methoxybenzyl 2-(2,6-dichloro-9H-purin-9-yl)hexadecanoate (150 mg, 0.266 mmol) in DCM (5 mL) was added trifluoroacetic acid (500 μL) at room temperature. Reaction mixture was stirred at room temperature for 2h. TLC analysis showed completion of the reaction. Solvents were evaporated under reduced pressure to dryness, reaction mixture was co-evaporated with acetonitrile (2×5 mL). Crude product was purified on an ACCQPrep HP125 system using a Waters Xbridge BEH C18 OBD prep column (5 um, 10×250 mm). Mobile phase A was Water and mobile phase B was Acetonitrile. 50 mg of crude was dissolved acetonitrile (5.0 mL) and loaded on column. Once loaded, a gradient was started with 70% mobile phase A, at 5 mL/min, and increased to 90% mobile phase B over 40 minutes. Compound was eluted at 90% acetonitrile in water at 50 min. Pure fractions were concentrated and dried under high vacuum to get pure compound 16. LCMS: m/z 442.99 $(M+H)^+$.

Compound 17: 2-(2,4-dichloro-7H-pyrrolo[2,3-d]pyrimidin-7-yl)hexadecanoic acid

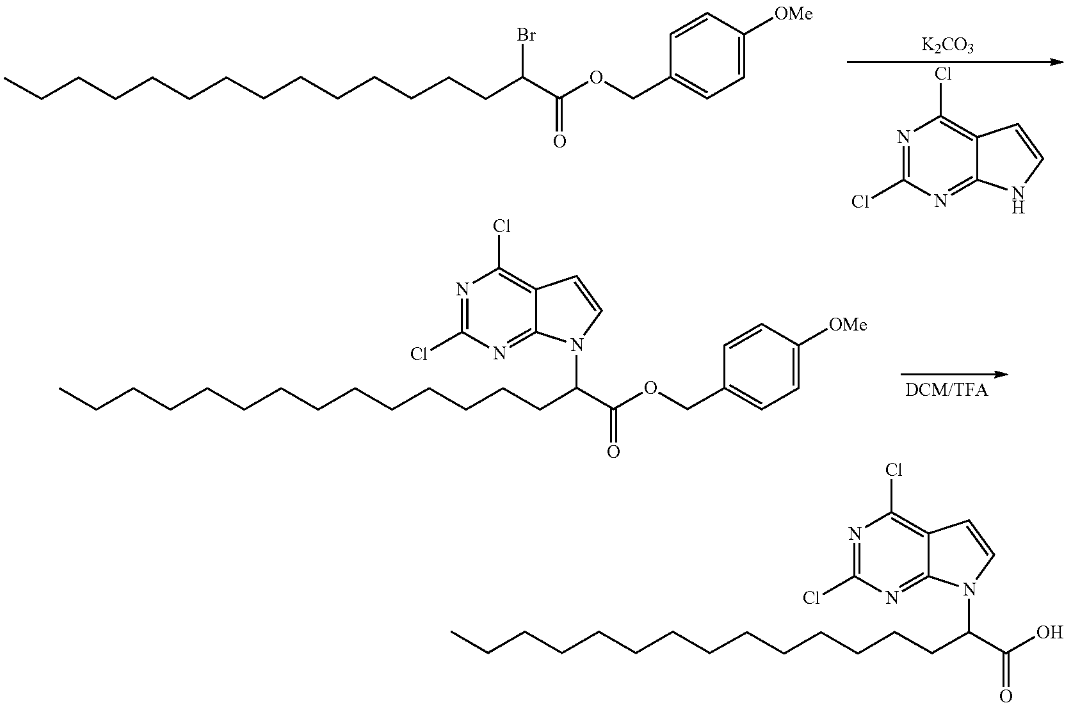

17

Step 1: To a solution of a 2,6-dicholoropurine (100 mg, 0.53 mmol) in DMF (5 mL) was added $K_2CO_3$ (146 mg, 1.06 mmol) and 4-methoxybenzyl 2-bromohexadecanoate (241 mg, 0.53 mmol). Reaction mixture was stirred at room temperature for two days under argon atm. TLC analysis showed completion of the reaction. Reaction mixture was diluted with DCM (50 mL) and washed with water (2×25 mL). Organic layers were dried over $Na_2SO_4$, concentrated under reduced pressure and dried under high vacuum to get crude product. Crude product was purified on combi flash silica gel column chromatography using 0-20% ethyl acetate gradient in hexane to get 240 mg 4-methoxybenzyl 2-(2,4-dichloro-7H-pyrrolo[2,3-d]pyrimidin-7-yl)hexadecanoate as white solid.

Step 2: To a solution of a 4-methoxybenzyl 2-(2,4-dichloro-7H-pyrrolo[2,3-d]pyrimidin-7-yl)hexadecanoate (240 mg, 0.42 mmol) in DCM (6.0 mL) was added trifluoroacetic acid (600 uL) at room temperature. Reaction mixture was stirred at room temperature for 2h. TLC analysis (Hexane:EtOAc, 80:20) showed completion of the reaction. Solvents were evaporated under reduced pressure to dryness, reaction mixture was co-evaporated with acetonitrile (2×5 mL). Crude product was purified on an ACCQPrep HP125 system using a Waters Xbridge BEH C18 OBD prep column (5 um, 10×250 mm). Mobile phase A was Water and mobile phase B was Acetonitrile. 50 mg of crude was dissolved acetonitrile (5.0 mL) and loaded on column. Once loaded, a gradient was started with 50% mobile phase A, at 5 mL/min, and increased to 100% mobile phase B over 17 minutes and continued over 28 min. Compound was eluted at 100% acetonitrile at 25 min. Pure fractions were concentrated and dried under high vacuum to get compound 17.

Compound 19: 2-(2,6-dichloro-9H-purin-9-yl)decanoic acid

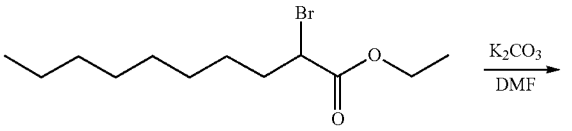

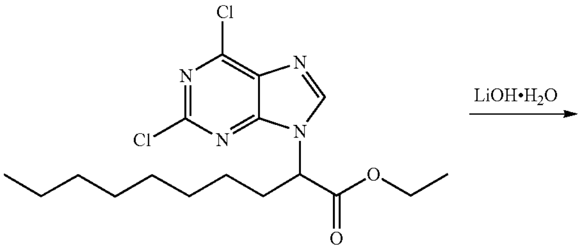

18

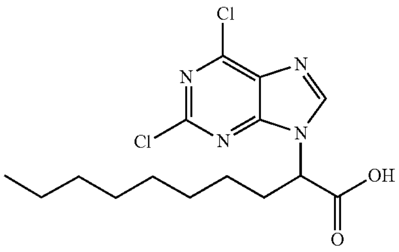

19

Step 1: To a solution of a 2,6-dicholoropurine (100 mg, 0.52 mmol) in DMF (2 mL) was added $K_2CO_3$ (146 mg, 1.05 mmol) and ethyl 2-bromodecanoate (177 mg, 0.63 mmol). Reaction mixture was stirred at room temperature for two days under argon atm. TLC analysis showed completion of the reaction. Reaction mixture was diluted with DCM (50 mL) and washed with water (2×25 mL). Organic layers were dried over $Na_2SO_4$, concentrated under reduced pressure and dried under high vacuum to get crude product. Crude product was purified on combi flash silica gel column chromatography using 0-20% ethyl acetate gradient in hexane to get 120 mg of ethyl 2-(2,6-dichloro-9H-purin-9-yl)decanoate (compound 18) as white solid.

Step 2: Lithium hydroxide monohydrate (11 mg, 0.256 mmol) was added to a solution of ethyl 2-(2,6-dichloro-9H-purin-9-yl)decanoate (50 mg, 0.12 mmol) in a mixture of THF: MeOH: $H_2O$ (3:1:1, 2.5 mL). Reaction mixture was stirred at room temperature for 1h. TLC analysis showed completion of the reaction. Solvents were evaporated under reduced pressure. The residue was dissolved in water (5.0 mL) and extracted with ethyl acetate (5.0 mL). The aqueous layer was acidified with aqueous potassium hydrogen sulfate to pH=3.0. And extracted with ethyl acetate (3×5 mL). The combined organic phases were washed with water (5.0 mL) and brine (5.0 mL) and dried over $Na_2SO_4$ and concentrated under reduced pressure to afford 50 mg of crude product. Crude product was purified on an ACCQPrep HP125 system using a Waters Xbridge BEH C18 OBD prep column (5 um, 10×250 mm). Mobile phase A was Water and mobile phase B was Acetonitrile. Crude was dissolved acetonitrile (5.0 mL) and loaded on column. Once loaded, a gradient was started with 70% mobile phase A, at 5 mL/min, and increased to 90% mobile phase B over 40 minutes, and continued 90% B over 50 min. Compound was eluted at 60% acetonitrile in water at 25 min. Pure fractions were concentrated and dried under high vacuum to get 23 mg of compound 19 as white solid. LCMS: m/z 357.09 $(M-H)^-$.

Compound 21: 2-chloro-6-(2-sulfonamidoethylamino)-9-(16-carbomethoxyhexadecyl)purine

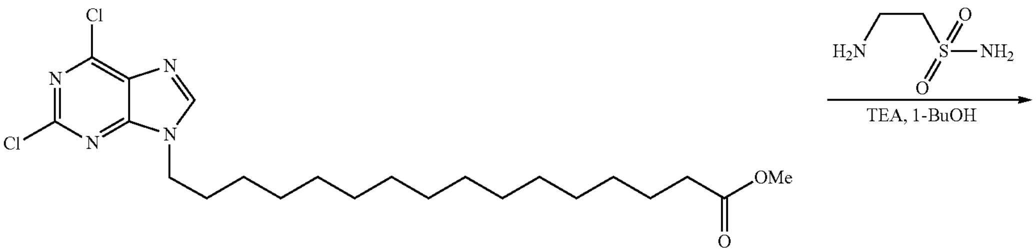

-continued

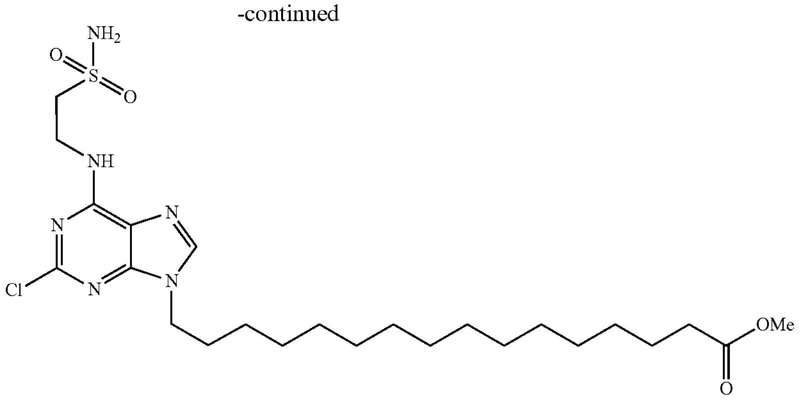

To a mixture of compound 20 (46 mg, 0.1 mmol) and 2-aminoethanesulfonamide (14 mg, 0.11 mmol) in 1-butanol (2 mL) under stirring TEA (0.1 mL) was added and the suspension was heated in oil bath at 85-90° C. for 4 h and TLC (DCM-MeOH 10%) indicated the absence of starting material. The reaction mixture was cooled to rt and the solvent was evaporated followed by high vac drying overnight. The white residue was partitioned between water (10 mL) and DCM (25 mL). DCM layer was washed with brine (5 mL), organic layer was dried over anhyd. $Na_2SO_4$, filtered, concentrated to provide compound 21 a white solid (43'mg, 79%); LCMS: m/z 546 (M+1) and $^1$H-NMR ($CDCl_3$+MeOH-$d_4$) δ 7.71 (s, 1H), 4.14 (t, 2H), 3.54 (s, 3H), 3.4 (t, 2H), 2.17 (t, 2H), 1.66 (m, 2H), 1.45 (m, 2H), 1.11-1.18 (m, 24H).

Compound 22: 6-((2-chloro-9-(4-methoxybenzyl)-9H-purin-6-yl)amino)hexanoic acid

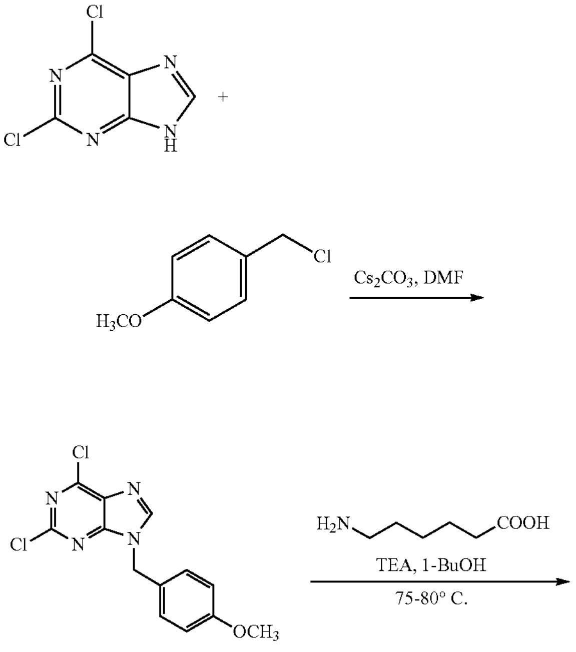

major

-continued

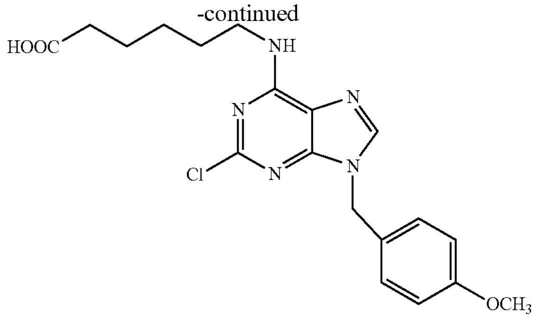

22

Step 1: To a mixture of 2,6-dichloropurine (1.89 g, 1 mmol) in anhyd. DMF (8 mL) 4-methoxybenzyl chloride (1.87 g, 1.2 mmol) was added followed by addition of cesium carbonate (3.25 g. 1 equiv.). The reaction mixture was heated in an oil bath slowly to 65-70° C. and maintained for 4-5 h. The progress of the reaction was monitored by TLC (DCM-MeOH 5%) and found to be complete. After cooling, DMF was removed, after the addition of water (50 mL), the reaction mixture was extracted with EtOAc (2×50 mL) and organic layer was washed with water (2×25 mL), brine (25 mL). Finally, organic layer was dried over anhyd. $Na_2SO_4$, filtered, and concentrated to give the crude reaction mixture, which was purified by Combi Flash using DCM-MeOH (0-10%). Two fractions were isolated in low yields with <5% of MeOH and first fraction, 9 isomer 450 mg (15%) and second fraction 7 regiomer 200 mg (7%).

Step 2: To 4-methoxybenzyl derivative obtained above (100 mg, 0.32 mmol) and 6-aminohexanoic acid (68 mg, 1.6 equiv.) in 1-butanol (5 mL) TEA (0.2 mL) was added. The suspension was heated in an oil bath at 75-80° C. for 5 h, monitoring the reaction by TLC (DCM-MeOH 2.5%). After the completion of reaction, concentrated, co-evaporated with acetonitrile (2×5 mL) and dried overnight under high vacuum. The resulting white solid was suspended in water (5 mL) treated with 1N HCl to convert the TEA salt. Extracted repeatedly with DCM (2×15 mL), the organic layer was washed with brine (5 mL), dried over anhyd. $Na_2SO_4$, filtered and concentrated to yield compound 22. $^1$H-NMR ($CDCl_3$) δ 7.58 (s, 1H), 7.25 (dd, 2H), 6.86 (d, 2H), 5.21 (s, 2H), 3.78 (s, 3H), 3.57 (2H), 2.31 (m, 4H), 1.67 (m, 4H), 1.44 (m, 2H).

Compound 23: methyl 16-(2-chloro-6-(methylamino)-7H-purin-7-yl)hexadecanoate

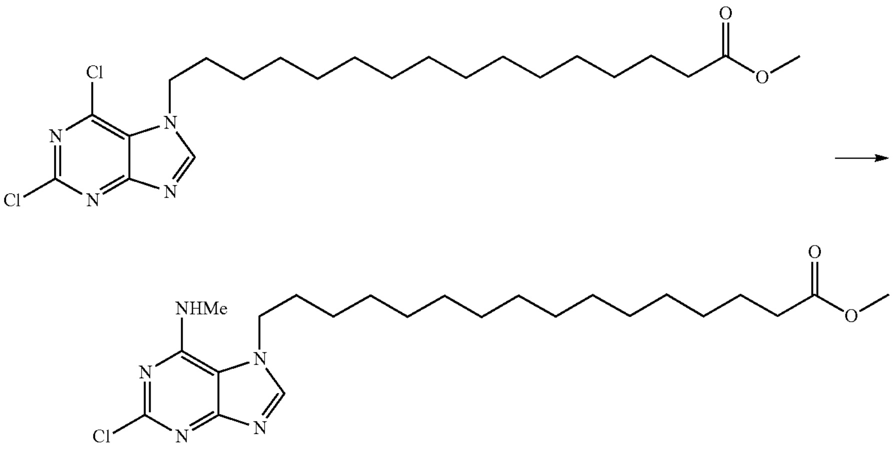

23

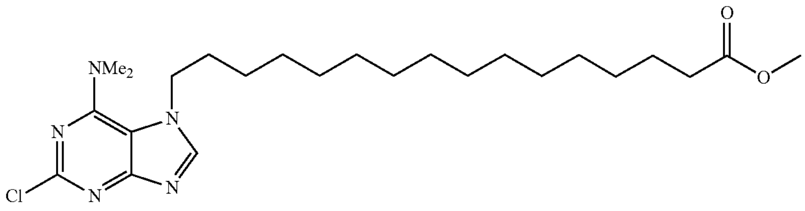

24

To a solution of compound 6 (15 mg, 0.03 mmol) in isopropanol (1 mL) was added methylamine (3eq, 40% in MeOH). The reaction mixture was stirred at 60° C. for 12h. Sat $NH_4Cl$ (0.5 mL) was added, stirred for 5 min. Solvent was evaporated. The crude was purified by combi flash reverse phase C18 silica gel column chromatography using 0-100% $CH_3CN$—$H_2O$ as gradient to provide compound 23 as a white solid. Yield 9 mg (60%); LCMS: m/z 452.3 (M+H); $^1$H-NMR ($CDCl_3$) δ 7.75 (s, 1H), 4.96 (m, 1H), 4.17 (m, 2H), 3.60 (s, 3H), 3.12 (m, 3H), 2.23 (m, 2H), 1.78 (m, 2H), 1.55 (m, 6H), 1.23 (18H).

Compound 24: methyl 16-(2-chloro-6-(dimethylamino)-7H-purin-7-yl)hexadecanoate

Compound 24 was prepared by following a procedure similar to that described for compound 23 using dimethylamine.HCl to get a white solid. LCMS: m/z 466.1(M+H); $^1$H-NMR ($CDCl_3$) δ 7.93 (s, 1H), 4.19 (m, 2H), 3.60 (s, 3H), 3.06 (m, 6H), 2.23 (m, 2H), 1.95(m, 211), 1.71 (m, 2H), 1.54 (m, 6H), 1.23 (16H).

Compound 25: 16-(2,6-dichloro-7H-purin-7-yl)hexadecan-1-ol

Compound 25 was prepared by following a procedure similar to that described for compound 1 from corresponding starting materials to provide a white solid. Yield 50 mg (12.2%). $^1$H NMR ($CDCl_3$) δ 8.22 (s, 1H), 4.44 (t, J=7.2 MHz, 2H), 3.66 (s, 3H), 2.30 (t, J=7.5 MHz, 2H), 1.91 (m, 2H), 1.59 (m, 211), 1.29 (m, 12H).

Compound 26: 2,6-dichloro-7-hexadecyl-7H-purine

Compound 26 was prepared by following a procedure similar to that described for compound 1 from corresponding starting materials to provide a white solid. Yield 75 mg (18.2%). $^1$H NMR ($CDCl_3$) δ 8.22 (s, 1H), 4.44 (t, J=6.9 MHz, 2H), 1.95 (m, 2H), 1.58 (s, 1H), 1.25 (m, 30H).

Compound 27: methyl 16-(6-(methylthio)-7H-purin-7-yl)hexadecanoate

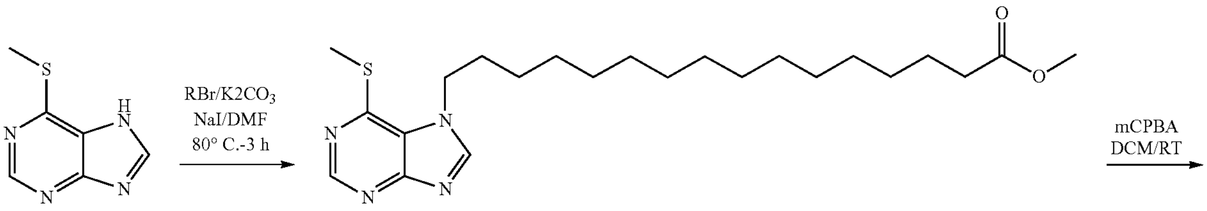

27

-continued

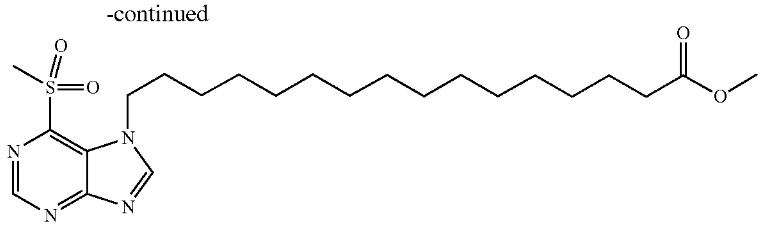

28

Compound 27 was prepared by following a procedure similar to that described for compound 1 from corresponding starting materials: LCMS: m/z 457(M+Na); $^1$H-NMR ($CDCl_3$) δ 8.74(s, 111), 7.90 (s, 1H), 4.24 (m, 1H), 3.55 (s, 3H), 2.65 (s, 3H), 2.15 (m, 2H), 1.90 (m, 3H), 1.79 (m, 4H), 1.23 (m, 20H).

Compound 28: methyl 16-(6-(methylsulfonyl)-7H-purin-7-yl)hexadecanoate

To a solution of compound 27 (0.31 g, 2 mmol) in DCM (0.5 mL) was added mCPBA (3 eq) in DCM (1 mL). Reaction was stirred for 12 h at rt. After the completion of the reaction, the reaction mixture was cooled and $NaHCO_3$ (1 M, 0.5 mL) followed by NaHSO3 (2M, 0.5 mL) was added and the layer was separated. Organic layer was dried over anhyd. $Na_2SO_4$. The crude was purified by CombiFlash using hexanes and EtOAc as eluent (0-100% EA/Hexane) to provide compound 28 as light white solid. LCMS: m/z 489.2 (M+Na); $^1$H-NMR ($CDCl_3$) δ 9.10 (s, 1H), 8.40 (s, 1H), 4.65(m, 211), 3.66 (s, 3H), 3.54(s, 311), 2.32 (m, 2H), 2.04 (m, 4H), 1.61 (m, 3H), 1.23 (m, 19H).

Several compounds were made by alternate synthetic routes as exemplified below:

Compound 29: methyl 16-(2,6-dichloro-8-methyl-7H-purin-7-yl)hexadecanoate

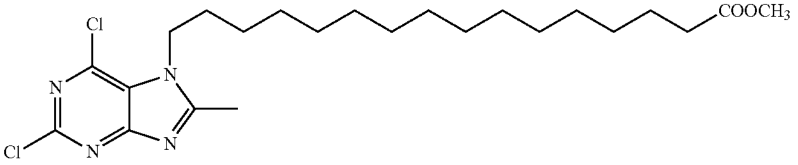 [SMILES: COC(=O)CCCCCCCCCCCCCCCn1c(C)nc2nc(Cl)nc(Cl)c21]

LCMS: m/z 493.1 (M+Na); $^1$H NMR (CDC13) δ 4.35 (dd, J=7.5 & 7.8, 2H), 3.66 (s, 3H), 2.70 (s, 3H), 2.29 (dd, J=7.5 & 7.8, 211), 1.82 (m, 211), 1.62 (m, 5H), 1.35 (m, 19H).

Compound 30: 16-(2,6-dicliloro-7H-purin-7-yl)hexadecanoic acid

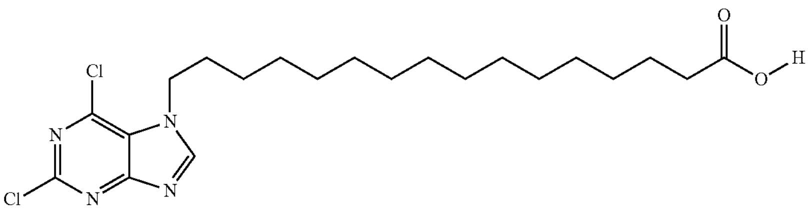 [SMILES: O=C(O)CCCCCCCCCCCCCCCn1cnc2nc(Cl)nc(Cl)c21]

LCMS: m/z 442.2 (M−H); $^1$H NMR (CDC13) δ 8.713 (s, 1H), 4.898 (t, 2H), 2.810 (t, 2H), 2.37 (m, 2H), 2.09 (m, 2H), 1.70 (m, 22H).

Compound 31: methyl 6-(2,6-dichloro-7H-purin-7-yl) hexanoate

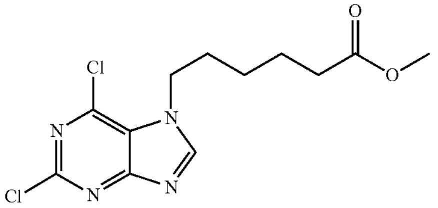 [SMILES: COC(=O)CCCCCn1cnc2nc(Cl)nc(Cl)c21]

LCMS: m/z 317.01 [M+H]; $^1$H NMR (CDCl3) δ 8.43 (s, 1H), 4.65 (t, 2H), 3.91 (s, 3H), 2.57 (t, 2H), 2.18 (t, 2H) 1.92 (t, 2H) 1.62 (m, 2H).

Compound 32: methyl 5-(2,6-dichloro-7H-purin-7-yl)pentanoate

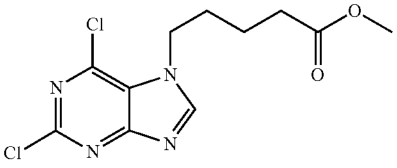 [SMILES: COC(=O)CCCCn1cnc2nc(Cl)nc(Cl)c21]

LCMS: m/z 303.12 (M+H); $^1$H NMR (DMSO) δ 8.89 (s, 1H), 4.44 (t, 2H), 3.55 (s, 3H), 2.34 (t, 2H), 1.83 (m, 2H), 1.51 (m, 2H).

Compound 33: 5-(2,6-dichloro-7H-purin-7-yl)pentyl acetate

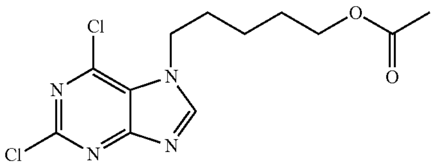 [SMILES: CC(=O)OCCCCCn1cnc2nc(Cl)nc(Cl)c21]

LCMS: m/z 317.05 (M+H). $^1$H NMR (CDCl3) δ 8.46 (s, 111), 4.67 (t, 2H), 4.37 (t, 2H), 2.00 (s, 3H), 1.65 (m, 2H).

Compound 34: methyl 16-(2,6-dichloro-8-methyl-9H-purin-9-yl)hexadecanoate

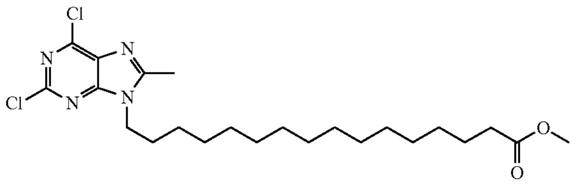 [SMILES: COC(=O)CCCCCCCCCCCCCCCn1c(C)nc2c(Cl)nc(Cl)nc21]

LCMS: m/z 493.1 (M+Na); $^1$H-NMR ($CDCl_3$) δ 4.35 (dd, J=7.5, 7.8, 2H), 3.66 (s, 3H), 2.70 (S, 3H), 2.29 (dd, J=7.5, 7.8, 2H), 1.82 (m, 2H), 1.34 (m, 24H).

Compound 35: 1,12-bis(2,6-dichloro-7H-purin-7-yl) dodecane

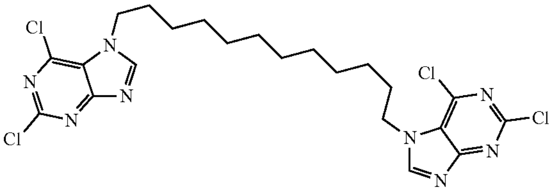 [SMILES: Clc1nc(Cl)c2c(ncn2CCCCCCCCCCCCn2cnc3nc(Cl)nc(Cl)c32)n1]

LCMS: m/Z 545.03 (M+H); $^1$H-NMR ($CDCl_3$) δ 8.16 (s, 2H), 4.25 (dd, J=6.9, 7.8, 4H), 1.80 (s, 411), 1.58 (s, 6H), 1.31 (bs, 6H), 1.25 (m, 4H).

Compound 36: ethyl 2-(2,6-dichloro-7H-purin-7-yl) decanoate

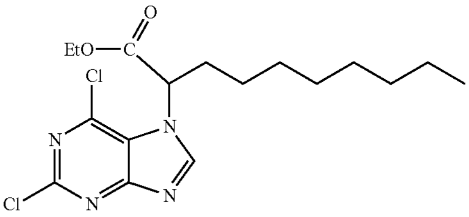 [SMILES: CCCCCCCCC(C(=O)OCC)n1cnc2nc(Cl)nc(Cl)c21]

LCMS: m/Z 387.1 (M+H); $^1$H-NMR ($CDCl_3$) δ 8.5 (s, 1H), 5.6(m, 1H), 4.28 (m, 2H), 2.34 (m, 1H), 2.21 (m, 1H), 1.28 (m, 18H).

Compound 37: methyl 4-(2,6-dichloro-7H-purin-7-yl)butanoate

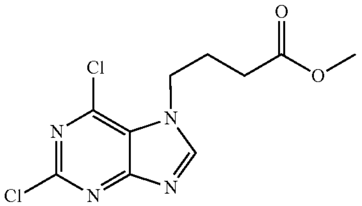 [SMILES: COC(=O)CCCn1cnc2nc(Cl)nc(Cl)c21]

LCMS: m/z 289.12 (M+H); $^1$H NMR δ 8.22 (s, 1H), 4.47 (t, 2H), 3.69 (s, 3H), 2.40 (t, 2H), 2.24 (m, 2H).

Compound 38: methyl 16-(6-chloro-2-fluoro-7H-purin-7-yl)hexadecanoate

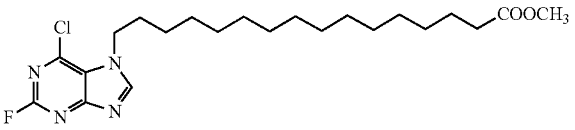 [SMILES: COC(=O)CCCCCCCCCCCCCCCn1cnc2nc(F)nc(Cl)c21]

LCMS: m/z 441.50 (M+H); $^1$H NMR (CDCl3) δ 8.57 (s, 1H), 4.81 (t, 2H), 4.00 (m, 3H), 2.62 (m, 2H), 2.25 (m, 2H), 1.93 (m, 2H), 2.61 (m, 22H).

Compound 39: methyl 16-(2-chloro-6-(methylsulfonyl)-7H-purin-7-yl) hexadecanoate

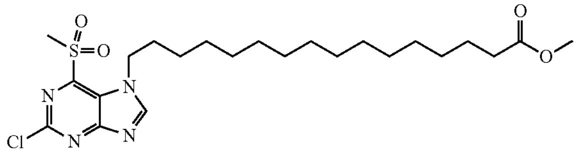 [SMILES: COC(=O)CCCCCCCCCCCCCCCn1cnc2nc(Cl)nc(S(C)(=O)=O)c21]

LCMS: m/Z 502.1 (M+H).

Compound 40: 10-(2,6-dichloro-7H-purin-7-yl)decan-1-ol

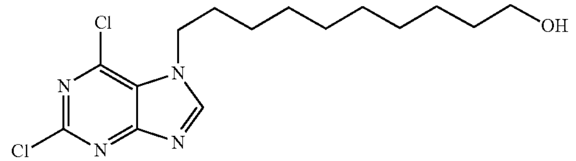 [SMILES: OCCCCCCCCCCn1cnc2nc(Cl)nc(Cl)c21]

LCMS: m/z 345.23 (M+H); $^1$H NMR (CDC13) δ 8.21 (s, 1H), 4.43 (t, 2H), 3.64 (t, 2H), 1.92 (t, 2H), 0.82 (m, 2h), 1.57 (m, 2H), 1.34 (m, 10H).

Compound 41: methyl 16-(7-chloro-1H-imidazo[4,5-b]pyridin-1-yl) hexadecanoate

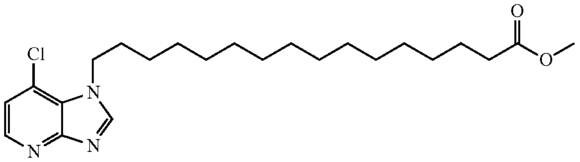 [SMILES: COC(=O)CCCCCCCCCCCCCCCn1cnc2nccc(Cl)c21]

LCMS: m/z 422.18 (M+H); $^1$H NMR (CDC13) δ 8.61 (d, 111), 8.59 (s, 1H), 7.57 (d, 1H), 4.60 (t, 2H), 3.97 (s, 3H), 2.61 (t, 2H), 2.24 (t, 211), 1.92 (m, 2H), 1.18 (m, 22H).

Compound 42: methyl 16-(7-chloro-3H-imidazo[4,5-b]pyridin-3-yl) hexadecanoate

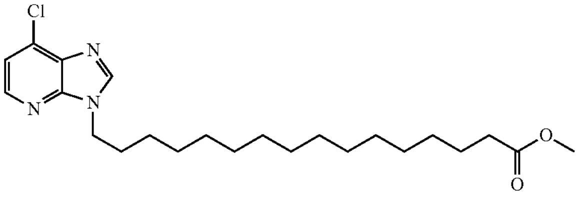 [SMILES: COC(=O)CCCCCCCCCCCCCCCn1cnc2c(Cl)ccnc21]

LCMS:m/z 422.18 (M+H); $^1$H NMR (CDC13) δ 8.57 (s, 1H), 8.31 (d, 1H), 7.42 (d, 1H), 4.26 (t, 2H), 3.55 (s, 3H), 2.28 (t, 211), 1.83 (m, 2H), 1.48 (m, 2H), 1.19 (m, 22H).

Compound 43: methyl 16-(4-chloro-1H-imidazo[4,5-c]pyridin-1-yl) hexadecanoate

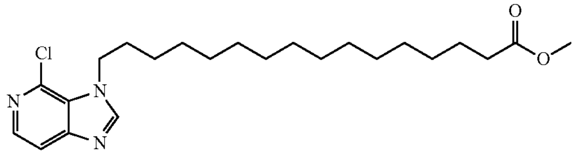 [SMILES: COC(=O)CCCCCCCCCCCCCCCn1cnc2ccnc(Cl)c21]

LCMS: m/z 422.18(M+H); $^1$H NMR (CDC13) δ $^1$H NMR (CDC13) δ 8.22 (d, 111), 7.99 (s, 1H), 7.63 (d, 1H), 4.51 (t, 211), 3.66 (s, 3H), 2.30 (t, 2H), 1.88 (t, 2H), 1.55 (t, 2H), 1.24 (m, 22H).

Compound 44: methyl 16-(4-chloro-3H-imidazo[4,5-c]pyridin-3-yl) hexadecanoate

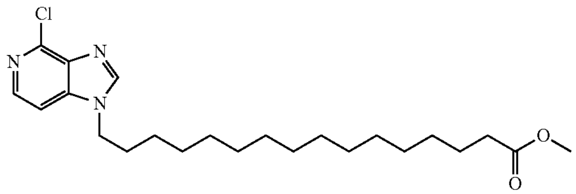 [SMILES: COC(=O)CCCCCCCCCCCCCCCn1cnc2c(Cl)nccc21]

LCMS: m/z 422.18 (M+H); $^1$H NMR (CDC13) δ 8.22 (d, 1H), 7.99 (s, 1H), 7.63 (d, 1H), 4.51 (t, 2H), 3.66 (s, 3H), 2.30 (t, 2H), 1.88 (t, 2H), 1.55 (t, 2H), 1.24 (m, 22H).

Compound 45: (6-(26-dichloro-7H-purin-7-yl) hexan-1-ol)

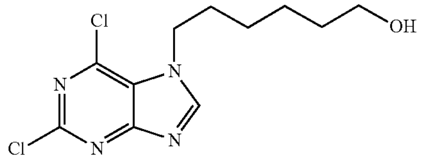 [SMILES: OCCCCCCn1cnc2nc(Cl)nc(Cl)c21]

LCMS: m/Z 288.96 (M+H); $^1$H NMR ($CDCl_3$) δ 8.22 (s, 1H), 4.46 (t, J=7.5 MHz, 2H), 3.65 (t, J=6.6 MHz, 2H), 1.95 (m, 2H), 1.58 (m, 2H), 1.43 (m, 5H).

Compound 46: (methyl 16-(2-acetamido-6-chloro-7H-purin-7-yl) hexadecanoate)

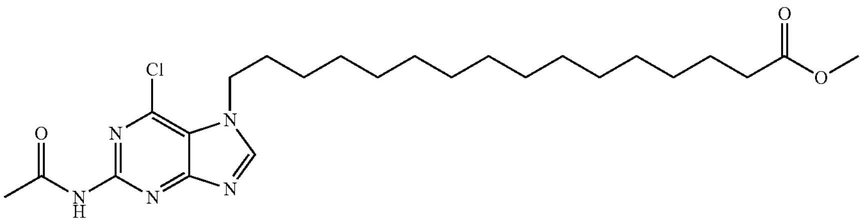 [SMILES: COC(=O)CCCCCCCCCCCCCCCn1cnc2nc(NC(C)=O)nc(Cl)c21]

LCMS: m/Z 502.41 (M+H); $^1$H NMR ($CDCl_3$) δ 8.11 (s, 1H), 8.00 (bs, 1H), 4.39 (t, J=7.5 MHz, 2H), 3.66 (s, 311), 2.61 (s, 3H), 2.29 (t, J=6.9 MHz, 2H) 1.90 (m, 2H), 1.60 (m, 3H), 1.24 (m, 24H).

Compound 47: (methyl 16-(2-acetamido-6-chloro-9H-purin-9-yl)hexadecanoate)

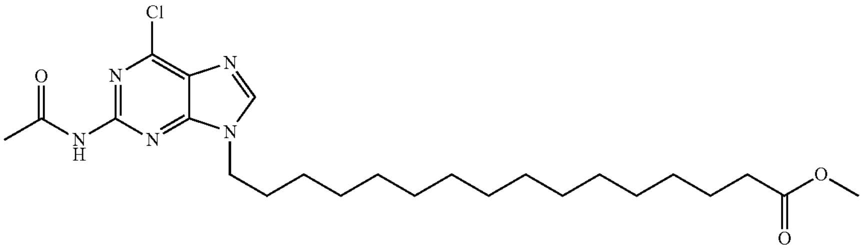 [SMILES: COC(=O)CCCCCCCCCCCCCCCn1cnc2c(Cl)nc(NC(C)=O)nc21]

LCMS: m/Z 502.41 (M+H). $^1$H NMR ($CDCl_3$) δ 8.03 (bs, 111), 7.99 (s, 1H) 4.19 (t, J=7.2 MHz, 2H), 3.66 (s, 311), 2.57 (s, 3H), 2.29 (t, J=7.5, 2H), 1.90 (m, 2H), 1.61 (m, 3H), 1.26 (m, 24H).

Compound 48: 2-(2-(2-(2-(2,6-dichloro-7H-purin-7-yl)ethoxy)ethoxy)ethoxy)ethan-1-ol)

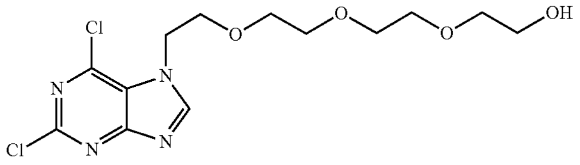 [SMILES: OCCOCCOCCOCCn1cnc2nc(Cl)nc(Cl)c21]

LCMS: m/Z 363.01(M−H); $^1$H NMR ($CDCl_3$) δ 8.44 (s, 1H), 4.66 (t, J=4.8, 2H), 3.88 (t, J=5.1, 2H), 3.75 (t, J=5.4, 211), 3.60 (m, 1011).

Compound 49: 2,6-dichloro-7-isopropyl-7H-purine

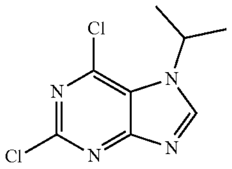

LCMS: m/z 231.95 (M+H); $^1$H NMR (DMSO) δ 9.05 (s, 1H), 5.13 (m, 1H) 1.56 (d, 6H).

Compound 50: (methyl 16-(2,4-dichloro-7H-pyrrolo [2,3-d]pyrimidin-7-yl)hexadecanoate)

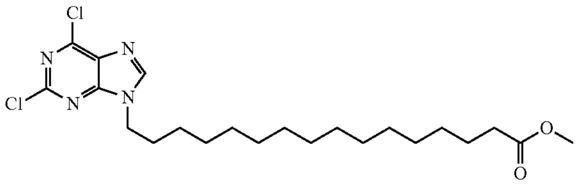 [SMILES: COC(=O)CCCCCCCCCCCCCCCn1cnc2c(Cl)nc(Cl)nc21]

$^1$H NMR ($CDCl_3$) δ 7.22 (d, J=3.6 MHz, 1H), 6.61 (d, J=3.3 MHz, 2H), 4.23 (t, J=7.5 MHz, 2H), 3.67 (s, 3H), 2.31 (t, J=7.5H, 2H), 1.82 (m, 2H), 1.62 (m, 2H), 1.25 (m, 22H).

Compound 51: 2-(2-(2-(2-(2,6-dichloro-9H-purin-9-yl)ethoxy)ethoxy)ethoxy)ethan-1-ol

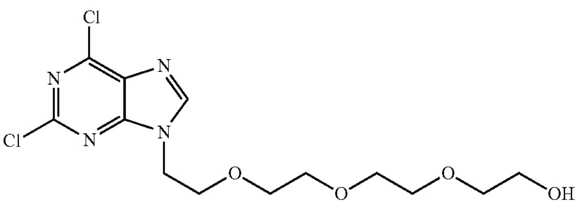 [SMILES: OCCOCCOCCOCCn1cnc2c(Cl)nc(Cl)nc21]

LCMS: m/z 365.1(M+H).

Compound 52: methyl 16-(2,6-dichloro-8-oxo-8,9-dihydro-7H-purin-7-yl)hexadecanoate

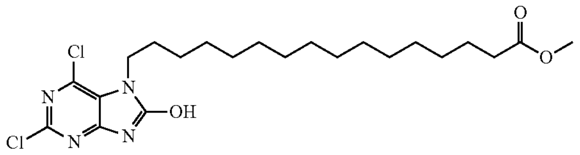 [SMILES: COC(=O)CCCCCCCCCCCCCCCn1c(O)nc2nc(Cl)nc(Cl)c21]

LCMS: m/z 471.20 (M+H); $^1$H NMR (CDCl3) δ 4.05 (t, 2H), 3.79 (s, 311), 2.42 (t, 2H), 1.91 (m, 2H), 1.36 (m, 24H).

Compound 53: methyl 16-(2,6-dichloro-8-oxo-7,8-dihydro-9H-purin-9-yl)hexadecanoate

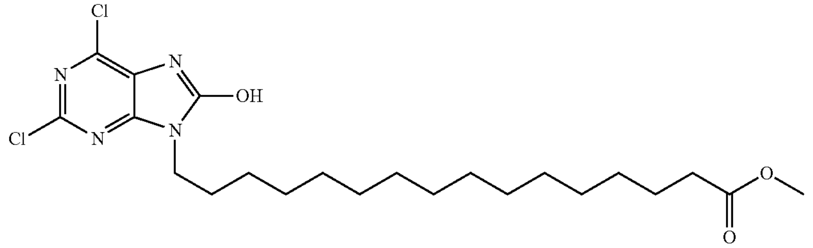 [SMILES: COC(=O)CCCCCCCCCCCCCCCn1c(O)nc2c(Cl)nc(Cl)nc21]

LCMS: m/z 471.26 (M+H); $^1$H NMR (CDCl3) δ 4.20 (t, 1H), 4.05 (t, 1H), 3.78 (s, 3H), 2.43 (t, 2H), 1.87 (m, 2H), 1.74 (m, 2H), 1.35 (m, 22H).

Compound 54: (E)-1,4-bis(2,6-dichloro-7H-purin-7-yl)but-2-ene

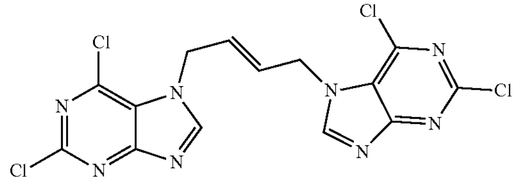 [SMILES: Clc1nc(Cl)c2c(ncn2C/C=C/Cn2cnc3nc(Cl)nc(Cl)c32)n1]

LCMS: m/z 428.87 (M+H); $^1$H NMR (DMSO) δ 8.81 (s, 2H), 5.77 (s, 211), 5.07 (s, 4H).

Compound 55: 1,4-bis(2,6-dichloro-7H-purin-7-yl)butane

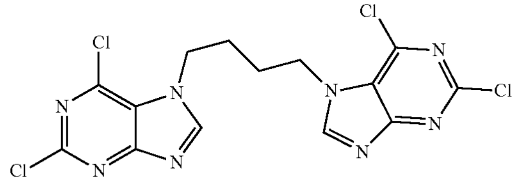 [SMILES: Clc1nc(Cl)c2c(ncn2CCCCn2cnc3nc(Cl)nc(Cl)c32)n1]

LCMS: m/z 430.91 (M+H); $^1$H NMR δ 8.84 (s, 2H), 4.45 (s, 4H), 1.84 (s, 4H).

Compound 56: methyl 2-(2,6-dichloro-7H-purin-7-yl)-2-methylpropanoate

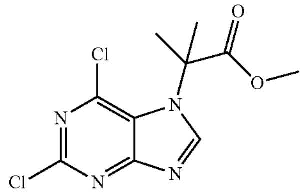 [SMILES: COC(=O)C(C)(C)n1cnc2nc(Cl)nc(Cl)c21]

LCMS: m/z 289.12 (M+H); $^1$H NMR δ 9.07 (s, 1H), 3.71 (s, 3H), 1.96 (s, 6H).

Compound 57: dimethyl 2,5-bis(2,6-dichloro-7H-purin-7-yl)hexanedioate

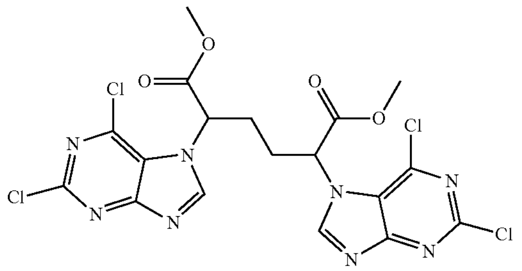 [SMILES: COC(=O)C(CCC(C(=O)OC)n1cnc2nc(Cl)nc(Cl)c21)n1cnc2nc(Cl)nc(Cl)c21]

LCMS: m/Z 548.9 (M+H); $^1$H-NMR ($CDCl_3$) δ 8.88 (s, 2H), 5.59 (bs,2H), 3.48 (bs, 6H), 2.13 (m, 1H), 1.75 (m, 1H), 1.53 (m, 1H), 1.32 (m, 1H).

Compound 58: (Z)-1,4-bis(2,6-dichloro-7H-purin-7-yl)but-2-ene

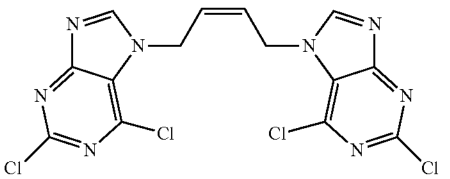 [SMILES: Clc1nc(Cl)c2c(ncn2C/C=C\Cn2cnc3nc(Cl)nc(Cl)c32)n1]

LCMS: m/z 428.26 (M+H); $^1$H NMR (DMSO) δ 8.03 (s, 2H), 6.55 (m, 2H), 4.164 (t, 4H).

Compound 59: 1,12-bis(2,6-dichloro-8-methyl-7H-purin-7-yl)dodecane

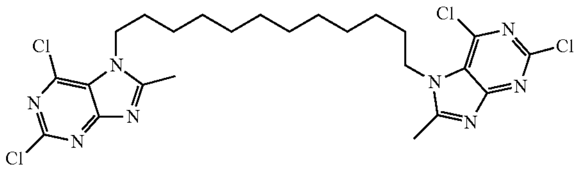 [SMILES: Cc1nc2nc(Cl)nc(Cl)c2n1CCCCCCCCCCCCn1c(C)nc2nc(Cl)nc(Cl)c21]

LCMS: m/z 571.25 (M+H), 573.16 (M+3H).

Compound 60: methyl 5-(2,6-dichloro-8-methyl-7H-purin-7-yl)pentanoate

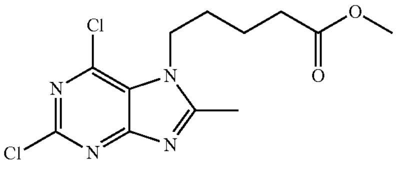 [SMILES: COC(=O)CCCCn1c(C)nc2nc(Cl)nc(Cl)c21]

LCMS: m/Z 318.1 (M+H); $^{1}$H-NMR ($CDCl_3$) δ 4.53 (m, 2H), 3.81 (s, 3H), 2.85 (s, 3H), 2.54 (m, 2H), 2.17 (m, 2H), 1.48 (m, 2H).

Compound 61: 1,10-bis(2,6-dichloro-8-methyl-7H-purin-7-yl)decane

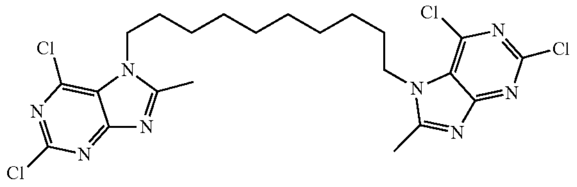 [SMILES: Cc1nc2nc(Cl)nc(Cl)c2n1CCCCCCCCCCn1c(C)nc2nc(Cl)nc(Cl)c21]

LCMS: m/z 543.07 (M+1), 545.15 (M+3H).

Compound 62: (6-(2,6-dichloro-8-methyl-7H-purin-7-yl)hexan-1-ol)

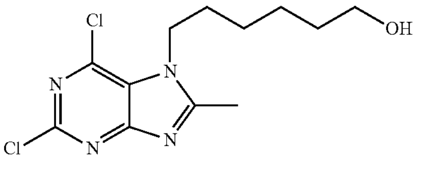 [SMILES: Cc1nc2nc(Cl)nc(Cl)c2n1CCCCCCO]

LCMS: m/Z 301.04 (M−H).

Compound 63: 1,8-bis(2,6-dichloro-8-methyl-7H-purin-7-yl)octane

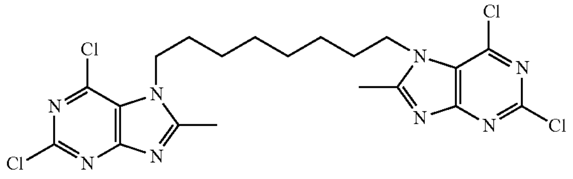 [SMILES: Cc1nc2nc(Cl)nc(Cl)c2n1CCCCCCCCn1c(C)nc2nc(Cl)nc(Cl)c21]

LCMS: m/z 515.08 (M+H), 517.22 (M+3H).

Compound 64: 1,4-bis(2,6-dichloro-8-methyl-7H-purin-7-yl)butane

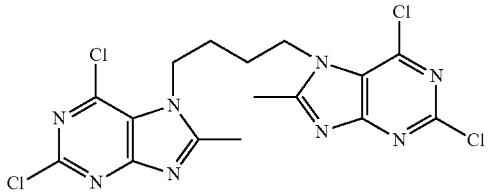 [SMILES: Cc1nc2nc(Cl)nc(Cl)c2n1CCCCn1c(C)nc2nc(Cl)nc(Cl)c21]

LCMS: m/z 458.84 (M+H), 460.98 (M+3H).

Compound 65: 2,6-dichloro-7-(6-chlorohexyl)-8-methyl-7H-purine

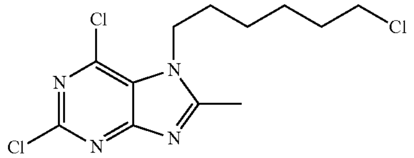 [SMILES: Cc1nc2nc(Cl)nc(Cl)c2n1CCCCCCCl]

LCMS: m/z 319.00 (M−H).

Compound 66: methyl 2-(2,6-dichloro-8-methyl-7H-purin-7-yl)acetate

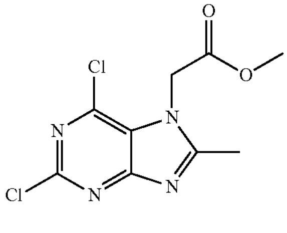 [SMILES: COC(=O)Cn1c(C)nc2nc(Cl)nc(Cl)c21]

LCMS: m/z 275.00 (M+H); $^{1}$H-NMR ($CD_3CN$) δ 5.38 (s, 2H), 3.96 (s, 3H), 2.79 (s, 3H).

Compound 67: 2,6-dichloro-7-(4-methoxybenzyl)-8-methyl-7H-purine

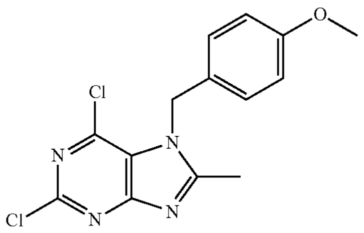 [SMILES: COc1ccc(Cn2c(C)nc3nc(Cl)nc(Cl)c32)cc1]

LCMS: m/z 323.1 (M+H).

Compound 68: 1-(4-((2,6-dichloro-7H-purin-7-yl)methyl)piperidin-1-yl)ethan-1-one

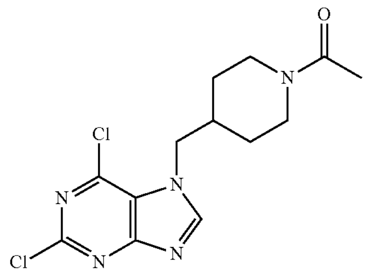 [SMILES: CC(=O)N1CCC(Cn2cnc3nc(Cl)nc(Cl)c32)CC1]

LCMS: m/Z 329.1 (M+H); $^1$H-NMR ($CDCl_3$) δ 8.65 (bs, 1H), 4.14 (m, 2H), 3.61 (m, 1H), 2.73 (m, 1H), 2.29 (s, 3H), 2.26 (m, 1H), 1.88 (bs, 1H), 1.77 (m, 1H), 0.98 (m, 2H), 0.87 (m, 2H).

Compound 69: methyl 16-(2-chloro-8-methyl-6-(methylsulfonyl)-7H-purin-7-yl)hexadecanoate

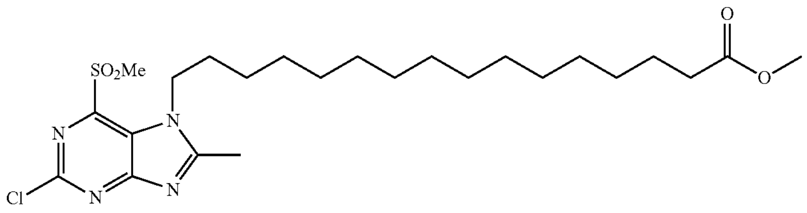 [SMILES: COC(=O)CCCCCCCCCCCCCCCn1c(C)nc2nc(Cl)nc(S(C)(=O)=O)c21]

LCMS: m/Z 516.1 (M+H).

Compound 70: methyl 16-(2,6-dichloro-8-(cyclopropylethynyl)-7H-purin-7-yl)hexadecanoate

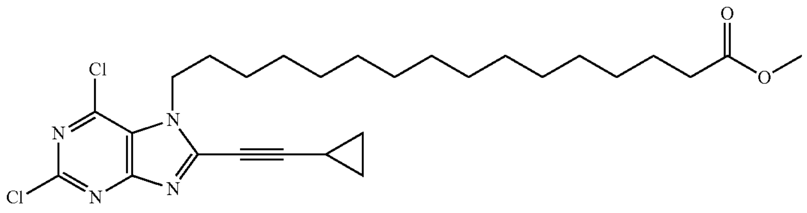 [SMILES: COC(=O)CCCCCCCCCCCCCCCn1c(C#CC2CC2)nc2nc(Cl)nc(Cl)c21]

LCMS: m/Z 521.3 (M+H); $^1$H-NMR ($CDCl_3$) δ 4.22 (m, 2H), 3.9 (m, 1H), 3.66 (s, 3H), 2.32 (m, 2H), 1.56 (bs, 6H), 1.25 (bs, 22H), 0.89 (m, 2H).

Compound 71: methyl 16-(2,6-dichloro-8-phenyl-7H-purin-7-yl)hexadecanoate

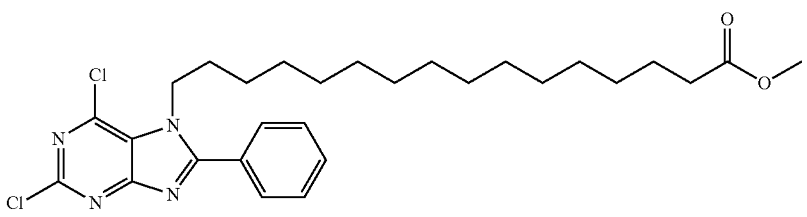 [SMILES: COC(=O)CCCCCCCCCCCCCCCn1c(-c2ccccc2)nc2nc(Cl)nc(Cl)c21]

LCMS: m/Z 533.6 (M+H); $^1$H-NMR ($CDCl_3$) δ 7.74 (m, 2H), 7.59 (m, 3H), 4.48 (m, 2H), 3.67 (s, 3H), 2.32 (m, 2H), 1.83 (m, 2H), 1.58 (bs, 6H), 1.25 (bs, 18H).
Compound 72: 16-(2,6-dichloro-8-methyl-7H-purin-7-yl)hexadecanoic acid
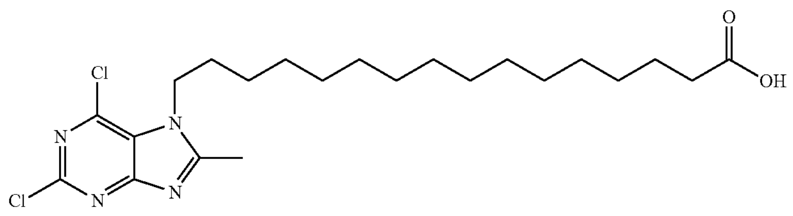 [SMILES: Cc1nc2nc(Cl)nc(Cl)c2n1CCCCCCCCCCCCCCCC(=O)O]
LCMS: m/Z 457.1 (M+H);
Compound 73: methyl 16-(2-chloro-8-methyl-6-(methylthio)-7H-purin-7-yl)hexadecanoate
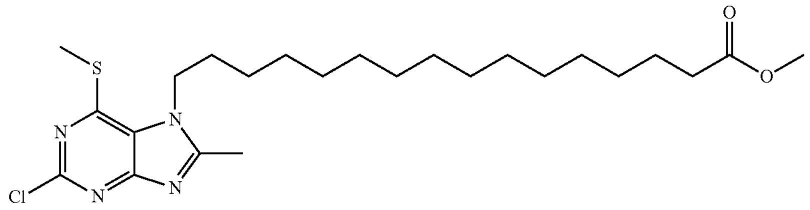 [SMILES: COC(=O)CCCCCCCCCCCCCCCn1c(C)nc2nc(Cl)nc(SC)c21]
LCMS: m/Z 483.6 (M+H);
Method 3:
Compound 74: methyl 16-(2-chloro-6-(isopropylsulfonyl)-8-methyl-7H-purin-7-yl)hexadecanoate
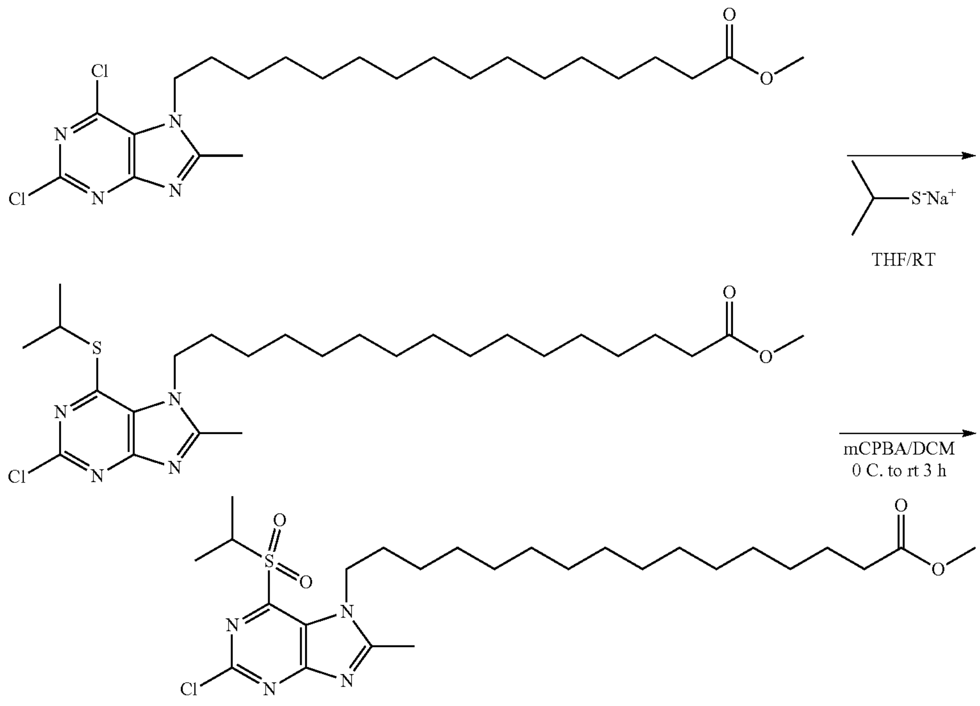

Step 1:Di-Cl compound (100 mg) was taken in THF and sodium 2-propanethiolate (1.3 eq) was added and stirred at room temperature for 3h. saturated $NH_4Cl$ (1 mL) was added. Ethyl acetate (5 mL) was added and extracted two times. After layer separation and drying, solvent was evaporated. The crude was taken in DMSO and purified by combi flash reverse phase C18 silica gel column chromatography using 0-100% $CH_3CN$—$H_2O$ as gradient to provide product as solid. The other fractions were isolated and identified two side products as 2,6-disubstituted thioether and carboxylic acid formed during the reaction.

Step 2: The C-6 thiol ether from above (30 mg) was taken in $CH_2Cl_2$ (2-3 mL) and cooled to 0° C. After 10 minutes mCPBA (75% assay, ~3 equivalent) was added at 0° C. and stirring continued for 3 h. The reaction mixture was further diluted with more $CH_2Cl_2$ (5 mL) and washed with saturated aqueous $NaHCO_3$ solution (2 mL×2), and then water (4 mL). The organic layer was dried ($Na_2SO_4$), filtered and concentrated. The crude was taken in DMSO and purified by combi flash reverse phase C18 silica gel column chromatography using 0-100% $CH_3CN$—$H_2O$ as gradient to provide product 74 as white solid. LCMS: m/Z 543.5 (M+H); $^1$H-NMR ($CDCl_3$) 4.57 (m, 2H), 4.30 (m, 2H), 3.66 (s, 3H), 2.77 (s, 3H), 2.30 (dd, J=7.5 Hz, 7.8 Hz, 2H), 1.84 (m, 2H), 1.60 (m, 211), 1.52 (d, J=6.9 Hz, 6H), 1.38-1.25 (broad m, 22H).

Compound 76: 16-(2,6-dichloro-8-methyl-9H-purin-9-yl)hexadecan-1-ol

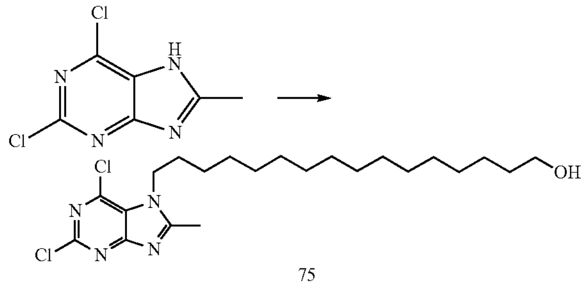

75

-continued

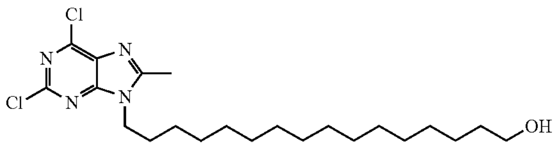

76

2,6-dichloro-8-methyl-purine (200 mg, 0.98 mmol), 16-bromohexadecanol (315 mg, 0.98 mmol), potassium carbonate (203 mg, 1.47 mmol), and sodium iodide (15 mg, 0.10 mmol) were all combined in a round-bottom flask under Argon. Anhydrous dimethylformamide (DMF) was added to this mixture and this was stirred at 80° C. for three hours. DMF was concentrated in vacuo and the crude was partitioned in ethyl acetate and water. Insoluble material was present and this was filtered off before separating the layers with a separatory funnel. The organic layer was dried over sodium sulfate, filtered, and concentrated. The crude mixture of isomers was then purified by flash chromatography in hexanes and ethyl acetate. About 32 mg (7%) of compound 75 (off-white solid) and 120 mg (27%) of compound 76 (white solid) were isolated.

Compound 75: LCMS: m/z 441.29 (M−H); m/z 443.34 (M+H)

Compound 76: LCMS: m/z 441.29 (M−H); m/z 443.31 (M+H); $^1$H NMR ($CDCl_3$) δ 4.19 (t, J=78 MHz, 2H), 3.65 (m, 2H), 3.69 (s, 3H), 1.82 (m, 2H), 1.60 (m, 2H), 1.30 (m, 26H)

Compound 77: 2,6-dichloro-7-hexadecyl-8-methyl-7H-purine

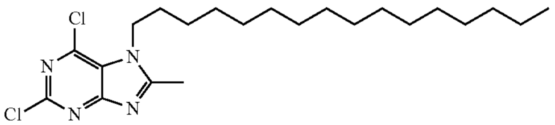 [SMILES: CCCCCCCCCCCCCCCCn1c(C)nc2nc(Cl)nc(Cl)c21]

Method 2B was utilized to provide the crude which was purified by combi flash silica gel column chromatography using 0-100% Ethyl acetate-Hexane as gradient to provide product 77 as white solid. LCMS: m/Z 427.2 (M+H).

Compound 78: ethyl 16-(2,6-dichloro-8-methyl-7H-purin-7-yl)hexadecanoate

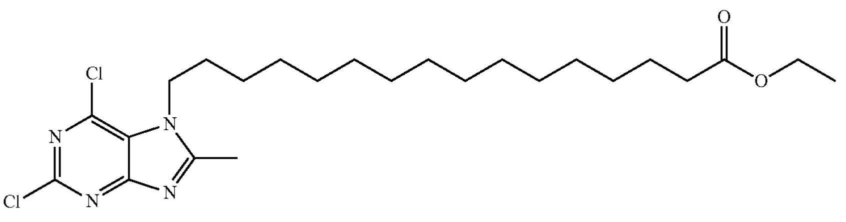 [SMILES: CCOC(=O)CCCCCCCCCCCCCCCn1c(C)nc2nc(Cl)nc(Cl)c21]

Method 4: To a solution of compound 29 (33 mg, 0.07 mmol) in ROH (0.3 mL) was added $H_2SO_{4(conc.)}$(1-3dps). The reaction mixture was stirred at 70° C. for 12h. Sat $NaHCO_3$ (0.1 mL) was added, stirred for 5 min. The crude was taken in DMSO and purified by combi flash reverse phase C18 silica gel column chromatography using 0-100% $CH_3CN$—$H_2O$ as gradient to provide compound 85 as a white solid.0.023 grams (68%). LCMS: m/Z 485.45 (M+H); $^1$H-NMR ($CDCl_3$) δ 4.35 (t, 2H), 4.02 (m, 2H), 3.32 (s, 3H), 2.25 (t, 2H), 1.74 (m, 2H), 1.49 (m, 2H) 1.21 (m, 22H) 1.15 (t, 3H).

Compound 79: isopropyl 16-(2,6-dichloro-8-methyl-7H-purin-7-yl)hexadecanoate

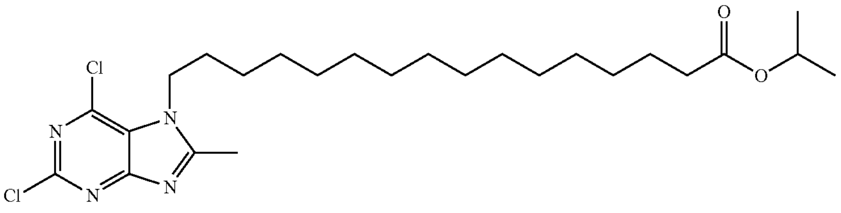 [SMILES: Cc1nc2nc(Cl)nc(Cl)c2n1CCCCCCCCCCCCCCCC(=O)OC(C)C]

Method 4 was utilized with corresponding ROH to provide product 79. Yield: 29 mg (85%). LCMS: m/Z 499.57 (M+H); $^1$H-NMR ($CDCl_3$) δ 4.99 (m, 1H), 4.35 (t, 2H), 2.70 (s, 3H), 2.25 (t, 2H), 1.81 (m, 2H), 1.59 (m, 2H), 1.25 (m, 22H), 1.21 (d, 6H).

Compound 80: methyl 5-(2,6-dichloro-8,9-dihydro-7H-purin-7-yl)-5-oxopentanoate

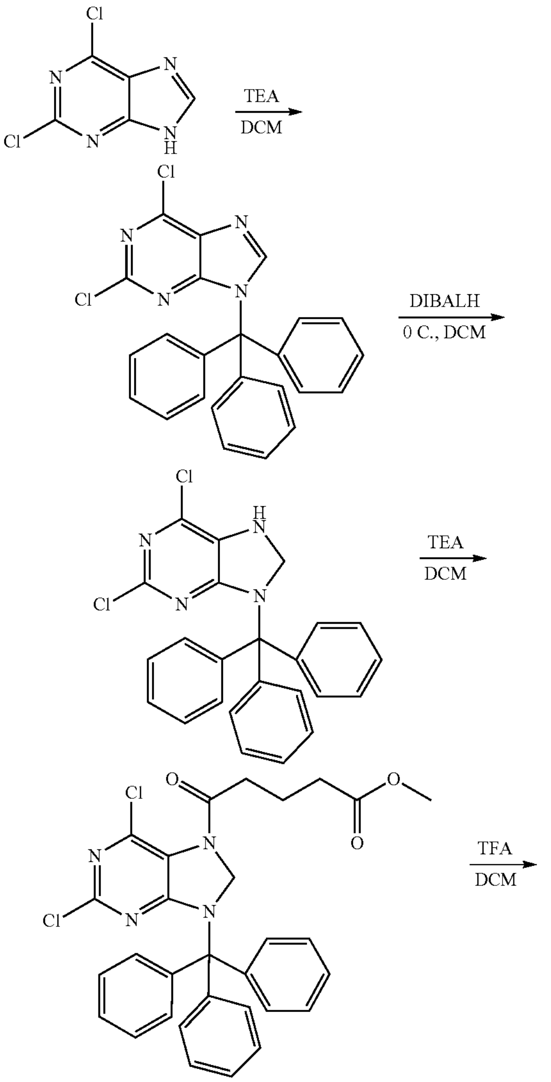

-continued

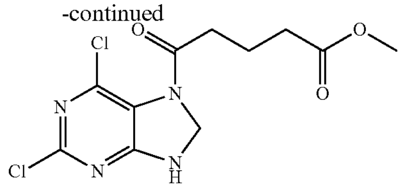

80

Step 1: 2,6-dichloropurine (3.0 g, 15.87 mmol) and trityl chloride (4.9 g, 17.4 mmol)) were stirred in 40 mL of dry dichloromethane (DCM). Triethylamine (2.4 g, 24.0 mmol) was added and the mixture became homogeneous. The reaction was stirred at ambient temperature for two hours. Silica gel was added and the reaction concentrated to dryness. The compound was purified by flash chromatography in hexanes and ethyl acetate to give 2.4 g (35%) of the product as a white solid. $^1$H NMR ($CDCl_3$) δ 8.15 (s, 2H), 7.34 (m, 9H), 7.16 (m, 6H).

Step 2: Step 1 product (2.2 g, 5.10 mmol) was dissolved in 20 mL anhydrous DCM and cooled in an ice bath. Diisobutyl aluminum hydride (DIBALH) (5 eq) was added slowly and reaction was stirred for 2 hours on ice. Once reaction was complete, quenched with saturated sodium sulfate and let warm to ambient temperature. The organic layer was extracted and passed through celite before being dried over sodium sulfate, filtered, and concentrated. LCMS: m/z 431.16 (M−H); $^1$H NMR ($CDCl_3$) δ 7.33 (m, 15H), 5.14 (s, 2H).

Step 3: Step 2 product (42 mg, 0.097 mmol) was dissolved in anhydrous DCM and to this was added triethylamine (30 mg, 0.146 mmol) and methyl-5-chloro-5-oxovalerate (19 mg, 0.117 mmol). The reaction was stirred for 12 h and appeared to go to completion by TLC (2:1 hexanes:ethyl acetate). The compound was purified by flash chromatography in hexanes and ethyl acetate to give 39 mg (72%) of product. $^1$H NMR ($CDCl_3$) δ 7.30 (m, 15H), 5.35 (s, 2H), 3.66 (s, 3H), 2.58 (m, 2H), 2.40 (m, 2H), 2.05 (m, 2H).

Step 4: Step 3 product (20 mg, 0.036 mmol) was dissolved in dichloromethane (DCM) and cooled in an ice bath. Trifluoroacetic acid (TFA) (0.1 mL) was added slowly and the solution allowed to warm to ambient temperature. LCMS showed the formation of the product and, once complete, the reaction was cooled in ice and quenched with triethylamine (0.1 mL). The product was extracted in DCM and washed with water and 5% sodium bicarbonate. The organic layer was then dried over sodium sulfate, filtered, and concentrated with silica gel. The crude was purified by flash chromatography in hexanes and ethyl acetate to give 7 mg (61%) of the compound as a white solid. LCMS: m/z 317.11 (M−H), m/z 319.00 (M+H); $^1$H-NMR ($CDCl_3$) δ 7.00 (s, 111), 5.48 (s, 2H), 3.67 (s, 3H), 2.59 (t, J=7.8 MHz, 2H), 2.44 (t, J=7.2 MHz, 211), 2.05 (m, 2H).

Compound 81: tert-butyl 16-(2,6-dichloro-8-methyl-7H-purin-7-yl)hexadecanoate

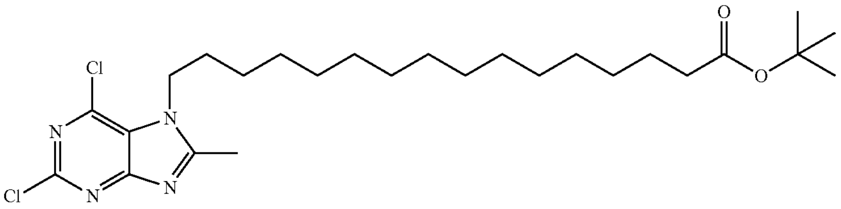 [SMILES: Cc1nc2nc(Cl)nc(Cl)c2n1CCCCCCCCCCCCCCCC(=O)OC(C)(C)C]

Method 4 was utilized with corresponding ROH to provide product 81. Yield: 5 mg (15%). LCMS: m/Z 513.44 (M+H); $^{1}$H-NMR ($CDCl_3$) δ 4.49 (m, 2H), 2.87 (s, 3H), 2.48 (m, 2H), 1.97 (m, 2H), 1.75 (m, 24H), 1.41 (s, 9H).

Compound 82: 2,6-dichloro-7,8-dimethyl-7H-purine

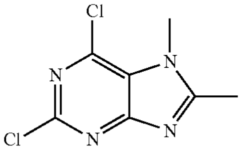

Method 1 was utilized to provide the crude which was purified by combi flash silica gel column chromatography using 0-100% Ethyl acetate-Hexane as gradient to provide product 82 as white solid. LCMS: m/Z 217.1 (M+H).

Compound 83: 2,6-dichloro-8,9-dimethyl-9H-purine

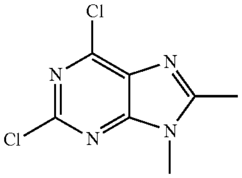

Method 1 was utilized to provide the crude which was purified by combi flash silica gel column chromatography using 0-100% Ethyl acetate-Hexane as gradient to provide product 83 as white solid. LCMS: m/Z 217.1 (M+H).

Compound 84: 2-hydroxyethyl 16-(2,6-dichloro-8-methyl-7H-purin-7-yl)hexadecanoate

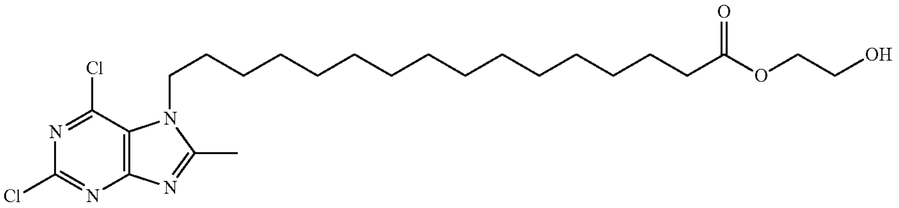

Method 4: To a solution of compound 74 (15 mg, 0.03 mmol) in ROH (0.3 mL) was added conc H2SO4(1dp). The reaction mixture was stirred at 70° C. for 12h. Sat $NaHCO_3$ (0.1 mL) was added, stirred for 5 min. The crude was taken in DMSO and purified by combi flash reverse phase C18 silica gel column chromatography using 0-100% $CH_3CN$—$H_2O$ as gradient to provide compound 85 as a white solid. LCMS: m/Z 501.2(M+H), 523.4(M+Na); $^{1}$H-NMR ($CDCl_3$) 4.42 (m, 211), 4.22 (m, 2H), 3.80 (m, 2H), 2.70 (s, 3H), 1.80 (m, 2H), 1.60 (m, 4H), 1.40-1.25 (broad m, 23H).

Compound 85: 2,3-dihydroxypropyl 16-(2,6-dichloro-8-methyl-7H-purin-7-yl)hexadecanoate

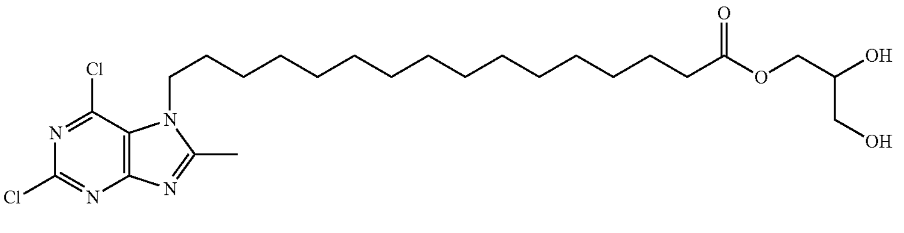

Method 4 was utilized with corresponding ROH to provide product 85. LCMS: m/Z 531.1 (M+H).

Compound 86: 7-(16-(2H-tetrazol-2-yl)hexadecyl)-2,6-dichloro-8-methyl-7H-purine

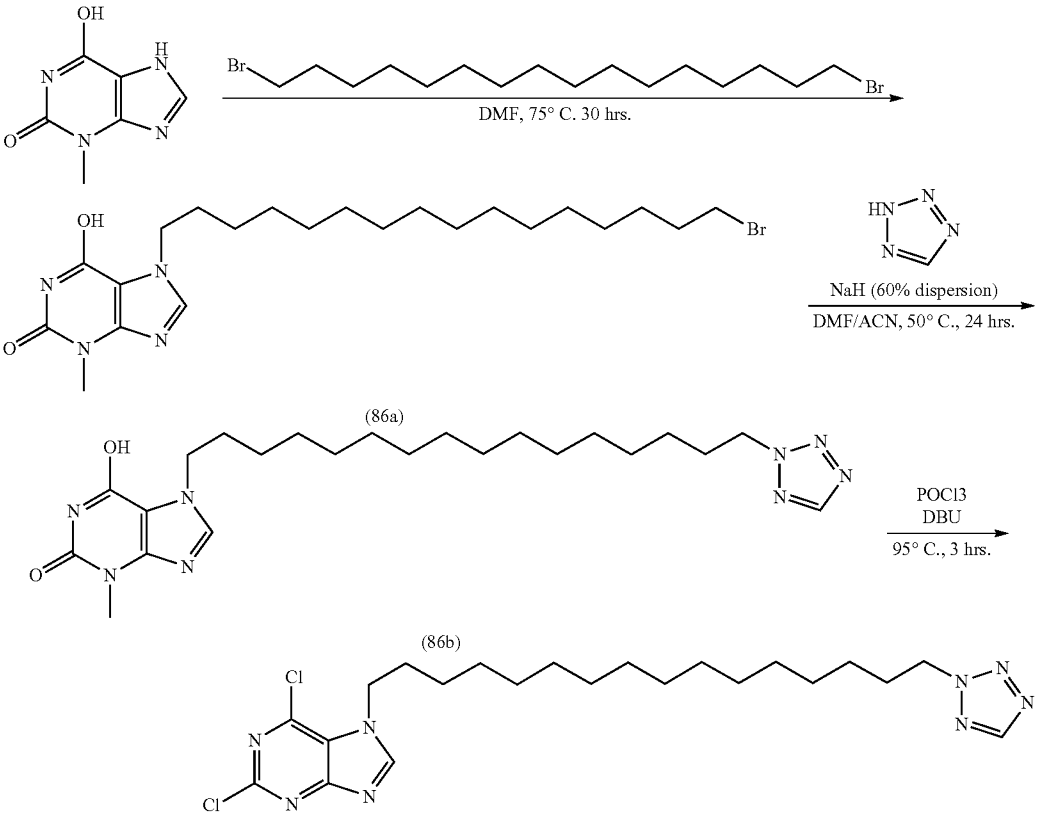

(86)

Step 1: To a solution of 1,16-dibromohexadecane (528 mg, 1.4 mmol) was added 150 mg of the potassium salt of 6-hydroxy-3-methyl-3,7-dihydro-2H-purin-2-one. Reaction was stirred at 75° C. for 30 hours. When complete a solid had precipitated from the reaction mixture. Solid was separated out and washed with MeOH (2×10 mL) and 10% $NaHCO_{3(aq.)}$(3×10 mL). Solid was then dried on high vacuum to obtain 511 mg. This was taken to next step without further purification. LCMS: m/Z 469.62 (M+H).

Step 2: 71 mgs. (3.0 mmol, 5.5 eq) was placed in sealed vial which was then purged with $Ar_{(g)}$. To this was added 3.25 mL of 3 wt. % tetrazole solution in $CH_3CN$ (0.11 mmol, 2.1 eq) and stirred at room temperature for 5 minutes and purged with $Ar_{(g)}$ again. To this vial was then added 250 mg of compound 86a in DMF. Reaction mixture became a cloudy white color and was allowed to stir at 50° C. for 12 hours. When complete, reaction was cooled to room temperature and quenched with methanol. Water was added and the mixture was centrifuged, and mother liquor was decanted and wet solid frozen and lyophilized. Solid was re-dissolved in DCM and to this was added 1.2 grams of silica gel. Solvents were removed and silica impregnated with crude compound was run through a flash column with a DCM: MeOH (0-5%) gradient to provide 27 mg (11%) of 7-(16-(2H-tetrazol-2-yl)hexadecyl)-6-hydroxy-3-methyl-3,7-dihydro-2H-purin-2-one (compound 86b) as a white powder. LCMS: m/Z 457.39 (M−H).

Step 3: Followed similar $POCl_3$ Procedure as shown in Method 2A. 4 mg (14%) of 7-(16-(2H-tetrazol-2-yl)hexadecyl)-2,6-dichloro-8-methyl-7H-purine (compound 86) as an off-white/yellow powder. LCMS: m/Z 495.35 (M+H) 493.64 (M−H); $^1$H-NMR ($CDCl_3$) δ 8.66 (s, 1H), 8.39 (s, 1H), 4.59 (m, 5H) 2.12 (m, 5H) 1.42 (m, 24H).

Compound 87: 16-(2,6-dichloro-8-methyl-7H-purin-7-yl)-1-(piperazin-1-yl)hexadecan-1-one

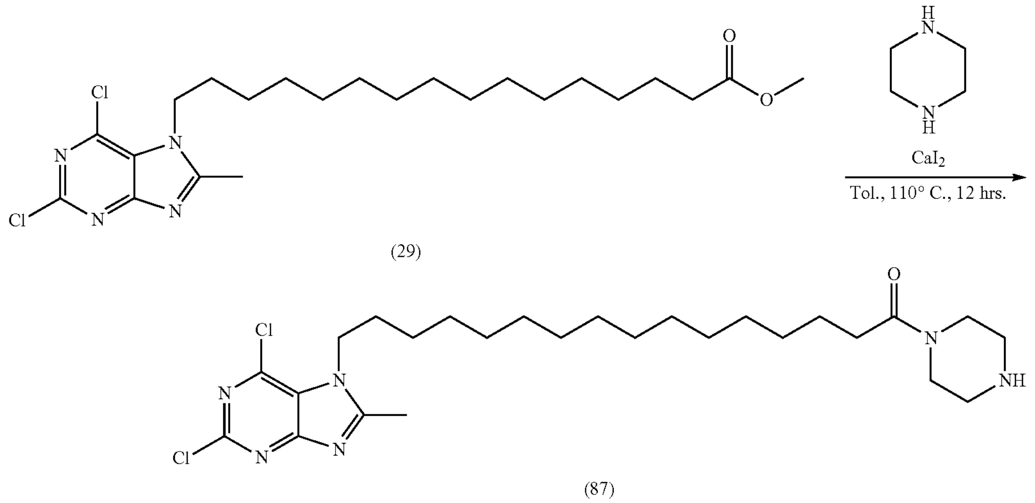

(29)

(87)

Compound 29 (33 mg, 0.070 mmol) and piperazine (19 mg, 0.22 mmol 3 eq) were dissolved in toluene. To this was added 12 mg (0.041 mmol). Reaction was heated to 110° C. with stirring for 12 h. After evaporation of toluene, the crude product was re-dissolved in ethyl acetate (EtOAc) and was washed with 0.5 mL sat. $NH_4Cl_{(aq.)}$. The crude product was re-dissolved in dimethyl sulfoxide (DMSO) and purified using a reverse phase column ($CH_3CN$: $H_2O$ 0-100%). Fractions were combined, frozen, and lyophilized to obtain 2 mg (5.4%) of 16-(2,6-dichloro-8-methyl-7H-purin-7-yl)-1-(piperazin-1-yl)hexadecan-1-one (compound 87).LCMS: m/Z 525.29 (M+H); $^1$H-NMR ($CDCl_3$) δ 4.35 (t, 2H), 3.81 (s, 3H), 3.52 (m, 4H), 3.23 (m, 4H), 2.78 (s, 2H), 2.44 (t, 2H), 1.61 (m, 2H), 1.24 (m, 22H).

Compound 88: 16-(2,6-dichloro-7H-purin-7-yl)hexadecyl dihydrogen phosphate

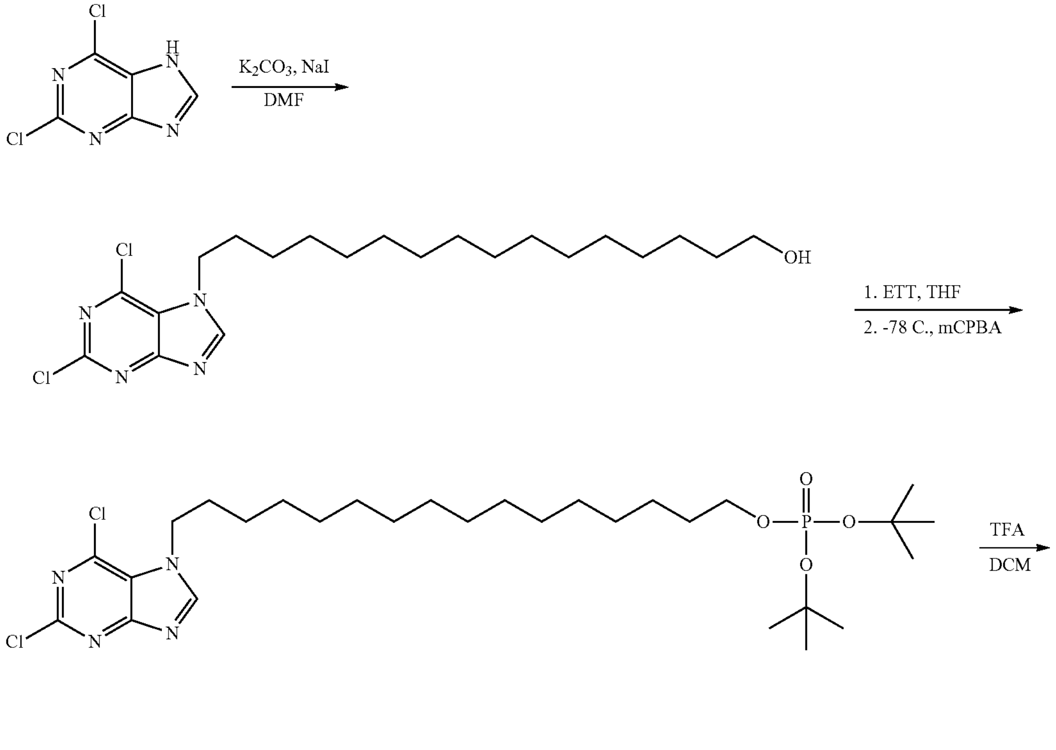

-continued

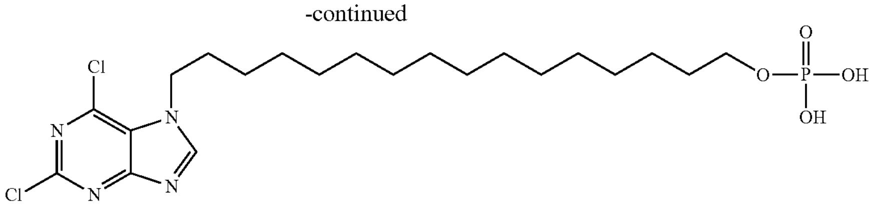

88

Step 1: Same procedure followed using method 1.

Step 2: Step 1 product (65 mg, 0.152 mmol) was dissolved in anhydrous tetrahydrofuran (THF). To this was added di-tertbutyl diethyl phosphoramidite (76 mg, 0.303 mmol) and 5-(ethylthio)-1H-tetrazole (99 mg, 0.76 mmol) at ambient temperature before the mixture was cooled to −78° C. Once cooled, 75% meta-Chloroperoxybenzoic acid (105 mg, 0.61 mmol) was added the reaction stirred at this temperature for 30 minutes before allowing to warm to ambient temperature. LCMS was used to monitor the reaction and, once complete, THF was removed in vacuo. The crude was purified by flash chromatography in hexanes and ethyl acetate but only 40 mg (42%) was isolated.

Step 3: Step 2 product (~40 mg) was dissolved in dichloromethane (DCM) and to this was added 1-2 drops of trifluoroacetic acid (TFA). This was stirred at ambient temperature overnight. LCMS showed the mass of the product. The crude product was subjected to flash column chromatography in dichloromethane and methanol. 2 mg (6%) of product 88 was isolated as white solid. LCMS: m/z 507.08 (M−H).

Compound 89: methyl 16-(2,6-dichloro-8-isopropyl-7H-purin-7-yl)hexadecanoate

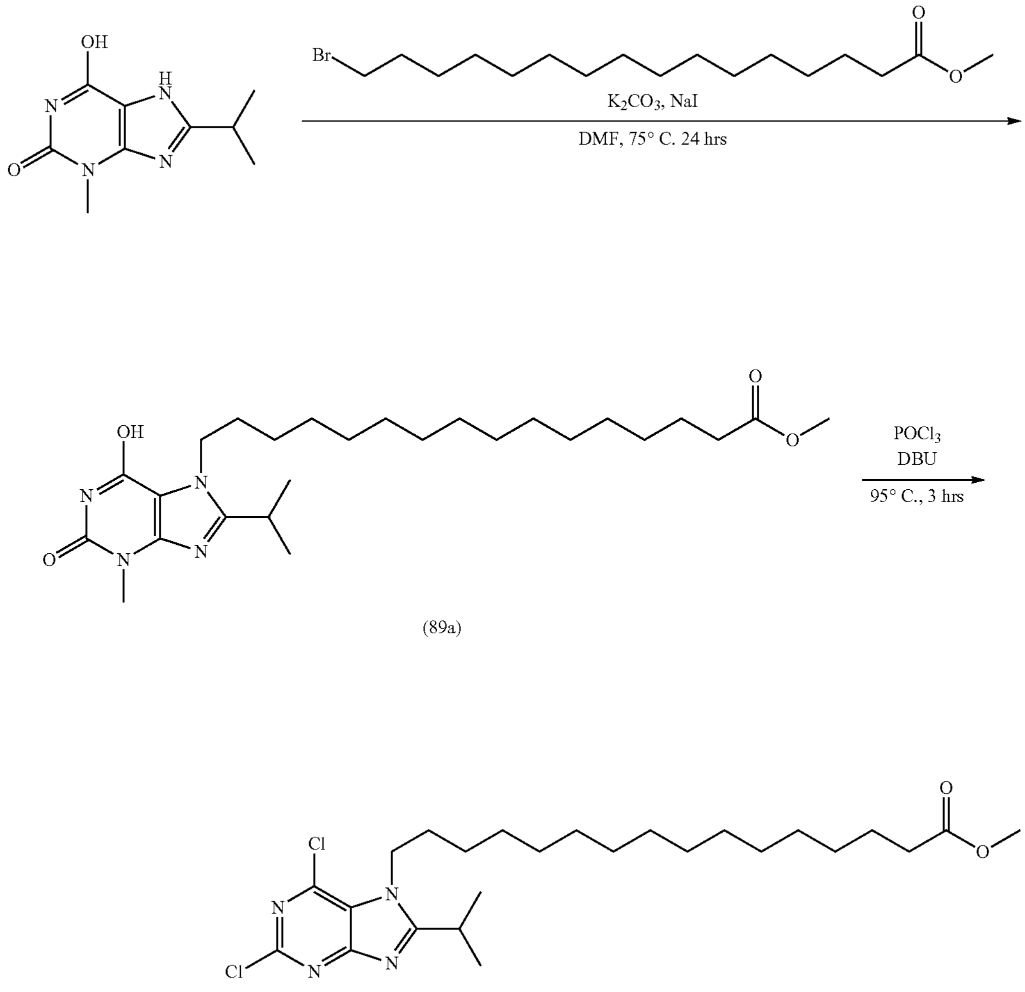

(89)

Step 1: Used similar method as described for method 2A. LCMS: m/Z 477.44 (M+H).

Step 2: Followed similar $POCl_3$ procedure as shown in Method 2A. 56 mg (40%) of methyl 16-(2,6-dichloro-8-isopropyl-7H-purin-7-yl)hexadecanoate (compound 89). LCMS: m/Z 499.19 (M+H); $^1$H-NMR ($CDCl_3$) δ 4.37 (t, 2H), 3.66 (s, 3H), 3.21 (m, 111), 2.30 (t, 2H), 1.82 (m, 2H), 1.61 (m, 2H), 1.48 (d, 6H), 1.27 (m, 22H).

Compound 90: 0-(2-cyanoethyl) 0-(16-(2,6-dichloro-7H-purin-7-yl)hexadecyl) O-hydrogen phosphorothioate IDC-99C3

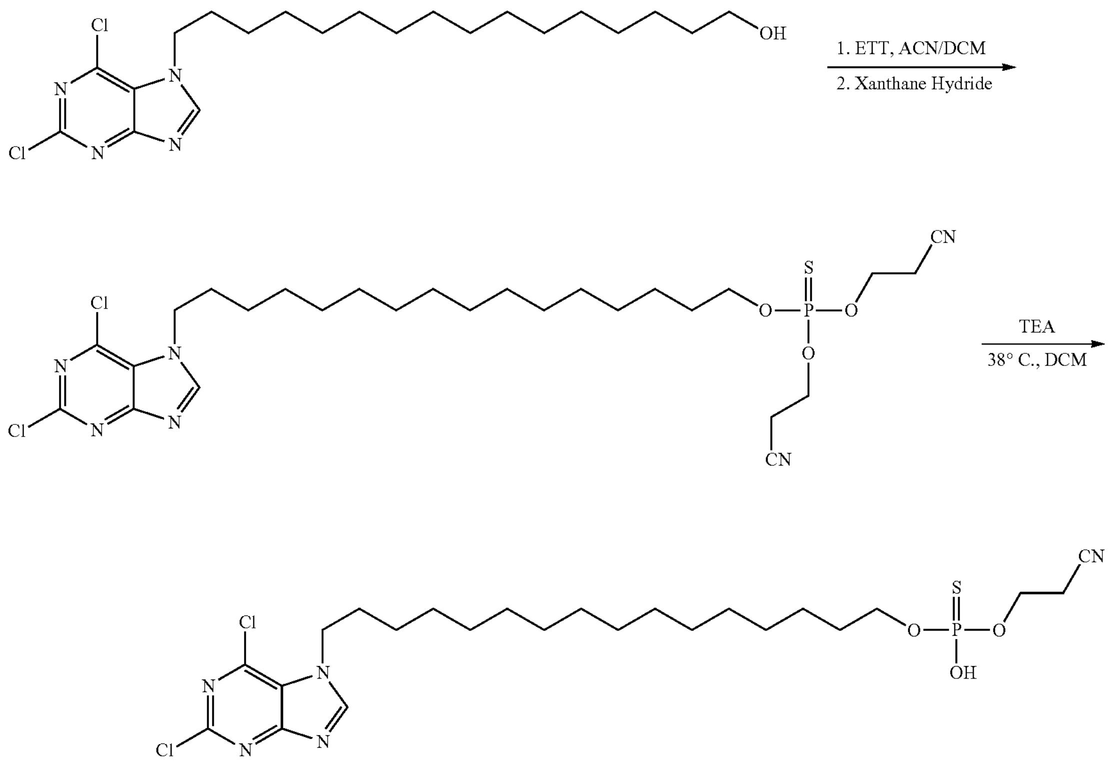

90

Step 1: Product from step 1 of compound 88 (28 mg, 0.065 mmol) and was dissolved in 6:1 anhydrous acetonitrile:anhydrous dichloromethane. To this was added bis(2-cyanethyl-N,N-diisopropyl phosphoramidite (27 mg, 0.098 mmol) and 5-(ethylthio)-1H-tetrazole (42 mg, 0.325 mmol). The reaction was stirred for 2.5 hours and LCMS showed no starting material remained. Xanthane Hydride was added, and the reaction stirred overnight. Solid was removed by centrifugation and then acetonitrile was removed in vacuo. The reaction mixture was partitioned in DCM and water. The organic layer was washed with 5% sodium bicarbonate, dried over sodium sulfate, filtered, and concentrated.

Step 2: Step 1 product was dissolved in DCM and to this was added triethylamine and heated to 38° over weekend. Washed with water, dried organic over sodium sulfate, filtered, and concentrated. The crude product was purified by HPLC using water/acetonitrile as gradient to get 22 mg of compound 90 as an oil. LCMS: m/z 576.30 (M−H).

Compound 91: Methyl 16-(2,6-dichloro-8-(chloromethyl)-7H-purin-7-yl)hexadecanoate

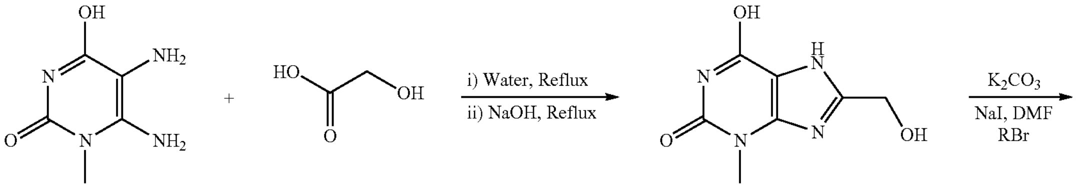

-continued

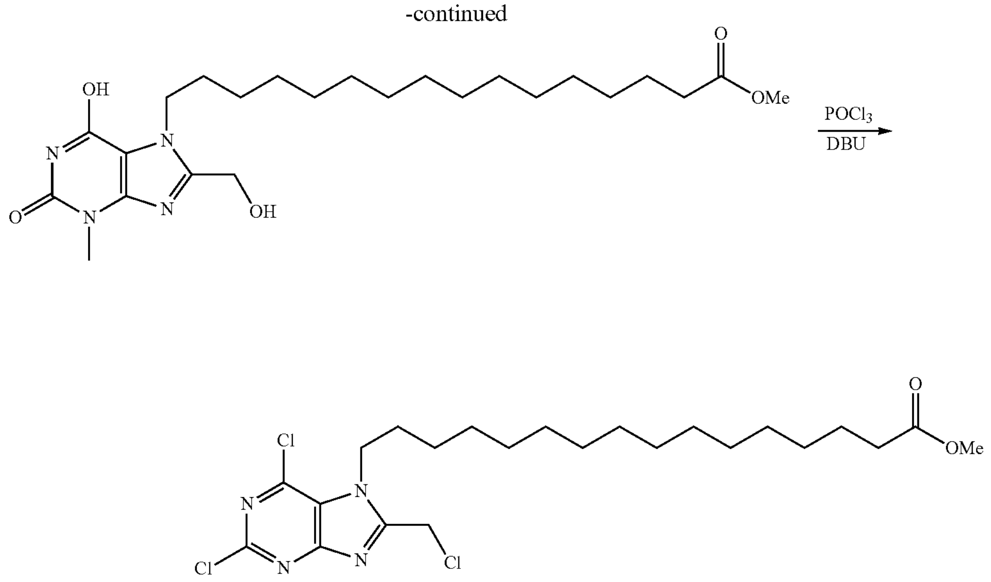

91

6-hydroy-8-(hydroxymethyl)-3-methyl-3,7-dihydro-2H-purin-2-one

To a solution of 5,6-Diamino-4-hydroxy-1-methylpyrimidin-2(1H)-one (5.0 g, 31.64 mmol) in water (75 mL) wad added glycolic acid was heated to reflux for 6 hours. After cooling to room temperature, NaOH in water (5.0 mL) was added, and the reaction mixture was heated at reflux for overnight. Reaction mixture was cooled to room temperature and then stirred at 0° C. for 15 minutes, the product was precipitated. The solid was collected by filtration, washed with ice-cold water (50 mL), followed by washing with diethyl ether (50 mL) and dried under high vacuum for overnight to get 5.03 g of pure product as light yellow solid. LCMS: m/Z 195.07 $(M-H)^+$. 1H-NMR (DMSO-D6): δ 4.39 (s, 2H), 3.51 (bs, 1H), 3.38 (bs, 1H), 3.34 (bs, 1H), 3.31 (s, 3H).

Methyl 16-(6-hydroxy-8-(hydroxymethyl)-3-methyl-2-oxo-2,3-dihydro-7H-purin-7-yl)hexadecanoate To a solution of 6-hydroy-8-(hydroxymethyl)-3-methyl-3,7-dihydro-2H-purin-2-one (100 mg, 0.5 mmol) in DMF (5.0 mL) was added $K_2CO_3$ (138 mg, 1 mmol), NaI (150 mg, 1 mmol) and 16-bromo methyl-hexadecanoate (197 mg, 0.55 mmol). Reaction mixture was stirred at 75° C. for 6 hours. Completion of the reaction was confirmed by LC-MS. DMF was evaporated under reduced pressure to dryness. Reaction mixture was suspended in water (20.0 mL) and product was extracted with 20% IPA in DCM (2×20 mL). Combined organic layers were dried over $Na_2SO_4$ and concentrated under reduced pressure to give crude product. Crude product was purified on combi-flash silica gel column chromatography using 0-10 MeOH in DCM to give 25 mg of pure product. LCMS: m/Z 487.4 $(M+Na)^+$, 463.44 $(M-H)^+$. $^1$H-NMR (DMSO-D6) δ 4.52 (s, 2H), 4.18 (m, 2H), 3.52 (s, 3H), 3.29 (s, 3H), 3.12 (bs, 1H), 2.91 (bs, 1H), 2.22 (t, J=7.5, 2H), 1.44 (m, 2H), 1.16 (m, 24H).

Step 3: Followed similar $POCl_3$ procedure as shown in Method 2A. Crude product was purified on combiflash silica get column chromatography using 0-5% MeOH in DCM to give 5 mg of pure product 91. LCMS: m/Z 505.24 $(M+H)^+$.

Compound 92: Methyl 16-(2,6-dichloro-8-(methoxymethyl)-7H-purin-7-yl)hexadecanoate

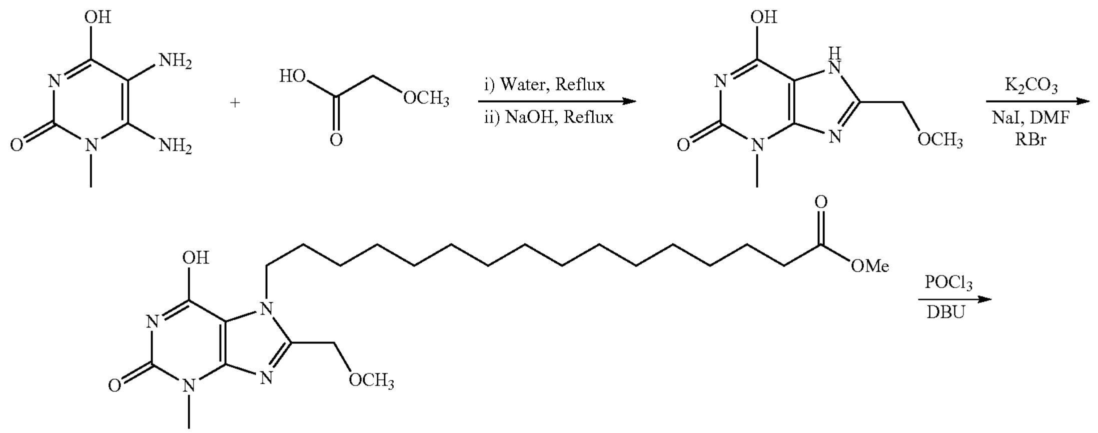

-continued

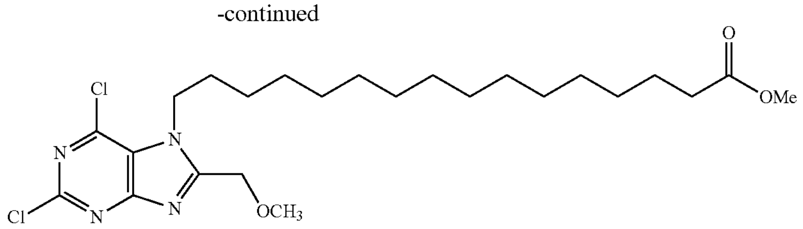

92

6-hydroxy-8-(methoxymethyl)-3-methyl-3,7-dihydro-2H-purin-2-one

To a solution of 5,6-Diamino-1-methylxanthine (0.5 g, 3.164 mmol) in water (5 mL) wad added methoxy acetic acid (0.57 g, 6.32 mmol) was heated to reflux for 3 hours. After cooling to room temperature, NaOH (215 mg, 5.37 mmol) in water (5.0 mL) was added, and the reaction mixture was heated at reflux for 5 hours. Reaction mixture was cooled to room temperature and then stirred at 0° C. for 15 minutes, the product was precipitated. The solid was collected by filtration, washed with ice-cold water (10 mL), followed by washing with diethyl ether (10 mL) and dried under high vacuum for overnight to get 50 mg or pure product as light yellow solid. LCMS: m/Z 210.96 $(M+H)^+$, 421.26 $(2M+H)^+$, 209.0 $(M-H)^+$, 419.18 $(2M-H)^+$.

Methyl 16-(6-hydroxy-8-(methoxymethyl)-3-methyl-2-oxo-2,3-dihydro-7H-purin-7-yl)hexadecanoate To a solution of 6-hydroxy-8-(methoxymethyl)-3-methyl-3,7-dihydro-2H-purin-2-one (50 mg, 0.238 mmol) in DMF (2.0 mL) was added $K_2CO_3$ (65 mg, 0.476 mmol), NaI (71 mg, 0.476 mmol) and 16-bromo methyl-hexadecanoate (91 mg, 0.261 mmol). Reaction mixture was stirred at 75° C. for 6 hours. Completion of the reaction was confirmed by LC-MS. DMF was evaporated under reduced pressure to dryness. Reaction mixture was suspended in water (25.0 mL) and product was extracted with 20% IPA in DCM (2×25 mL). Combined organic layers were dried over $Na_2SO_4$ and concentrated under reduced pressure to give crude product. Crude product was purified on combi-flash silicagel column chromatography using 0-10% MeOH in DCM to give 50 mg of pure product. LCMS: m/Z 477.44 $(M-H)^+$.

Step 3: Followed similar $POCl_3$ procedure as shown in Method 2A. Crude product was purified on combiflash silica get column chromatography using 0-5% MeOH in DCM to give 20 mg of pure product. LCMS: m/Z 523.21 (M+Na)+.

Compound 93: Methyl 16-(2,6-dichloro-8-(hydroxymethyl)-7H-purin-7-yl)hexadecanoate

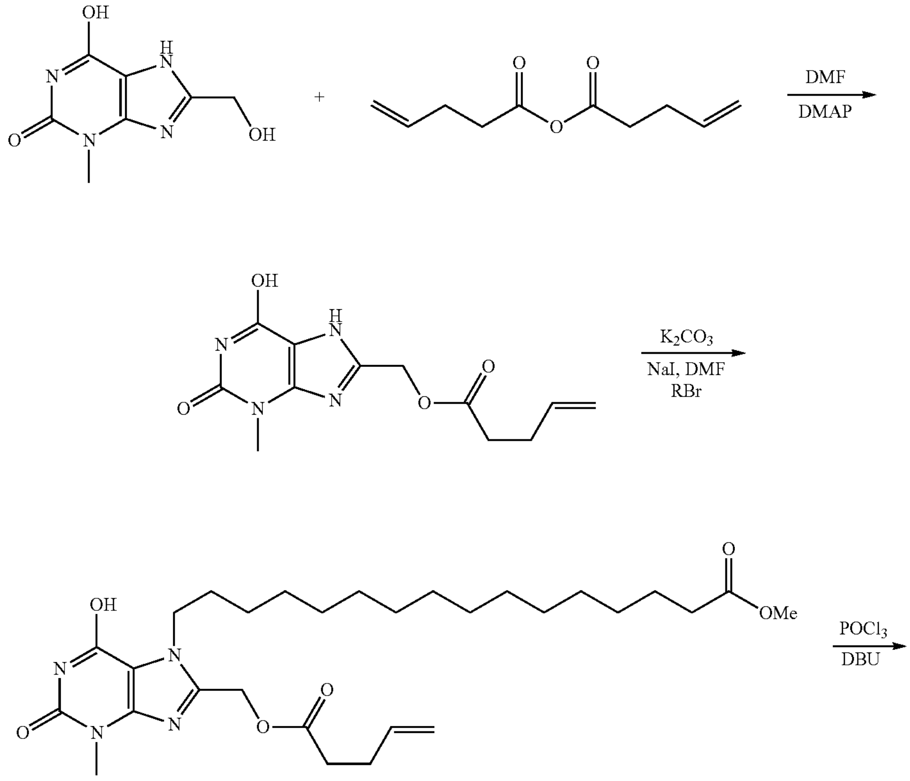

-continued

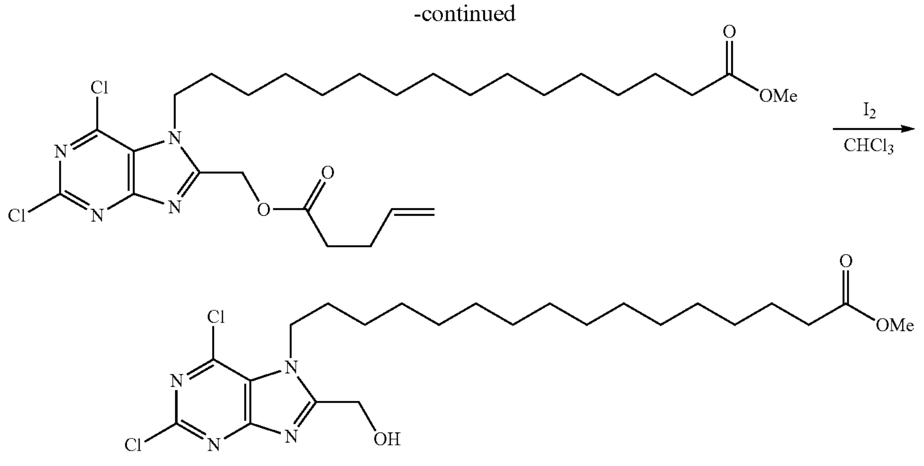

93

(6-hydroxy-3-methyl-2-oxo-3,7-dihydro-2H-purin-8-yl)methyl pent-4-enoate

Pentenoic anhydride was added to a suspension of 6-hydroxy-8-(hydroxymethyl)-3-methyl-3,7-dihydro-2H-purin-2-one (3.4 g, 17.33 mmol) in DMF (70.0 mL) at room temperature. DMAP (420 mg, 3.44 mmol) was added to reaction mixture. Reaction mixture was turned into solution in 15-30 minutes under stirring. Reaction mixture was stirred at room temperature for 2h. Reaction progress was monitored by LC-MS. After stirring for two hours, solvents were evaporated under reduced pressure to dryness. Reaction mixture was dissolved in 20% IPA in DCM (400 mL) and washed with water (150 mL). Water was back extracted with 20% IPA in DCM (100 mL). Combined organic layers were dried over $Na_2SO_4$and concentrated under reduced pressure to dryness. Product was dried under high vacuum overnight to get 4.21 g of pure product as light yellow solid. LCMS: m/Z 279.22 $(M+H)^+$, 557.2 $(2M+H)^+$, 277.08 $(M-H)^+$, 555.31 $(2M-H)^+$.

Methyl 16-(6-hydroxy-3-methyl-2-oxo-8-((pent-4-enoyloxy)methyl)-2,3-dihydro-7H-purin-7-yl)hexadecanoate To a solution of (6-hydroxy-3-methyl-2-oxo-3,7-dihydro-2H-purin-8-yl)methyl pent-4-enoate (2.0 g, 7.19 mmol) in DMF (60.0 mL) was added $K_2CO_3$ (1.98 g, 14.38 mmol), NaI (2.14 g, 14.38 mmol) and 16-bromo methyl-hexadecanoate (2.75 g, 7.9 mmol). Reaction mixture was stirred at 75° C. for 4 hours. Reaction progress was monitored by LC-MS, which showed completion of the reaction. DMF was evaporated under reduced pressure to dryness. Reaction mixture was suspended in water (100.0 mL) and product was extracted with 20% IPA in DCM (2×150 mL). Combined organic layers were dried over $Na_2SO_4$ and concentrated under reduced pressure to give crude product. Crude product was purified on combi-flash silicagel column chromatography using 0-10 MeOH in DCM to give 1.6 g of pure product. LCMS: m/Z 569.49 $(M+Na)^+$, 545.53 $(M-H)^+$.

Methyl 16-(2,6-dichloro-8-((pent-4-enoyloxy)methyl)-7H-purin-7-yl)hexadecanoate $POCl_3$ (11.0 mL) was added to a Methyl 16-(6-hydroxy-3-methyl-2-oxo-8-((pent-4-enoyloxy)methyl)-2,3-dihydro-7H-purin-7-yl)hexadecanoate (1.1 g, 2.01 mmol) in a scintillation glass vial. The mixture was then placed in a pre-heated heating block at 65° C., and heated at that temperature for 5-10 min. DBU (0.887 mL, 5.84 mmol) was then added dropwise via syringe to the stirring mixture at 65° C. (some fuming was observed during the addition of DBU). Reaction mixture was then heated at 90° C. overnight. Reaction mixture was turned to dark brown solution. Completion of reaction was confirmed by LC-MS. In a 2.0 L Erlenmeyer flask containing a large stir bar and a thermometer, was added 5% aq. $NaHCO_3$ (500 mL) and this solution was stirred and cooled in an ice-water bath to −5° C. (internal temperature). The reaction mixture was then added in small portions to the stirring cold solutions, keeping the internal temperature 0-8° C. Slid $NaHCO_3$ (30 g) was also added in small portion at intervals to neutralize the excess $POCl_3$ and to get the final brown mixture to pH 7-7.5, maintaining the internal temperature between 0-8° C. at all time during the neutralization. After the addition the mixture was stirred at 0-5° C. for 10-15 min. The ice-water bath was then removed, and the mixture was stirred at room temperature 10 min. The mixture was extracted with 20% IPA in DCM (2×100 mL). Combined organic layers were dried over $Na_2SO_4$ and concentrated under reduced pressure to get 1.2 g of pure product as brown semi-solid. LCMS: m/Z 591.43 (M+Na)+.

Methyl 16-(2,6-dichloro-8-(hydroxymethyl)-7H-purin-7-yl)hexadecanoate $I_2$ (667 mg, 2.63 mmol) was added to a solution of Methyl 16-(2,6-dichloro-8-((pent-4-enoyloxy)methyl)-7H-purin-7-yl)hexadecanoate (500 mg, 0.877 mmol) in $CHCl_3$ (50.0 mL). Reaction mixture was stirred at room temperature for overnight. Completion of the reaction was confirmed by LC-MS. Solvents were evaporated under reduced pressure. Reaction mixture was diluted with ethyl acetate (100.0 mL) and washed 5% aq. $NaHSO_3$ (50.0 mL) solution to removed color of iodine. Organic solvents were dried over $Na_2SO_4$ and concentrated under reduced pressure to get crude product. Crude product was purified on combi-flash silicagel column chromatography using 0-5% methanol in DCM to give 420 mg of pure product 93. LCMS: m/Z 487.23 $(M+H)^+$, 485.53 $(M-H)^+$. $^1$H-NMR ($CDCl_3$): δ 4.99 (s, 2H), 4.42 (m, 2H), 3.9 (bs, 1H) 566 (s, 311), 2.29 (t, J=7.5, 2H), 1.85 (m, 2H), 1.24 (m, 24H).

Compound 94: 16-(2,6-dichloro-8-methyl-7H-purin-7yl)-N-methylhexadecanamide

Compound 95: 16-(2,6-dichloro-8-methyl-9H-purin-9yl)-N-methylhexadecanamide

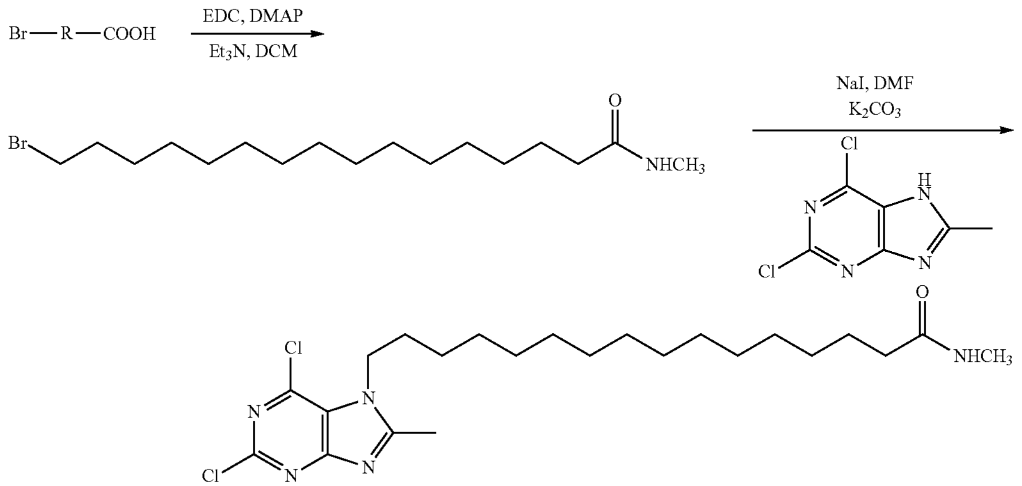

94

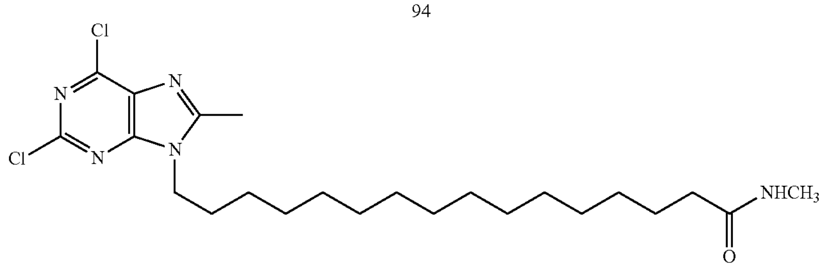

95

Step 1: 16-bromo-N-methylhexadecanamide: Dissolve the 16-bromohexadecanoic acid in DCM (75 mL), cool the reaction mixture to 0° C. Added EDC.HCl (1.543 g, 8.05 mmol) to reaction mixture, followed by addition of DMAP (73 mg, 0.596 mmol), methylamine hydrochloride (483 mg, 7.156 mmol) and triethylamine (2.077, 14.91 mmol). Allowed the reaction mixture to warm to room temperature stirred for overnight. Added Sat. $NH_4Cl$ solution to the reaction mixture (25 mL). Extract the reaction mixture with DCM (2×100 mL). Washed the combined organic layers with brine (50 mL), dried over $Na_2SO_4$ and concentrated under reduced pressure to dryness. Purified crude reaction mixture by combiflash silicagel column chromatography using 0-10% MeOH in DCM. Product fraction were started eluting at DCM and up to 10% MeOH in DCM. Product fraction were identified by TLC using phosphomolybdic acid staining. Pure fractions were combined and evaporated under reduced pressure to dryness to give 1.57 g of pure product as light brown solid. LCMS: m/Z 348.19 $(M+H)^+$. $^1$H-NMR ($CDCl_3$) δ 5.4 (bs, 111), 3.40 (t, J=7.2, 2H), 2.81 (d, J=4.5, 3H), 2.15 (t, J=7.5, 2H), 1.84 (m, 211), 1.24 (m, 24H).

Step 2: Followed similar procedure as described in method 1. Crude product was purified on combi-flash silicagel column chromatography using 0-80% ethyl acetate in hexane gradient method to give 40 mg of pure 94 (7-isomer) and 340 mg of pure 95 (9-isomer). Product 94: LCMS: m/Z 492.32 $(M+Na)^+$, 468.42 $(M-H)^+$. $^1$H-NMR ($CDCl_3$) δ 5.45 (bs, 1H), 4.34 (m, 211), 2.8 (d, 3H), 2.7 (s, 3H), 2.16 (t, J=7.5, 2H), 1.8 (m, 211), 2.24 (m, 24H).

95: 16-(2,6-dichloro-8-methyl-9H-purin-9yl)-N-methylhexadecanamide: LCMS: m/Z 492.32 $(M+Na)^+$, 468.23 $(M-H)^+$ Compound 96: isopropyl 16-(2-chloro-6-(isopropylsulfonyl)-8-methyl-7H-purin-7-yl)hexadecanoate

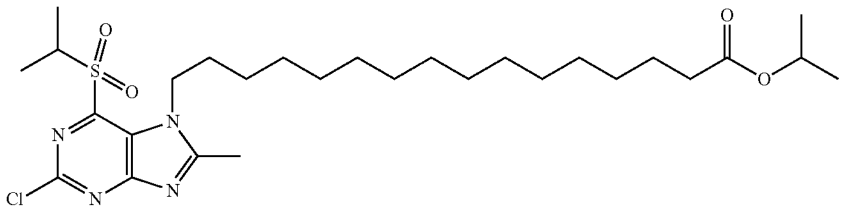 [SMILES: Cc1nc2nc(Cl)nc(S(=O)(=O)C(C)C)c2n1CCCCCCCCCCCCCCCC(=O)OC(C)C]

Method 4 was utilized with corresponding ROH to provide product 96. LCMS: m/Z 571.1 (M+H); $^1$H-NMR ($CDCl_3$): δ 4.80 (m, 1H), 4.55 (m, 2H), 4.40 (m, 111), 2.75 (s, 3H), 2.30 (m, 2H), 1.80 (m, 4H), 1.52 (d, J=6.9 Hz, 611), 1.38-1.25 (broad m, 2811).

Compound 97: 2-chloro-7-hexadecyl-6-(isopropylsulfonyl)-8-methyl-7H-purine

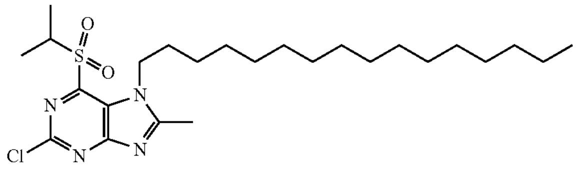 [SMILES: CCCCCCCCCCCCCCCCn1c(C)nc2nc(Cl)nc(S(=O)(=O)C(C)C)c21]

Method 3 was utilized with corresponding 2,6-DiCl intermediate to provide product 97. LCMS: m/Z 499.2 (M+H); $^1$H-NMR ($CDCl_3$) 4.58 (m, 2H), 4.45 (m, 1H), 2.72 (s, 3H), 1.82 (m, 2H), 1.52 (d, J=6.9 Hz, 6H), 1.38-1.25 (broad m, 26H), 0.85 (t, 3H).

Compound 98: 2-hydroxypropyl 16-(2,6-dichloro-8-methyl-7H-purin-7-yl)hexadecanoate

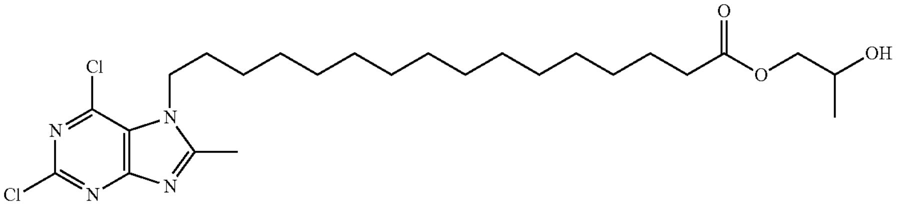 [SMILES: Cc1nc2nc(Cl)nc(Cl)c2n1CCCCCCCCCCCCCCCC(=O)OCC(C)O]

Method 4 was utilized with corresponding ROH to provide product 98. LCMS: m/Z 515.2 (M+H).

Compound 99: 2-(2-ethoxyethoxy)ethyl 16-(2,6-dichloro-8-methyl-7H-purin-7-yl)hexadecanoate

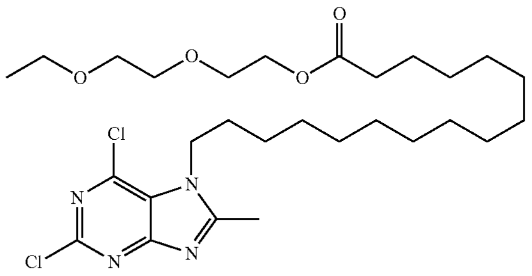 [SMILES: CCOCCOCCOC(=O)CCCCCCCCCCCCCCCn1c(C)nc2nc(Cl)nc(Cl)c21]

Method 4 was utilized with corresponding ROH to provide product 99. LCMS: m/Z 573.3 (M+H).

Compound 100: 2,6-dichloro-8-methyl-9-(15-(1-methyl-1H-tetrazol-5-yl)pentadecyl)-9H-purine

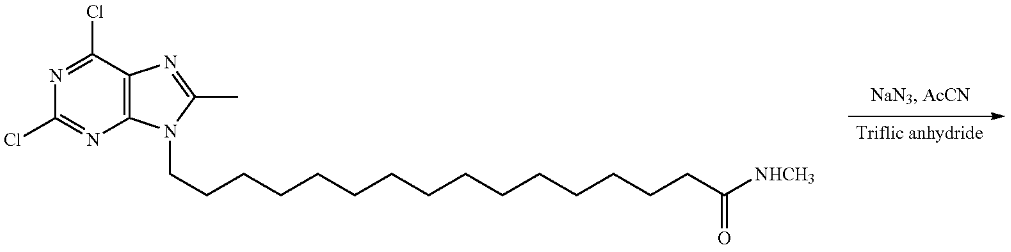

95

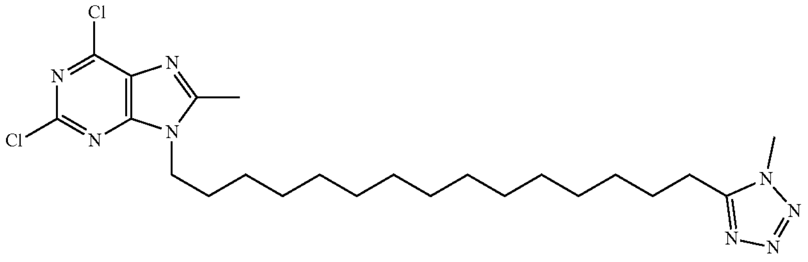

100

Triflic anhydride (47 mg, 0.168 mmol) was added to a stirred suspension of 16-(2,6-dichloro-8-methyl-7H-purin-7yl)-N-methylhexadecanamide (20 mg, 0.042 mmol) and sodium azide (8 mg, 0.126 mmol) in acetonitrile (4.0 mL) under nitrogen atmosphere. Reaction mixture was rapidly turned into homogenous solution. Reaction mixture was stirred at room temperature for 5 hours. Completion of reaction was confirmed by LC-MS. Reaction mixture was poured into a 5% $NaHCO_3$ solution. Extracted the reaction mixture with ethyl acetate (2×20 mL). Washed the combined organic phases with brine (20.0 mL) and dried over $Na_2SO_4$. Solvents were evaporated under reduced pressure to dryness. Crude product was purified by silicagel gradient column chromatography using 0-80% ethyl acetate in hexane. Product was eluted at 70% ethyl acetate. Product fractions were collected, and solvents were evaporated under reduced pressure to get 20 mg of product as light color solid. LCMS: m/Z 495.47 $(M+H)^+$, 517.29 $(M+Na)^+$, 493.52 $(M-H)^+$.

Compound 101: 2,6-dichloro-8-methyl-7-(15-(1-methyl-1H-tetrazol-5-yl)pentadecyl)-7H-purine

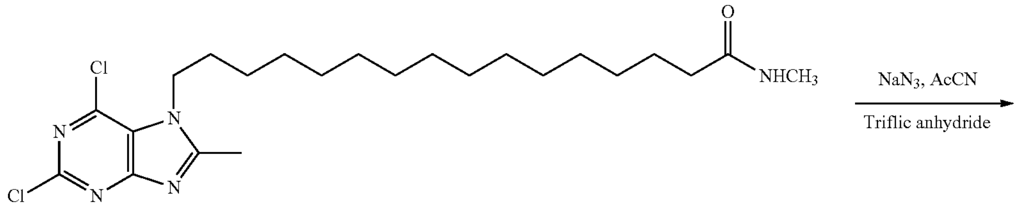

94

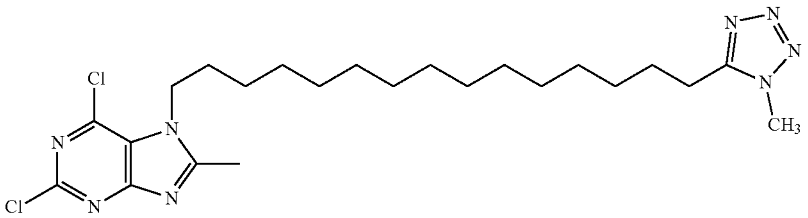

101

Utilized similar procedure detailed in the preparation of compound 100 was utilized starting from compound 94. Crude product was purified by silicagel gradient column chromatography using 0-80% ethyl acetate in hexane Product was eluted at 70% ethyl acetate. Product fractions were collected, and solvents were evaporated under reduced pressure to get 35 mg of pure product. LCMS: m/Z 495.35 $(M+H)^+$, 517.41 $(M+Na)^+$, 493.45 $(M-H)^+$. $^1$H-NMR ($CDCl_3$) δ 4.17 (m, 2H), 3.99 (s, 3H), 2.84 (m, 2H), 2.71 (s, 3H), 1.8 (m, 2H), 2.25 (m, 24H).

Compound 102: 4-(10-(2,6-dichloro-8-methyl-7H-purin-7-yl)decyl)morpholine

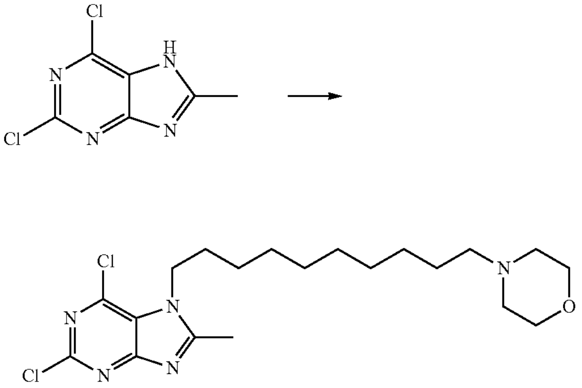

102

Method 1 was utilized to synthesis 102. The crude was purified by flash chromatography is DCM and methanol but only 1.5 mg (2%) of the 7-isomer was isolated as an oily solid. LCMS: m/z 428.37 (M+H); $^1$H-NMR (CDCl3) δ 4.35 (t, J=7.8 MHz, 2H), 3.72 (t, J=4.5 MHz, 4H), 2.70 (s, 3H), 2.43 (m, 4H), 2.31 (t, J=7.2 MHz, 2H), 1.80 (m, 4H), 1.35 (m, 12H).

Compound 103 (RM-108-187): (E)-1,4-bis(2,6-dichloro-8-methyl-7H-purin-7-yl)but-2-ene

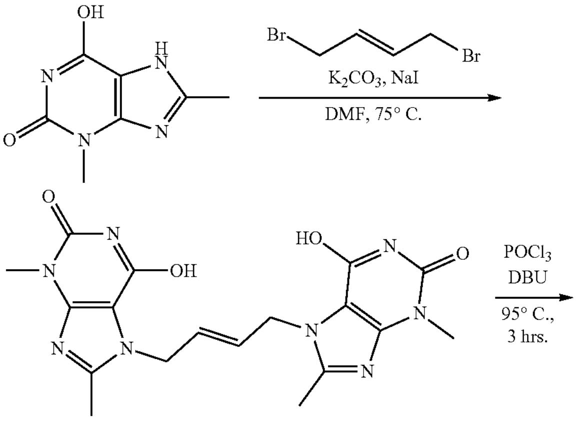

(103a)

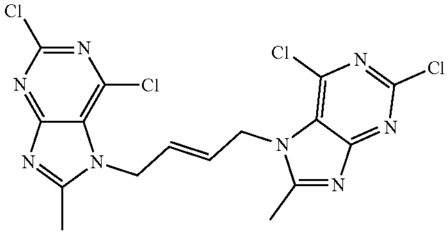

(103)

Step 1: Compound 103a was prepared in the same manner as described in Method 1. 366 mgs. (54%) of (E)-7,7'-(but-2-ene-1,4-diyl)bis(6-hydroxy-3,8-dimethyl-3,7-dihydro-2H-purin-2-one) as a tan powder.

Step 2: Utilized $POCl_3$ procedure as described in method 2A. Obtained 0.54 mg (0.12%) of (E)-1,4-bis(2,6-dichloro-8-methyl-7H-purin-7-yl)but-2-ene. LCMS: m/Z 455.12 (M-H).

Compound 104 (R)-2,3-dihydroxypropyl 16-(2,6-dichloro-8-methyl-7H-purin-7-yl)hexadecanoate

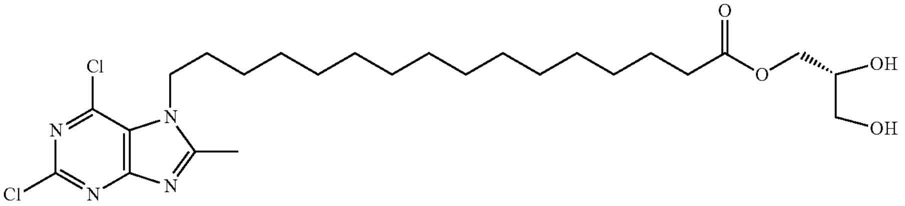 [SMILES: Cc1nc2nc(Cl)nc(Cl)c2n1CCCCCCCCCCCCCCCC(=O)OC[C@H](O)CO]

Method 4 was utilized with corresponding ROH to provide product 104. LCMS: m/Z 531.2 (M+H).

Compound 105: 4-(16-(2,6-dichloro-8-methyl-7H-purin-7-yl)hexadecyl)morpholine

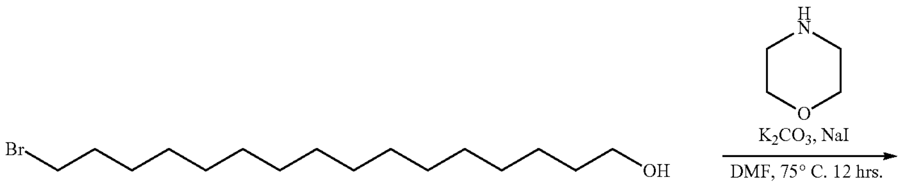

-continued

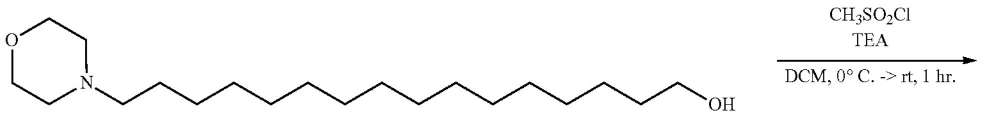

(105a)

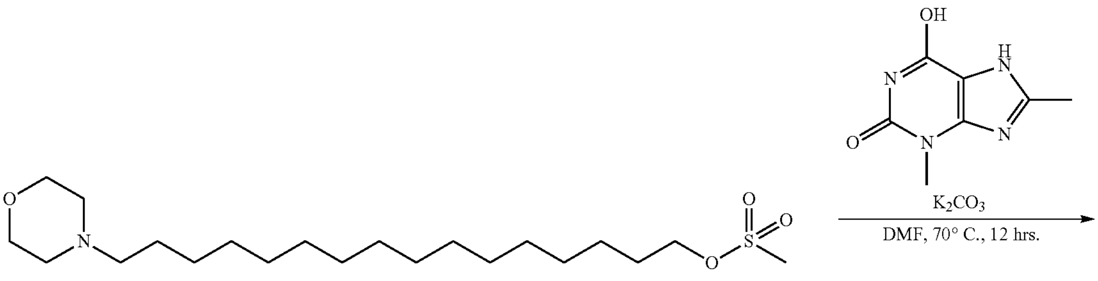

(105b)

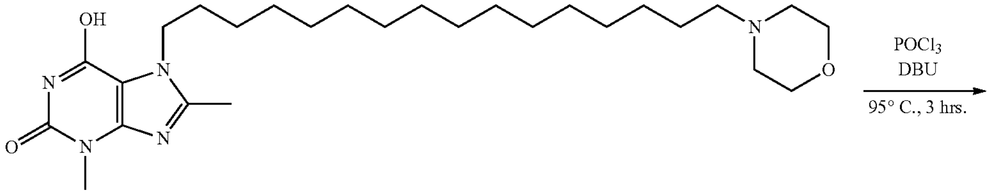

(105c)

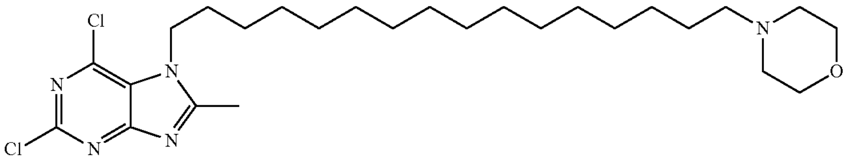

(105)

Step 1: Compound 105a was prepared in a similar manner described in method 1. 183 mg (84%) of 16-morpholinohexadecan-1-ol (compound 105a). LCMS: m/Z 326.46 (M+H).

Step 2: 16-morpholinohexadecan-1-ol was dissolved in anhydrous DCM. Flask was then purged with Ar(s) and placed in ice bath. To this was added 116 mg (1.2 mmol) triethylamine (TEA) and $CH_3SO_2C_1$(89 mg, 0.78 mmol) and diluted with DCM. Reaction was allowed to warm to room temperature and stirred for around 1 hour. Water was then added and layers were separated and aqueous portion extracted with DCM (3x5 mL). Organic layer was separated, dried and concentrated to provide 225 mg (99%) of 16-morpholinohexadecyl methanesulfonate (compound 105b) as a flaky white solid. LCMS: m/Z 406.63 (M+H).

Step 3: Utilized similar procedure as described in method 1. 196 mg (71%) of 6-hydroxy-3,8-dimethyl-7-(16-morpholinohexadecyl)-3,7-dihydro-2H-purin-2-one (compound 105c). LCMS: m/Z 490.43 (M+H).

Step 4: Utilized similar procedure as described in method 2A, 14 mg (26%) of 4-(16-(2,6-dichloro-8-methyl-7H-purin-7-yl)hexadecyl)morpholine (compound 105). LCMS: m/Z 512.42 (M+H); $^1$H-NMR ($CDCl_3$) δ 4.36 (t, 2H), 3.72 (t, 4H), 2.71 (s, 3H), 2.43 (m, 4H), 2.31 (t, 2H), 1.79 (m, 2H), 1.47 (m, 2H), 1.25 (m, 24H).

Compound 106: 1,3-dihydroxypropan-2-yl 16-(2,6-dichloro-8-methyl-7H-purin-7-yl)hexadecanoate

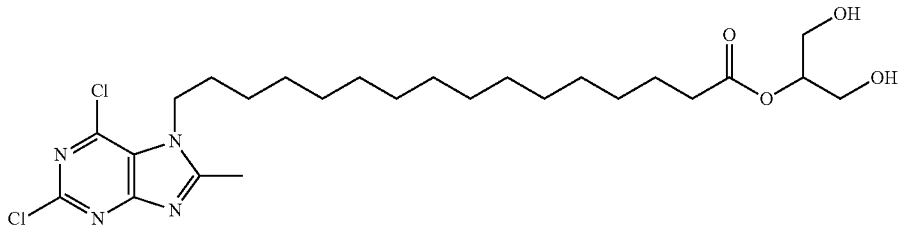 [SMILES: Cc1nc2nc(Cl)nc(Cl)c2n1CCCCCCCCCCCCCCCC(=O)OC(CO)CO]

Method 4 was utilized with corresponding ROH to provide product 106. LCMS: m/Z 531.5 (M+H).

Compound 107: (S)-2,3-dihydroxypropyl 16-(2,6-dichloro-8-methyl-7H-purin-7-yl)hexadecanoate

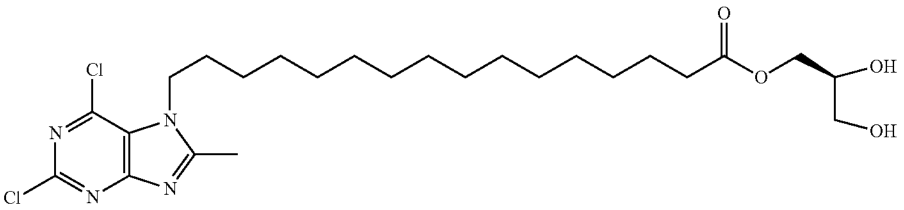 [SMILES: Cc1nc2nc(Cl)nc(Cl)c2n1CCCCCCCCCCCCCCCC(=O)OC[C@@H](O)CO]

Method 4 was utilized with corresponding ROH to provide product 107. LCMS: m/Z 531.5 (M+H).

Compound 108: methyl 16-(2-chloro-6-(2-(dimethylamino)ethoxy)-8-methyl-7H-purin-7-yl)hexadecanoate

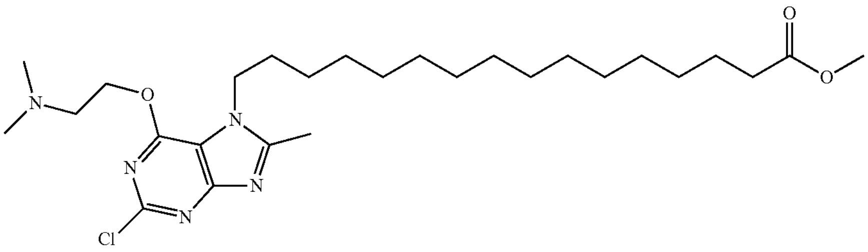

Method 4 was utilized with corresponding ROH to provide product 108. LCMS: m/Z 524.3 (M+H).

Compound 109: isopropyl 16-(2-chloro-8-methyl-6-(methylsulfonyl)-7H-purin-7-yl)hexadecanoate

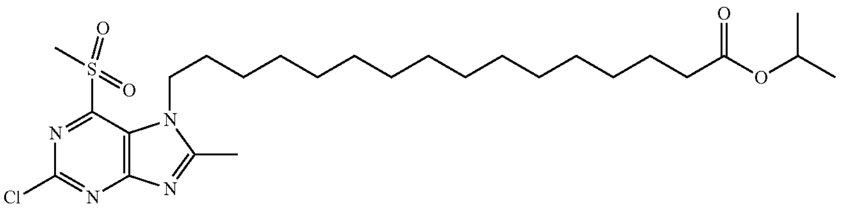 [SMILES: Cc1nc2nc(Cl)nc(S(C)(=O)=O)c2n1CCCCCCCCCCCCCCCC(=O)OC(C)C]

Method 3 was utilized with corresponding 2,6-DiCl intermediate to provide product 109; LCMS: m/Z 543.4 (M+H); 565.4 (M+Na+).

Compound 110: (16-(2,6-dichloro-8-methyl-7H-purin-7-yl)hexadecyl)phosphonic acid

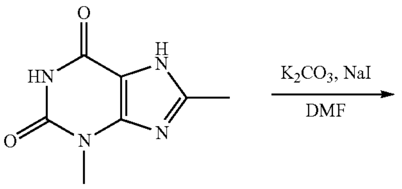

-continued

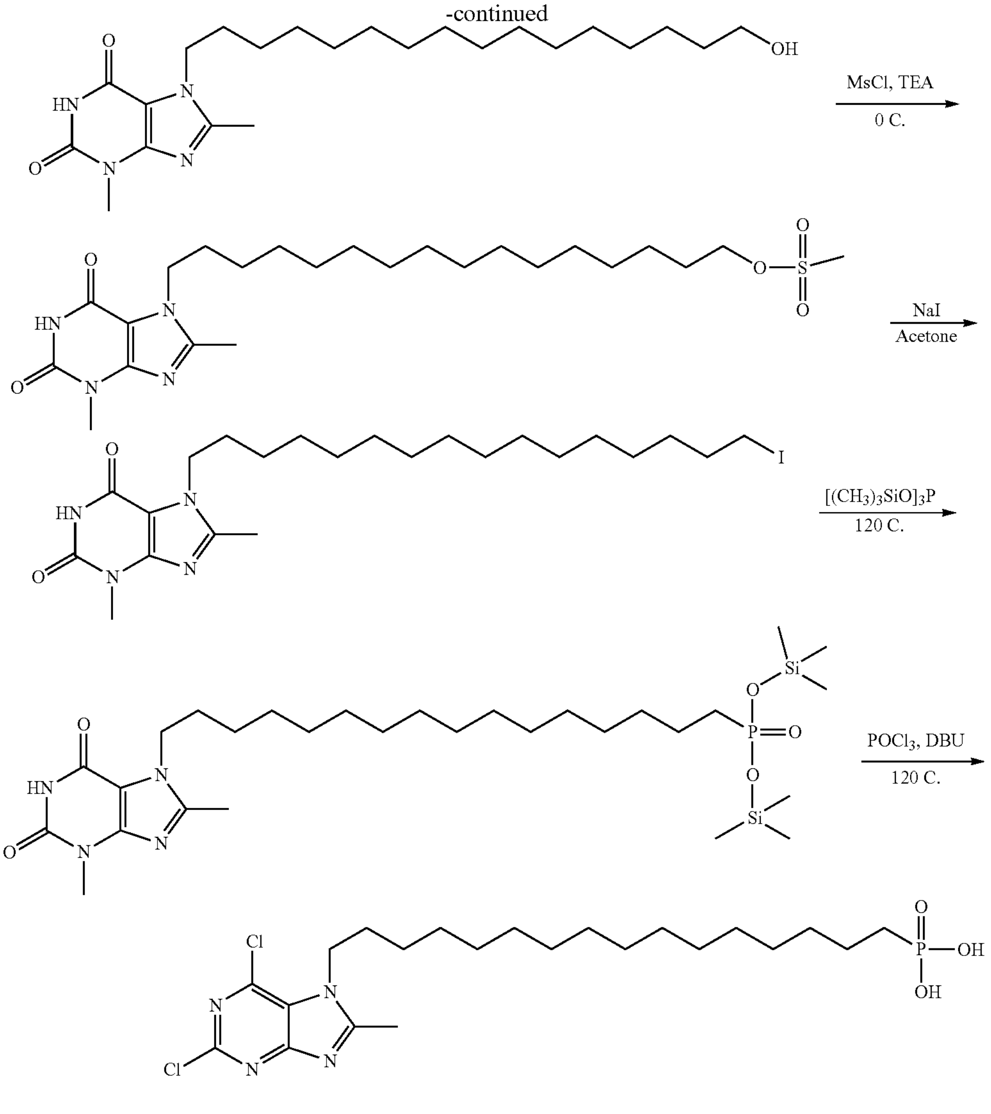

110

Step 1: 8-methylxanthine (100 mg, 0.56 mmol), 16-bromohexadecanol (176 mg, 0.56 mmol), potassium carbonate (116 mg, 0.84 mmol), and sodium iodide (9 mg, 0.06 mmol) were all combined in a round-bottom flask under Argon. Anhydrous dimethylformamide (DMF, 2 mL) was added to this mixture and this was stirred at 100° C. for three hours. DMF was concentrated in vacuo and the crude was partitioned in dichloromethane (DCM) and water. The organic layer was washed dried over sodium sulfate, filtered, and concentrated. The crude was purified by flash chromatography (DCM/MeOH 0-30%) and 110 mg of the product was isolated as solid. $^{1}$H-NMR ($CDCl_3$) δ 8.05 (s, 1H), 4.19 (t, J=7.8 MHz, 2H), 3.63 (m, 2H), 3.51 (s, 3H), 2.46 (s, 3H), 1.80 (m, 2H), 1.58 (m, 4H), 1.27 (m, 24H).

Step 2: Step 1 product (50 mg, 0.12 mmol) was stirred in dry dichloromethane (DCM) and cooled in an ice bath. Triethylamine (0.033 mL, 0.24 mmol) and methane sulfonyl chloride (0.011 mL, 0.14 mmol) were added and the reaction warmed to ambient temperature for 12 h. The reaction was quenched with water and extracted in DCM. The organic layer was washed with 5% sodium bicarbonate, dried over sodium sulfate, and concentrated to give about 60 mg of crude which was taken on to the next step.

Step 3: Step 2 product (60 mg, 0.12 mmol) was stirred in dry acetone. To this was added sodium iodide (90 mg, 0.60 mmol) and the reaction was heated 56° C. Upon heating, the mixture became homogeneous and was monitored by TLC (95:5 DCM:Methanol). After 2 hours, acetone was removed in vacuo and the crude partitioned in DCM and water. The organic layer was washed with 10% sodium thiosulfate, dried over sodium sulfate, filtered, and concentrated to give about 57 mg.

Step 4: To step 3 product (55 mg, 0.11 mmol) was added tris(trimethylsilyl)phosphite and this mixture was heated to 120° C. for two hours. The reaction was concentrated to remove excess phosphite reagent. This was taken as is onto the final step.

Step 5: Step 4 product was stirred in Xylenes and to this was added $POCl_3$ (0.13 mL) and DBU (0.13 mL). The mixture was heated to 120° C. and, after 3 hours, the mass of the product was seen by LCMS. After cooling, crude was washed with water and 5% sodium bicarbonate. The organic layers were combined, dried over sodium sulfate, filtered, and concentrated. The crude was purified by RPHPLC to provide around 1 mg of product. LCMS: m/z 505.38 (M−H), m/z 507.40 (M+H).

Compound 111: 16-(2-chloro-6-(isopropylsulfonyl)-8-methyl-7H-purin-7-yl)hexadecan-1-ol and compound 112: 16-(2-chloro-6-(isopropylsulfonyl)-8-methyl-8,9-dihydro-7H-purin-7-yl)hexadecan-1-ol

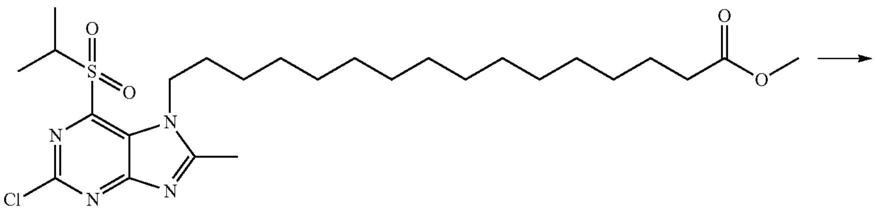

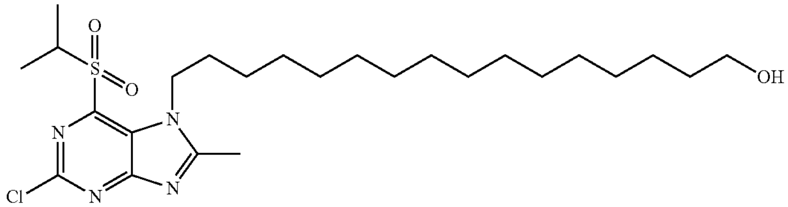

111

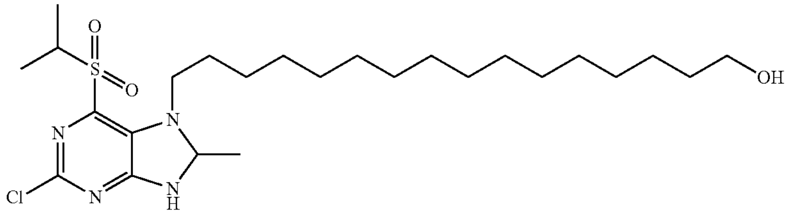

112

Compound 74 (50 mg, 0.092 mmol) was dissolved in dry dichloromethane (DCM) and cooled in an ice bath. DIBALH (1 M in DCM) was added (0.184 mL, 0.184 mmol) and the reaction let warm to ambient temperature. After one hour, LCMS showed mostly starting material, so the reaction was cooled in ice and another 3 equivalents of DIBALH were added. The reaction was quenched by adding ethyl acetate and concentrated. The crude was partitioned in DCM and water and then washed organic with 5% sodium bicarbonate. Dried the organic layer over sodium sulfate, filtered, and concentrated. The two products were separated by RPHPLC in water and acetonitrile (0-100%). About 5 mg (11%) of compound 111 was isolated as an oil and about 15 mg (32%) of compound 112 was isolated as a white semi solid.

Compound 111: 1H-NMR (CDCl3) δ 4.57 (t, J=8.4 MHz, 2H), 4.43 (m, 1H), 3.64 (t, J=6.6 MHz, 2H), 2.77 (s, 3H), 1.81 (m, 4H), 1.51 (d, J=6.3 MHz, 6H), 1.25 (m, 18H).

Compound 112: 1H-NMR (CDCl3) δ 8.21 (bs, 1H), 5.56 (m, 1H), 4.04 (m, 2H), 3.64 (t, J=6.6 MHz, 2H), 3.23 (m, 1H), 1.58 (m, 11H), 1.36 (d, J=7.2 MHz, 6H), 1.27 (m, 24H).

Compound 113: 2,6-dichloro-8-methyl-7-(10-(4-methylpiperazin-1-yl)decyl)-7H-purine

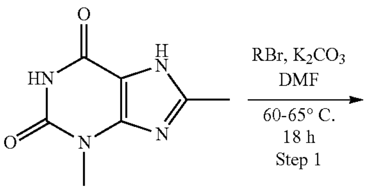

-continued

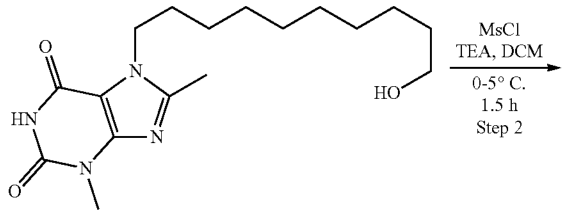

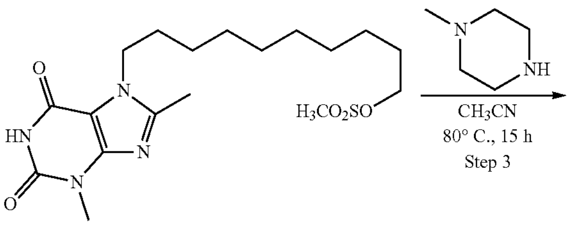

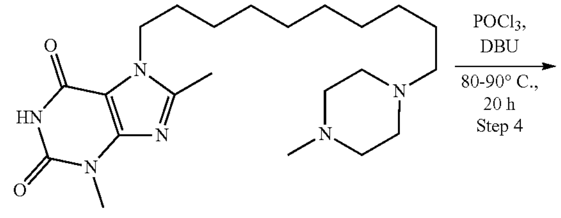

-continued

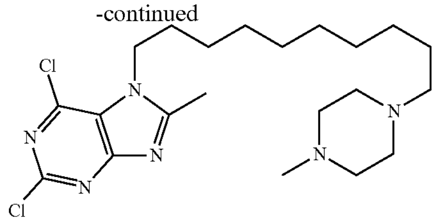

113

Step 1: 8-Methylxanthine (2 g, 11.1 mmol) and potassium carbonate (2.3 g, 16.65 mmol) were weighed in a 250 mL 1N RB flask containing a stir bar. Anhydrous DMF (60 mL) was added and the heterogeneous mixture was stirred for 5-10 min. 10-Bromo-1-decanol (2.9 g, 12.21 mmol) was then added and the yellow mixture was immersed in a pre-heated oil-bath and heated at 60-65° C. for 18 h. After the heating, the flask was cooled to room temperature. The mixture was poured into stirring ice-water and the white precipitate formed was filtered, collected on a Buchner funnel and washed with additional water. The white solid was dried under high vacuum overnight. The solid was then stirred with MTBE/hexanes (10 mL/40 mL) to remove the excess 10-bromodecanol. The solid was filtered, washed with hexanes and dried under high vacuum to give the desired product (3.14 g, 84%) as a white solid. LCMS: m/Z 337.35 (M+H), 335.33 (M−H); $^1$H-NMR ($CDCl_3$ with 0.03% v/v TMS) δ 8.37 (bs, 1H), 4.20 (m, 2H), 3.64 (m, 2H), 3.52 (s, 3H), 2.47 (s, 3H), 1.78 (m, 2H), 1.55 (m, 2H), 1.42-1.2 (m, 12H).

Step 2: To a well cooled solution of alkylated xanthene derivative (170 mg, 0.5 mmol) in DCM (5 mL), TEA (0.3 mL, 4 eq) was added. To this mixture, a solution of $MeSO_2Cl$ (0.3 mL, 4 eq) in DCM (1 mL) was added dropwise and reaction mixture was stirred as such for 12 h. The reaction mixture was extracted in DCM (20 mL), washing with water (10 ml), $NaHCO_3$ (5%, 10 ml) followed by brine (5 mL), and dried over $Na_2SO_4$. The crude product was purified by Combi Flash using DCM-MeOH (0-5%) to give the product mesylate (116 mg, 56%), LCMS: m/Z 413.4 (M−H).

Step 3: The mesylate (120 mg, 0.289 mmolq) was weighed in a 50 mL 1N RB flask containing a stir bar. Anhydrous acetonitrile (10 mL) was added and the heterogeneous mixture was stirred for 5-10 min. N-Methylpiperazine (67 mg, 0.666 mmol) was then added in a single portion and the yellow mixture was immersed in a pre-heated oil-bath and heated at 80-85° C. (oil-bath temperature) overnight. TLC (DCM/MeOH, 9:1) showed that the reaction was complete. The solvent was evaporated in vacuo and the yellow oil was dissolved in DCM. Silica gel (600 mg) was added to make a slurry. The DCM was evaporated to get the crude product as a solid load on silica gel. The crude was purified by automated column chromatography using DCM/MeOH as a gradient to give the desired product (90 mg, 75%) as a white foamy solid that was dried under high vacuum. An aliquot was analyzed by LCMS and HPLC and showed the desired mass and purity of 93%. It was carried forward to the next step. HPLC purity 93%; LCMS: 419.29 (M+H).

Step 4: The N-methylpiperazine derivative (90 mg, 0.215 mmol) was transferred to a glass vial containing a stir bar. $POCl_3$ (1.5 mL) was added and the mixture was stirred and immersed in a pre-heated oil-bath (60° C.) and heated for 2-3 min. DBU (120 mg, 0.789 mmol) was added dropwise and the brown mixture was heated at 85-90° C. (oil-bath temperature) overnight. After cooling to room temperature, an aliquot was analyzed by LCMS which showed that all starting material was consumed and also showed the desired mass. The reaction mixture was quenched by dropwise addition to a cold (0-5° C.) aqueous solution of 5% sodium bicarbonate. Water (2 mL) and solid $NaHCO_3$ were added intermittently with stirring till the pH of the mixture was 7-7.5. The mixture as then extracted with dichloromethane (2×10 mL). The combined organic layer was dried over anhydrous sodium sulfate, filtered and the solvent evaporated in vacuo to give the crude product as a red oil. The crude was purified by reverse-phase preparative HPLC to give the desired product. After evaporation of solvent and lyophilization, the pure product 113 (45.7 mg, 48%) was obtained as a red oil. HPLC purity 96.8%. LCMS: m/Z 441.38 (M+H); $^1$H-NMR ($CDCl_3$ with 0.03% v/v TMS, 300 MHz): δ 5.46 (bs, 3H), 4.36 (m, 2H), 2.71 (bs, 8H), 2.47 (m, 2H), 2.39 (s, 3H), 2.02 (s, 3H), 1.82 (m, 2H), 1.51 (m, 2H), 1.52 (d, J=6.9 Hz, 6H), 1.44-1.26 (m, 10H).

Compound 114: Methyl 16-(2-chlolro-8-(hydroxymethyl)-6-(isopropylsulfonyl)-7H-purin-7-yl) hexadecanoate

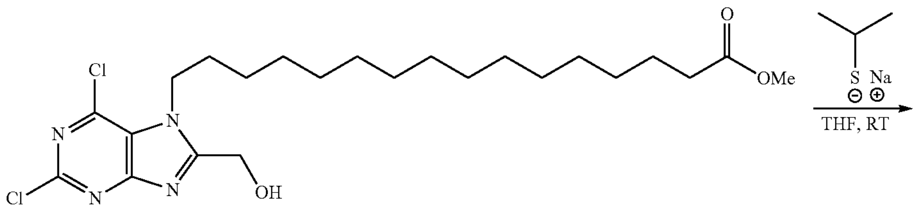

93

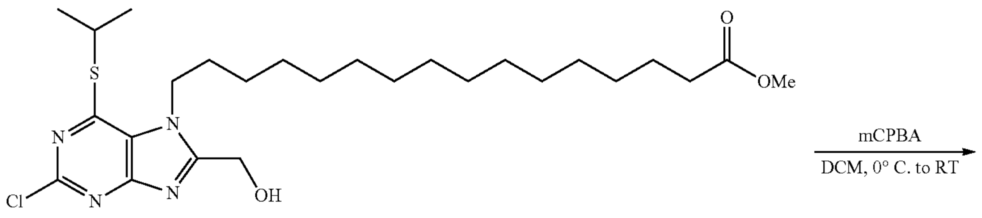

-continued

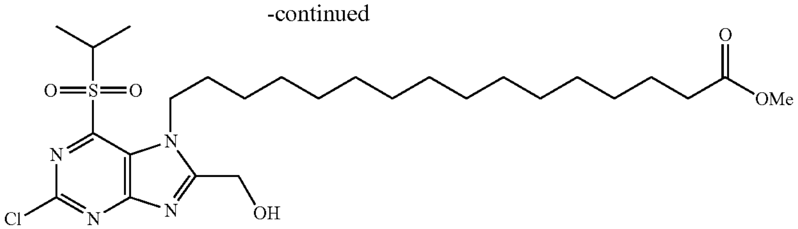

114

Method 3 was utilized to provide the crude product in step 2 which was purified on C18 reverse phase gradient column chromatography using Solvent A: Water and Solvent B: Acetonitrile. Pure fractions were combined and lyophilized to get 30 mg of pure product. LCMS: m/Z 559.57 $(M+H)^+$, 582.76 (M+Na)+. $^1$H-NMR ($CDCl_3$) δ 5.04 (s, 2H), 4.6 (m, 2H), 4.45 (m, 1H), 3.68 (s, 3H), 3.6 (bs, 1H) 2.3 (m, 2H), 1.9 (m, 2H), 1.6 (m, 2H), 1.54 (d, J=0.9, 3H), 1.52 (d, J=1.2, 3H), 1.2 (m, 22H)

Compound 115: 4-(10-(2-chloro-6-(isopropylsulfonyl)-8-methyl-7H-purin-7-yl)decyl)-4-(11-oxidanyl)-414-morpholine

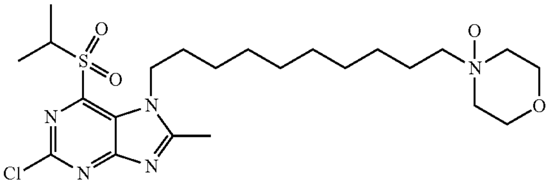

Method 3 was utilized with corresponding 2,6-DiCl intermediate to provide product 115. LCMS: m/Z 516.5 (M+H).

Compound 116: methyl 4-(2,6-dichloro-8-methyl-7H-purin-7-yl)butanoate

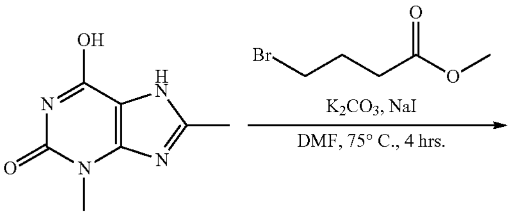

-continued

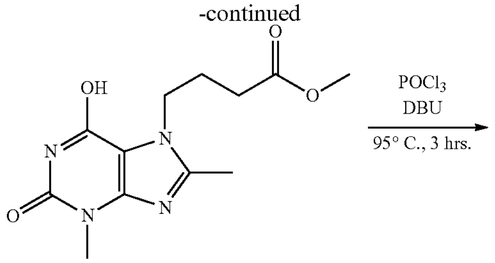

(116a)

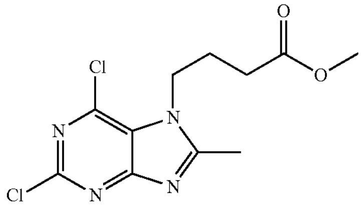

(116)

Step 1: Compound 116a was prepared in the same manner as described in method 1. Obtained 437 mgs. (54%); LCMS: m/Z 281.18 (M+H).

Step 2: $POCl_3$ procedure (as described in method 2b). Obtained 88 mgs. (20%) compound 116 as white solid. LCMS: m/Z 303.05 (M+H); $^1$H-NMR ($CDCl_3$) δ 4.45 (t, 2H), 3.68 (s, 3H), 2.73 (s, 3H), 2.47 (m, 2H), 2.13 (m, 2H).

Compound 117: methyl 16-(2,6-dichloro-8-(diethylamino)-7H-purin-7-yl)hexadecanoate

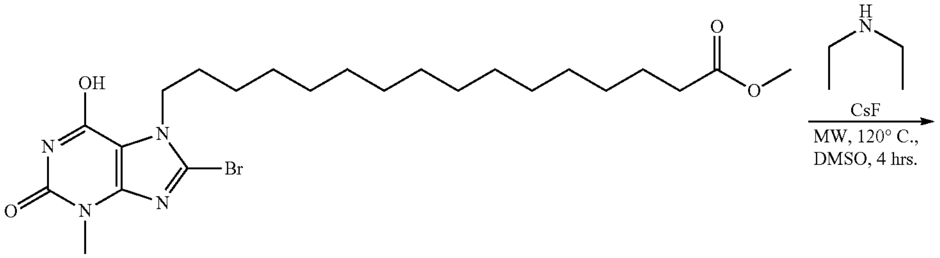

-continued

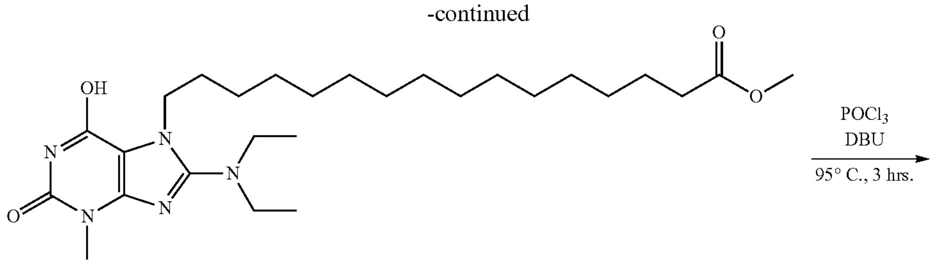

(117a)

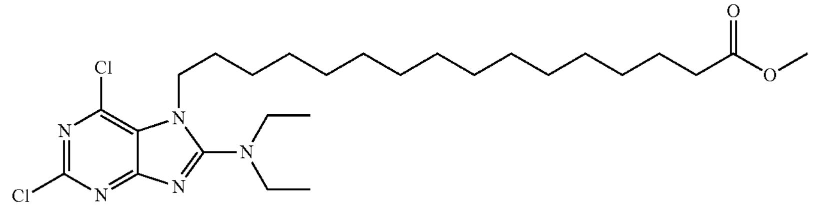

(117)

Step 1: methyl 16-(8-bromo-6-hydroxy-3-methyl-2-oxo-2,3-dihydro-7H-purin-7-yl)hexadecanoate (200 mg, 0.39 mmol), diethylamine (DEA) (153 mg, 2.09 mmol), and CsF (128 mg, 0.84 mmol) were dissolved in DMSO in a microwave vial. Vial was heated in microwave reactor for 4 hours at 120° C. Cloudy solution turned translucent brown. Reaction contents were poured into cold water and then centrifuged 3 mins. Mother liquor was decanted, and the wet solids were frozen and lyophilized. Obtained 135 mgs. (68%) of compound 117a as a brown low melting solid. LCMS: m/Z 506.39 (M+H).

Step 2: $POCl_3$ Procedure (as described in method 2b). Obtained 40 mgs. (28%) (compound 117). LCMS: m/Z 528.51 (M+H); $^1$H-NMR ($CDCl_3$) δ 4.18 (t, 2H), 3.65 (s, 3H), 3.47 (q, 4H), 2.25 (t, 2H), 1.64 (m, 2H), 1.26 (m, 30H).

Compound 118: methyl 4-(2-chloro-6-(isopropylsulfonyl)-8-methyl-7H-purin-7-yl)butanoate

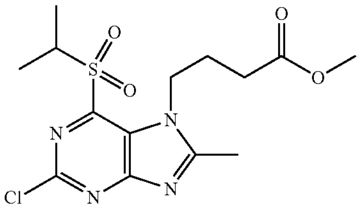 [SMILES: COC(=O)CCCn1c(C)nc2nc(Cl)nc(S(=O)(=O)C(C)C)c21]

Method 3 was utilized with corresponding 2,6-DiCl intermediate to provide product 118. LCMS: m/Z 375.2 (M+H); $^1$H-NMR ($CDCl_3$): δ 4.62 (m, 2H), 4.40 (m, 1H), 3.7 (m, 3H), 2.55 (s, 3H), 2.51 (m, 2H), 2.15 (m, 2H), 1.52 (d, J=6.9 Hz, 6H).

Compound 119: (2,6-dichloro-7-hexadecyl-7H-purin-8-yl)methanol

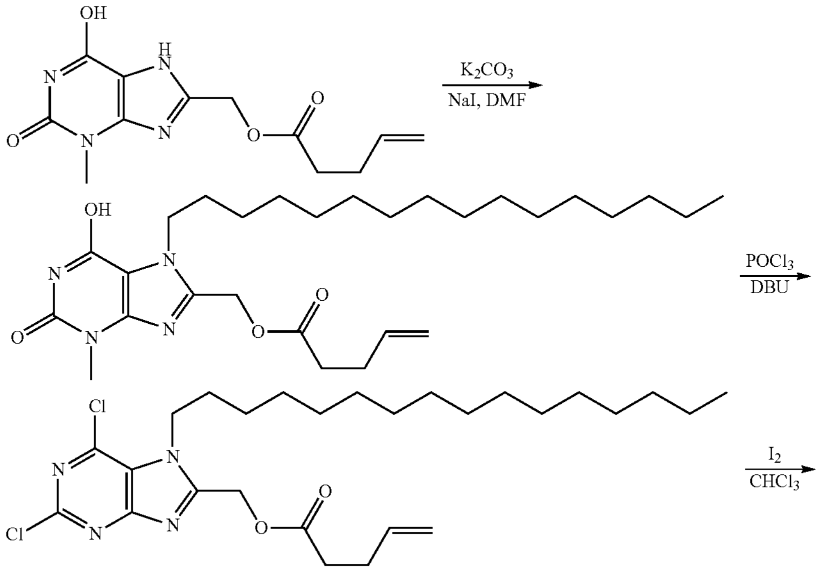

-continued

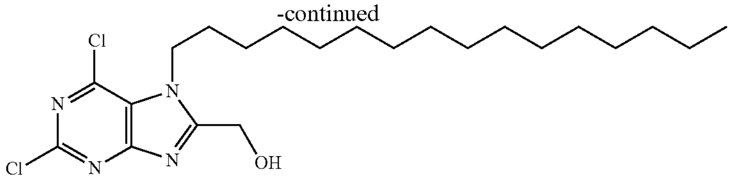

119

Step 1: Followed similar procedure as described in method 1. Crude product was purified on combi-flash silicagel column chromatography using 0-5 MeOH in DCM to give 400 mg of pure product. LCMS: m/Z 503.05 $(M+H)^+$. $^1H$-NMR ($CDCl_3$): δ 8.18 (bs, 1H), 5.8 (m, 1H), 5.18 (s, 2H), 5.03 (m, 2H), 4.28 (m, 2H), 3.54 (m, 4H), 2.48 (i, 2H), 2.41 (m, 2H), 1.8 (m, 2H), 1.25 (m, 28H).

Step 2: $POCl_3$ Procedure (as described in method 2b). Combined organic layers were dried over $Na_2SO_4$ and concentrated under reduced pressure to get 234 mg of product as brown semi-solid. LCMS: m/Z 525.11 $(M+H)^+$, 523.34 $(M-H)^+$. $^1H$-NMR ($CDCl_3$) δ 5.8 (m, 1H), 5.39 (s, 2H), 5.04 (m, 2H), 4.42 (m, 211), 2.56 (m, 2H), 2.42 (m, 2H), 2.4 (m, 3H), 1.36 (m, 28H)

Step 3:12 (325 mg, 1.284 mmol) was added to a solution of (2,6-dichloro-7-hexadecyl-7H-purin-8-yl)methyl pent-4-enoate (225 mg, 0.428 mmol) in $CHCl_3$ (25.0 mL). Reaction mixture was stirred at room temperature for overnight. Completion of the reaction was confirmed by LC-MS. Solvents were evaporated under reduced pressure. Reaction mixture was diluted with ethyl acetate (50.0 mL) and washed 5% aq. $NaHSO_3$ (25.0 mL) solution to removed color of iodine. Organic solvents were dried over $Na_2SO_4$ and concentrated under reduced pressure to get crude product. Crude product was purified on combi-flash silicagel column chromatography using 0-5% methanol in DCM to give 45 mg of pure product. LCMS: m/Z 443.18 $(M+H)^+$, 441.29 $(M-H)^+$. $^1H$-NMR ($CDCl_3$) δ 5.0 (s, 2H), 4.42 (m, 2H), 1.9 (brs, 1H), 1.87 (m, 2H), 1.25 (m, 26H), 0.87 (m, 3H).

Compound 120: methyl 5-(2,6-dichloro-8-methyl-7H-purin-7-yl)pentanoate

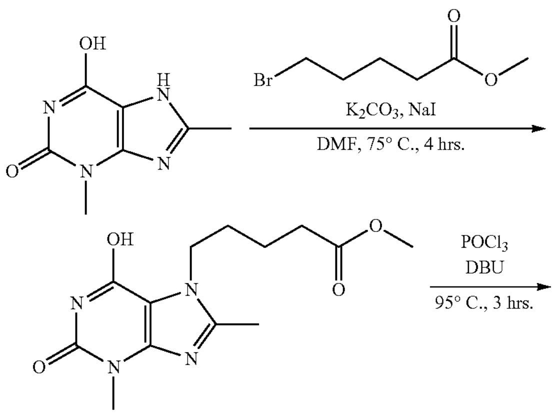

(120a)

-continued

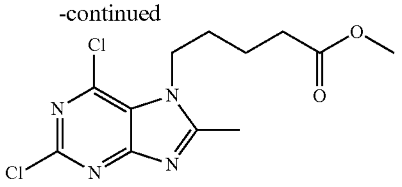

(120)

Step 1: Compound 120a was prepared in the same manner as described in method 1. Obtained 480 mgs. (58%) of compound 120a.LCMS: m/Z 295.25 (M+H).

Step 2: $POCl_3$ Procedure (as described in method 2b). Obtained 96 mgs. (19%) of compound 120. LCMS: m/Z 317.20 (M+H); $^1H$-NMR ($CDCl_3$) δ 4.40 (t, 2H), 3.69 (s, 3H), 2.72 (s, 311), 2.38 (m, 2H), 1.87 (m, 2H), 1.70 (m, 2H).

Compound 121: methyl 5-(2-chloro-6-(isopropylsulfonyl)-8-methyl-7H-purin-7-yl)pentanoate

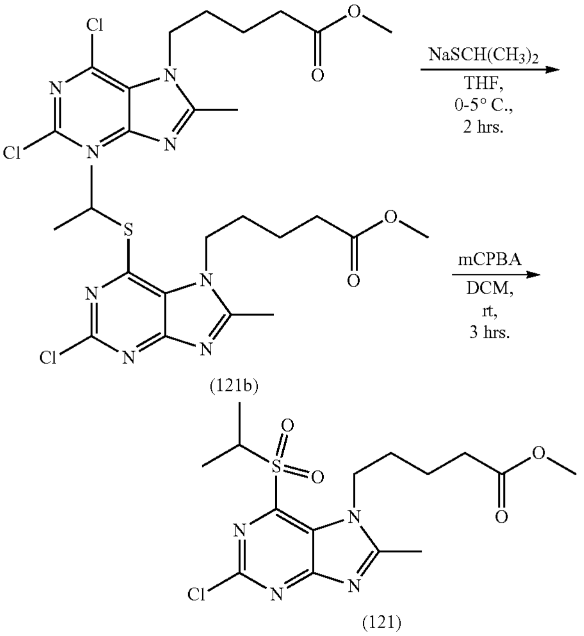

(121b)

(121)

Method 3 was utilized with corresponding 2,6-DiCl intermediate to provide product in two steps.

Step 1: compound 121b obtained as waxy yellow solid. Used in next step without further purification. LCMS: m/Z 357.13 (M+H).

Step 2: Obtained 18 mg (39%) compound 121 as a clear viscous oil. LCMS: m/Z 389.24 (M+H); $^1H$-NMR ($CDCl_3$) δ 4.61 (t, 2H), 4.43 (m, 1H), 3.68 (s, 3H), 2.79 (s, 3H), 2.42 (t, 2H), 1.91 (m, 2H), 1.78 (m, 2H), 1.54 (d, 6H).

Compound 122: (2-chloro-7-hexadecyl-6-(isopropylsulfonyl)-7H-purin-8-yl)methanol

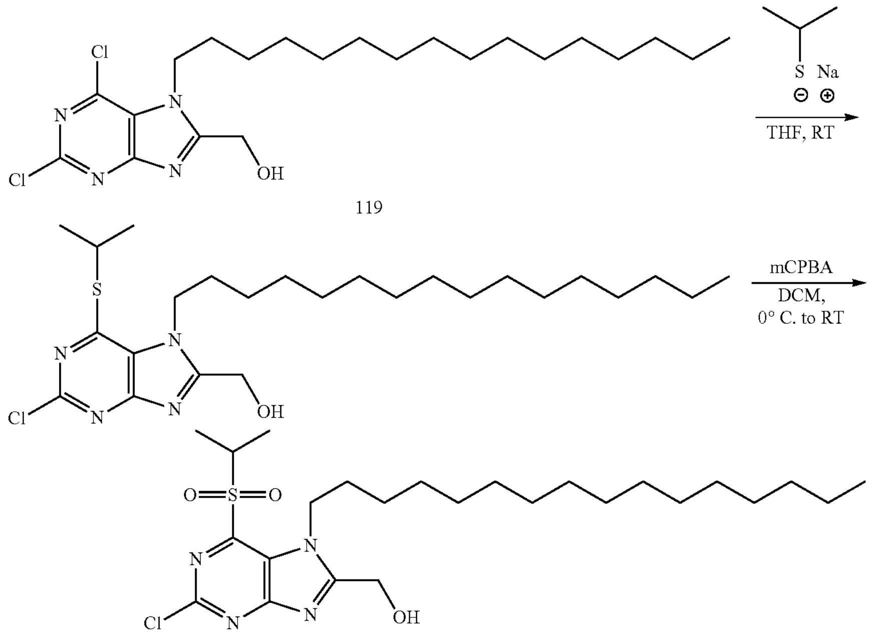

119

122

Method 3 was utilized with corresponding 2,6-DiCl intermediate to provide product in two steps.

Step 1: 43 mg of crude product. LCMS: m/Z 483.32 $(M+H)^+$

Step 2: Crude product was purified on C18 reverse phase gradient column chromatography using Solvent A: Water and Solvent B: Acetonitrile. Pure fractions were combined and lyophilized to get 15 mg of pure product. LCMS: m/Z 515.28 $(M+H)^+$.

Compound 123: Methyl 10-(2,6-dichloro-8-methyl-7H-purin-7-yl)decanoate

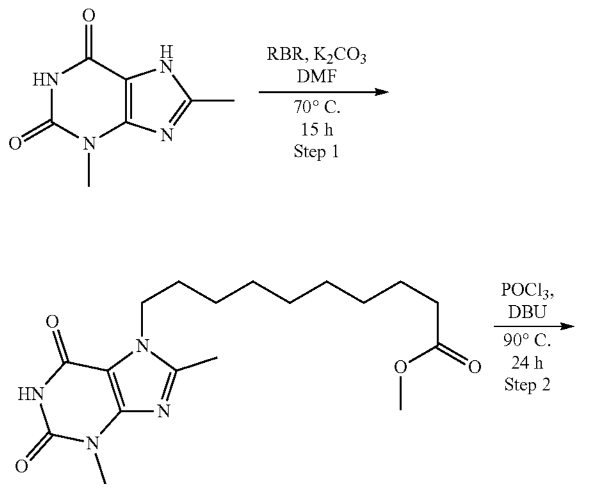

-continued

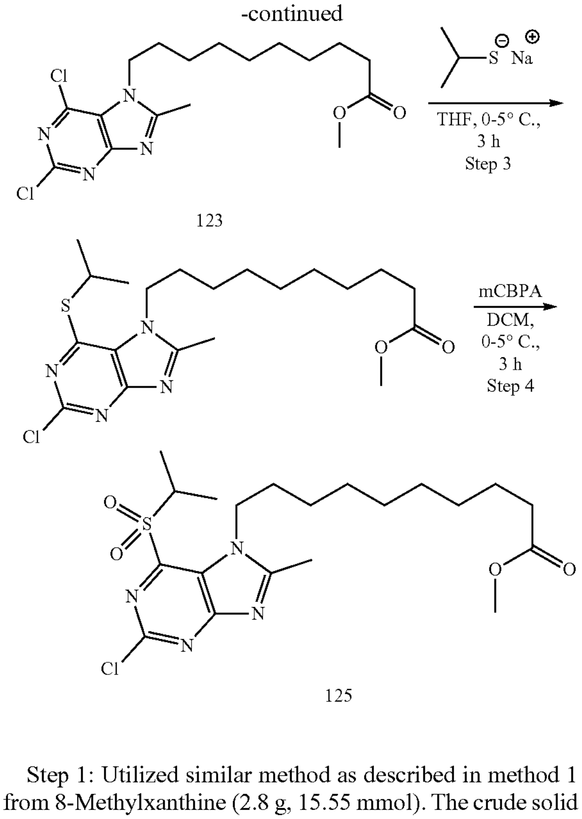

123

125

Step 1: Utilized similar method as described in method 1 from 8-Methylxanthine (2.8 g, 15.55 mmol). The crude solid was filtered and dried under high vacuum to give the desired product (4.66 g, 82%) as a white solid. $^1$H-NMR ($CDCl_3$ with 0.03% v/v TMS) δ 8.26 (bs, 1H), 4.20 (t, J=7.4 Hz, 2H), 3.67 (s, 3H), 3.52 (s, 3H), 2.47 (s, 3H), 2.30 (t, J=7.4 Hz, 2H), 1.78 (m, 2H), 1.60 (m, 2H), 1.4-1.2 (m, 1OH).

Step 2: $POCl_3$ Procedure (as described in method 2b). Compound 123 (4.13 g, 87%) as an orange solid. HPLC purity 95%; LCMS: m/Z 385.14 (M+H), 387.16 (M−H); $^1$H-NMR ($CDCl_3$ with 0.03% v/v TMS) δ 4.36 (m, 2H), 3.67 (s, 3H), 2.71 (s, 3H), 2.30 (t, J=7.5 Hz, 2H), 1.83 (m, 2H), 1.61 (m, 2H), 1.49-1.22 (m, 10H).

Compound 125: Methyl 10-(2-chloro-6-(isopropylsulfonyl)-8-methyl-7H-purin-7-yl)decanoate Step 3: Method 3 was utilized with corresponding 2,6-DiCl intermediate to provide product in two steps from product 123.

Crude sulfide (544 mg) was obtained as a viscous orange oil. After drying under high vacuum, the oil slowly solidified to a low-melting orange solid on standing. LCMS: m/Z 449.09 (M+Na). $^1$H-NMR ($CDCl_3$ with 0.03% v/v TMS, 300 MHz): δ 4.38 (sept, J=6.9 Hz, 1H), 4.28 (m, 2H), 3.67 (s, 3H), 2.62 (s, 3H), 2.31 (t, J=7.4 Hz, 2H), 1.80 (m, 2H), 1.62 (m, 2H), 1.50 (d, J=6.9 Hz, 6H), 1.46-1.22 (m, 10H).

Step 4: The crude sulfide (274 mg, 0.642 mmol, 1 eq) was converted to the sulfone which was purified by reverse-phase preparative HPLC followed by lyophilization to get the pure product (167 mg, 57%) as a viscous pale yellow oil. LCMS: m/Z 459.13 (M+H), 457.17 (M−H); $^1$H-NMR ($CDCl_3$ with 0.03% v/v TMS, 300 MHz): δ 4.57 (m, 2H), 4.43 (sept, J=6.9 Hz, 1H), 3.67 (s, 3H), 2.78 (s, 3H), 2.30 (t, J=7.2 Hz, 2H), 1.84 (m, 2H), 1.61 (m, 2H), 1.52 (d, J=6.9 Hz, 6H), 1.46-1.24 (m, 10H).

Compound 124: methyl 10-(2-chloro-6-(isopropylsulfinyl)-8-methyl-7H-purin-7-yl)decanoate

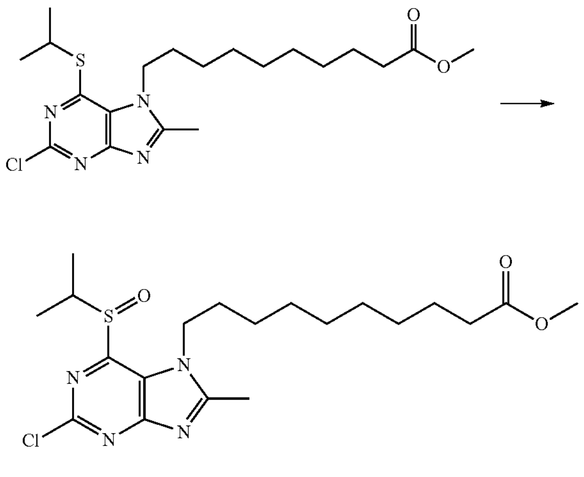

Sulfide from step 3 (30 mg, 0.07 mmol) was dissolved in aqueous methanol and to this was added oxone (22 mg, 0.14 mmol). This was stirred for 12 h and was concentrated to remove methanol and then partitioned in DCM and water. The organic layer was dried over sodium sulfate, filtered, and concentrated. The compound was then purified by reverse phase HPLC [RPHPLC] in water and acetonitrile [0-100%] to give 16 mg (52%) as a white solid. LCMS: m/z 443.31 (M+H); $^1$H-NMR (CDCl3) δ 4.76 (m, 1H), 4.36 (m, 1H), 3.80 (m, 1H), 3.66 (s, 3H), 2.75 (s, 3H), 2.26 (t, J=7.8 MHz, 2H), 1.78 (m, 1H), 1.58 (m, 3H), 1.36 (d, J=7.2 MHz, 6H), 1.28 (m, 12H).

Compound 126: Methyl 16-(2,6-dicyano-8-methyl-7H-purin-7-yl)hexadecanoate

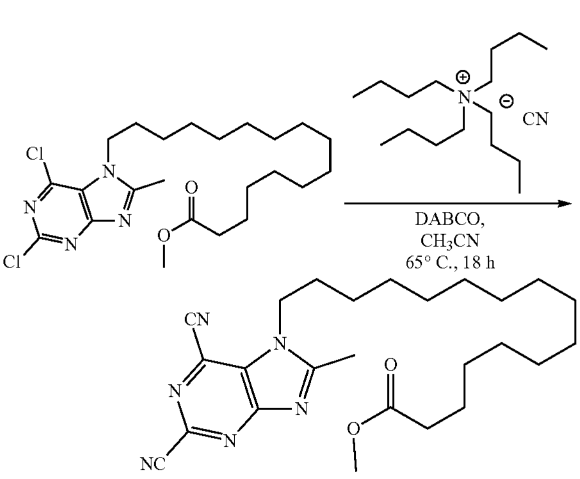

126

To a solution of the dichloro derivative (150 mg, 0.32 mmol) in acetonitrile (5 mL) was added tetra-n-butylammonium cyanide (129 mg, 0.48 mmol) and DABCO (54 mg, 0.48 mmol). The dark brown reaction mixture was heated at 65° C. for 12 h. After cooling to room temperature, the mixture was poured into a separatory funnel containing ethyl acetate and water. The aqueous layer was separated and re-extracted with ethyl acetate. The combined organic layer was washed with water and passed through a cotton plug to remove insoluble matter. The clear brown organic layer was evaporated in vacuo to get a dark brown solid which was treated with acetonitrile/methanol. On standing, an insoluble solid precipitated out. The mixture was centrifuged and the solid was separated from the supernatant. The solvent was evaporated in vacuo and the residue was further purified by reverse-phase preparative HPLC to obtain the desired product (6 mg) as a brown solid. LCMS: m/Z 453.32 (M+H), 451.05 (M−H); $^1$H-NMR ($CDCl_3$ with 0.03% v/v TMS, 300 MHz): δ 4.29 (m, 2H), 3.67 (s, 3H), 2.55 (s, 3H), 2.30 (t, J=7.4 Hz, 2H), 1.80 (m, 2H), 1.61 (m, 2H), 1.4-1.2 (m, 22H).

Compound 127: 4-(10-(2-chloro-6-(isopropylsulfinyl)-8-methyl-7H-purin-7-yl)decyl)morpholine 4-oxide and compound 129: 4-(10-(2-chloro-6-(isopropylthio)-8-methyl-7H-purin-7-yl)decyl)morpholine 4-oxide

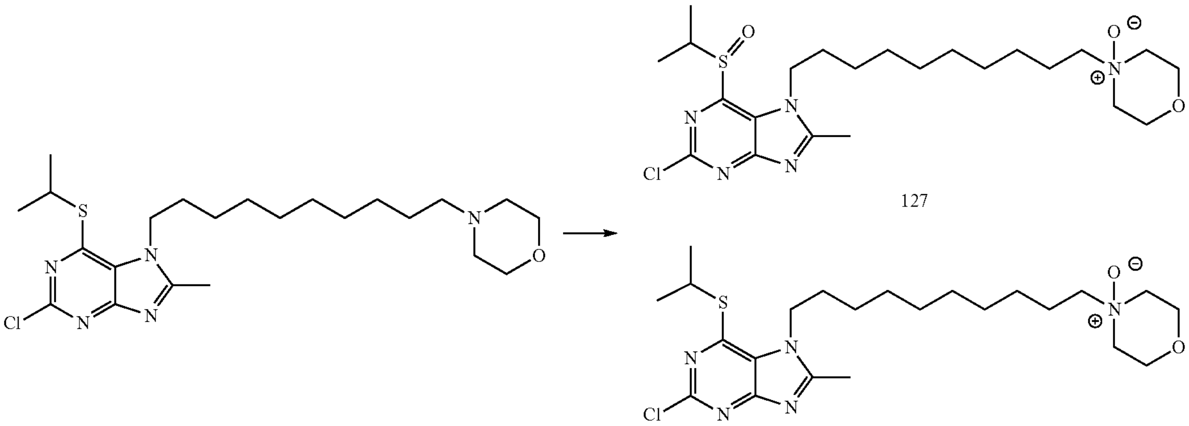

127

129

Sulfide (50 mg, 0.107 mmol) was dissolved in methanol. Oxone was added and the reaction for stirred for 48 h. The reaction mixture was concentrated to remove methanol and then partitioned in DCM and water. The organic layer was dried over sodium sulfate, filtered, and concentrated. The sulfoxide and sulfide were separated by RPHPLC with 0.02 M ammonium acetate and acetonitrile. Each compound was then desalted by passing through C18 in just water and acetonitrile.

Compound 127:10 mg (10%): LCMS: m/z 500.28 (M+H).

Compound 129: 2 mg (3%) LCMS: m/z 484.33 (M+H) $^1$H-NMR (CDCl3) δ 4.40 (m, 2H), 4.25 (m, 2H), 3.23 (m, 4H), 3.06 (d, J=11.1 MHz, 2H), 2.58 (m, 5H), 1.95 (m, 2H), 1.78 (m, 2H), 1.47, (d, J=6.6 MHz 6H), 1.31 (in, 12H).

Compound 128: methyl 16-(2-chloro-6-(isopropylsulfinyl)-8-methyl-7H-purin-7-yl)hexadecanoate

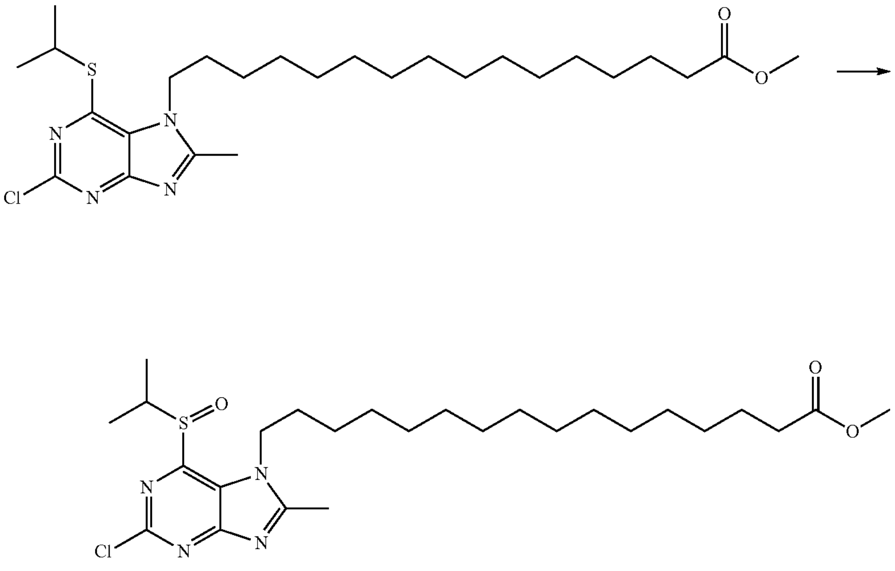

Sulfide (50 mg, 0.098 mmol) was dissolved in aqueous methanol and to this was added oxone (30 mg, 0.196 mmol). This was stirred for 12 h. The reaction was concentrated to remove methanol and then partitioned in DCM and water. The organic layer was dried over sodium sulfate, filtered, and concentrated. The compound was then purified by RPHPLC in water and acetonitrile to give 16 mg (31%) as a white solid. LCMS: m/z 527.31 (M+H); $^1$H-NMR (CDCl3) δ 4.76 (m, 1H), 4.36 (m, 1H), 3.80 (m, 1H), 3.66 (s, 3H), 2.75 (s, 3H), 2.30 (t, J=7.8 MHz, 2H), 1.77, (in, 1H), 1.61 (m, 31), 1.34 (d, J=7.2 MHz, 6H), 1.24 (m, 24H).

Compound 130: methyl (R)-6-((1-(2,6-dichloro-8-methyl-7H-purin-7-yl)hexyl)pyrrolidin-3-yl)oxy) hexanoate

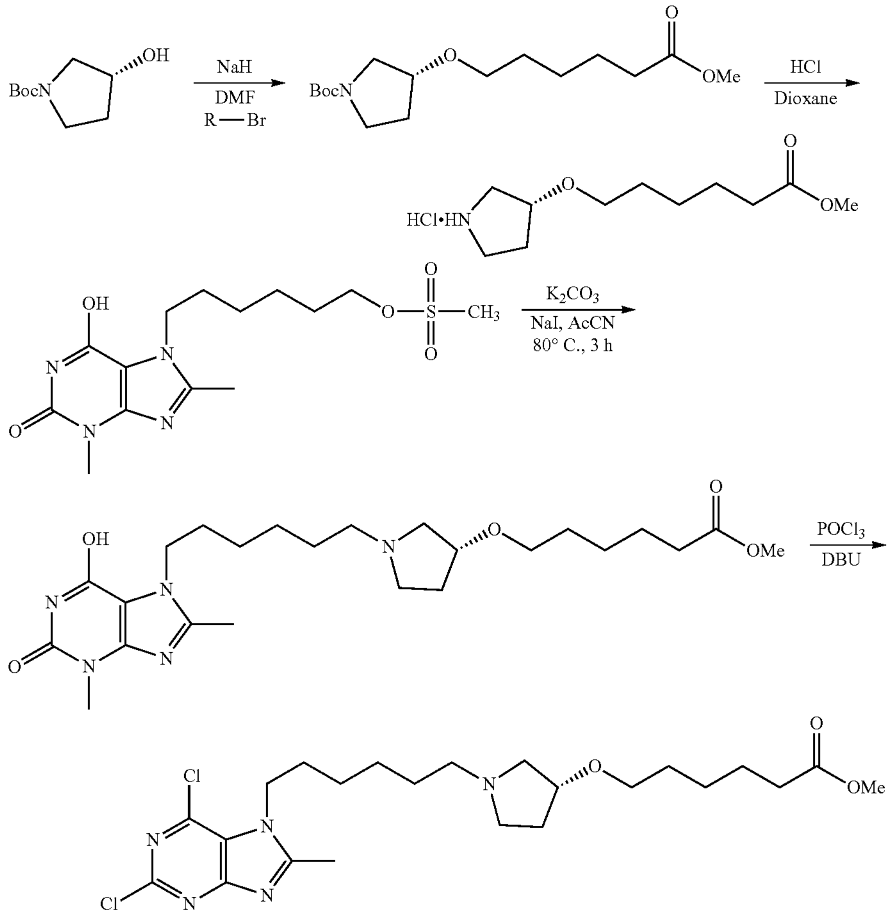

130

Step 1: A solution of (R)-(−)-N-Boc-3-pyrrolidinol (1.0 g, 5.34 mmol) in DMF (5.0 mL) was added dropwise to a suspension of NaH (320 mg, 8.0 mmol, 60% w/w dispersion in mineral oil) in DMF (10.0 mL) at 0° C. The reaction mixture was allowed to warm to room temperature and was stirred for 1 hour. 6-bromo-hexanoic acid methyl ester (1.67 g, 8.0 mmol) in DMF (5.0 mL) was added to reaction mixture. Reaction mixture was stirred at room temperature for overnight. The reaction mixture was partitioned between DCM (50.0 mL) and water (50.0 mL). DCM layer was collected, aqueous layer was re extracted with DCM (25.0 mL). Combined organic layers were dried over $Na_2SO_4$ and concentrated under reduced pressure to get crude product. Crude product was purified on combi-flash silica gel column chromatography using 0-50% ethyl acetate in hexane. Pure fractions were evaporated under reduced pressure to dryness to ger 190 mg of pure product. LCMS: m/Z 316.5 $(M+H)^+$. $^1$H-NMR ($CDCl_3$) δ 3.98 (m, 1H), 3.66 (s, 3H), 3.4 (m, 6H), 2.31 (t, J=7.5, 2H), 1.95 (m, 2H), 1.61 (m, 4H), 1.45 (s, 9H), 1.39 (m, 2H).

Step 2: HCl in dioxane solution (1.0 mL, 4.0 M) was added to a reaction mixture containing tert-butyl (R)-3-((6-methoxy-6-oxohexyl)oxy)pyrrolidine-1-carboxylate (190 mg, 0.602 mmol). Reaction mixture was stirred at room temperature for 1 hour. Solvents were evaporated under reduced pressure and was re-dissolved in dioxane (50.0 μL) and precipitated by adding diethyl ether (5.0 mL). Product was collected by centrifugation and dried under high vacuum to get 130 mg of product as off-white solid. LCMS: m/Z 216.21 $(M+H)^+$. $^1$H NMR ($CDCl_3$) δ 4.15 (m, 1H), 3.66 (s, 3H), 3.4 (m, 6H), 2.31 (t, J=7.5, 2H), 2.3 (m, 1H), 2.0 (m, 1H), 1.79 (m, 1H), 1.59 (m, 411), 1.35 (m, 2H).

Step 3: A solid 6-(6-hydroxy-3,8-dimethyl-2-oxo-2,3-dihydro-7H-purin-7-yl)hexyl methanesulfonate (170 mg, 0.476 mmol) was added to a mixture Methyl (R)-6-(pyrrolidin-3-yloxy)hexanoate hydrochloride (120 mg, 0.476 mmol), $K_2CO_3$ (131 mg, 0.952 mmol) and NaI (35 mg, 0.238 mmol) in acetonitrile (10.0 mL). Reaction mixture was heated to 80° C. for 3 h and then was cooled to room temperature. The reaction mixture was diluted with DCM (15.0 mL) and concentrated under reduced pressure. The residue was dissolved in DCM (25.0 mL) and washed with water (20.0 mL). Organic layer was dried over $Na_2SO_4$ and concentrated under reduced pressure and was purified on combiflash silica gel column chromatography using 1% $Et_3N$ in DCM to get 150 mg of pure product. LCMS: m/Z 478.36 $(M+H)^+$, 476.14 $(M-H)^+$. $^1$H-NMR (CDCl3) δ 4.21 (m, 2H), 4.0 (m, 111), 3.66 (s, 3H), 3.51 (s, 3H), 3.35 (m, 2H) 2.88 (m, 2H), 2.7 (m, 2H), 2.48 (m, 2H) 2.46 (s, 3H), 2.3 (t, J=7.5, 2H), 2.1 (m, 1H), 1.8 (m, 2H), 1.56 (m, 2H), 1.58 (m, 611), 1.38 (m, 6H).

Step 4: $POCl_3$ Procedure as described in method 2b was followed. Crude product was purified on $C_{1s}$ reverse phase gradient column chromatography using solvent A: Water and solvent B: Acetonitrile, pure fractions were collected and lyophilized to get 15 mg of pure product 130. LCMS: m/Z 500.34 $(M+H)^+$. $^1$H-NMR ($CDCl_3$) δ 4.36 (m, 2H), 4.05 (m, 1H), 3.67 (s, 3H), 3.37 (m, 2H) 3.2 (m, 2H), 2.95 (m, 2H), 2.71 (s, 3H), 2.65 (m, 2H), 2.31 (t, J=7.5, 2H), 2.04 (m, 211), 1.85 (m, 2H), 1.6 (m, 6H), 1.39 (m, 6H).

Compound 131: 16-(2-chloro-6-(isopropylsulfonyl)-8-methyl-7H-purin-7-yl)-N-methylhexadecaanamide

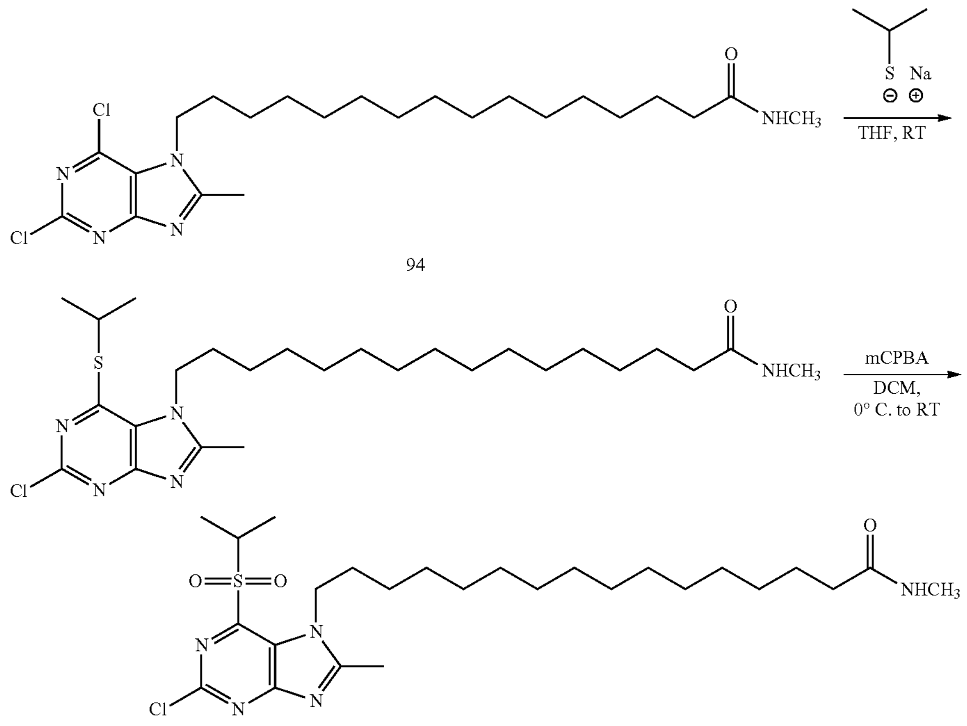

94

131

Method 3 was utilized with corresponding 2,6-DiCl intermediate to provide product in two steps.

Step 1: Crude product was dissolved in DCM (50 mL) passed through silica plug, solvents were evaporated under reduced pressure to give 40 mg of sulfide.

Step 2: Crude product was purified on C18 reverse phase gradient column chromatography using water and acetonitrile to get 15 mg of product. LCMS: m/Z 542.43 $(M+H)^+$. $^1$H-NMR ($CDCl_3$): δ 5.4 (bs, 111), 4.54 (m, 2H), 4.4 (m, 1H), 2.8 (d, 3H), 2.76 (s, 3H), 2.15 (t, J=7.5, 2H), 1.57 (m, 2H), 1.52 (d, 3H), 1.49 (d, 3H), 2.24 (m, 24H).

Compound 132: (R)-(2,2-dimethyl-1,3-dioxolan-4-yl)methyl 16-(2-chloro-6-(isopropylsulfonyl)-8-methyl-7H-purin-7-yl)hexadecanoate

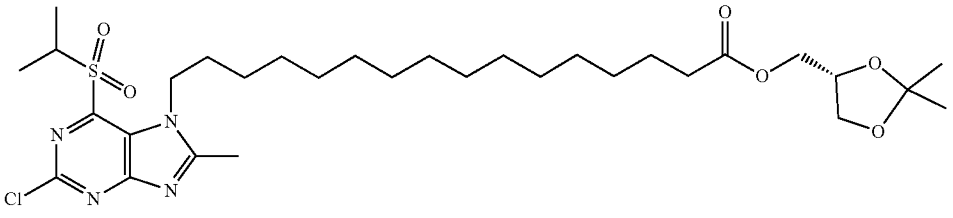 [SMILES: Cc1nc2nc(Cl)nc(S(=O)(=O)C(C)C)c2n1CCCCCCCCCCCCCCCC(=O)OC[C@H]1COC(C)(C)O1]

Method 4 was utilized with corresponding ROH which provided both 132 and 133 which were separated by c18 column chromatography using 0-100% ACN-Water to provide products. Compound 132; LCMS: m/Z 643.3 (M+H).

Compound 133: (R)-2,3-dihydroxypropyl 16-(2-chloro-6-(isopropylsulfonyl)-8-methyl-7H-purin-7-yl)hexadecanoate

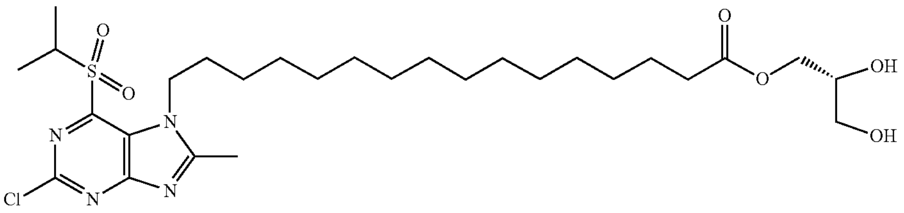 [SMILES: Cc1nc2nc(Cl)nc(S(=O)(=O)C(C)C)c2n1CCCCCCCCCCCCCCCC(=O)OC[C@H](O)CO]

Compound 133; LCMS: m/Z 603.3 (M+H).

Compound 134: (S)-(2,2-dimethyl-1,3-dioxolan-4-yl)methyl 16-(2-chloro-6-(isopropylsulfonyl)-8-methyl-7H-purin-7-yl)hexadecanoate

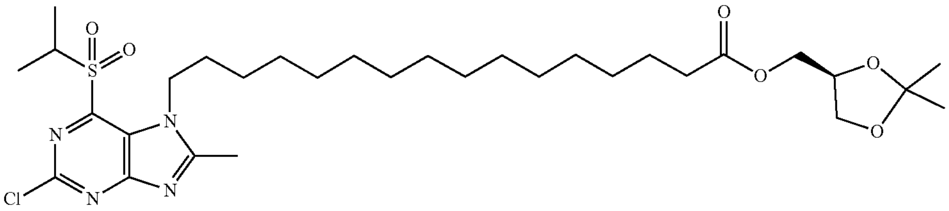 [SMILES: Cc1nc2nc(Cl)nc(S(=O)(=O)C(C)C)c2n1CCCCCCCCCCCCCCCC(=O)OC[C@@H]1COC(C)(C)O1]

Method 4 was utilized with corresponding ROH which provided both 134 and 135 which were separated by c18 column chromatography using 0-100% ACN-Water to provide products. Compound 134; LCMS: m/Z 643.3 (M+H).

Compound 135: (S)-2,3-dihydroxypropyl 16-(2-chloro-6-(isopropylsulfonyl)-8-methyl-7H-purin-7-yl)hexadecanoate

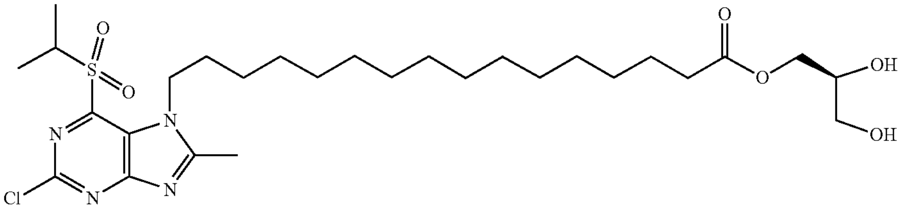 [SMILES: Cc1nc2nc(Cl)nc(S(=O)(=O)C(C)C)c2n1CCCCCCCCCCCCCCCC(=O)OC[C@@H](O)CO]

LCMS: m/Z 603.3 (M+H); $^{1}$H-NMR ($CDCl_3$) 4.57 (m, 2H), 4.28 (m, 2H), 4.18 (m, 2H), 3.94 (m, 1H), 3.85 (m, 1H), 3.66 (m, 2H), 2.77 (s, 3H), 2.35 (dd, J=7.2 Hz, 7.5 Hz, 2H), 1.82 (m, 2H), 1.62 (m, 3H), 1.52 (d, J=6.9 Hz), 1.41-1.25 (broad m, 22H).

Compound 136: 4-(10-(2-chloro-6-(isopropylsulfinyl)-8-methyl-7H-purin-7-yl)decyl)morpholine Compound 137: 4-(10-(2-chloro-6-(isopropylsulfonyl)-8-methyl-7H-purin-7-yl)decyl)morpholine

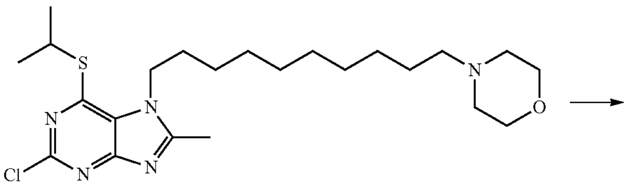

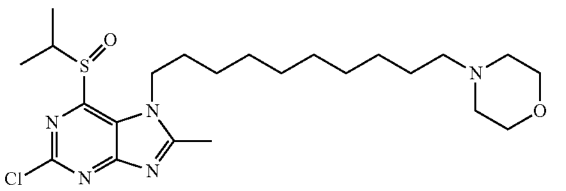

136

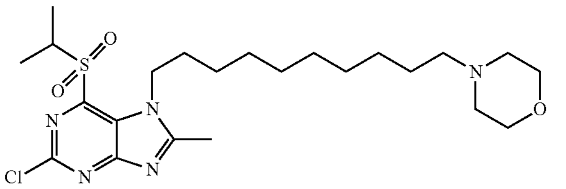

137

Sulfide (50 mg, 0.107 mmol) was dissolved in ethyl acetate and cooled in an ice bath. To this solution was added 0.2 mL of 4M HCl in dioxane. Solid began to precipitate immediately, and the mixture was stirred on ice for 30 minutes before letting warm to ambient temperature for 12 h. The ethyl acetate was decanted and the solid washed with more ethyl acetate, to remove any remaining free base, and then dried under vacuum. The salt was then taken (31 mg, 0.062 mmol) and dissolved in methanol. Oxone was added and the reaction let stir for 12 h. The reaction mixture was concentrated to remove methanol and then partitioned in DCM and water. The organic layer was dried over sodium sulfate, filtered, and concentrated. The crude was subjected to RPHPLC with 0.02 M ammonium acetate and acetonitrile as solvent and fractions were isolated. After evaporation, each compound was then desalted by passing through C18 in just water and acetonitrile.

Compound 136: 5 mg (10%); LCMS: m/z 484.21 (M+H); $^1$H-NMR (CDCl3) δ 4.76 (m, 1H), 4.36 (m, 1H), 3.78 (m, 1H), 3.75 (m, 4H), 2.75 (s, 3H), 2.50 (m, 4H), 2.36 (t, J=7.5 MHz, 2H), 1.77, (m, 1H), 1.49 (m, 1H), 1.34 (d, J=7.2 MHz, 6H), 1.26 (m, 14H).

Compound 137: 1.5 mg (3%) LCMS: m/z 500.34 (M+H)

Compound 138. 2-chloro-7-hexadecyl-8-methyl-7H-purin-6-amine

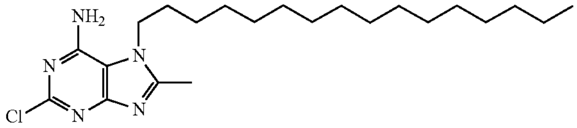 [SMILES: CCCCCCCCCCCCCCCCn1c(C)nc2nc(Cl)nc(N)c21]

Di-Cl compound (50 mg) was dissolved in ethanol. To this solution was added NH3 in EtOH (10eq). The reaction mixture was heated at 60° C. for 12 h. The reaction mixture was concentrated to remove ethanol. The semi solid was taken in hexane and washed several times in hexane and filtered to provide the product 138. LCMS: m/Z 408.3 (M+H); Compound 139. 16-(2-chloro-6-(isopropylsulfonyl)-8-methyl-7H-purin-7-yl)hexadecanoic acid

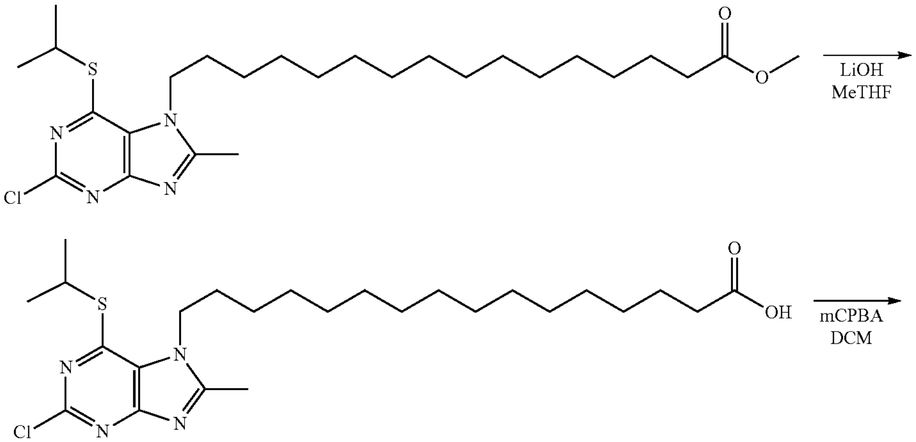

-continued

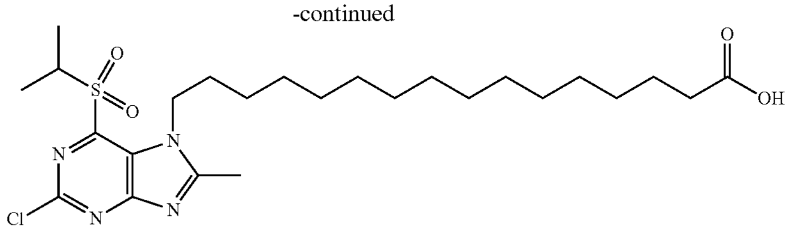

139

Step 1: To a solution of the sulfide analog (500 mg) in Methyl THF (2 mL) was added LiOH (3eq) in water (1 mL). The reaction was stirred for 4 h at rt. After cooling, 1N HCl (1 mL) was added, and the reaction mixture was extracted with EtOAc (2×10 ml). After drying, the evaporation of organic layer provided a yellowish solid, which was taken to next step without further purification. LCMS: m/Z 497.3 (M+H).

Step 2: Method 3 was utilized to oxidize the above sulfide using mCPBA to provide product 139. LCMS: m/Z 529.3 (M+H).

Compound 140 2-chloro-6-(isopropylsulfonyl)-8-methyl-7-(15-(1-methyl-1H-tetrazol-5-yl)pentadecyl)-7H-purine

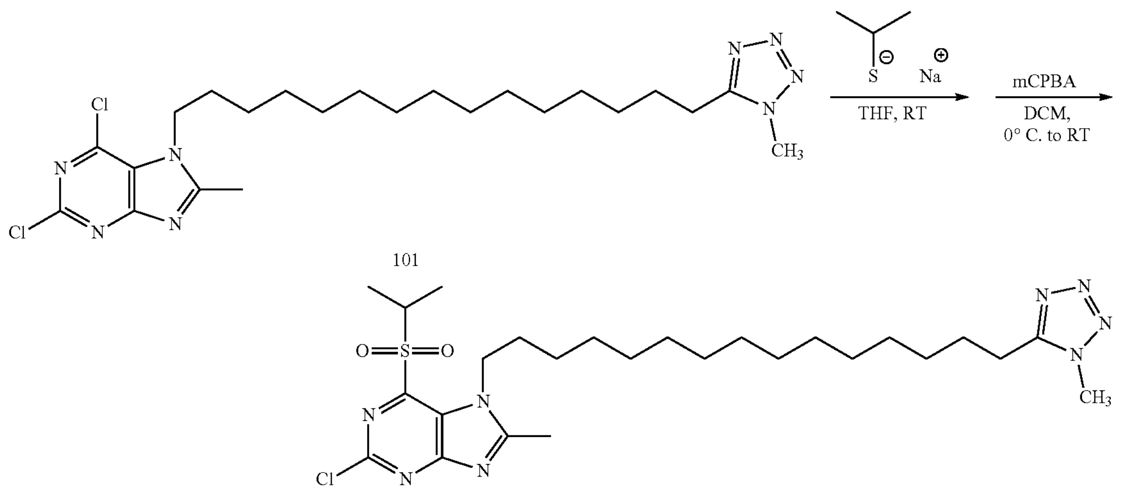

Method 3 was utilized with corresponding 2,6-DiCl intermediate to provide product in two steps. Organic layers were dried over $Na_2SO_4$ and concentrated under reduced pressure to give 30 mg of crude product. LCMS: m/Z 567.39 $(M+H)^+$.

Compound 141: Methyl 7-((8-(2,6-dichloro-8-methyl-7H-purin-7-yl)octyl)(methyl)amino)heptanoate

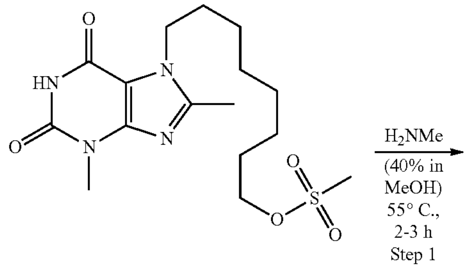

-continued

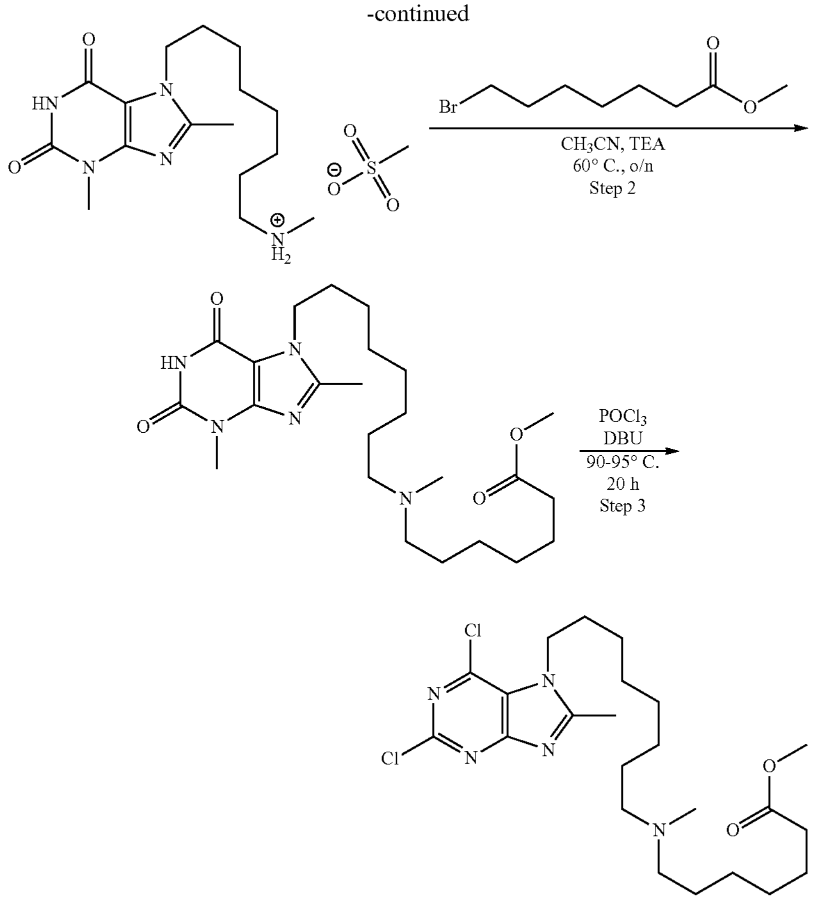

141

Step 1: The mesylate (0.450 g, 1.164 mmol) was weighed in a 40 mL glass vial containing a stir bar. Methylamine (40% in methanol, 12 mL) was added and the clear colorless solution was heated at 40-45° C. in an oil-bath. Methanol was evaporated in vacuo and the residue was taken up in DCM (20 mL). The organic layer was washed with water, dried over anhydrous $Na_2SO_4$, filtered and the solvent evaporated DCM in vacuo to get the mesylate salt of the amine as a foamy solid (485 mg, quantitative) that was carried over to the next step. LCMS: m/Z 322.30 (M+H), 320.09 (M−H); $^1$H-NMR ($CDCl_3$ w/0.03% v/v TMS, 300 MHz): δ 4.21 (t, J=7.6 Hz, 2H), 3.52 (s, 3H), 2.94 (m, 2H), 2.79 (s, 3H), 2.71 (s, 3H), 2.47 (s, 3H), 1.78 (m, 4H), 1.42-1.24 (m, 8H).

Step 2: The mesylate salt of the amine (472 mg, 1.13 mmol) was dissolved in $CH_3CN$ (10 mL) in a 40 mL glass vial. TEA (0.29 g, 2.83 mmol, 0.4 mL) was added and the solution was stirred. Methyl 7-bromoheptanoate (379 mg, 1.7 mmol) was added and the mixture was heated for 20 h at 60° C. on a heating block. After 20 h, LCMS and TLC (DCM/MeOH, 9:1) showed the mass of the desired product. Acetonitrile was evaporated in vacuo and the crude material was dissolved in DCM (30 mL) and washed with water (20 mL). The organic layer was dried over anhydrous $Na_2SO_4$ and the crude was purified by automated column chromatography using DCM/methanol as the eluent system to give the pure product (330 mg, 63%) as a white foamy solid. HPLC purity 95%. LCMS: m/Z 464.04 (M+H), 462.09 (M−H); $^1$H-NMR ($CDCl_3$ w/0.03% v/v TMS, 300 MHz): δ 8.49 (bs, 1H), 4.21 (t, J=7.6 Hz, 2H), 3.67 (s, 3H), 3.53 (s, 3H), 2.99 (m, 4H), 2.76 (s, 3H), 2.48 (s, 3H), 2.32 (t, J=7.1 Hz, 2H), 1.98-1.72 (m, 6H), 1.63 (m, 2H), 1.42-1.24 (m, 12H). Step 3: $POCl_3$ Procedure as described in method 2b was followed. The crude was purified by reverse-phase HPLC gave the desired product (10 mg) as a brown oil. LCMS: m/Z 486.35 (M+H), 484.27 (M−H); HPLC purity 99.5%; $^1$H-NMR ($CDCl_3$ with 0.03% v/v TMS) 4.36 (m, 2H), 3.67 (s, 3H), 2.71 (s, 3H), 2.31 (m, 6H), 2.20 (s, 3H), 1.82 (m, 2H), 1.63 (m, 2H), 1.52-1.2 (m, 18H).

Compound 142

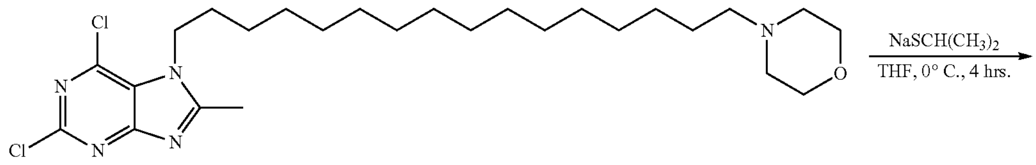

-continued

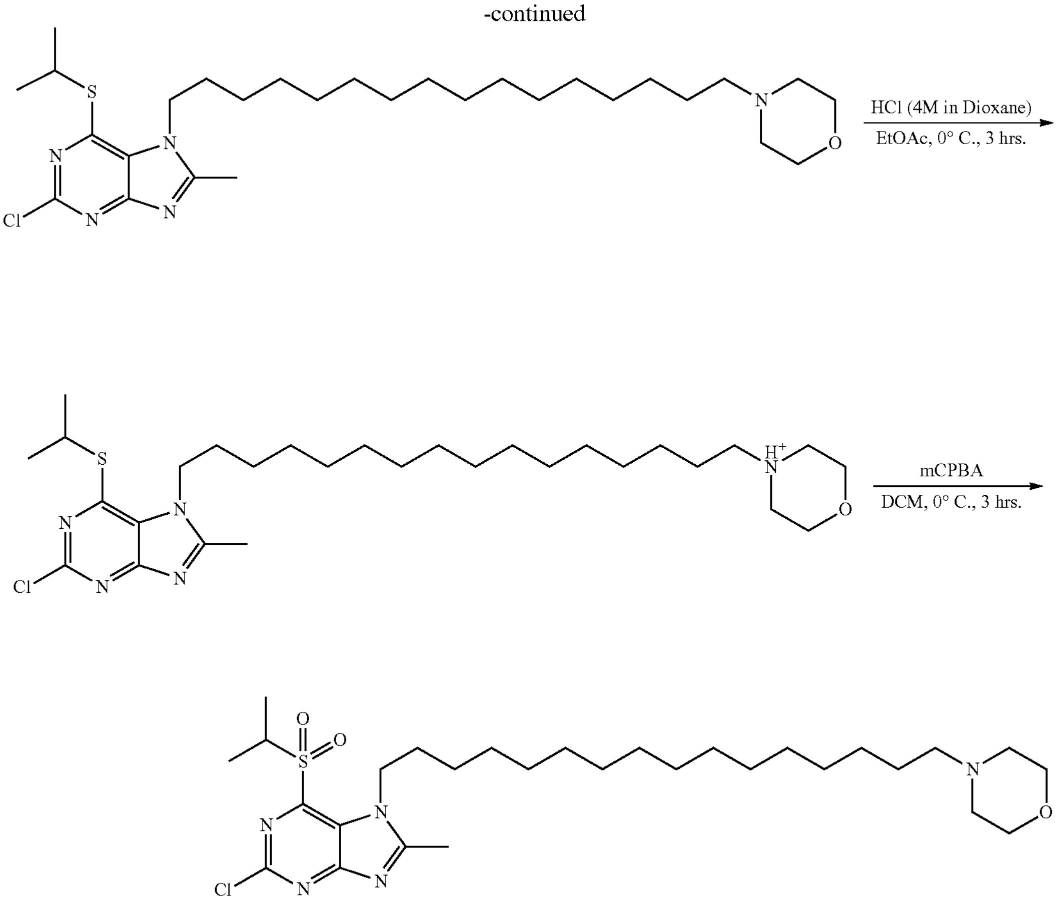

Step 1: Method 3 was utilized with corresponding 2,6-DiCl intermediate to provide product. Crude was purified on a reverse phase C18 column eluting with $CH_3CN$: $H_2O$ (0-100%). Fractions were collected, reduced, frozen, and lyophilized to provide 40 mg of 4-(16-(2-chloro-6-(isopropylthio)-8-methyl-7H-purin-7-yl)hexadecyl)morpholine. (67%). LCMS: m/Z 552.51 (M+H)

Step 2: 4-(16-(2-chloro-6-(isopropylthio)-8-methyl-7H-purin-7-yl)hexadecyl)morpholine was dissolved in EtOAc and placed in an ice bath (0-5° C.). To this was added 0.1 mL of 4M HCl in dioxane. White solid crashed out immediately. Reaction was kept stirring at (0-5° C.) for 3 hours. At this point the reaction mixture was centrifuged at 2500 rpm for 3 minutes. Mother liquor was decanted off and kept aside. Wet solids were dried on high vacuum. Used without further purification or structure elucidation.

Step 3: Product from step 2 was dissolved in DCM and was placed on an ice bath (0-5° C.). To this was added mCPBA (32 mg, 0.19 mmol) and was dissolved in additional cold DCM. Reaction was kept for 3 hours and was quenched with 200 μL of 10% $Na_2SO_{3(aq.)}$. Reaction mixture was then washed once with 2.0 mL of saturated $NaHCO_{3(aq.)}$. DCM was removed in vacuo. Crude residue was redissolved in DMSO and passed through a reverse phase C18 column eluting with $CH_3CN$: $H_2O$ (0-100%). Fractions were collected, frozen, and lyophilized to obtain 1.9 mgs. of 142 as transparent crystals (7%). LCMS: m/Z 584.40 (M+H); m/Z 582.00 (M−H); $^1$H-NMR ($CDCl_3$) δ 4.57 (t, 2H), 4.40 (m, 1H), 3.73 (m, 4H), 2.77 (s, 3H), 2.44 (m, 4H), 2.29 (t, 2H), 1.85 (m, 2H), 1.53 (d, 6H), 1.26 (m, 26H).

143: (3R)-1-(6-(2-chloro-6-(isopropylsulfonyl)-8-methyl-7H-purin-7-yl)hexyl)-3-((6-methoxy-6-oxohexyl)oxy)pyrrolidin-1-ium chloride

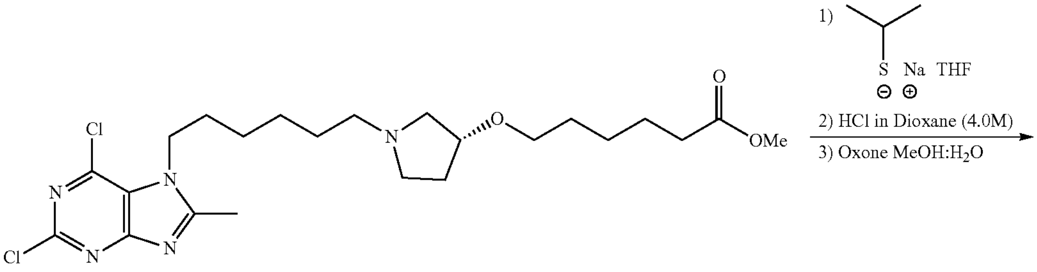

-continued

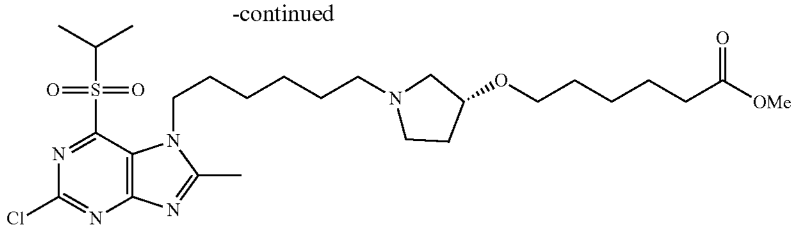

143

Step 1: Method 3 was utilized with corresponding 2,6-DiCl intermediate to provide product. Methyl LCMS: m/Z 540.17 $(M+H)^+$.

Step 2: HCl in dioxane solution (1.0 mL, 4.0 M) was added to a reaction mixture containing methyl (R)-6-((1-(6-(2-chloro-6-(isopropylthio)-8-methyl-7H-purin-7-yl)hexyl) pyrrolidin-3-yl)oxy)hexanoate (10 mg, 0.02 mmol) and was stirred at room temperature for 1 hour. Solvents were evaporated under reduced pressure and dried under vacuum to get the product. Product (salt) was re-dissolved in MeOH (500 μL) and cooled to 0° C. A solution of $KHSO_5$ (30 mg, 0.1 mmol) in water (500 mL) was added and the resulting slurry was stirred at room temperature for 4 hours. Methanol was evaporated and product was extracted with EtOAc (2×5 mL), combined organic layers were dried over $Na_2SO_4$ and concentrated under reduced pressure to get crude product. Crude product was purified on C18 reverse phase gradient chromatography by using 0.02 M ammonium acetate as buffered solvent A and Acetonitrile as solvent B. Pure fraction were combined, desalted and lyophilized to get 0.6 mg of pure product. LCMS: m/Z 572.3 $(M+H)^+$.

Compound 144. 2-hydroxyethyl 16-(2-chloro-6-(isopropylsulfonyl)-8-methyl-7H-purin-7-yl)hexadecanoate

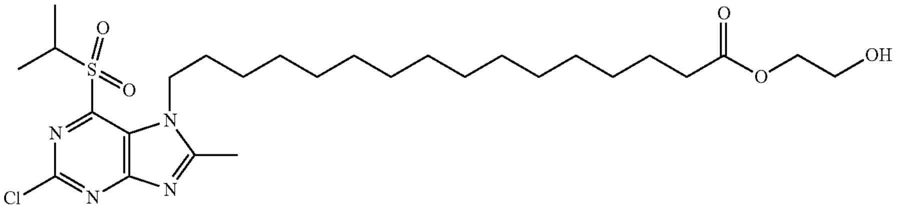 [SMILES: Cc1nc2nc(Cl)nc(S(=O)(=O)C(C)C)c2n1CCCCCCCCCCCCCCCC(=O)OCCO]

Method 4 was utilized with corresponding ROH which provided a crude which was purified by c18 column chromatography using 0-100% ACN-Water to provide product 144. LCMS: m/Z 573.3 (M+H).

Compound 145. 16-(2-chloro-6-(isopropylsulfonyl)-8-methyl-7H-purin-7-yl)-1-morpholinohexadecan-1-one

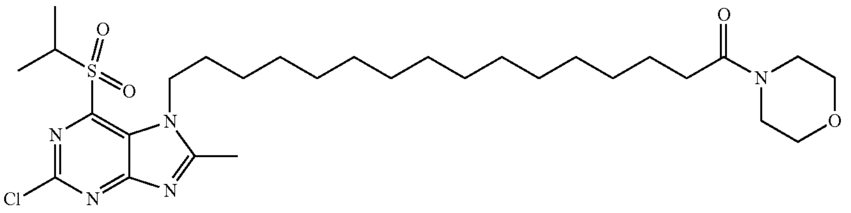 [SMILES: Cc1nc2nc(Cl)nc(S(=O)(=O)C(C)C)c2n1CCCCCCCCCCCCCCCC(=O)N1CCOCC1]

To a solution of the acid (100 mg) in DMF (1 mL) was added EDC (1.5eq) and HOBt (1.5eq) followed by DIEA (1.5eq). Morpholine (1.5eq) was later added and the reaction was stirred for 12 h at rt. After cooling, sat $NaHCO_3$ (1 mL) was added, and the reaction mixture was extracted with EtOAc (2×10 ml). After drying, the evaporation of organic layer, provided a crude which was purified by c18 column chromatography using 0-100% ACN-Water to provide product 145 LCMS: m/Z 598.3 (M+H).

Compound 146: isopropyl 16-(2-chloro-6-((2-hydroxyethyl)sulfonyl)-8-methyl-7H-purin-7-yl)hexadecanoate

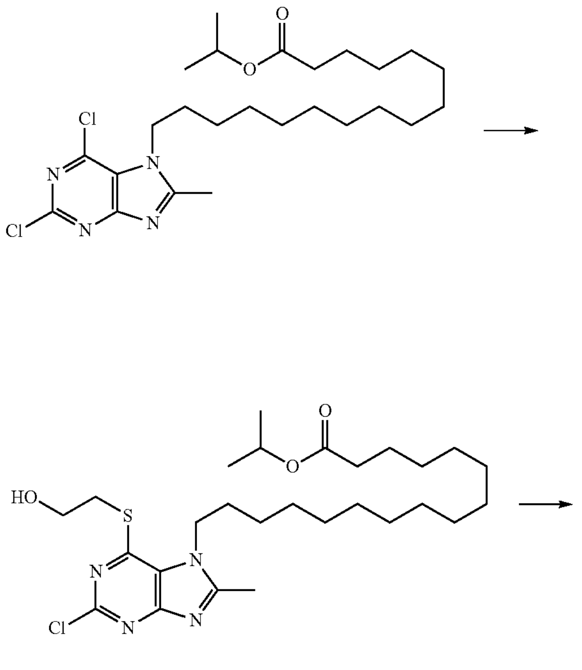

-continued

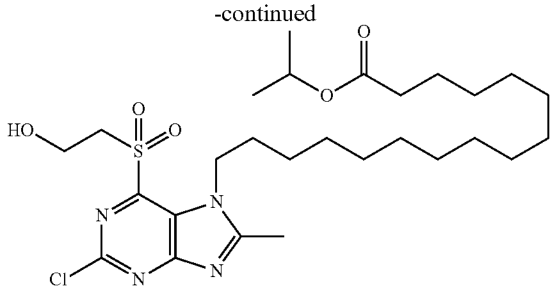

146

Step 1: Isopropyl 16-(2,6-dichloro-8-methyl-7H-purin-7-yl)hexadecanoate (50 mg, 0.100 mmol), was dissolved in anhydrous acetonitrile (1.5 mL) and to this was added 2-mercaptoehtanol (16 mg, 0.200 mmol), and triethylamine (0.034 mL, 0.240 mmol). The reaction was heated to 80° C. and monitored by LCMS. After 6 hours, the reaction was complete and concentrated to remove acetonitrile. The crude was the purified by flash chromatography in dichloromethane and methanol. About 45 mg (83% yield) was recovered as a white solid. LCMS: m/z 541.17 (M+H); $^1$H-NMR ($CDCl_3$) δ 5.00 (m, 1H), 4.29 (t, J=7.5 MHz, 2H), 4.04 (m, 2H), 3.58 (t, J=5.4 MHz, 2H), 3.29 (m, 1H), 2.64 (s, 3H), 2.25 (t, J=6.9 MHz), 2H), 1.82 (m, 2H), 1.61 (m, 2H), 1.24 (m, 28H). Step 2: Step 1 product (23 mg, 0.042 mmol) was dissolved in 1 mL anhydrous DCM and cooled in an ice bath. To this solution was added 70% mCPBA (21 mg, 0.085 mmol) and the reaction mixture was allowed to warm to ambient temperature. An additional 8 mg of mCPBA was added and the reaction stirred for 14 hours. Upon completion, the reaction was quenched with 5% sodium bicarbonate and shaken vigorously. The aqueous layer was extracted multiple times with DCM to extract all product. The organic layer was dried over sodium sulfate, filtered, and concentrated to provide the crude and was purified by RPHPLC in water and acetonitrile to give about 12 mg (50% yield) of the desired compound 146 as a white solid. LCMS: m/z 573.12 (M+H); $^1$H-NMR ($CDCl_3$) δ 5.02 (m, 1H), 4.55 (t, J=8.1 MHz, 2H), 4.29 (t, J=5.1 MHz, 2H), 4.03 (m, 2H), 2.80 (s, 3H), 2.27 (t, J=6.9 MHz, 2H), 1.86 (m, 2H), 1.62 (m, 2H), 1.24 (m, 28H).

Compound 147: methyl 16-(6-((2-aminoethyl)sulfonyl)-2-chloro-8-methyl-7H-purin-7-yl)hexadecanoate

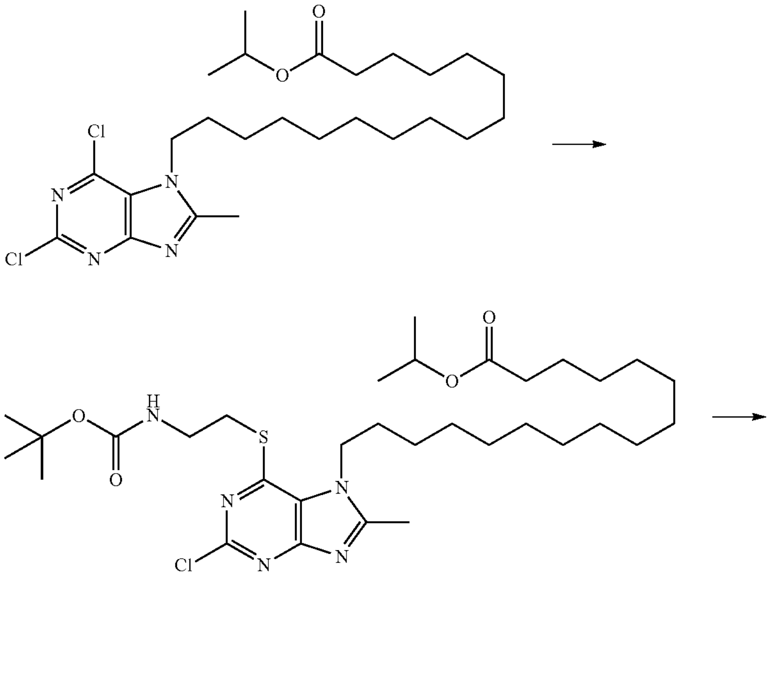

-continued

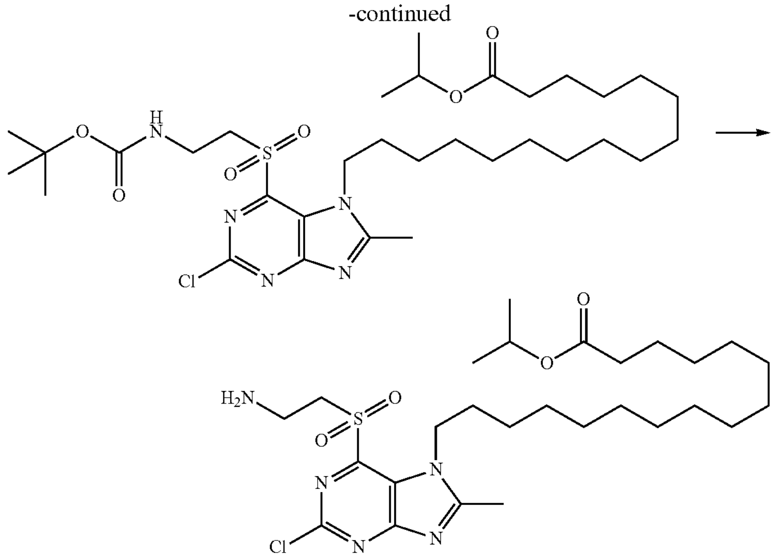

147

Step 1: Isopropyl 16-(2,6-dichloro-8-methyl-7H-purin-7-yl)hexadecanoate (50 mg, 0.100 mmol), was dissolved in anhydrous acetonitrile (1.5 mL) and to this was added 2-(Boc-amino)ethanethiol (36 mg, 0.200 mmol), and 60% sodium hydride (10 mg, 0.240 mmol). The reaction was heated to 80° C. and monitored by LCMS. After 6 hours, the reaction was complete and concentrated to remove acetonitrile. The crude was the purified by flash chromatography in dichloromethane and methanol. About 45 mg (70% yield) was recovered as a white solid. LCMS: m/z 640.48 (M+H); $^1$H-NMR ($CDCl_3$) δ 5.20 (bs, 1H), 5.00 (m, 1H), 4.27 (t, J=7.8 MHz, 2H), 3.52 (m, 4H), 2.63 (s, 3H), 2.25 (t, J=6.9 MHz, 2H), 1.80 (m, 2H), 1.60 (m, 3H), 1.35 (m, 37H)

Step 2: Step 1 product (25 ing, 0.039 mmol) was dissolved in 1 mL anhydrous DCM and cooled in an ice bath. To this solution was added 70% mCPBA (19 mg, 0.078 mmol) and the reaction mixture was allowed to warm to ambient temperature. An additional 8 mg of mCPBA was added and the reaction stirred for 14 hours. Upon completion, the reaction was quenched with 5% sodium bicarbonate and shaken vigorously. The aqueous layer was extracted multiple times with DCM to extract all product. The organic layer was dried over sodium sulfate, filtered, and concentrated to give about 23 mg (88% yield) of crude which was taken on to the next step without purification. LCMS: m/z 672.17 (M+H).

Step 3: Step 2 crude product (23 ing, 0.034 mmol) was dissolved in 2 mL methanol. To this solution was added about 0.1 mL of 4M HCl in dioxane and the reaction was stirred at ambient temperature for 14 hours. The mixture was concentrated to remove methanol and purified by RPHPLC in 0.02 M ammonium acetate and acetonitrile. The desired compound was then desalted by passing through C18 again in water and acetonitrile. 3 mg (17% yield) of the compound 147 was recovered as a white solid. LCMS: m/z 542.05 (M−H), 544.39 (M+H); $^1$H-NMR (DMSO) S 4.15 (m, 2H), 3.71 (m, 2H), 3.51 (s, 3H), 2.74 (m, 2H), 2.44 (s, 3H), 2.21 (t, J=7.5 MHz, 2H), 1.60 (m, 2H), 1.47 (m, 2H), 1.14 (m, 24H).

Compound 148: methyl (16-(2-chloro-6-(isopropylsulfonyl)-8-methyl-7H-purin-7-yl)hexadecanoyl)-L-valinate

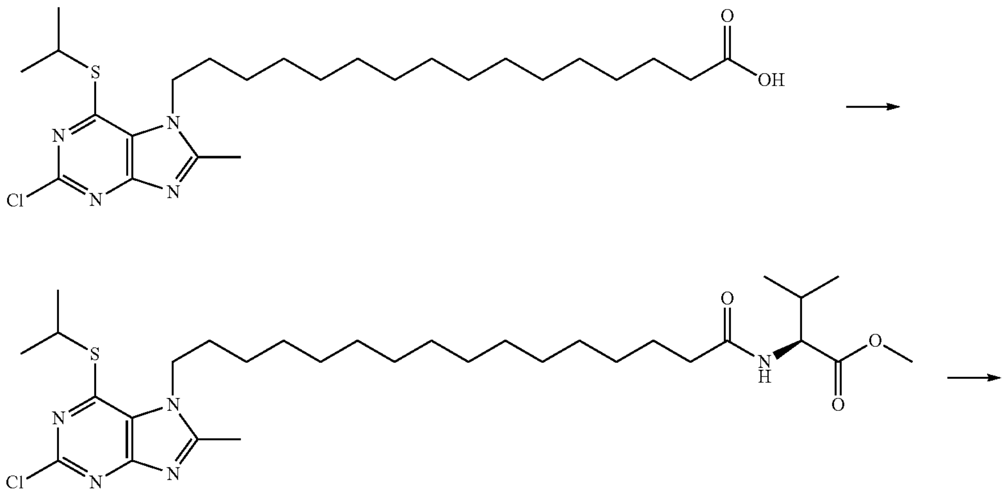

-continued

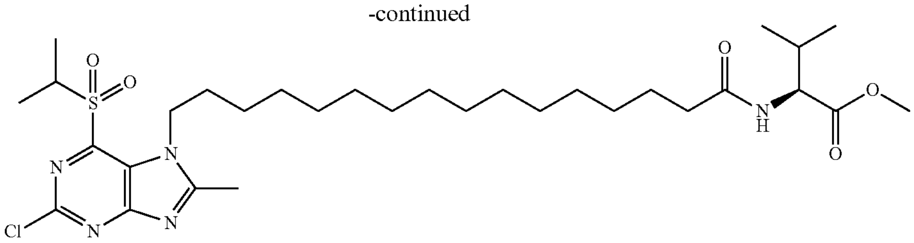

148

Step 1: Compound acid (30 mg, 0.061 mmol), EDC (26 mg, 0.134 mmol), and HOBT (18 mg, 0.134 mmol) were combined and stirred in 2 mL anhydrous DMF. To this mixture was added valine methyl ester (11 mg, 0.067 mmol) and triethylamnine (0.01 mL, 0.067 mmol). The reaction was stirred at ambient temperature for 14 hours. The reaction was quenched with water and the product was extracted in ethyl acetate. The organic was dried over sodium sulfate, filtered, and concentrated to give 60 mg of crude. Purification by RPH1PLC in water and acetonitrile gave 32 mg (86% yield) of the product as an oil. LCMS: m/z 608.23 (M−H), 610.21 (M+H); $^1$H-NMR ($CDCl_3$) δ 5.90 (m, 1H), 4.60 (m, 11H), 4.40 (m, 11H), 4.27 (t, J=8.4, 211), 3.74 (s, 311), 2.63 (s, 311), 2.23 (t, J=6.9 MHz, 211), 2.15 (m, 11H), 1.80 (in, 211), 1.60 (in, 411), 1.49 (d, J=7.2 MHz, 611), 1.29 (in, 22), 0.93 (n, 61).

Step 3: Step 2 product (31 mg, 0.051 mmol) was dissolved in dry DCM and cooled in an ice bath. To this mixture was added 70% mCPBA (25 mg, 0.102 mmol) and stirred a ambient temperature for 4 hours. The reaction was quenched with 5% sodium bicarbonate and extracted multiple times with DCM. The organic was dried over sodium sulfate, filtered, and concentrated. The crude was purified by RPHPLC in water and acetonitrile to give 20 mg of compound 148 as an oil. LCMS: m/z 640.17 (M−H), 642.08 (M+H); $^1$H-NMR ($CDCl_3$) δ 5.89 (m, 1H), 4.56 (m, 3H), 4.43 (in, 111)),3.74 (s, 3H), 2.78 s, 3), 2.24 (t, J=6.9 MHz, 211), 2.16 (m, 1H), 1.84 (m, 2H), 1.62 (m, 4H), 1.52 (d, J=6.9 MHz, 61H), 1.25 (m, 22H), 0.93 (mi, 61).

Compound 149: 16-(2-chloro-6-(isopropylsulfonyl)-8-methyl-7H-purin-7-yl)hexadecanamide

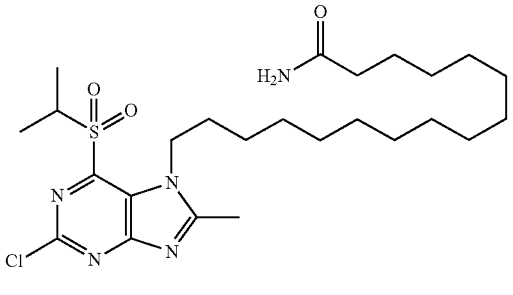 [SMILES: Cc1nc2nc(Cl)nc(S(=O)(=O)C(C)C)c2n1CCCCCCCCCCCCCCCC(N)=O]

Similar procedure used for synthesis of compound 145 was utilized. LCMS: m/Z 528.5 (M+H);

Compound 150.16-(2-chloro-6-(isopropylsulfonyl)-8-methyl-7H-purin-7-yl)-N,N-dimethylhexadecanamide

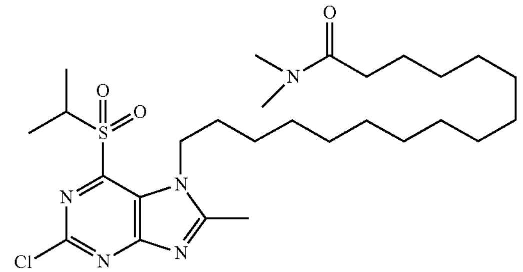 [SMILES: Cc1nc2nc(Cl)nc(S(=O)(=O)C(C)C)c2n1CCCCCCCCCCCCCCCC(=O)N(C)C]

Similar procedure used for synthesis of compound 145 was utilized. LCMS: m/Z 556.3 (M+H);

Compound 151: 8-(2,6-dichloro-8-methyl-7H-purin-7-yl)octyl acetate

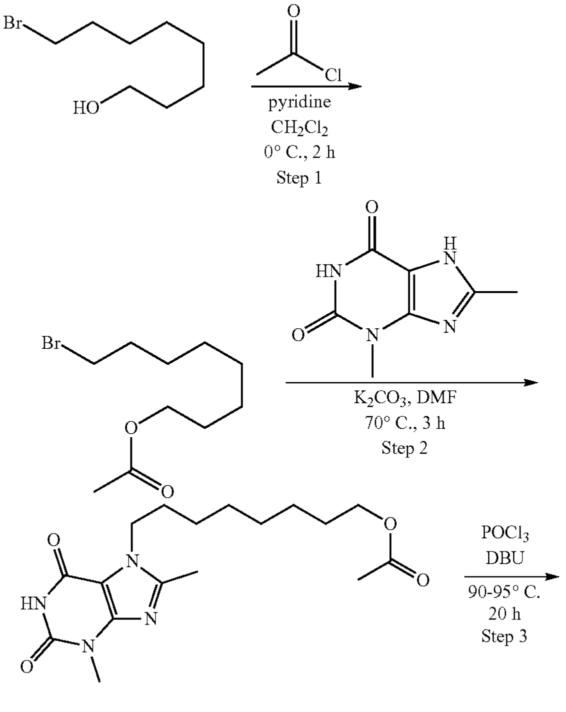

-continued

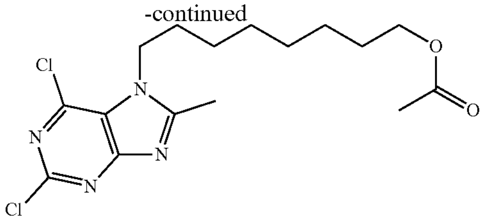

151

Step 1: 8-bromo-1-octanol (3.0 g, 14.35 mmol) was dissolved in anhydrous $CH_2Cl_2$ (40 mL) and the solution was cooled to 0-5° C. in an ice-water bath. Pyridine (2.9 mL, 35.86 mmol) was added and after stirring for 2-3 min, acetyl chloride (1.3 mL, 18.66 mmol) was added dropwise. The reaction mixture was stirred at 0-5° C. for 1.5 h and then quenched with water (30 mL). Additional DCM (50 mL) was added and after extraction, the organic layer was separated, and the aqueous layer was re-extracted with DCM (30 mL). The combined organic layer was dried over anhydrous $Na_2SO_4$, filtered and the solvent evaporated in vacuo to obtain the crude product (3.55 g, 98.6%) as a pale-yellow liquid that was dried under high vacuum and carried to the next step. $^1$H-NMR ($CDCl_3$ with 0.03% v/v TMS) δ 4.05 (t, J=6.8 Hz, 2H), 3.41 (t, J=7.1 Hz, 2H), 2.05 (s, 3H), 1.86 (m, 2H), 1.62 (m, 2H), 1.50-1.26 (m, 8H).

Step 2: 8-Methylxanthine (0.72 g, 3.98 mmol) was weighed in a 100 mL 1N RB flask and anhydrous DMF (20 mL) was added. The heterogeneous mixture was stirred and heated in a pre-heated oil-bath at 70° C. until the solid dissolved. $K_2CO_3$ (0.825 g, 5.97 mmol) was added followed by the addition of the bromo derivative (1.2 g, 4.78 mmol). The mixture was heated at 70° C. for 5 h. LCMS showed the mass of the desired product. The mixture was cooled to room temperature and DCM (70 mL) was added. The mixture was extracted with water (4-5x) and the organic layer was dried over anhydrous $Na_2SO_4$, filtered and the solvent evaporated in vacuo to obtain the crude product. The crude was purified by automated column chromatography using a gradient of ethyl acetate/DCM to yield the pure product (1.2 g, 86%) as a white solid. LCMS: 351.29 (M+H), 349.02 (M−H). $^1$H-NMR ($CDCl_3$ with 0.03% v/v TMS) δ 8.60 (bs, 1H), 4.21 (t, J=7.1 Hz, 2H), 4.04 (t, J=6.8 Hz, 2H), 3.53 (s, 3H), 2.47 (s, 3H), 2.05 (s, 3H), 1.80 (m, 2H), 1.61 (m, 2H), 1.42-1.22 (m, 8H).

Step 3: $POCl_3$ Procedure as described in method 2b was followed. The crude was purified by passing it through a pad of silica gel using a gradient of hexanes/EtOAc (1:1 then 2:1 and 3:1) to yield the pure product (1.05 g, 83%) as a golden yellow oil. LCMS: 373.29 (M+H). $^1$H-NMR ($CDCl_3$ with 0.03% v/v TMS) δ 4.37 (m, 2H), 4.05 (t, J=6.8 Hz, 2H), 2.71 (s, 3H), 2.05 (s, 3H), 1.83 (m, 2H), 1.62 (m, 2H), 1.46-1.28 (m, 811).

Compound 152: Methyl 7-((8-(2-chloro-6-(isopropylsulfonyl)-8-methyl-7H-purin-7-yl)octyl)(methyl)-amino)heptanoate

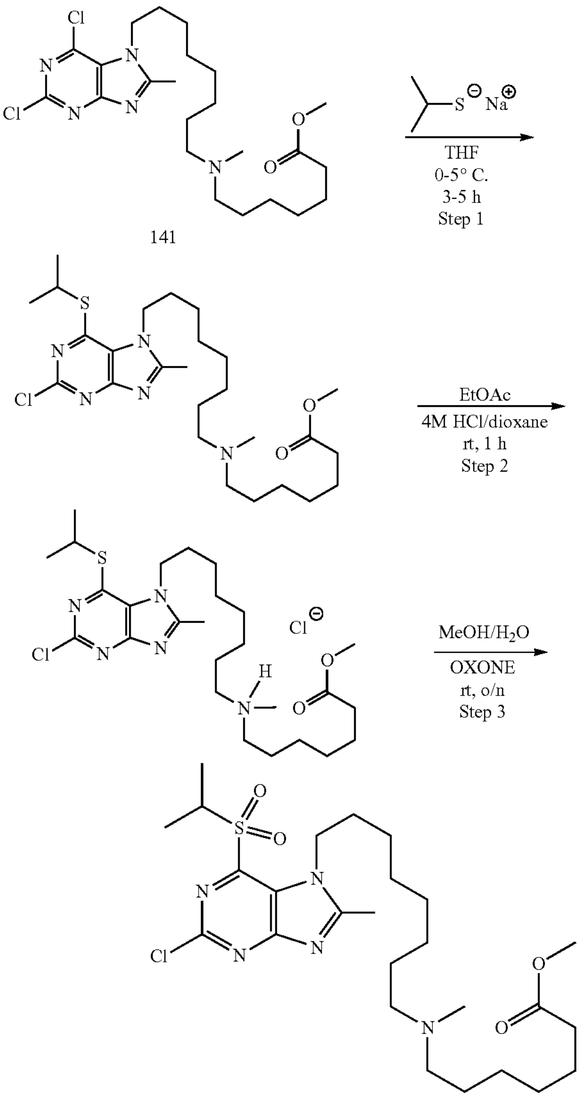

141

152

Step 1: Method 3 was utilized with corresponding 2,6-DiCl intermediate to provide crude sulfide (230 mg, 63%) as a red oil that was taken to the next step. LCMS: m/Z 526.30 (M+H); $^1$H-NMR ($CDCl_3$ with 0.03% v/v TMS) δ 4.39 (sept, J=6.9 Hz, 1H), 4.27 (m, 2H), 3.66 (s, 3H), 2.62 (s, 3H), 2.37 (m, 4H), 2.30 (t, J=7.4 Hz, 2H), 2.26 (s, 3H), 1.79 (m, 2H), 1.62 (m, 2H), 1.49 (d, J=6.9 Hz, 611), 1.42-1.20 (m, 16H).

Step 2: The crude sulfide (215 g, 0.409 mmol) was dissolved in ethyl acetate (5 mL) to give a clear orange solution. To the stirring solution at room temperature was added dropwise 4M HCl/dioxane (0.5 mL) and a white precipitate was formed. The mixture was stirred for 30 min at room temperature. Ethyl acetate was carefully pipetted off from the white solid. The solid was again centrifuged with ethyl acetate (20 mL) and the supernatant was carefully pipetted off. The white solid (233 mg) was dried under high vacuum and carried to the next step.

Step 3: The hydrochloride salt (150 mg, 0.267 mmol) was dissolved in MeOH/water (1:1, 16 mL). After stirring for 2 min, oxone (164 mg, 0.534 mmol) was added as a solid and the mixture was stirred at room temperature for 20 h. LCMS showed that all the starting material was converted to the sulfone. Methanol was evaporated in vacuo and the aqueous layer was extracted with DCM (2×15 mL). The combined organic layer was dried over anhydrous $Na_2SO_4$, filtered and the solvent evaporated in vacuo to give the crude as a viscous colorless oil (88 mg) that was purified by preparative HPLC to give the desired product (41 mg, 41%) as a yellow oil. LCMS: m/Z 558.31 (M+H), 556.23 (M−H); HPLC purity 98.8%; $^1$H-NMR ($CDCl_3$ with 0.03% v/v TMS) δ 4.57 (m, 2H), 4.43 (sept, J=6.3 Hz, 1H), 3.66 (s, 3H), 2.77 (s, 3H), 2.31 (m, 6H), 2.21 (s, 3H), 1.84 (m, 2H), 1.62 (m, 2H), 1.52 (d, J=6.3 Hz, 6H), 1.50-1.2 (m, 16H).

Compound 153: Methyl 4-(4-(6-(2,6-dichloro-8-methyl-7H-purin-7-yl)hexyl)piperazin-1-yl)butanoate

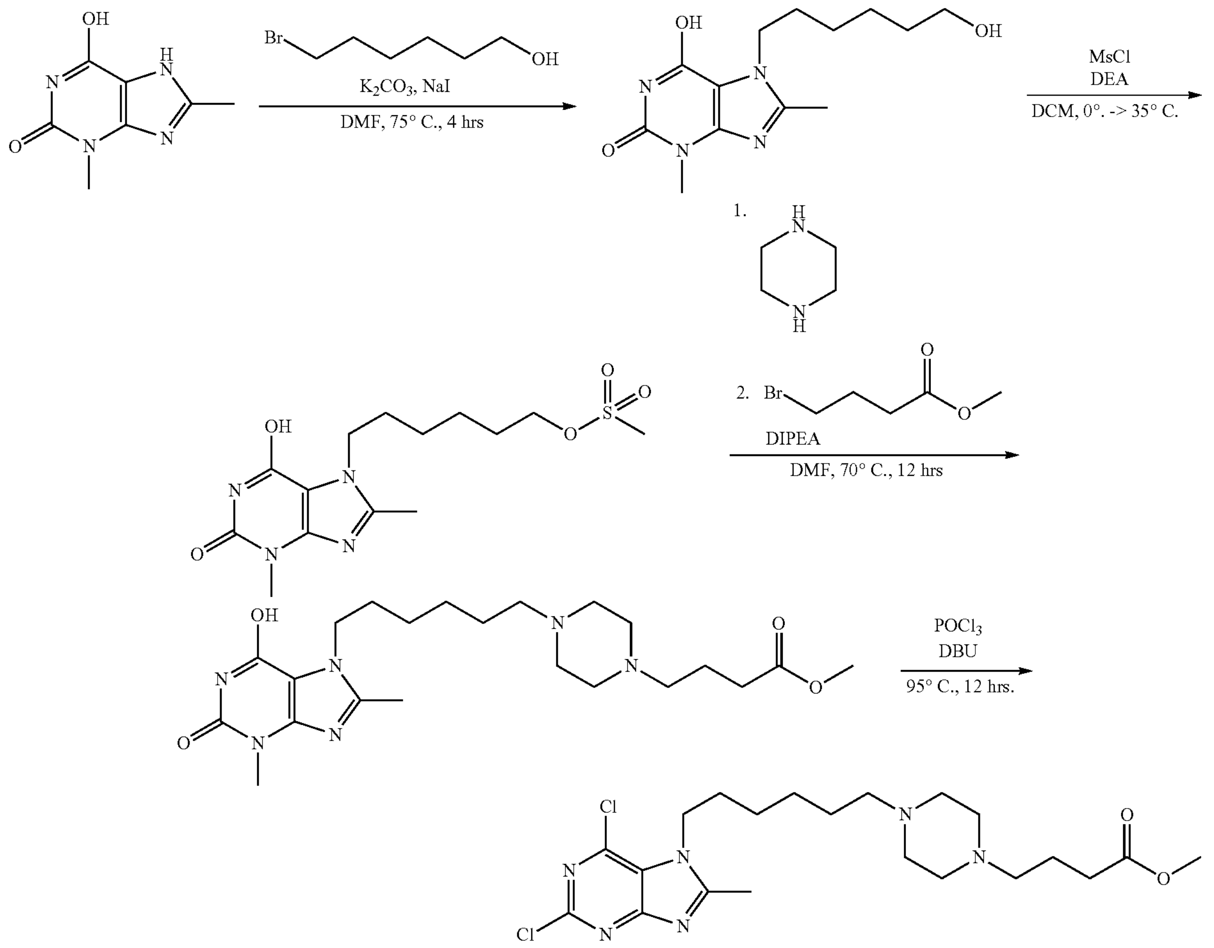

153

Step 1: $K_2CO_3$ mediated alkylation procedure as described in method 1 was followed. Obtained 3.0 g (96%) of 6-hydroxy-7-(6-hydroxyhexyl)-3,8-dimethyl-3,7-dihydro-2H-purin-2-one. LCMS: m/Z 281.20 (M+H) 279.19

Step 2: 6-hydroxy-7-(6-hydroxyhexyl)-3,8-dimethyl-3,7-dihydro-2H-purin-2-one (3.0 g, 10.7 mmol) was dissolved in DCM and cooled to 0° C. on ice bath. To this was added 2.24 mL (1.63 g, 16.2 mmol) triethylamine followed by 1.53 g (13.4 mmol) of MsCl dissolved in cold DCM dropwise. Reaction was kept at 0° C. for around 15 minutes then was taken off of the ice bath and heated slightly to 35° C. for around 3 hours. 3.0 mL $H_2O$ was added followed by DCM. After evaporation of organic layer, crude material was redissolved in EtOAc (50 mL) and was washed with 5% $NaHCO_{3(aq)}$ (1×25 mL), 1.0 M $HCl_{(aq)}$ (1×25 mL), and brine (1×25 mL). The organics were then removed in vacuum and obtained 3.58 g of yellowish solid 6-(6-hydroxy-3,8-dimethyl-2-oxo-2,3-dihydro-7H-purin-7-yl)hexyl methanesulfonate (94%). LCMS: m/Z 359.08 (M+H)

Step 3: 6-(6-hydroxy-3,8-dimethyl-2-oxo-2,3-dihydro-7H-purin-7-yl)hexyl methanesulfonate (250 mg, 0.70 mmol), piperazine (67 mg, 0.78 mmol) and 186 mg (1.4 mmol) of DIPEA were dissolved in DMF and taken to 70° C. To the solution was then added 139 mg (0.77 mmol, 1.1 equiv.) of methyl 4-bromobutyrate and solution was allowed to react for 12 additional hours. When reaction was complete, the vial was cooled to room temperature and solvents were then removed en vacuo. The crude mixture was then dissolved in DMSO with sonication and passed through a reverse phase column eluting with ACN:$H_2O$ (0-100%). Obtained 300 mg (96%) of methyl 4-(4-(6-(6-hydroxy-3,8- dimethyl-2-oxo-2,3-dihydro-7H-purin-7-yl)hexyl)piperazin-1-yl)butanoate as a dark viscous oil. LCMS: m/Z 449.29 (M+H).

Step 4: $POCl_3$ Procedure was followed. Obtained 32 mg of methyl 4-(4-(6-(2,6-dichloro-8-methyl-7H-purin-7-yl) hexyl)piperazin-1-yl)butanoate from reverse phase column. LCMS: m/Z 471.23 (M+H); $^1$H-NMR ($CDCl_3$) δ 4.38 (t, 2H), 3.68 (s, 3H), 3.48 (m, 10H), 3.16 (m, 2H) 2.73 (s, 3H), 2.50 (t, 2H), 2.04 (m, 4H), 1.33 (m, 6H).

Compound 154: methyl 16-(2,6-dichloro-8-(morpholinomethyl)-7H-purin-7-yl)hexadecanoate under high vacuum to get 200 mg of product, which was used for next reaction without further purification. LCMS: m/Z 266.33 $(M+H)^+$.

Step 3: To a solution of 6-hydroxy-3-methyl-8-(morpholinomethyl)-3,7-dihydro-2H-purin-2-one (200 mg, 0.75 mmol) in DMF (5.0 mL) was added $K_2CO_3$ (208 mg, 1.5 mmol), NaI (56 mg, 0.37 mmol) and 16-bromo methylhexadecanoate (290 mg, 0.82 mmol). Reaction mixture was stirred at 75° C. for 4 hours. DMF was evaporated under reduced pressure to dryness. Reaction mixture was suspended in water (25.0 mL) and product was extracted with 20% IPA in DCM (2×50 mL). Combined organic layers were

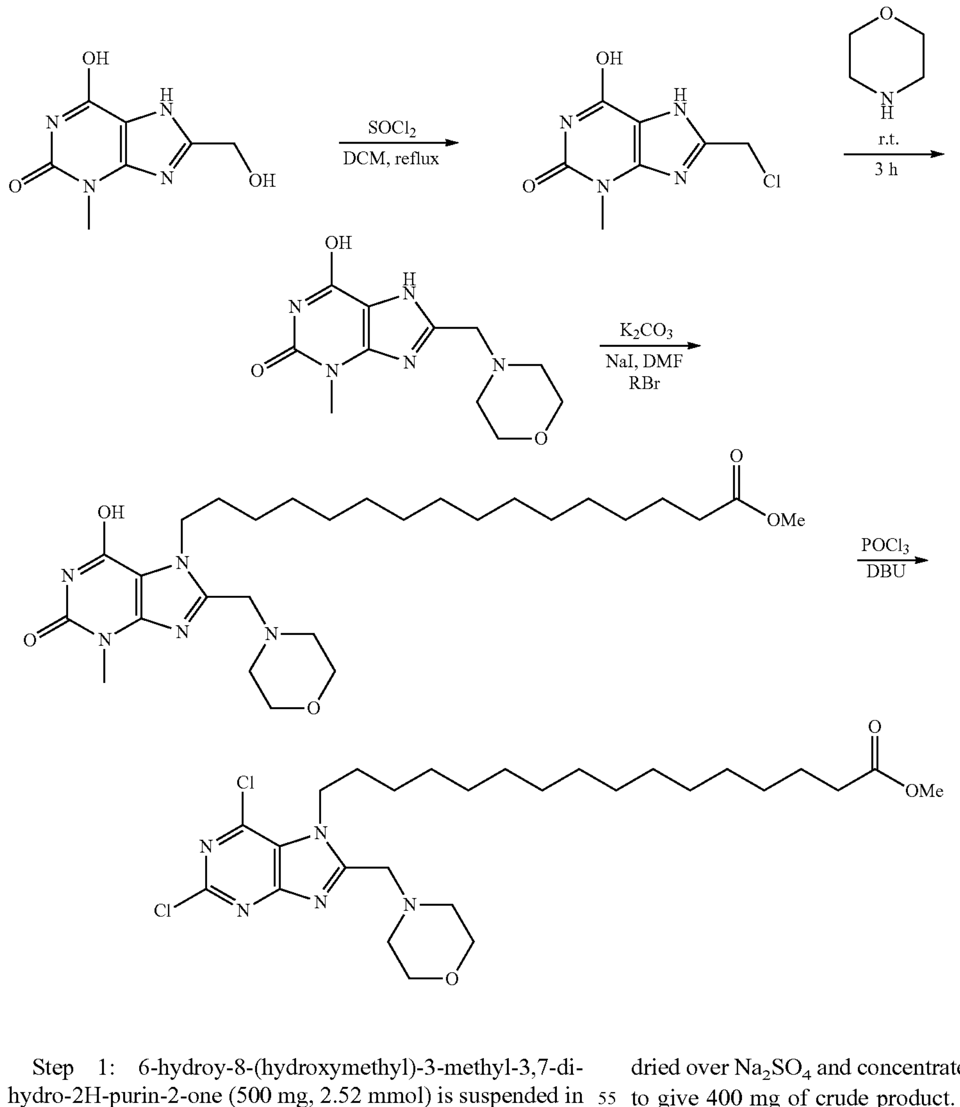

Step 1: 6-hydroy-8-(hydroxymethyl)-3-methyl-3,7-dihydro-2H-purin-2-one (500 mg, 2.52 mmol) is suspended in DCM (20 mL). $SOCl_2$ (550 μL) was added to the reaction mixture, which was heated at reflux for 30 hours with oil bath. Solvents were evaporated under reduced pressure and the crude product was purified on silica gel column chromatography using 0-20% MeOH in DCM gradient method to get 125 mg pure compound. LCMS: m/Z 215.2 $(M+H)^+$, 213.12 $(M-H)^+$, 427.36 $(2M-H)^+$.

Step 2: Morpholine (5.0 mL) was added to a 8-(chloromethyl)-6-hydroxy-3-methyl-3,7-dihydro-2H-purin-2-one (250 mg, 1.16 mmol) in scintillation glass vial. Reaction mixture was stirred for 3 hours at room temperature. Solvent was evaporated under reduced pressure to dryness and dried dried over $Na_2SO_4$ and concentrated under reduced pressure to give 400 mg of crude product. 200 mg of crude product was purified on combi-flash silica gel gradient column chromatography using 0-5% MeOH in DCM (1% $Et_3N$ in DCM) to give 150 mg of pure product. LCMS: m/Z 534.37 $(M+H)^+$, 532.42 $(M-H)^+$.

Step 4: $POCl_3$ Procedure as described in method 2b was followed. Crude product was purified on combi-flash on C18 reverse phase chromatography by using water as solvent A and acetonitrile B. Pure fractions were combined and lyophilized to get 10 mg of pure product as light brown solid. LCMS: m/Z 556.67 $(M+H)^+$, 578.1 (M+Na)+.

Compound 155: Methyl 7-((8-(2,6-dichloro-8-methyl-7H-purin-7-yl)octyl)amino)heptanoate

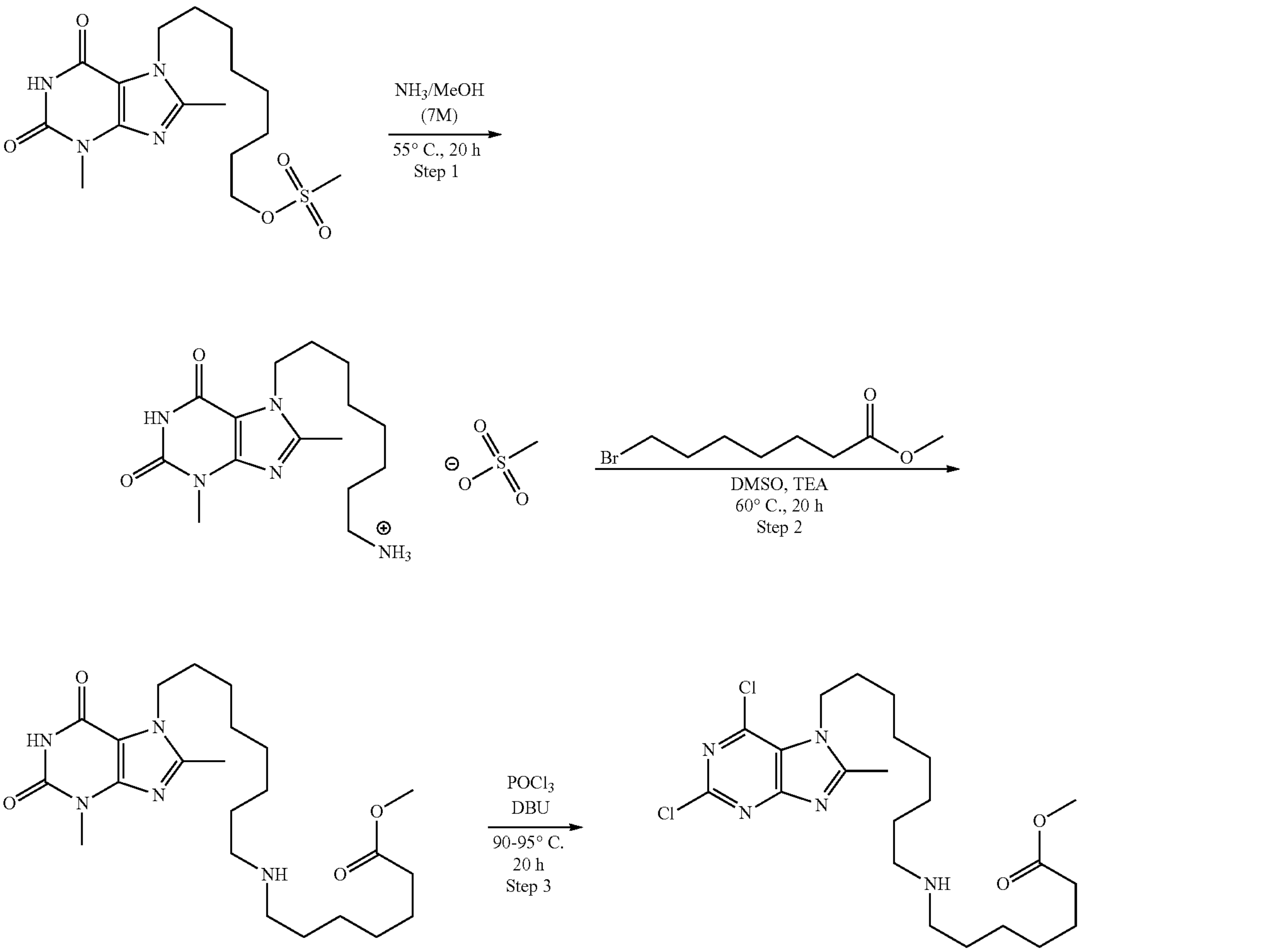

155

Step 1: The mesylate (1 g, 2.59 mmol) was weighed in 200 mL thick-walled pressure glass vessel containing a stir bar. Ammonia (7.0 M solution in methanol) (40 mL) was added and the vessel was tightly sealed. After stirring the mixture for 2 min, the vessel was placed in a pre-heated oil-bath and clear pale-yellow solution was heated for 20 h at 55° C. After 20 h, the vessel was removed from the oil-bath and allowed to cool to room temperature. LCMS indicated that all starting material was consumed and showed the mass of the desired product. Methanol from the mixture was evaporated in vacuo to give the mesylate salt of the amine (1.06 g, quantitative) as a white foamy solid. LCMS: m/Z 308.24 (M+H), 306.23 (M−H); $^{1}$H-NMR (DMSO-$d_6$ w/0.03% v/v TMS, 300 MHz): δ 7.71 (bs, 3H), 4.16 (t, J=6.0 Hz, 2H), 3.32 (s, 3H), 2.75 (m, 2H), 2.42 (s, 3H), 2.33 (d, J=3.0 Hz, 3H), 1.68 (m, 2H), 1.52 (m, 2H), 1.34-1.2 (m, 8H).

Step 2: The mesylate salt of the amine (1 g, 2.48 mmol) was dissolved in DMSO (15 mL) in a 100 mL 1N RB flask. TEA (1 mL, 7.43 mmol) was added and the solution was stirred. Methyl 7-bromoheptanoate (608 mg, 2.73 mmol) was added and the mixture was heated in an oil-bath at 65° C. for 20 h. LCMS showed the mass of the desired product. The mixture was poured into ice water and stirred. 5% aqueous $NaHCO_3$ (5 mL) and DCM (20 mL) was added. After stirring for 10-15 min, the mixture was poured into a separatory funnel and the organic layer was separated. The aqueous layer was re-extracted with DCM. The combined organic layer was dried over anhydrous $Na_2SO_4$, filtered and the solvent evaporated in vacuo to obtain the crude product as an orange oil that was purified by automated column chromatography using DCM/methanol as the eluent system to give the pure product (322 mg, 29%) as a white solid. LCMS: m/Z 450.30 (M+H), 448.35 (M−H); $^{1}$H-NMR ($CDCl_3$ w/0.03% v/v TMS, 300 MHz): δ 4.20 (t, J=7.4 Hz, 2H), 3.66 (s, 3H), 3.52 (s, 3H), 2.61 (m, 4H), 2.47 (s, 3H), 2.31 (t, J=7.7 Hz, 2H), 1.78 (m, 2H), 1.68-1.48 (m, 6H), 1.4-1.2 (m, 12H).

Step 3: $POCl_3$ Procedure as described in method 2b was followed. The crude product that was purified by reverse phase HPLC to obtain the pure product (46.8 mg, 19%) as a sticky yellow solid. HPLC purity 99.6%; LCMS: m/Z 472.23 (M+H); $^{1}$H-NMR ($CDCl_3$ with 0.03% v/v TMS) 6 9.50 (bs, 1H), 4.38 (t, J=7.7 Hz, 2H), 3.66 (s, 3H), 2.90 (m, 4H), 2.73 (s, 3H), 2.29 (t, J=7.2 Hz, 2H), 1.96-1.72 (m, 6H), 1.62 (m, 2H), 1.46-1.20 (m, 12H).

Compound 156: Methyl 6-((1-(6-(2,6-dichloro-8-methyl-7H-purin-7-yl)hexyl)piperidin-4-yl)oxy) hexanoate

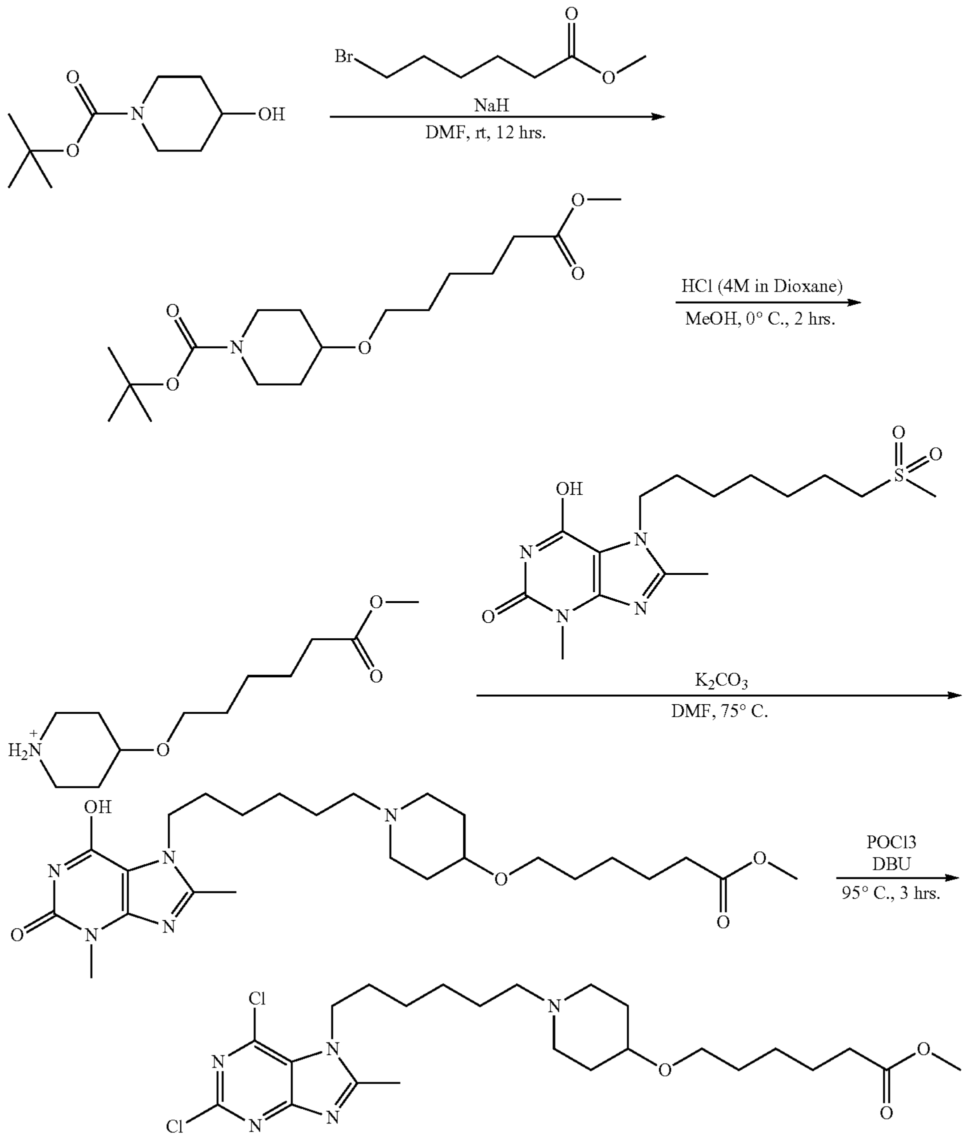

Step 1: 1.0 g (5.02 mmol) tert-butyl 4-hydroxypiperidine-1-carboxylate was dissolved in DMF at 25° C. To this was added 309 mg (12.9 mmol) of NaH in two portions. To this cloudy suspension was added 1.30 g (6.22 mmol) of methyl 6-bromohexanoate dropwise over a period of five minutes. Reaction was kept for 12 hours at 25° C. After then, reaction contents were poured onto ice. Aqueous solution was extracted with EtOAc (2×50 mL). After drying organic layer was evaporated to obtain ~3 g of crude oil. Crude was purified by reverse phase column eluting with ACN:$H_2O$ (0-100%). Fractions were collected, frozen, and lyophilized to obtain 171 mg (10%) of tert-butyl 4-((6-methoxy-6-oxohexyl)oxy)piperidine-1-carboxylate. LCMS: m/Z 330.31 (M+H) 328.73 (M−H); $^1$H-NMR ($CDCl_3$) δ 3.73 (m, 1H), 3.67 (s, 3H), 3.40 (m, 3H) 3.22 (m, 1H), 3.07 (m, 2H), 2.33 (m, 2H), 1.85 (m, 3H), 1.65 (m, 5H), 1.45 (m, 11H).

Step 2: 171 mg (0.52 mmol) tert-butyl 4-((6-methoxy-6-oxohexyl)oxy)piperidine-1-carboxylate was dissolved in MeOH and placed on an ice bath. To this was added 0.3 mL (1.2 mmol) of a 4M solution of HCl in dioxane. Reaction was stirred at 0° C. for about 2 hours and then methanol was removed en vacuo to obtain 160 mg of the hydrochloride salt of methyl 6-(piperidin-4-yloxy)hexanoate. LCMS: m/Z 230.27 (M+H).

Step 3: The HCl salt of methyl 6-(piperidin-4-yloxy) hexanoate and 116 mg (0.84 mmol) $K_2CO_3$ were dissolved in DMF. To this solution was added 275 mg (0.77 mmol) of 6-(6-hydroxy-3,8-dimethyl-2-oxo-2,3-dihydro-7H-purin-7-yl)hexyl methanesulfonate. Reaction was stirred at 75° C. When starting material was consumed the reaction was cooled to room temperature and the solvents were removed en vacuo. Crude was dissolved in DMSO with sonication and injected into a reverse phase column eluting with ACN:$H_2O$ (0-100%). Fractions were collected, frozen, and lyophilized to obtain 90 mg of methyl 6-((1-(6-(6-hydroxy-3,8-dimethyl-2-oxo-2,3-dihydro-7H-purin-7-yl)hexyl)piperidin-4-yl)oxy)hexanoate as a tan powder (26%). LCMS: m/Z 492.27 (M+H)

Step 4: $POCl_3$ procedure was followed. Obtained 1.5 mg (1.6%) of methyl 6-((1-(6-(2,6-dichloro-8-methyl-7H-purin-7-yl)hexyl)piperidin-4-yl)oxy)hexanoate. LCMS: m/Z 514.27 (M+H).

Compound 157: 16-(2,6-dichloro-8-methyl-7H-purin-7-yl)hexadecanenitrile

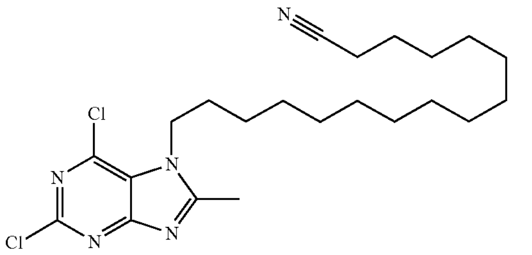 [SMILES: Cc1nc2nc(Cl)nc(Cl)c2n1CCCCCCCCCCCCCCCC#N]

POCl3 procedure as described in method 2A was followed to obtain 16-(2,6-dichloro-8-methyl-7H-purin-7-yl)hexadecanenitrile product. LCMS m/z 438.13 (M+H)$^1$H-NMR ($CDCl_3$) δ 4.35 (t, 2H), 2.70 (s, 3H), 2.33 (t, 2H), 1.84 (m, 2H), 1.70 (m, 4H), 1.25 (m, 26H).

Compound 158: Cyclopropylmethyl 16-(2-chloro-6-(isopropylsulfonyl)-8-methyl-7H-purin-7-yl)hexadecanoate

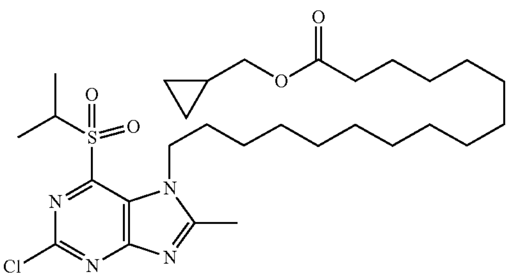 [SMILES: Cc1nc2nc(Cl)nc(S(=O)(=O)C(C)C)c2n1CCCCCCCCCCCCCCCC(=O)OCC1CC1]

Method 4 was utilized with corresponding ROH which provided a crude which was purified by c18 column chromatography using 0-100% ACN-Water to provide product 158. LCMS: m/Z 583.3 (M+H); $^1$H-NMR ($CDCl_3$) 4.57 (m, 2H), 4.30 (m, 2H), 4.20 (m, 1H), 3.91 (d, J=7.5 Hz, 1H), 2.77 (s, 3H), 2.31 (dd, J=7.5 Hz, 7.8 Hz, 2H), 1.84 (m, 2H), 1.60 (m, 2H), 1.52 (d, J=7.2 Hz, 6H), 1.38-1.25 (broad m, 22H). 0.57 (m, 2H),).26 (m,2H).

Compound 159: Isobutyl 16-(2-chloro-6-(isopropylsulfonyl)-8-methyl-7H-purin-7-yl)hexadecanoate

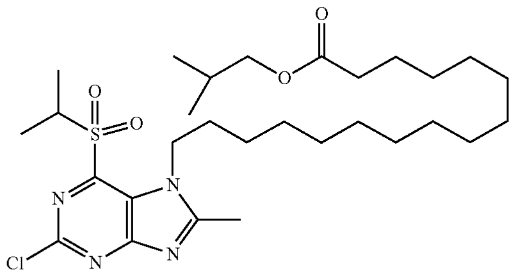 [SMILES: Cc1nc2nc(Cl)nc(S(=O)(=O)C(C)C)c2n1CCCCCCCCCCCCCCCC(=O)OCC(C)C]

Method 4 was utilized with corresponding ROH which provided a crude which was purified by c18 column chromatography using 0-100% ACN-Water to provide product 159. LCMS: m/Z 585.4 (M+H);

Compound 160: Methyl-d3 16-(2-chloro-6-(isopropylsulfonyl)-8-methyl-7H-purin-7-yl)hexadecanoate

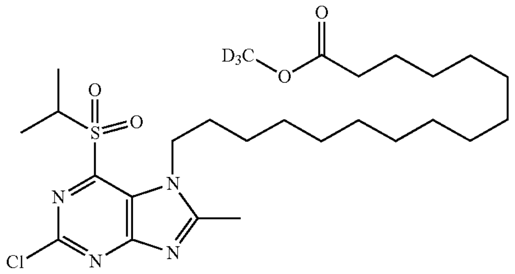 [SMILES: [2H]C([2H])([2H])OC(=O)CCCCCCCCCCCCCCCn1c(C)nc2nc(Cl)nc(S(=O)(=O)C(C)C)c21]

Method 4 was utilized with corresponding ROH which provided a crude which was purified by c18 column chromatography using 0-100% ACN-Water to provide product 160. LCMS: m/Z 546.3 (M+H); $^1$H-NMR ($CDCl_3$) 4.57 (m, 2H), 4.45 (m, 1H), 2.77 (s, 3H), 2.30 (dd, J=7.5 Hz, 7.8 Hz, 2H), 1.84 (m, 2H), 1.61 (m, 2H), 1.52 (d, J=6.9 Hz, 6H), 1.38-1.25 (broad m, 22H).

Compound 161: Methyl 15-(2,6-dichloro-8-methyl-7H-purin-7-yl)pentadecanoate

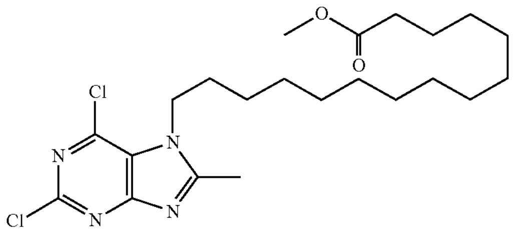 [SMILES: COC(=O)CCCCCCCCCCCCCCn1c(C)nc2nc(Cl)nc(Cl)c21]

Method 2B was utilized with corresponding RBr which provided a crude which was purified by c18 column chromatography using 0-100% ACN-Water to provide product 161. LCMS: m/Z 457.3 (M+H); $^1$H-NMR ($CDCl_3$) 4.37 (m, 2H), 3.66 (s, 3H), 2.70 (s, 3H), 2.29 (dd, J=6.9 Hz, 7.8 Hz, 2H), 1.81 (m, 2H), 1.60 (m, 2H), 1.38-1.25 (broad m, 20H).

Compound 162: Methyl 15-(2-chloro-6-(isopropylsulfonyl)-8-methyl-7H-purin-7-yl)pentadecanoate

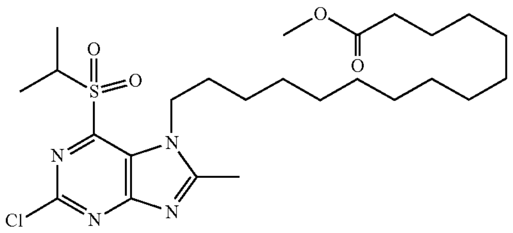 [SMILES: COC(=O)CCCCCCCCCCCCCCn1c(C)nc2nc(Cl)nc(S(=O)(=O)C(C)C)c21]

Method 3 was utilized from corresponding product 161 to provide sulfide intermediate which was oxidized by mCPBA, to provide crude product which was purified by c18 column chromatography using 0-100% ACN-Water to provide product 162. LCMS: m/Z 529.3 (M+H); $^1$H-NMR ($CDCl_3$) 4.57 (m, 2H), 4.23 (m, 1H), 3.66 (s, 3H), 2.77 (s, 3H), 2.30 (dd, J=7.5 Hz, 7.8 Hz, 2H), 1.83 (m, 2H), 1.61 (m, 2H), 1.51 (d, J=6.9 Hz, 6H), 1.38-1.25 (broad m, 20H).

Compound 163: 16-(2,6-dichloro-8-methyl-7H-purin-7-yl)hexadecan-1-amine

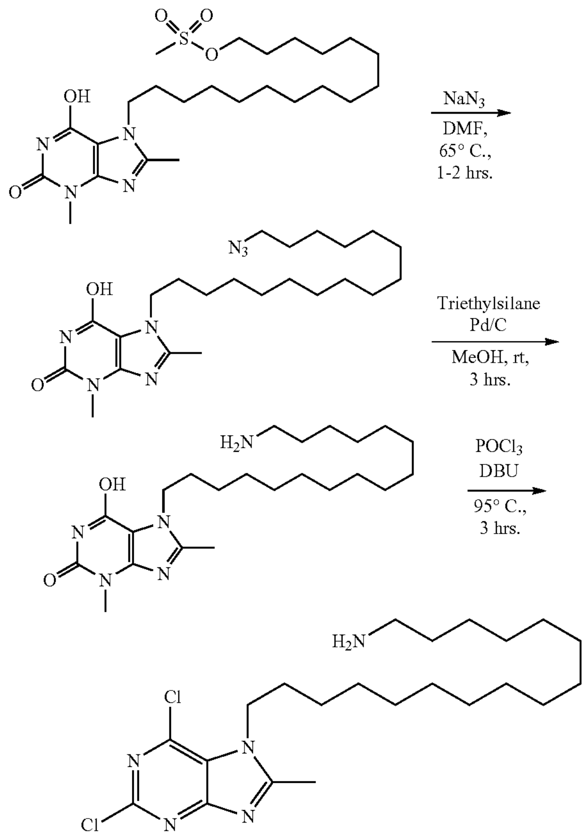

Step 1 550 mgs (1.1 mmol) of 16-(6-hydroxy-3,8-dimethyl-2-oxo-2,3-dihydro-7H-purin-7-yl)hexadecyl methanesulfonate was dissolved in DMF. To this was added sodium azide (655 mgs 10.1 mmol) and the reaction was heated to 65° C. After 2h, reaction mixture were poured into a beaker of ice and the precipitated solid was filtered off and washed with water (2×25 mL) and 5 wt % $NaHCO_{3(aq.)}$ (2×10 mL). Obtained 270 mgs (55%) of 7-(16-azidohexadecyl)-6-hydroxy-3,8-dimethyl-3,7-dihydro-2H-purin-2-one as an off-white crystalline powder. LCMS: m/Z 446.21 (M+H) 444.25 (M−H); $^1$H-NMR ($CDCl_3$) δ 11.01 (bs, 1H) 4.16 (t, 2H), 3.36 (s, 3H), 2.51 (s, 3H), 1.69 (m, 2H), 1.53 (m, 2H), 1.24 (m, 26H).

Step 2: The azide product from above (50 mgs, 0.11 mmol) was dissolved in MeOH. To this was added 1 mg (0.08 mol %) Pd/C (10 wt % Pd) and 0.12 mL (88 mgs, 0.76 mmol) of triethylsilane dropwise over five minutes. Reaction was kept stirring for 3 hours at which time LCMS indicated completion. The reaction mixture was passed through a pad of celite which was then washed with DCM. The filtrate was reduced en vacuo to obtained 30 mg (64%) of 7-(16-aminohexadecyl)-6-hydroxy-3,8-dimethyl-3,7-dihydro-2H-purin-2-one as low melting greenish-white solid. LCMS: m/Z 420.22 (M+H) $^1$H-NMR ($CDCl_3$) δ 4.20 (t, 2H), 3.52 (s, 3H), 2.69 (t, 2H), 2.47 (s, 3H), 1.79 (m, 2H), 1.45 (m, 2H), 1.25 (m, 27).

Step 3: POCl3 procedure as described in method 2A was followed to obtain 5 mgs (16%) of 16-(2,6-dichloro-8-methyl-7H-purin-7-yl)hexadecan-1-amine. LCMS: m/Z 442.41 (M+H) 463.02 (M+Na); $^1$H-NMR ($CDCl_3$) δ 4.35 (t, 2H), 3.60 (t, 2H), 2.67 (s, 3H), 1.70 (m, 2H), 1.32 (m, 4H), 1.22 (m, 24H).

Compound 164 16-(2-chloro-6-(isopropylsulfonyl)-8-methyl-7H-purin-7-yl)hexadecanenitrile IDC-594C3

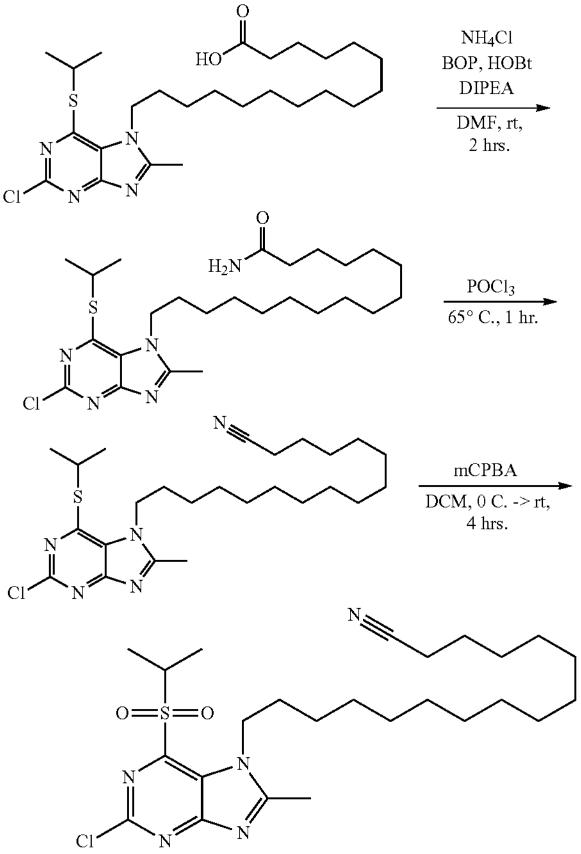

Step 1: 16-(2-chloro-6-(isopropylthio)-8-methyl-7H-purin-7-yl)hexadecanoic acid (350 mgs, 0.70 mmol) was dissolved in DMF along with $NH_4Cl$ (80 mugs, 1.5 mmol). In another vial (Benzotriazol-1-yloxy)tris(dimethylamino) phosphonium hexafluorophosphate (467 mg, 1.06 mmol) and Benzotriazol-1-ol (143 mg, 1.06 mmol) were taken DMF and stirred at 25° C. for ~5 minutes. The contents were then added to the first vial and DIPEA (0.49 mL, 2.83 mmol) was added dropwise to reaction. Reaction was mostly complete by 30 mins. The reaction mixture was diluted with EtOAc and the organics were washed with water (2×20 mL) and brine (1×20 mL). The EtOAc was removed in vacuo and the crude material redissolved in DCM. Silica was added and was purified on normal phase column eluting DCM: MeOH (0-5%) gradient. Fractions were collected and reduced to obtain 250 mgs (72%) of 16-(2-chloro-6-(isopropylthio)-8-methyl-7H-purin-7-yl)hexadecanamide as a transparent-whitish solid. LCMS: m/Z 496.05 (M+H) 494.41 (M−H).

solved in DCM and placed on ice bath (0-5° C.). To this was added mCPBA (60%, 67 mg, 0.39 mmol) dissolved in cold DCM dropwise. Reaction was taken off of ice and let stir at room temperature. When reaction was complete it was quenched with 1.5 mL of 5 wt % $NaS_2O_{5(aq.)}$. Solvents were removed en vacuo and the crude residue was redissolved in DMSO and purified on a reverse phase column eluting ACN:$H_2O$ (0-100%). Fractions were collected, frozen, and lyophilized to obtain 9 mgs (28%) of 16-(2-chloro-6-(isopropylsulfonyl)-8-methyl-7H-purin-7-yl)hexadecanenitrile as a flaky white solid. LCMS: m/Z 510.23 (M+H) 508.28 (M−H); $^1$H-NMR ($CDCl_3$) δ 4.57 (t, 2H), 4.43 (5m, 1H), 2.77 (s, 3H), 2.33 (t, 2H), 1.81 (m, 2H), 1.65 (m, 2H), 1.53 (d, 6H), 1.25 (m, 22H).

Compound 165: 5-(15-(2-chloro-6-(isopropylsulfonyl)-8-methyl-7H-purin-7-yl)pentadecyl)-1,3,4-oxadiazol-2(3H)-one

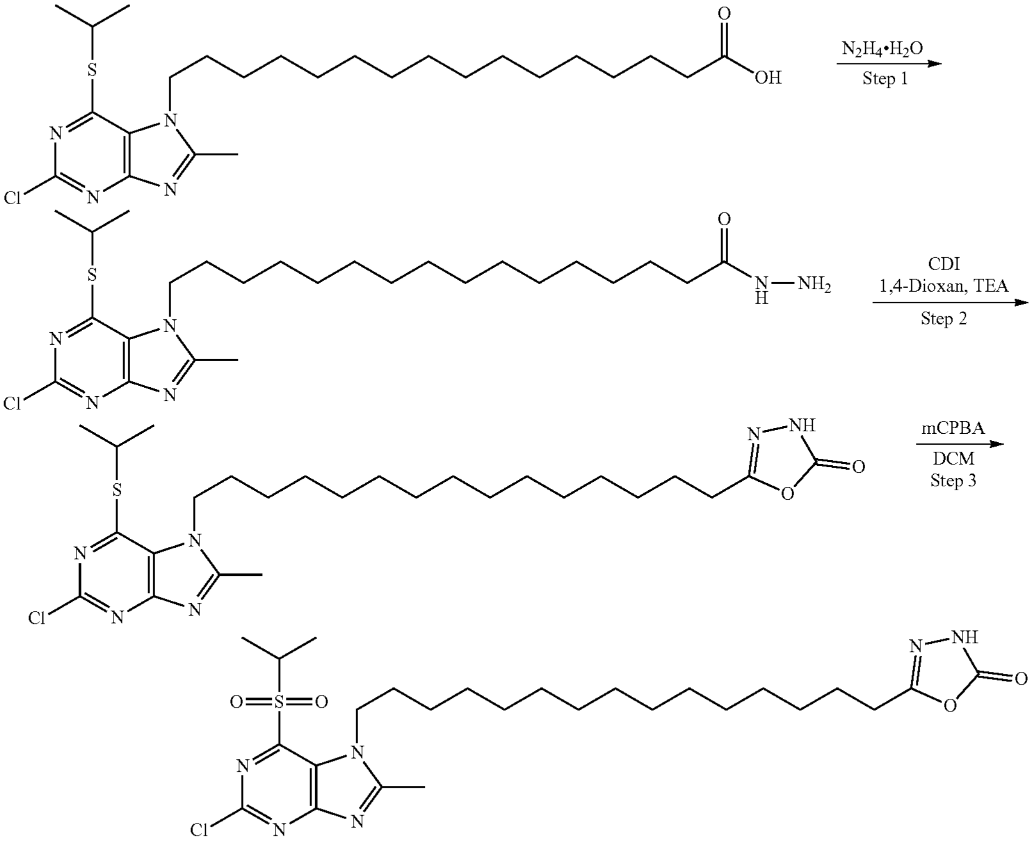

Step 2: POCl3 procedure as described in method 2A was followed. When complete, the reaction contents were slowly added dropwise to a cold solution of saturated $NaHCO_{3(aq.)}$. Then to this solution was added solid $NaHCO_3$ until the pH was tested to be 6-7. Then the aqueous solution was extracted with DCM (2×30 mL). Solvents were removed to obtain ~200 mgs (84%) of 16-(2-chloro-6-(isopropylthio)-8-methyl-7H-purin-7-yl)hexadecanenitrile as a transparent, very thick oil or low melting solid. LCMS: m/Z 478.21 (M+H).

Step 3: 16-(2-chloro-6-(isopropylthio)-8-methyl-7H-purin-7-yl)hexadecanenitrile (30 mgs, 0.06 mmol) was dis- Step 1: To a suspension of methyl ester (250 mg, 0.49 mmol) in methanol (6 mL) under stirring at r. t. excess hydrazine hydrate (1 mL) was added dropwise. The almost clear dark reaction mixture was heated at 50° C. overnight. The reaction mixture was cooled to room temperature, concentrated under rotavap and the residue was extracted in DCM (15 mL), washed with water (2×5 mL), brine and dried over $Na_2SO_4$ (anhyd). DCM extract was filtered, concentrated, to give the crude reaction mixture. Crude product was purified by silica column chromatography using DCM-MeOH (0-5%). The pure product (80 mg, 32%) was isolated.

LCMS: m/z 511.12 (M+H); $^1$H NMR ($CDCl_3$) δ 6.88 (s, br, 1H), 4.39 (m, 1H), 4.32 (t, 2H), 3.90 (s, br., 2H), 2.60 (s, 3H) 2.13 (m, 2H), 1.79 (m, 2H), 1.60 (m, 2H), 1.45 (d, 6H), 1.34 (m, 22H).

Step 2: To a solution of carboxylic acid hydrazide (38 mg, 0.074 mmol) in a vial CDI (20 mg, 1.7 eq) and 1,4-dioxane (anhyd. 1 mL) followed by the addition of TEA (anhyd. 0.1 mL). The reaction mixture was heated at 90° C. for 2 h. The reaction mixture was cooled, concentrated, extracted in DCM (2x5 mL), washed with water (3 ml), brine (2 ml), dried over anhyd. $Na_2SO_4$. The mixture was filtered, concentrated to give the clean product (35 mg, 88%) LCMS: m/z 537.20 (M+H); $^1$H NMR ($CDCl_3$) δ 9.25 (s, br., 1H), 4.39 (m, 1H), 4.27 (t, 2H), 2.63 (s, 3H) 2.55 (m, 2H), 1.79 (m, 2H), 1.68 (m, 2H), 1.49 (d, 6H), 1.30 (m, 22H).

Step 3: To a solution of oxadiazalone derivative (35 mg, 0.077 mmol) in DCM (2 mL) cooled in ice-cold water, mCPBA (77%, 53 mg, 3 eq) was added slowly. The reaction mixture was stirred overnight, and the disappearance of the starting material was detected by TLC. The reaction mixture was diluted with DCM (10 mL), quenched with $NaHSO_3$ (5%, 3 ml), washed thoroughly repeatedly with $NaHCO_3$ (5%, 3x 5 mL), brine (5 mL) and organic layer was dried over anhyd. $Na_2SO_4$. The mixture was filtered, concentrated to give the crude product, which was purified using silica column using a mixture of hexane: EtOAC to isolate the pure sulfone derivative of oxadiazolone. LCMS: m/z 567.22 (M−H); m/z 569.07 (M+H); $^1$H NMR ($CDCl_3$) δ 8.41 (s, br., 1H), 4.57 (t, 2H), 4.43 (m, 1H), 2.77 (s, 3H) 2.55 (m, 2H), 1.81 (m, 2H), 1.69 (m, 2H), 1.52 (d, 6H), 1.53 (m, 22H).

Compound 166: N-(16-(2,6-dichloro-8-methyl-7H-purin-7-yl)hexadecyl)acetamide TDC-59

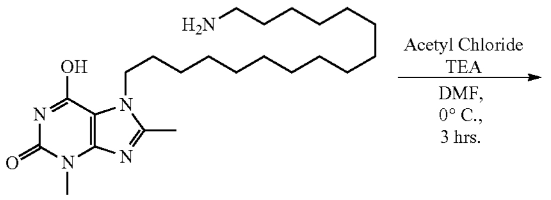

-continued

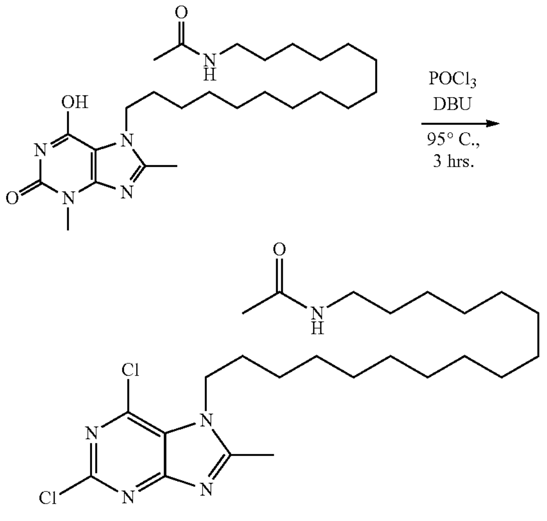

Step 1: 7-(16-aminohexadecyl)-6-hydroxy-3,8-dimethyl-3,7-dihydro-2H-purin-2-one (100 mgs (0.24 mmol) was dissolved in DMF and to this was added 0.04 mL (29 mgs, 0.29 mmol) of TEA. The reaction mixture was cooled to 0° C. and to this was added 0.03 mL (33 mgs, 0.42 mmol) of acetyl chloride dropwise, and was stirred for around 4 hours at 0° C. The reaction mixture was poured onto ice. The resulting precipitate was filtered off. Obtained 60 mgs (54%) of N-(16-(6-hydroxy-3,8-dimethyl-2-oxo-2,3-dihydro-7H-purin-7-yl)hexadecyl)acetamide as a yellow crystalline, impure solid. LCMS: m/z 462.4 (M+H).

Step 2: POCl3 procedure as described in method 2A was followed to obtain 2 mgs (3.2%) of N-(16-(2,6-dichloro-8-methyl-7H-purin-7-yl)hexadecyl)acetamide as a tan/white powder. LCMS: m/Z 484 (M+H); $^1$H NMR (CDCl3) 5 5.44 (bs, 1H), 4.37 (t, 2H), 3.25 (m, 2H), 2.72 (s, 3H), 1.99 (s, 3H), 1.84 (t, 2H), 1.50 (m, 2H), 1.26 (m, 24H).

Compound 167: 3-(15-(2-chloro-6-(isopropylsulfonyl)-8-methyl-7H-purin-7-yl)pentadecyl)-4-methyl-1,2,4-oxadiazol-5(4H)-one

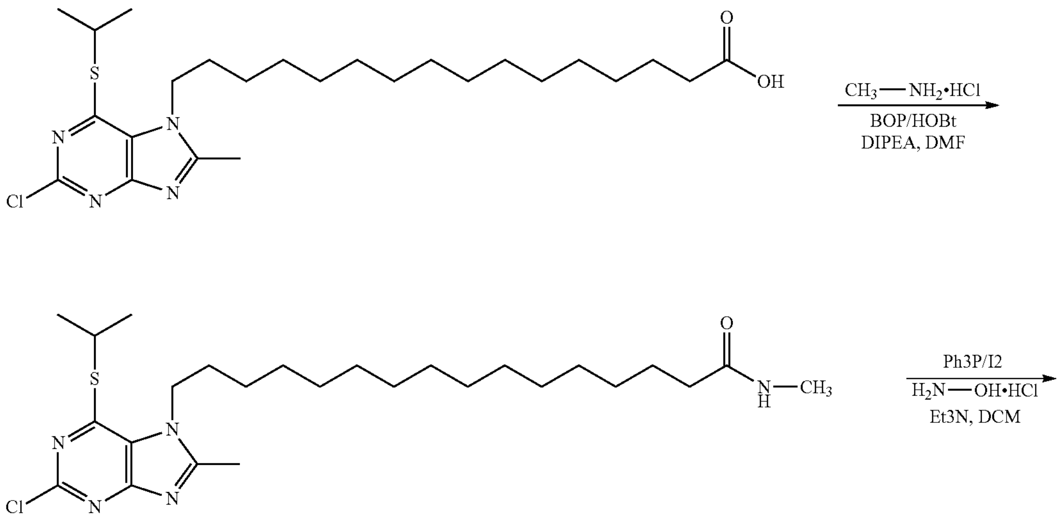

-continued

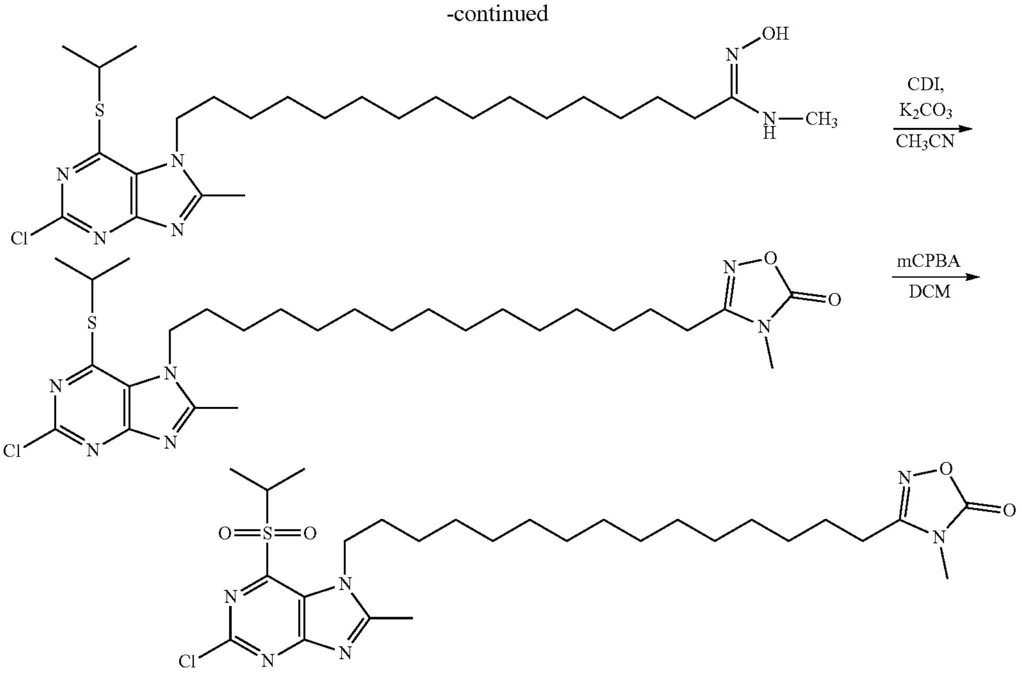

Step 1 A solution of BOP (Benzotriazol-lyloxy)tris(dimethylamino)phosphonium hexafluorophosphate) (597 mg, 1.35 mmol) and HOBt (182 mg, 1.35 mmol) in DMF (5.0 mL) was added dropwise to a stirred solution of 16-(2-chloro-6-(isopropylthio)-8-methyl-7H-purin-7-yl)hexadecanoic acid (610 mg, 1.22 mmol) and $MeNH_2{\cdot}HCl$ (91 mg, 1.35 mmol) in DMF (5.0 mL) at 0° C. under argon atmosphere. DIPEA (472 μL, 2.7 mmol) was added dropwise to the reaction mixture. Reaction mixture was then stirred at r. t. for 2h. Completion of the reaction was confirmed by LC-MS. Water (5.0 mL) was added to reaction mixture and stirred for 5 min. Solvents were evaporated under reduced pressure. Reaction mixture was suspended in DCM (50 mL), washed with water (40 mL) and brine (40 mL). Organic layer was dried over $Na_2SO_4$ and concentrated under reduced pressure to dryness to give crude residue. Crude product was purified on Combi-flash silica gel gradient column chromatography using 0-5% MeOH in DCM to get 380 mg of desire product as light yellow solid. LCMS: m/Z 510.04 $(M+H)^+$.

Step 2: To a solution of iodine (249 mg, 0.981 mmol) and triphenylphosphine (257 mg, 0.981 mmol) in dry DCM (10 mL) was added 16-(2-chloro-6-(isopropylthio)-8-methyl-7H-purin-7-yl)-N-methylhexadecanamide (350 mg, 0.654 mmol), triethyl amine (455 μL, 3.27 mmol) and hydroxylamine hydrochloride (68 mg, 0.981 mmol) at 0° C. Reaction mixture was then warmed up to r. t. and stirred for 3h. Completion of the reaction was confirmed by LC-MS. Reaction mixture was concentrated under reduced pressure. Crude product was purified on Combi-flash silica gel gradient column chromatography using 0-10% MeOH in DCM to give 250 mg of desire product as light gummy solid. LCMS: m/Z 525 $(M+H)^+$.

Step 3: To a solution of 16-(2-chloro-6-(isopropylthio)-8-methyl-7H-purin-7-yl)-N'-hydroxy-N-methylhexadecanimidamide (225 mg, 0.428 mmol) in acetonitrile (5.0 mL) was added 1,1'-carbonyl diimidazole (83 mg, 0.51 mmol), followed by $K_2CO_3$ (295 mg, 2.14 mmol). The resulting mixture was stirred at r. t. for 15 min. Completion of the reaction was confirmed by LC-MS. Reaction mixture was concentrated under reduced pressure to dryness. Crude product was purified by Combi-flash silica gel gradient column chromatography using 0-5% MeOH in DCM to get 100 mg of desire product as gummy solid. LCMS: m/Z 551 $(M+H)^+$.

Step 4: To a cooled solution (ice-water bath) of 3-(15-(2-chloro-6-(isopropylthio)-8-methyl-7H-purin-7-yl)pentadecyl)-4-methyl-1,2,4-oxadiazol-5(4H)-one (30 mg, 0.054 mmol) in DCM (1.0 mL) was added mCPBA (77%, 36 mg, 0.162 mmol) at one portion, and reaction mixture was stirred at this temperature for 30 min. Reaction mixture was warmed up to room temperature and stirred for 2 hours. Completion of the reaction was confirmed by LC-MS. DCM (20 mL) was added to reaction mixture and washed with 5% aq. $NaHCO_3$. (2×10 mL). Organic layers were dried over $Na_2SO_4$ and concentrated under reduced pressure to give crude product, which was purified on $C_{18}$ reverse phase gradient chromatography using Solvent A: water and solvent B: acetonitrile, product was eluted at 80% acetonitrile, pure fractions were combined and lyophilized to get 20 mg of desire product as fluffy white solid. LCMS: m/Z 583 $(M+H)^+$. $^1H$-NMR ($CDCl_3$) δ 4.54 (m, 2H), 4.43 (m, 1H), 3.2 (s, 3H), 2.77 (s, 3H), 2.53 (m, 2H) 1.85 (m, 2H), 1.71 (m, 2H), 1.53 (s, 3H), 1.5 (s, 3H), 1.25 (m, 22H).

Compound 168: methyl 7-((8-(2-chloro-6-(isopropylsulfonyl)-8-methyl-7H-purin-7-yl)octyl)amino) heptanoate

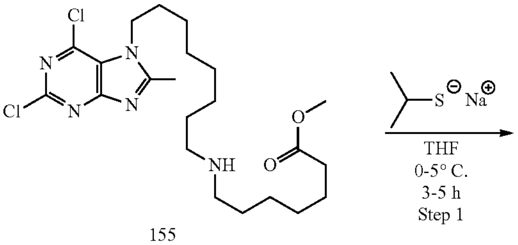

155

-continued

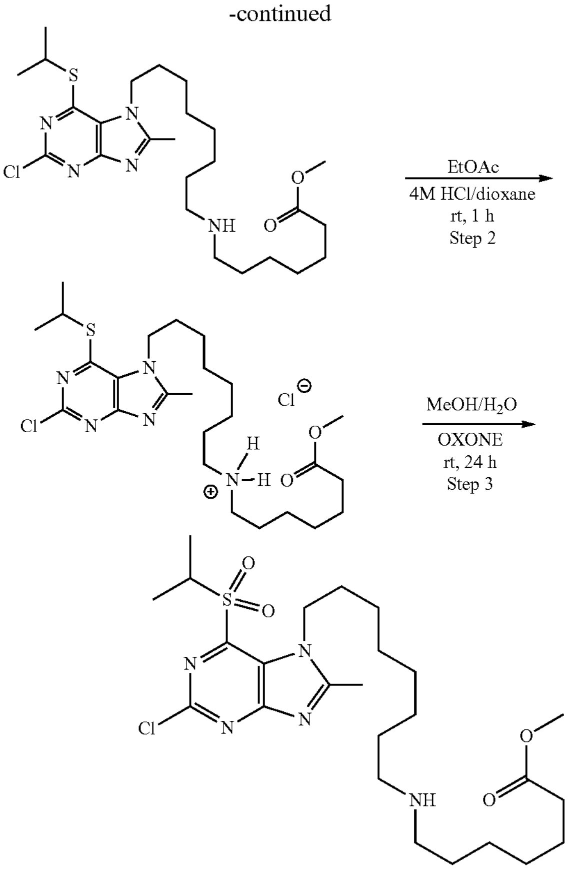

168

Step 1: Following the general procedure, the crude dichloropurine derivative 155 (~320 mg, 0.677 mmol) gave the pure sulfide after reverse-phase chromatography (54 mg, 15.7%) as an orange oil that was taken to the next step. LCMS: m/Z 512 (M+H); $^1$H-NMR (CDCl3 with 0.03% v/v TMS) 8 4.38 (sept, J=6.9 Hz, 1H), 4.29 (m, 2H), 3.65 (s, 3H), 2.88 (m, 4H), 2.65 (s, 3H), 2.28 (t, J=7.4 Hz, 2H), 1.79 (m, 6H), 1.59 (m, 2H), 1.49 (d, J=6.9 Hz, 6H), 1.4-1.24 (m, 12H).

Step 2: The sulfide (48 mg, 0.102 mmol) was dissolved in ethyl acetate (3 mL) to give a slightly cloudy yellow solution. To the stirring solution at room temperature was added dropwise 4M HCl/dioxane (1.0 mL) and a white precipitate was formed. The mixture was stirred for 30 min at room temperature. Ethyl acetate was carefully pipetted off from the white solid. The solid was again centrifuged with ethyl acetate (3 mL) and the supernatant was carefully pipetted off. The white solid (~54 mg) was dried under high vacuum and carried to the next step.

Step 3: The hydrochloride salt (54 mg, 0.098 mmol) was dissolved in MeOH/water (1:1, 5 mL). After stirring for 2 min, oxone (184 mg, 0.6 mmol) was added as a solid and the mixture was stirred at room temperature for 20 h. LCMS showed that all the starting material was converted to the sulfone. After quenching with 5% aqueous ammonium chloride (3-4 mL), the methanol was evaporated in vacuo and the aqueous layer was extracted with DCM (2x15 mL). The combined organic layer was dried over anhydrous $Na_2SO_4$, filtered and the solvent evaporated in vacuo to give the crude as a red oil (52 mg) that was purified by preparative HPLC to give the desired product (6 mg, 11.8%) as an orange oil. LCMS: m/Z 544 (M+H); HPLC purity 90%; $^1$H-NMR ($CDCl_3$ with 0.03% v/v TMS) δ 4.57 (m, 2H), 4.43 (sept, J=7.1 Hz, 1H), 3.66 (s, 3H), 2.78 (s, 3H), 2.66 (m, 4H), 2.30 (t, J=7.2 Hz, 2H), 1.84 (m, 2H), 1.61 (m, 6H), 1.52 (d, J=6.9 Hz, 6H), 1.44-1.26 (m, 12H).

Example 2: Protocol for Testing STING Antagonistic Activity of Exemplary Compounds of the Disclosure in THP-1 and RAW Cells Cells and Cell Culture Conditions THP-1 dual cells (InvivoGen) were cultured under 5% $CO_2$ at 37° C. in RPMI containing 10% fetal bovine serum (FBS), 100 IU mL-1 penicillin and 100 pg mL-1 streptomycin. RAW-ISG cells (InvivoGen) were cultured under 5% $CO_2$ at 37° C. in DMEM containing 10% fetal bovine serum (FBS), 100 IU mL-1 penicillin and 100 pg mL-1 streptomycin. THP-1 dual cells were seeded into the 96 well assay plate on the day of assay whereas RAW cells were seeded into the 96 well assay plate 18 hours before the assay.

Cell-based ISG54 promoter-reporter luciferase measurements of IRF activity in THP-1 dual cells:

50,000 cells seeded in a 96-well flat bottom white assay plate were treated with different concentrations (10 uM to 0.01 uM) of compounds for 1 h followed by STING induction with either 30 nM SB 11285 or 10ug/mL 2'-3' cGAMP. The cells were then incubated for 20 hours @37° C. in CO2 incubator before measuring IRF activation by using Quanti-Luc (InvivoGen). The % inhibition was calculated as 100-{[(luminescence of COI treated well/luminescence of non-COI treated well)/100]X 100}. $IC_{50}$ was calculated by plotting in Xlfit.

Cell-based ISG54 promoter-reporter luciferase measurements of IRF activity in RAW-ISG cells 50,000 cells seeded in a 96-well flat bottom white assay plate were treated with different concentrations (10 uM to 0.01 uM) of compounds for 1 h followed by STING induction with either 1 μM SB 11285 or 10 μg/mL 2'-3' cGAMP. The cells were then incubated for 20 hours @37° C. in CO2 incubator before measuring IRF activation by using Quanti-Luc (InvivoGen). The % inhibition was calculated as 100-{[(luminescence of COI treated well/luminescence of non-COI treated well)/100]X 100}. $IC_{50}$ was calculated by plotting in Xlfit.

Protocol to evaluate STING antagonist compounds in THP1-Dual-WT cells

THP1-Dual-WT cells (InvivoGen) were plated into 96-well flat bottom plate at 5x10∝cells/140 μL/well in triplicate. Cells were then treated with diluted antagonist compounds at 10 μL/well for 1 h, followed by treatment with compounds or 2'3'-cGAMP/lipo mixture for 18 h. The levels of IRF activity were determined using Quanti-luc (InvivoGen) and calculated against IRF activity in DMSO-treated cells. $IC_{50}$and $CC_{50}$ values were calculated using Xlfit.

Inhibition of IRF3 in THP-1 cells using a synthetic STING agonist

THP-1 dual WT cells were plated in 96-well plates. The cells were pre-treated with the test compounds THP1-Dual-WT cells in 96-well plate were pre-treated with antagonist compound for 1 h, followed by stimulation with a synthetic STING agonist for 18 h. The levels of IRF activity were determined using Quanti-luc and IC50 values compared with that of the DMSO-treated cells.

Inhibition of IRF3 in THP-1 cells using a natural STING agonist 2'3'-cGAMP

THP1-Dual-WT cells in 96-well plate were pre-treated with antagonist compound for 1 h, followed by stimulation with 2'3'-cGAMP (10 μM) for 19 h. The levels of IRF activity were determined using Quanti-luc and calculated against IRF activity in DMSO-treated cells.

Evaluation of antagonist compounds in RAW-WT cells using natural STING agonist 2'3'-cGAMP RAW-WT cells in 96-well plate were pre-treated with antagonist compound for 1 h, followed by stimulation with 2'3'-cGAMP (10 μM) for 18 h. The levels of IRF activity were determined using Quanti-luc and IC50 values compared with that of the DMSO-treated cells.

Screening of compounds for antagonistic activity using HEK-92-derived SZ-14 cells SZ14 cells in 96-well plate were pre-treated with antagonists for 1 h, followed by stimulation with SB 11285 (0.5 μM) for 5 h. The levels of ISG54 ISRE-luc activity were determined using Steady-Glo buffer and calculated against ISRE-luc activity in DMSO-treated cells.

Evaluation of activity of compounds in THP-1 cells for their inhibition of STING, LPS, ppp-dsRNA & Poly IC induction: THP-1 cells were treated with different concentrations (10 uM to 0.01 μM) of Compounds for 1 h followed by STING/TLR3/TLR4/RIG-I/TLR7/9 activation by corresponding agonists. Lipofectamine (LTX) was used along with dsRNA, 2'-3'cGAMP & VACV-70. The cells were then incubated for 20 hours @37° C. before measuring IRF activation by using Quanti-Luc. The % inhibition was calculated as 100-[(luminescence of COI treated well/luminescence of non COI treated well)/100]X 100. Cytotoxicity was measured by using Cell Titer Glo.

1. Cmd 6 weakly inhibits dsDNA-induced cGAS-STING-IRF/NF-κB signaling pathway
2. Cmd 6 weakly inhibits 3p-hpRNA-induced RIG-I-IRF/NF-κB signaling pathway
3. Cmd 6 does not affect TLR7/9 signaling pathways. Cmd 6 seems to inhibit LPS-induced TLR4/NF-κB activation in RAW-WT cells, but not in THPI-WT cells.

Evaluation of activity of compounds in RAW cells for their inhibition of STING induction:

THP-1 cells were treated with different concentrations (10 uM to 0.01 uM) of compounds for 1 h followed by STING activation by different concentrations of 2'-3'cGAMP (with Lipofectamine LTX). The cells were then incubated for 20 hours @37° C. before measuring IRF activation by using Quanti-Luc. The % inhibition was calculated as 100-[(luminescence of COI treated well/luminescence of non COI treated well)/100]X 100. Cytotoxicity was measured by using Cell Titer Glo.

Evaluation of activity of compounds in TREX-1 KO and STING GOF M155 mutant THP-1 cells:

(a) THP-1 cells were treated with different concentrations (10 uM to 0.01 uM) of compounds and incubated for 20 hours @37° C. before measuring IRF activation by using Quanti-Luc. The % inhibition was calculated as 100-[(luminescence of COI treated well/luminescence of non COI treated well)/100]X 100.

(b) THPl-TREX1 KO-cells or THP1-KI STING-M155 (GoF) cells in 96-well plate were treated with compounds or vehicle DMSO once daily for 3 days. Cells were cultured for around 22 h and the levels of IRF activity were determined using Quanti-luc before adding new additional compounds. Culture media were not changed during the treatment. The IRF activity was normalized against IRF activity in DMSO-treated cells. IC50 values were calculated using Xlfit.

Evaluating STING antagonist activity of compounds in human PBMCs against natural STING ligand 2'-3'cGAMP: Human PBMCs were treated with 3 uM of each compound followed by addition of 200 uM 2'-3'cGAMP. The cells were then incubated for 20 hours @37° C. before collecting supernatants and measuring secreted cytokines by ELISA. The statistical significance was calculated by student's t test.

Evaluating of activity of compounds in THP-1 cells & RAW macrophages for inhibition of STING activation: THP-1 cells were treated with different concentrations (10 uM to 0.01 uM) of compounds for 1 h followed by STING activation by adding 10ug/mL 2'-3' cGAMP. The cells were then incubated for 20 hours @37° C. before measuring IRF activation by using Quanti-Luc. The % inhibition was calculated as 100-[(luminescence of COI treated well/luminescence of non COI treated well)/100]X 100. Cytotoxicity was measured by using Cell Titer Glo.

Evaluating STING antagonist activity of compounds in human PBMCs against natural STING ligand 2'-3'cGAMP: Human PBMCs were treated with 6.25 uM of each compound followed by addition of 200 uM 2'-3'cGAMP. The cells were then incubated for 20 hours @37° C. before collecting supernatants and measuring secreted cytokines by ELISA. The statistical significance was calculated by student's t test.

In vivo evaluation of antagonistic activity of compounds in mice Mice were pretreated with vehicle or compounds (50 mg/kg) via i.p. injection for 1 h, followed by treatment with synthetic STING agonist (2 mg/kg. i.p.). Blood, spleen, and liver samples were collected at 1 h, 4h, and 24 h post-agonist treatment. The production of IFN-β was monitored using ELISA. The basal level of IFN-β in untreated mice (n=2) was undetectable in all tested tissues. Mice were pretreated with vehicle or Compounds (50 mg/kg) via i.p. injection for 1 h, followed by treatment with synthetic STING agonist (2 mg/kg. i.p.). Blood, spleen, and liver samples were collected at 1 h, 4h, and 24 h post-agonist treatment. The production of RANTES was monitored using ELISA. The basal level of RANTES in untreated mice (n=2), blood (undetectable), spleen (26.6 ng/g of spleen), liver (6.17 ng/g of liver).

Mice were pretreated with vehicle or compounds (10 mg/kg) via i.p. injection for 1 h, followed by treatment with 2'3'-cGAMP (10 mg/kg. i.p.). Blood samples were collected at 4 h and 6 h post-cGAMP treatment. The production of IFN-β was monitored using ELISA.

Evaluating stability of compounds in Simulated Gastric fluid (SGF) & Simulated intestinal fluidsSIF: Each test compound was incubated in either total SIF or SGF at a final concentration of 100 M of compound. The incubations were carried out at 37° C. for different time points that includes 0, 0.5 h, 1 h, 2 h, 4 h, and 6 h after which quenched by addition of Acetonitrile. The samples were then frozen in dry ice for at least 10 minutes to precipitate out the proteins followed by high speed centrifugation to collect clear supernatant for analysis by HPLC. Stability of the compounds were calculated from the rate of disappearance of test compound.

TABLE 2
Antagonist Activity of Exemplary Compounds
| Compound Number | Structure | $IC_{50}$ |
|---|---|---|
| 1 | 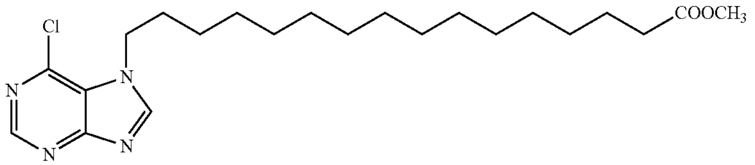 [SMILES: COC(=O)CCCCCCCCCCCCCCCn1cnc2ncnc(Cl)c21] | B |
| 2 | 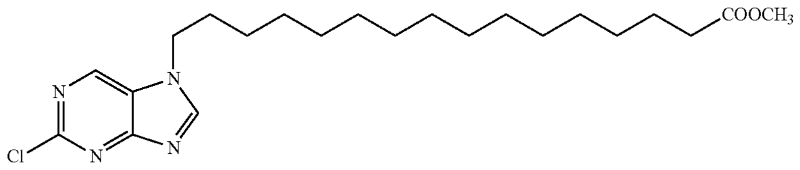 [SMILES: COC(=O)CCCCCCCCCCCCCCCn1cnc2nc(Cl)ncc21] | D |
| 3 | 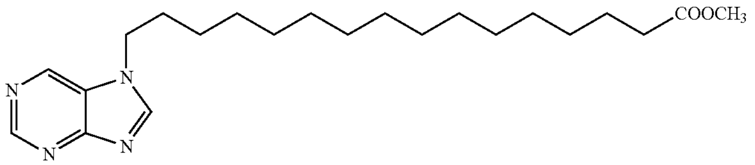 [SMILES: COC(=O)CCCCCCCCCCCCCCCn1cnc2ncncc21] | E |
| 4 | 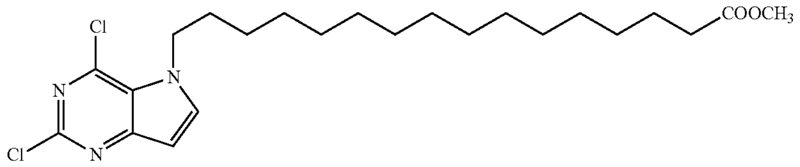 [SMILES: COC(=O)CCCCCCCCCCCCCCCn1ccc2nc(Cl)nc(Cl)c21] | E |
| 5 | 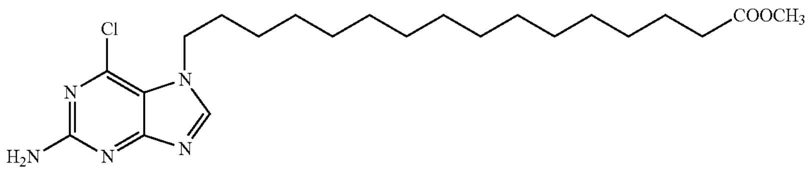 [SMILES: COC(=O)CCCCCCCCCCCCCCCn1cnc2nc(N)nc(Cl)c21] | C |
| 6 | 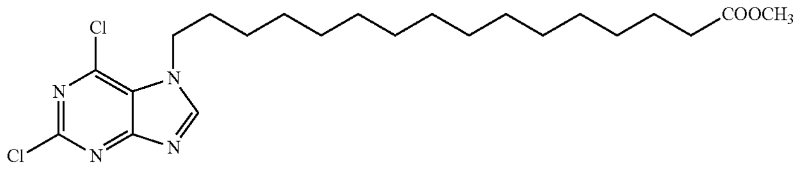 [SMILES: COC(=O)CCCCCCCCCCCCCCCn1cnc2nc(Cl)nc(Cl)c21] | A |
| 7 | 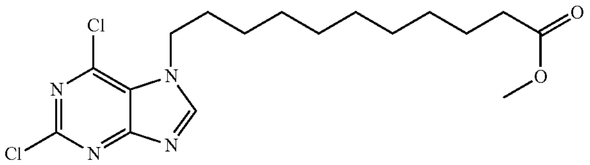 [SMILES: COC(=O)CCCCCCCCCCn1cnc2nc(Cl)nc(Cl)c21] | A |
| 8 | 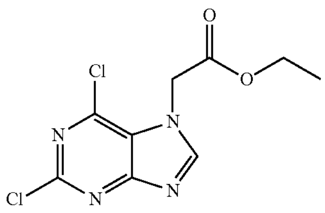 [SMILES: CCOC(=O)Cn1cnc2nc(Cl)nc(Cl)c21] | A |

TABLE 2-continued
| Compound Number | Structure | $IC_{50}$ |
|---|---|---|
| Antagonist Activity of Exemplary Compounds | | |
| 9 | 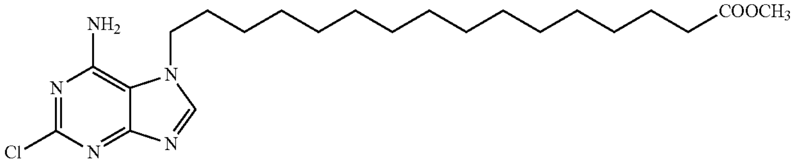 [SMILES: COC(=O)CCCCCCCCCCCCCCCn1cnc2nc(Cl)nc(N)c21] | B |
| 10 | 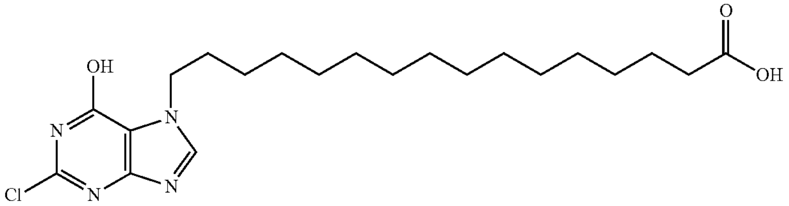 [SMILES: O=C(O)CCCCCCCCCCCCCCCn1cnc2nc(Cl)nc(O)c21] | E |
| 11 | 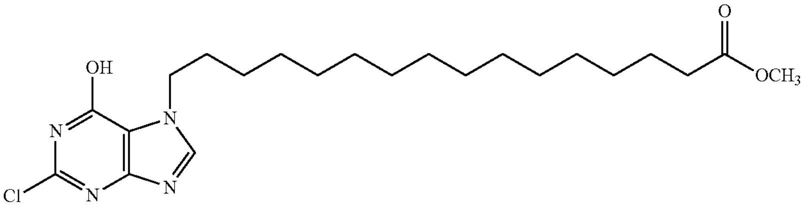 [SMILES: COC(=O)CCCCCCCCCCCCCCCn1cnc2nc(Cl)nc(O)c21] | D |
| 12 | 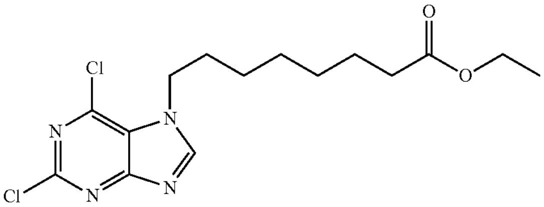 [SMILES: CCOC(=O)CCCCCCCn1cnc2nc(Cl)nc(Cl)c21] | A |
| 13 | 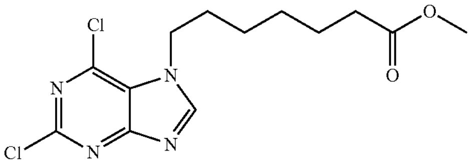 [SMILES: COC(=O)CCCCCCn1cnc2nc(Cl)nc(Cl)c21] | A |
| 14 | 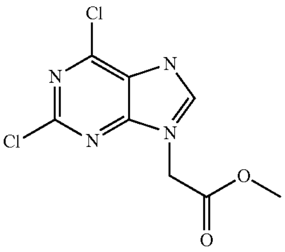 | E |
| 15 | 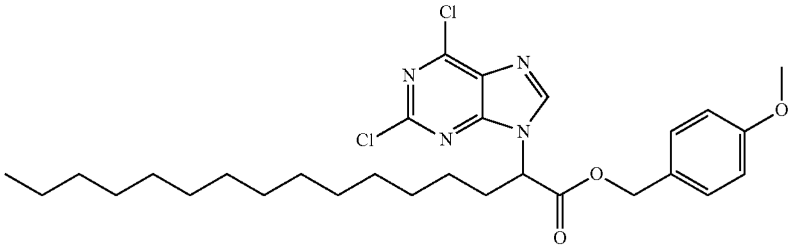 [SMILES: CCCCCCCCCCCCCCC(C(=O)OCc1ccc(OC)cc1)n1cnc2c(Cl)nc(Cl)nc21] | E |

TABLE 2-continued
| Antagonist Activity of Exemplary Compounds | | |
|---|---|---|
| Compound Number | Structure | IC$_{50}$ |
| 16 | 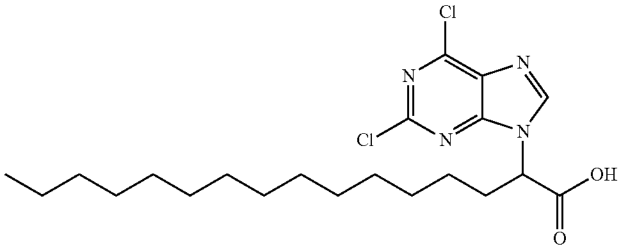 [SMILES: CCCCCCCCCCCCCCC(C(=O)O)n1cnc2c(Cl)nc(Cl)nc21] | D |
| 17 | 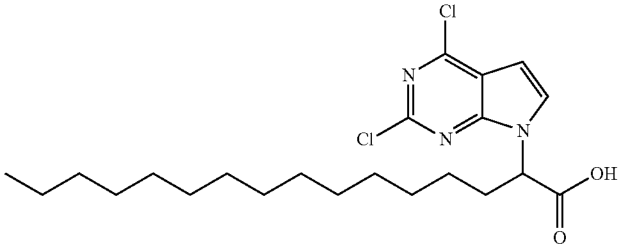 [SMILES: CCCCCCCCCCCCCCC(C(=O)O)n1ccc2c(Cl)nc(Cl)nc21] | E |
| 18 | 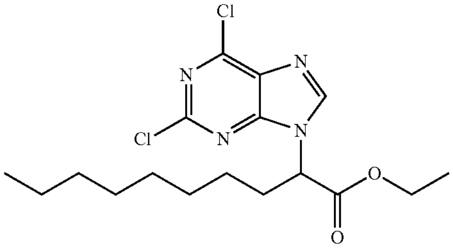 [SMILES: CCCCCCCCC(C(=O)OCC)n1cnc2c(Cl)nc(Cl)nc21] | B |
| 19 | 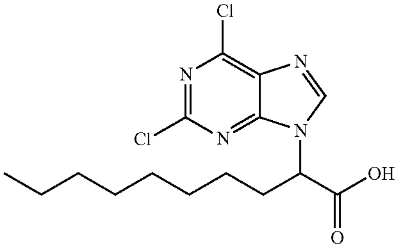 [SMILES: CCCCCCCCC(C(=O)O)n1cnc2c(Cl)nc(Cl)nc21] | C |
| 20 | 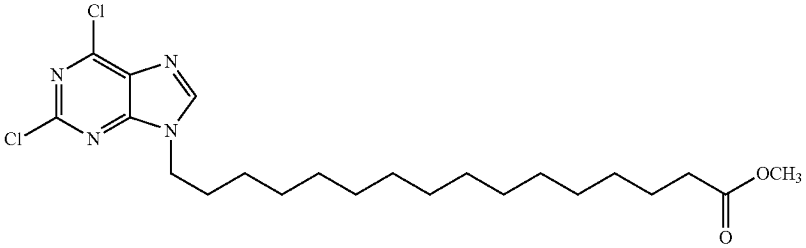 [SMILES: COC(=O)CCCCCCCCCCCCCCCn1cnc2c(Cl)nc(Cl)nc21] | C |

TABLE 2-continued
Antagonist Activity of Exemplary Compounds
| Compound Number | Structure | $IC_{50}$ |
|---|---|---|
| 21 | 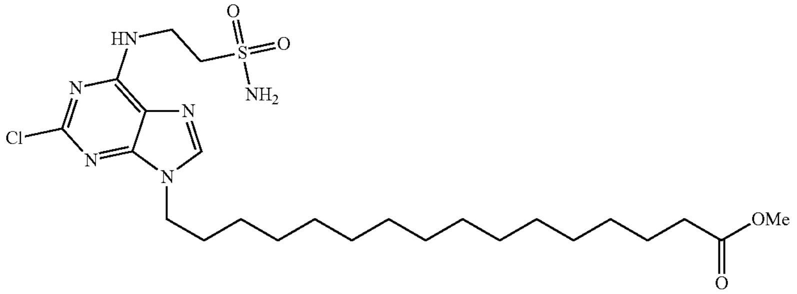 [SMILES: COC(=O)CCCCCCCCCCCCCCCn1cnc2c(NCCS(N)(=O)=O)nc(Cl)nc21] | D |
| 22 | 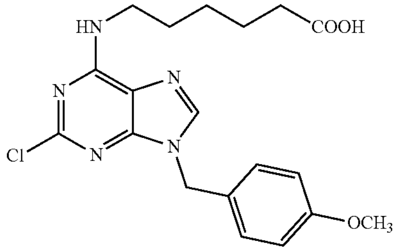 [SMILES: COc1ccc(Cn2cnc3c(NCCCCCC(=O)O)nc(Cl)nc32)cc1] | E |
| 23 | 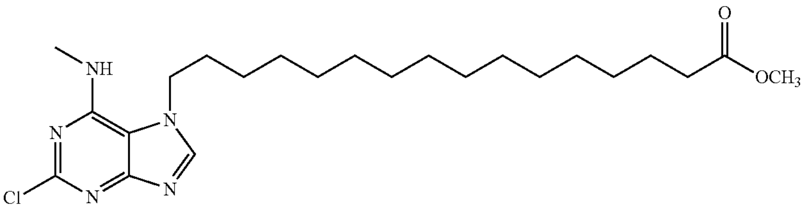 [SMILES: CNc1nc(Cl)nc2ncn(CCCCCCCCCCCCCCCC(=O)OC)c12] | E |
| 24 | 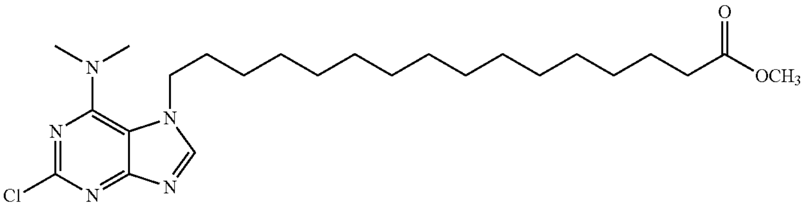 [SMILES: COC(=O)CCCCCCCCCCCCCCCn1cnc2nc(Cl)nc(N(C)C)c21] | B |
| 25 | 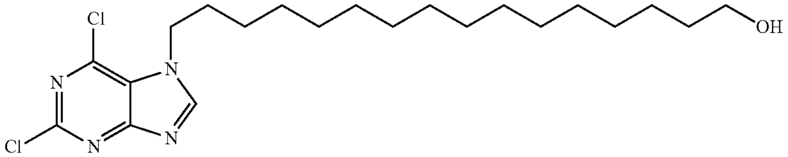 [SMILES: OCCCCCCCCCCCCCCCCn1cnc2nc(Cl)nc(Cl)c21] | A |
| 26 | 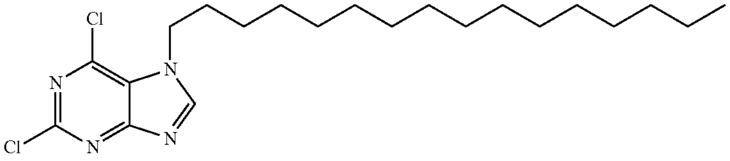 [SMILES: CCCCCCCCCCCCCCCCn1cnc2nc(Cl)nc(Cl)c21] | A |
| 27 | 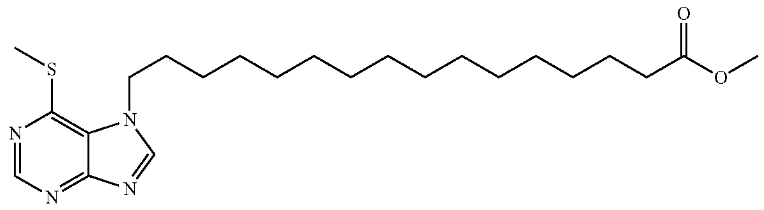 [SMILES: COC(=O)CCCCCCCCCCCCCCCn1cnc2ncnc(SC)c21] | C |

TABLE 2-continued
| Antagonist Activity of Exemplary Compounds | | |
|---|---|---|
| Compound Number | Structure | $IC_{50}$ |
| 28 | 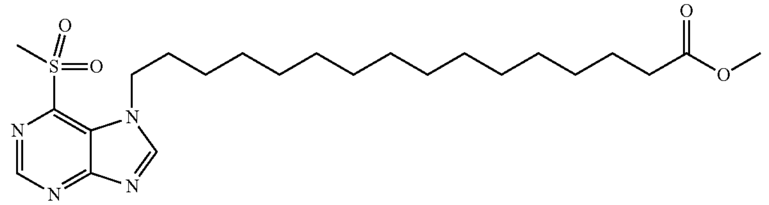 [SMILES: COC(=O)CCCCCCCCCCCCCCCn1cnc2ncnc(S(C)(=O)=O)c21] | A |
| 29 | 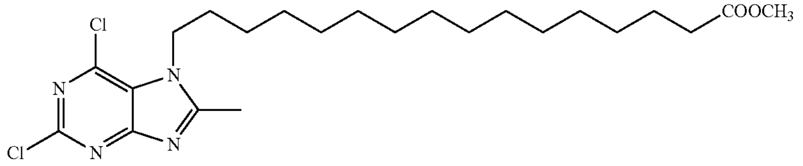 [SMILES: COC(=O)CCCCCCCCCCCCCCCn1c(C)nc2nc(Cl)nc(Cl)c21] | A |
| 30 | 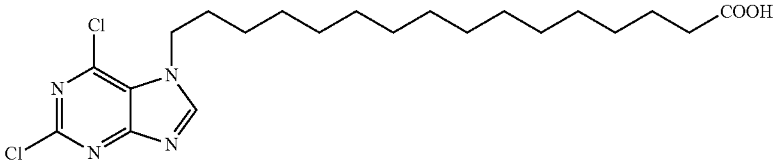 [SMILES: O=C(O)CCCCCCCCCCCCCCCn1cnc2nc(Cl)nc(Cl)c21] | B |
| 31 | 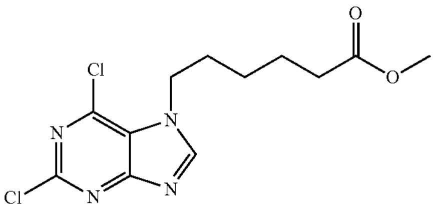 [SMILES: COC(=O)CCCCCn1cnc2nc(Cl)nc(Cl)c21] | B |
| 32 | 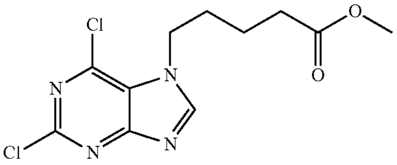 [SMILES: COC(=O)CCCCn1cnc2nc(Cl)nc(Cl)c21] | B |
| 33 | 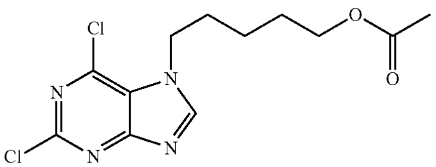 [SMILES: CC(=O)OCCCCCn1cnc2nc(Cl)nc(Cl)c21] | B |
| 34 | 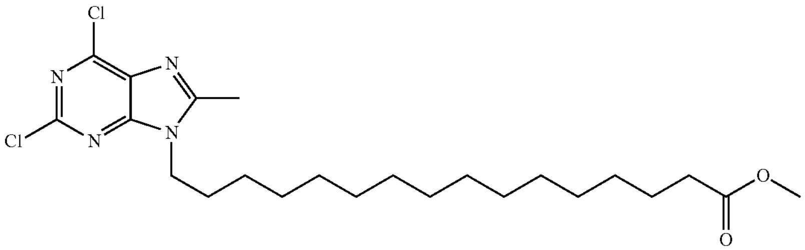 [SMILES: COC(=O)CCCCCCCCCCCCCCCn1c(C)nc2c(Cl)nc(Cl)nc21] | D |

TABLE 2-continued
| Antagonist Activity of Exemplary Compounds | | |
|---|---|---|
| Compound Number | Structure | $IC_{50}$ |
| 35 | 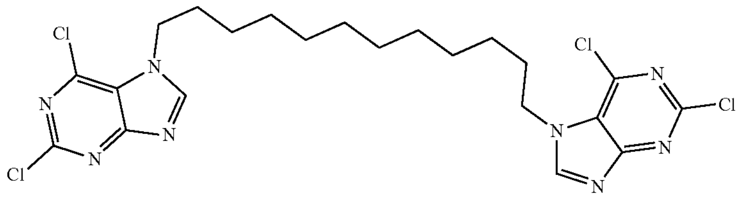 [SMILES: Clc1nc(Cl)c2c(ncn2CCCCCCCCCCCCn2cnc3nc(Cl)nc(Cl)c32)n1] | B |
| 36 | 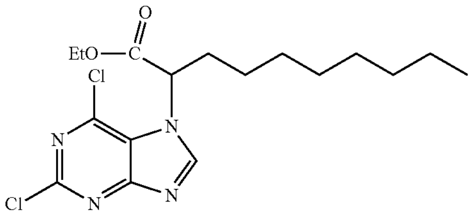 [SMILES: CCCCCCCCC(C(=O)OCC)n1cnc2nc(Cl)nc(Cl)c21] | B |
| 37 | 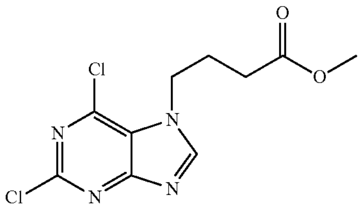 [SMILES: COC(=O)CCCn1cnc2nc(Cl)nc(Cl)c21] | C |
| 38 | 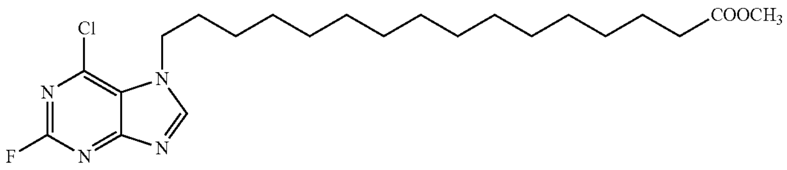 [SMILES: COC(=O)CCCCCCCCCCCCCCCn1cnc2nc(F)nc(Cl)c21] | B |
| 39 | 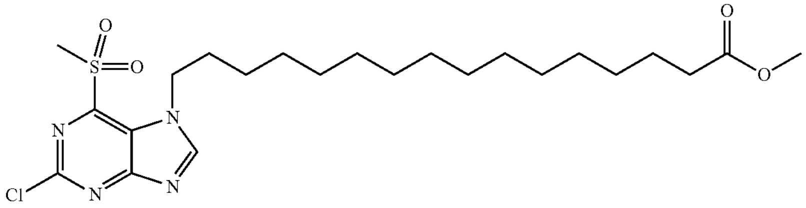 [SMILES: COC(=O)CCCCCCCCCCCCCCCn1cnc2nc(Cl)nc(S(C)(=O)=O)c21] | E |
| 40 | 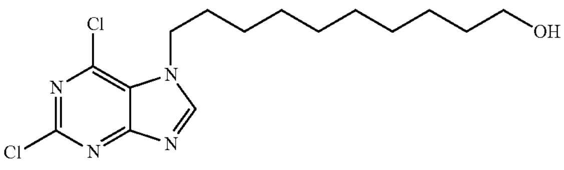 [SMILES: OCCCCCCCCCCn1cnc2nc(Cl)nc(Cl)c21] | A |
| 41 | 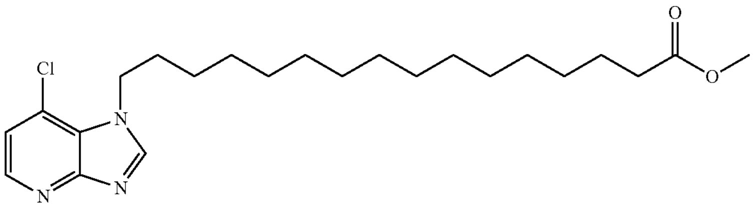 [SMILES: COC(=O)CCCCCCCCCCCCCCCn1cnc2nccc(Cl)c21] | E |

TABLE 2-continued
Antagonist Activity of Exemplary Compounds
| Compound Number | Structure | $IC_{50}$ |
| --- | --- | --- |
| 42 | 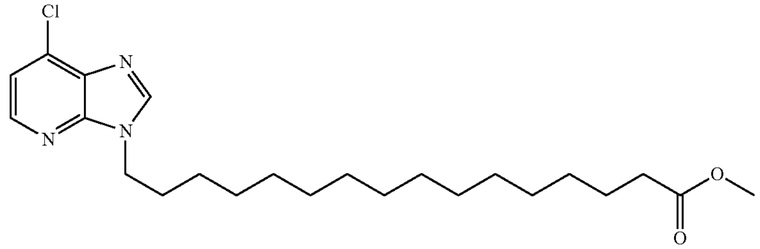 [SMILES: COC(=O)CCCCCCCCCCCCCCCn1cnc2c(Cl)ccnc21] | E |
| 43 | 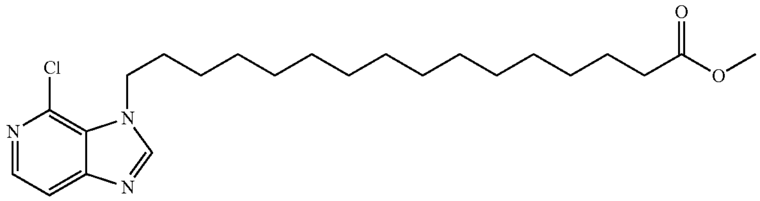 [SMILES: COC(=O)CCCCCCCCCCCCCCCn1cnc2ccnc(Cl)c21] | E |
| 44 | 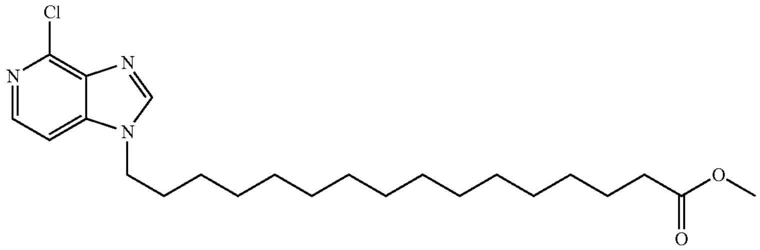 [SMILES: COC(=O)CCCCCCCCCCCCCCCn1cnc2c(Cl)nccc21] | E |
| 45 | 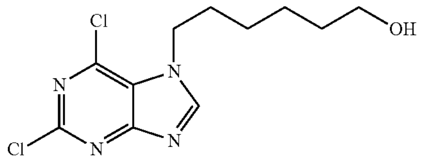 [SMILES: OCCCCCCn1cnc2nc(Cl)nc(Cl)c21] | B |
| 46 | 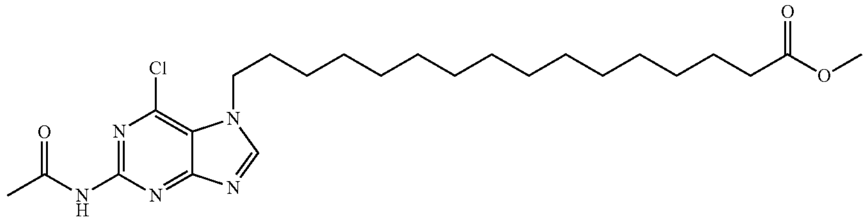 [SMILES: COC(=O)CCCCCCCCCCCCCCCn1cnc2nc(NC(C)=O)nc(Cl)c21] | E |
| 47 | 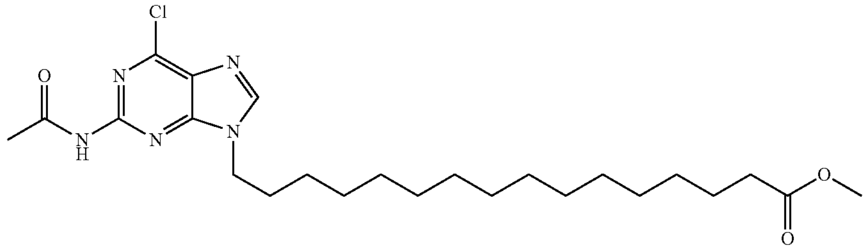 [SMILES: COC(=O)CCCCCCCCCCCCCCCn1cnc2c(Cl)nc(NC(C)=O)nc21] | E |
| 48 | 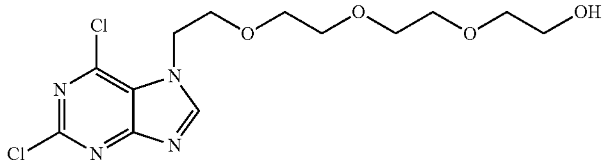 [SMILES: OCCOCCOCCOCCn1cnc2nc(Cl)nc(Cl)c21] | B |

TABLE 2-continued
Antagonist Activity of Exemplary Compounds
| Compound Number | Structure | $IC_{50}$ |
|---|---|---|
| 49 | 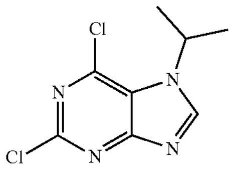 | E |
| 50 | 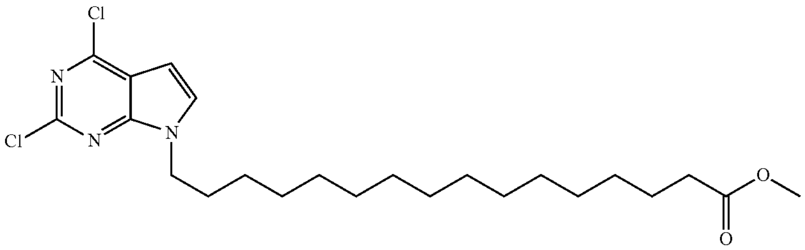 [SMILES: COC(=O)CCCCCCCCCCCCCCCn1ccc2c(Cl)nc(Cl)nc21] | E |
| 51 | 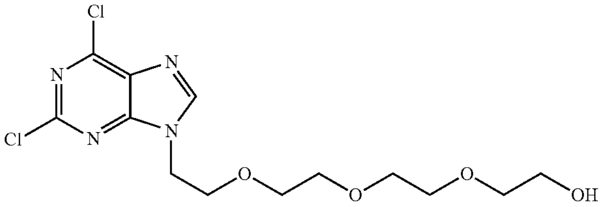 [SMILES: OCCOCCOCCOCCn1cnc2c(Cl)nc(Cl)nc21] | E |
| 52 | 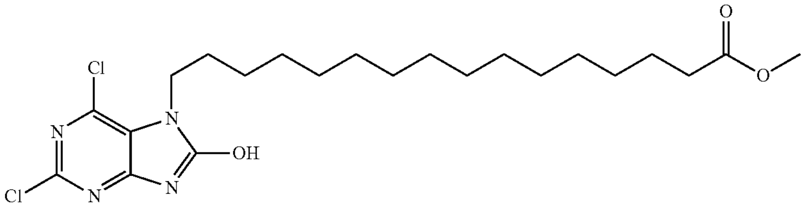 [SMILES: COC(=O)CCCCCCCCCCCCCCCn1c(O)nc2nc(Cl)nc(Cl)c21] | E |
| 53 | 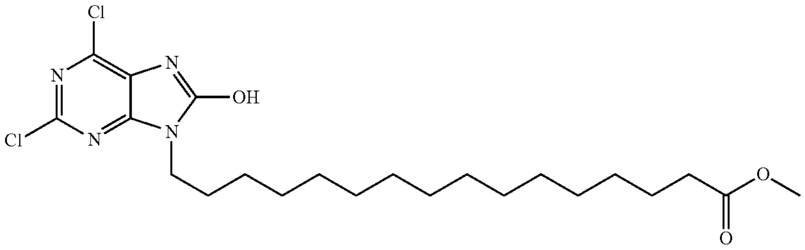 [SMILES: COC(=O)CCCCCCCCCCCCCCCn1c(O)nc2c(Cl)nc(Cl)nc21] | E |
| 54 | 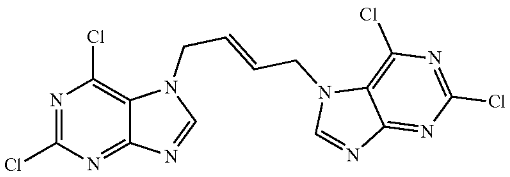 [SMILES: Clc1nc(Cl)c2c(ncn2C/C=C/Cn2cnc3nc(Cl)nc(Cl)c32)n1] | B |
| 55 | 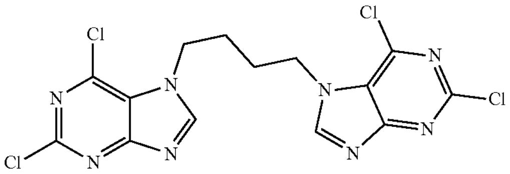 [SMILES: Clc1nc(Cl)c2c(ncn2CCCCn2cnc3nc(Cl)nc(Cl)c32)n1] | C |

TABLE 2-continued
| Antagonist Activity of Exemplary Compounds | | |
|---|---|---|
| Compound Number | Structure | $IC_{50}$ |
| 56 | 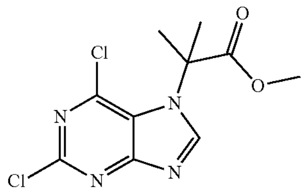 [SMILES: COC(=O)C(C)(C)n1cnc2nc(Cl)nc(Cl)c21] | E |
| 57 | 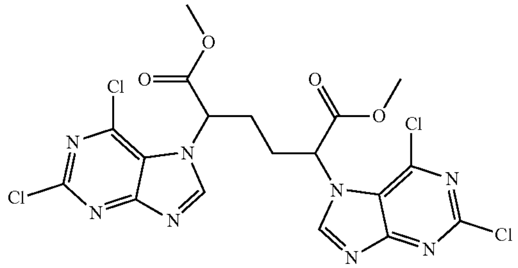 [SMILES: COC(=O)C(CCC(C(=O)OC)n1cnc2nc(Cl)nc(Cl)c21)n1cnc2nc(Cl)nc(Cl)c21] | B |
| 58 | 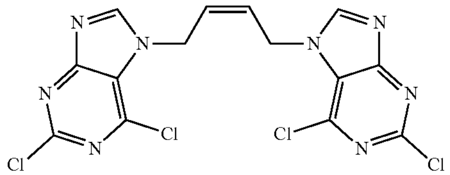 [SMILES: Clc1nc(Cl)c2c(ncn2C/C=C\Cn2cnc3nc(Cl)nc(Cl)c32)n1] | E |
| 59 | 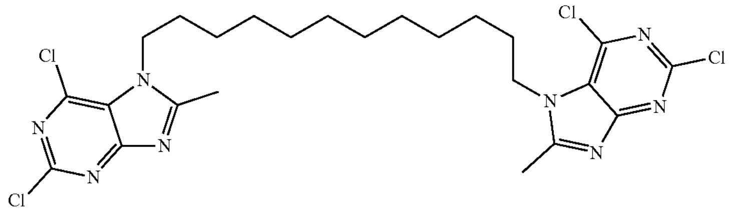 [SMILES: Cc1nc2nc(Cl)nc(Cl)c2n1CCCCCCCCCCCCn1c(C)nc2nc(Cl)nc(Cl)c21] | A |
| 60 | 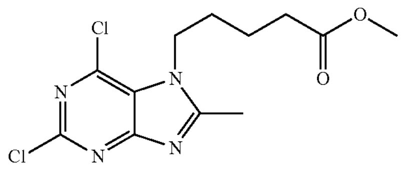 [SMILES: COC(=O)CCCCn1c(C)nc2nc(Cl)nc(Cl)c21] | C |
| 61 | 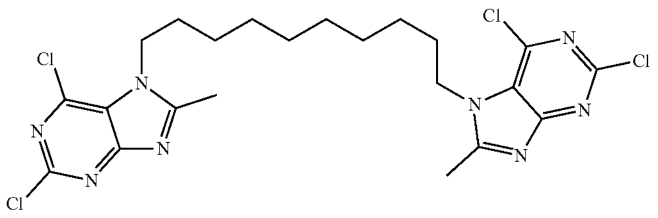 [SMILES: Cc1nc2nc(Cl)nc(Cl)c2n1CCCCCCCCCCn1c(C)nc2nc(Cl)nc(Cl)c21] | A |
| 62 | 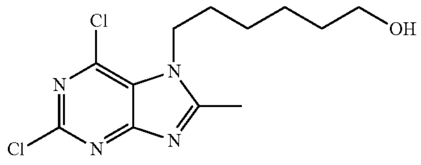 [SMILES: Cc1nc2nc(Cl)nc(Cl)c2n1CCCCCCO] | B |

TABLE 2-continued
| Antagonist Activity of Exemplary Compounds | | |
|---|---|---|
| Compound Number | Structure | $IC_{50}$ |
| 63 | 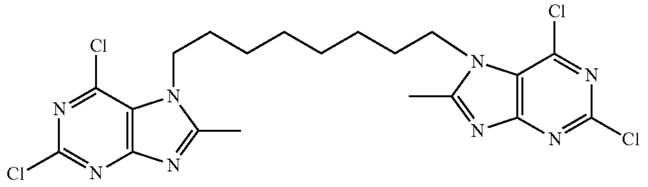 [SMILES: Cc1nc2nc(Cl)nc(Cl)c2n1CCCCCCCCn1c(C)nc2nc(Cl)nc(Cl)c21] | A |
| 64 | 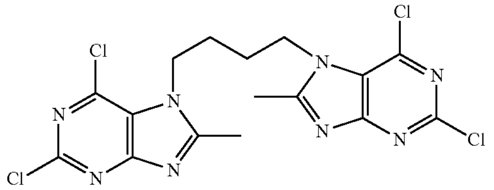 [SMILES: Cc1nc2nc(Cl)nc(Cl)c2n1CCCCn1c(C)nc2nc(Cl)nc(Cl)c21] | E |
| 65 | 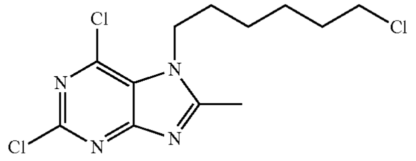 [SMILES: Cc1nc2nc(Cl)nc(Cl)c2n1CCCCCCCl] | B |
| 66 | 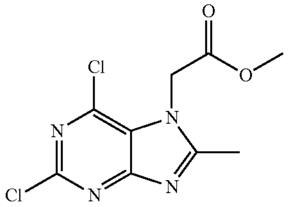 [SMILES: COC(=O)Cn1c(C)nc2nc(Cl)nc(Cl)c21] | B |
| 67 | 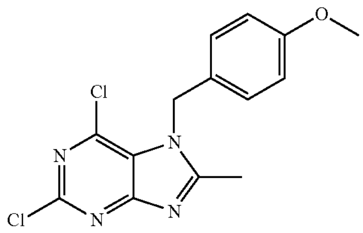 [SMILES: COc1ccc(Cn2c(C)nc3nc(Cl)nc(Cl)c32)cc1] | B |
| 68 | 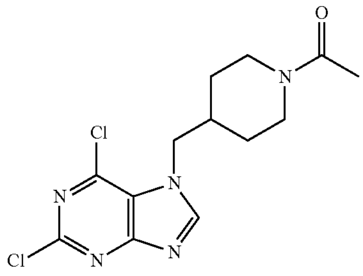 [SMILES: CC(=O)N1CCC(Cn2cnc3nc(Cl)nc(Cl)c32)CC1] | C |
| 69 | 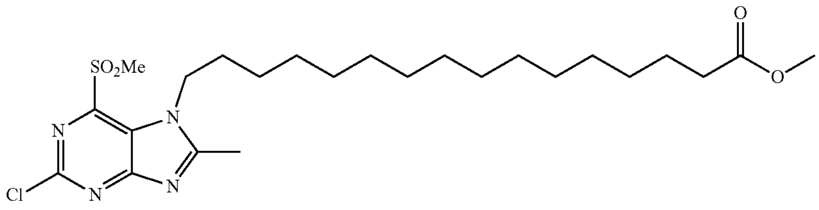 [SMILES: COC(=O)CCCCCCCCCCCCCCCn1c(C)nc2nc(Cl)nc(S(C)(=O)=O)c21] | A |

TABLE 2-continued
| Antagonist Activity of Exemplary Compounds | | |
|---|---|---|
| Compound Number | Structure | $IC_{50}$ |
| 70 | 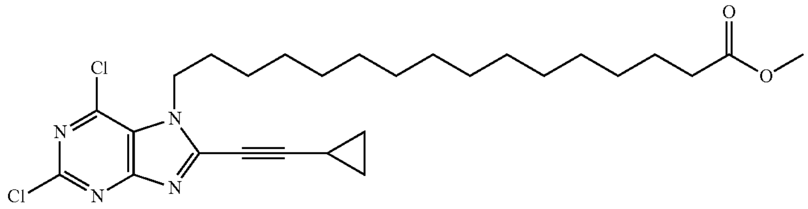 [SMILES: COC(=O)CCCCCCCCCCCCCCCn1c(C#CC2CC2)nc2nc(Cl)nc(Cl)c21] | B |
| 71 | 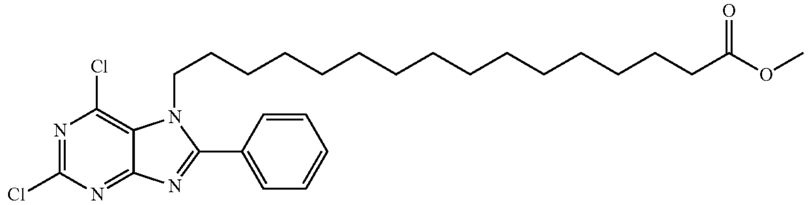 [SMILES: COC(=O)CCCCCCCCCCCCCCCn1c(-c2ccccc2)nc2nc(Cl)nc(Cl)c21] | B |
| 72 | 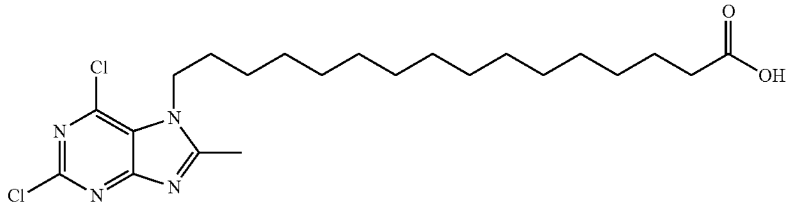 [SMILES: Cc1nc2nc(Cl)nc(Cl)c2n1CCCCCCCCCCCCCCCC(=O)O] | D |
| 73 | 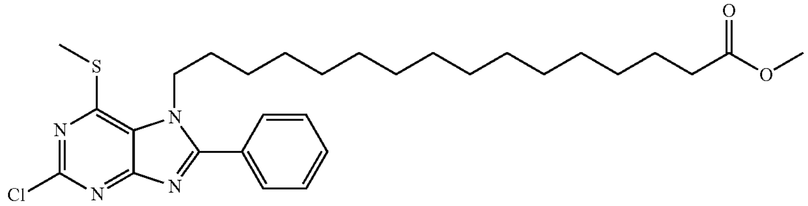 [SMILES: COC(=O)CCCCCCCCCCCCCCCn1c(-c2ccccc2)nc2nc(Cl)nc(SC)c21] | D |
| 74 | 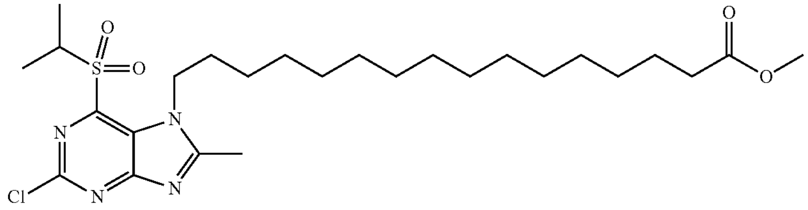 [SMILES: COC(=O)CCCCCCCCCCCCCCCn1c(C)nc2nc(Cl)nc(S(=O)(=O)C(C)C)c21] | A |
| 75 | 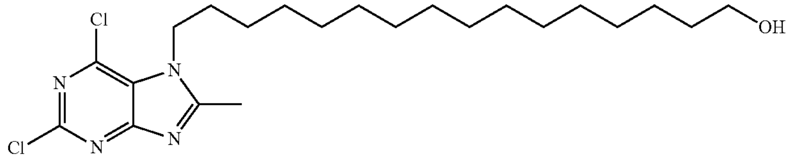 [SMILES: Cc1nc2nc(Cl)nc(Cl)c2n1CCCCCCCCCCCCCCCCO] | A |
| 76 | 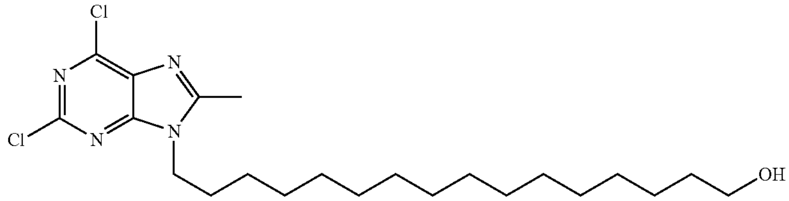 [SMILES: Cc1nc2c(Cl)nc(Cl)nc2n1CCCCCCCCCCCCCCCCO] | C |

TABLE 2-continued
| Antagonist Activity of Exemplary Compounds | | |
|---|---|---|
| Compound Number | Structure | $IC_{50}$ |
| 77 | 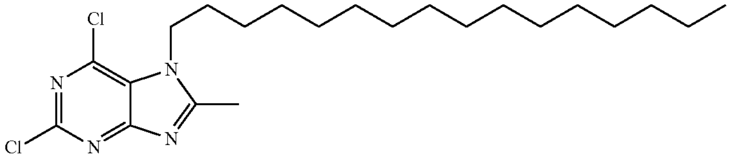 [SMILES: CCCCCCCCCCCCCCCCn1c(C)nc2nc(Cl)nc(Cl)c21] | A |
| 78 | 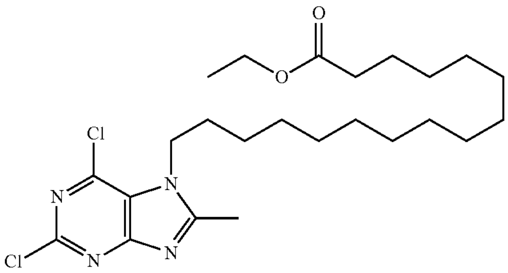 [SMILES: CCOC(=O)CCCCCCCCCCCCCCCn1c(C)nc2nc(Cl)nc(Cl)c21] | A |
| 79 | 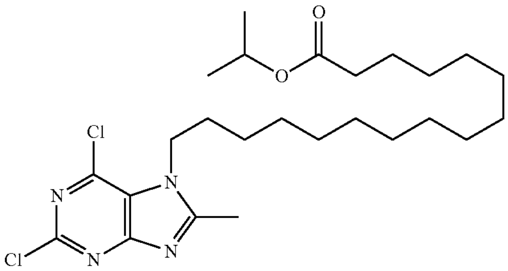 [SMILES: Cc1nc2nc(Cl)nc(Cl)c2n1CCCCCCCCCCCCCCCC(=O)OC(C)C] | A |
| 80 | 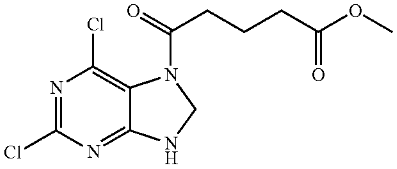 [SMILES: COC(=O)CCCC(=O)N1CNc2nc(Cl)nc(Cl)c21] | E |
| 81 | 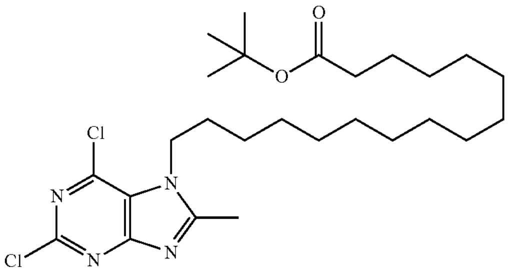 [SMILES: Cc1nc2nc(Cl)nc(Cl)c2n1CCCCCCCCCCCCCCCC(=O)OC(C)(C)C] | B |
| 82 | 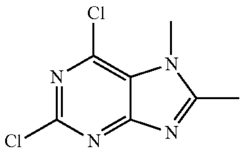 | C |
| 83 | 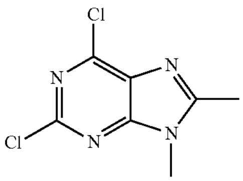 | E |

TABLE 2-continued
| Antagonist Activity of Exemplary Compounds | | |
|---|---|---|
| Compound Number | Structure | $IC_{50}$ |
| 84 | 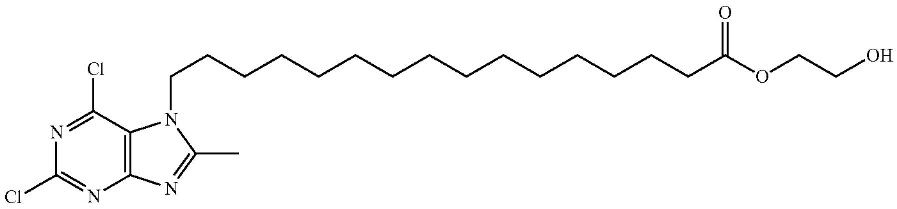 | B |
| 85 | 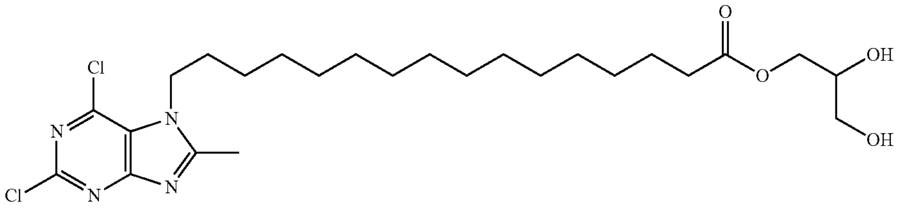 | B |
| 86 | 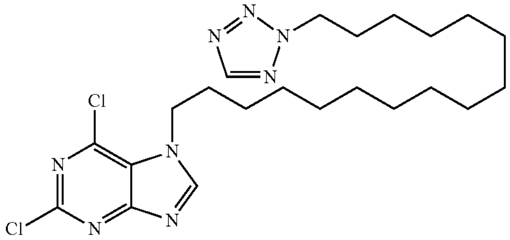 [SMILES: Clc1nc(Cl)c2c(ncn2CCCCCCCCCCCCCCCCn2ncnn2)n1] | B |
| 87 | 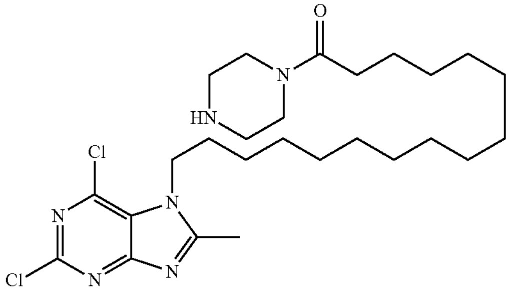 [SMILES: Cc1nc2nc(Cl)nc(Cl)c2n1CCCCCCCCCCCCCCCC(=O)N1CCNCC1] | D |
| 88 | 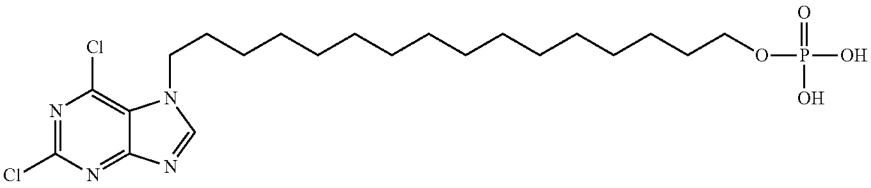 | E |
| 89 | 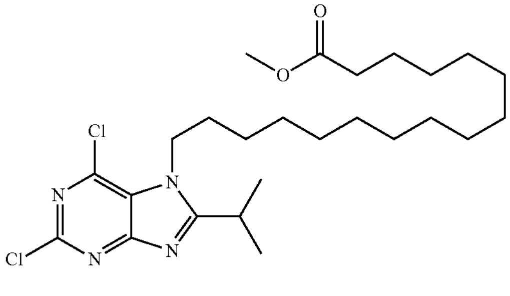 [SMILES: COC(=O)CCCCCCCCCCCCCCCn1c(C(C)C)nc2nc(Cl)nc(Cl)c21] | A |

TABLE 2-continued
| Antagonist Activity of Exemplary Compounds | | |
|---|---|---|
| Compound Number | Structure | $IC_{50}$ |
| 90 | 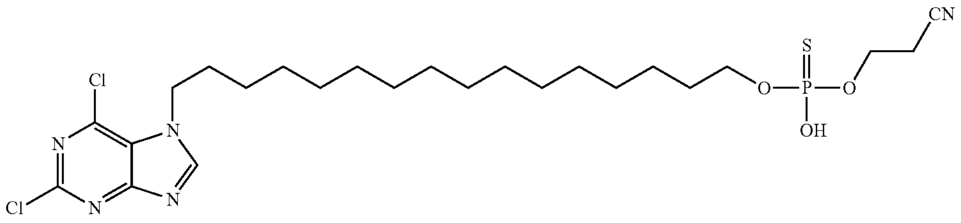 [SMILES: N#CCCOP(O)(=S)OCCCCCCCCCCCCCCCCn1cnc2nc(Cl)nc(Cl)c21] | C |
| 91 | 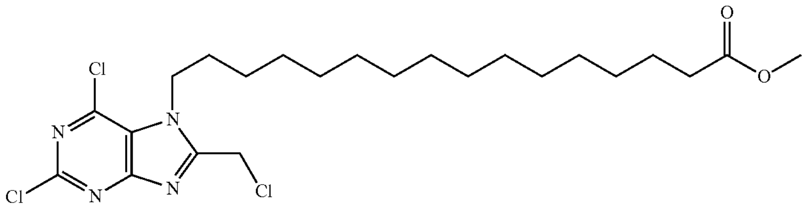 [SMILES: COC(=O)CCCCCCCCCCCCCCCn1c(CCl)nc2nc(Cl)nc(Cl)c21] | A |
| 92 | 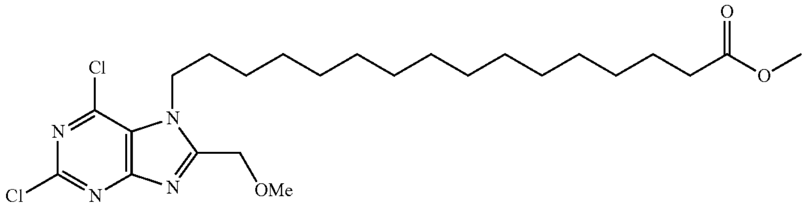 [SMILES: COCc1nc2nc(Cl)nc(Cl)c2n1CCCCCCCCCCCCCCCC(=O)OC] | A |
| 93 | 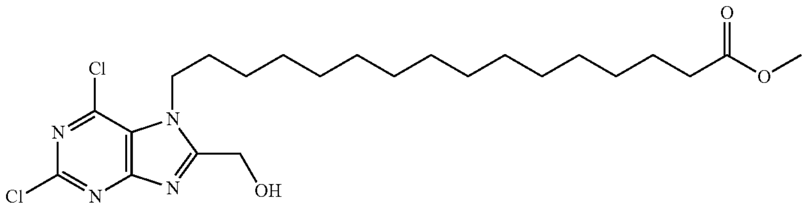 [SMILES: COC(=O)CCCCCCCCCCCCCCCn1c(CO)nc2nc(Cl)nc(Cl)c21] | A |
| 94 | 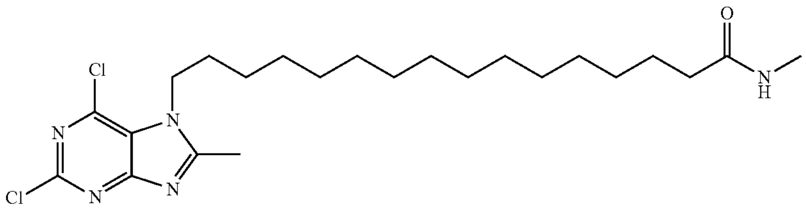 [SMILES: CNC(=O)CCCCCCCCCCCCCCCn1c(C)nc2nc(Cl)nc(Cl)c21] | A |
| 95 | 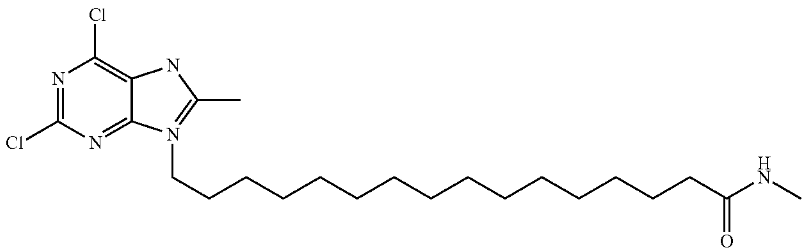 | E |

TABLE 2-continued
| Antagonist Activity of Exemplary Compounds | | |
|---|---|---|
| Compound Number | Structure | $IC_{50}$ |
| 96 | 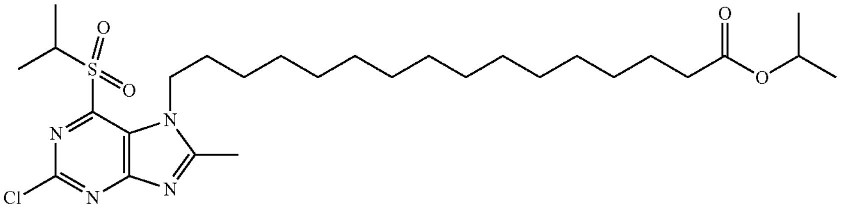 [SMILES: Cc1nc2nc(Cl)nc(S(=O)(=O)C(C)C)c2n1CCCCCCCCCCCCCCCC(=O)OC(C)C] | A |
| 97 | 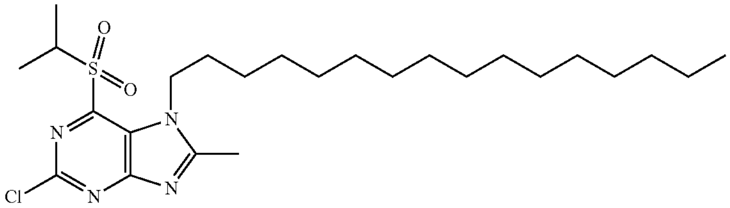 [SMILES: CCCCCCCCCCCCCCCCn1c(C)nc2nc(Cl)nc(S(=O)(=O)C(C)C)c21] | A |
| 98 | 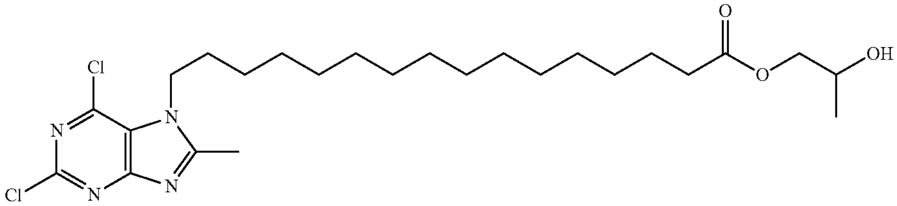 [SMILES: Cc1nc2nc(Cl)nc(Cl)c2n1CCCCCCCCCCCCCCCC(=O)OCC(C)O] | B |
| 99 | 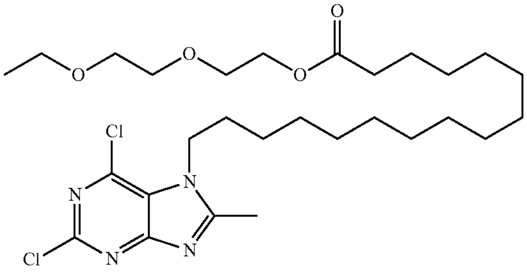 [SMILES: CCOCCOCCOC(=O)CCCCCCCCCCCCCCCn1c(C)nc2nc(Cl)nc(Cl)c21] | B |
| 100 | 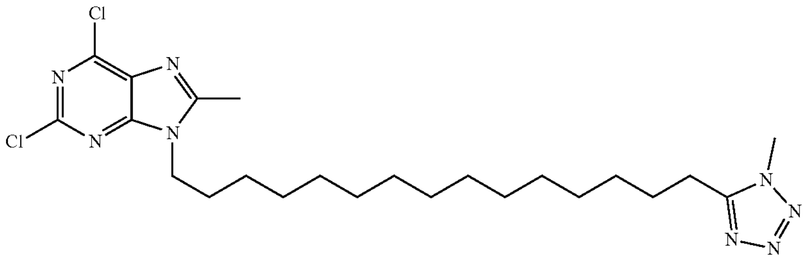 [SMILES: Cc1nc2c(Cl)nc(Cl)nc2n1CCCCCCCCCCCCCCCc1nnnn1C] | C |
| 101 | 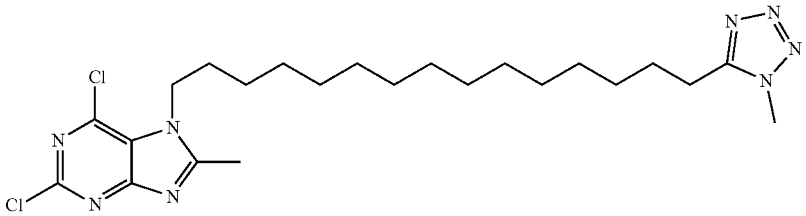 [SMILES: Cc1nc2nc(Cl)nc(Cl)c2n1CCCCCCCCCCCCCCCc1nnnn1C] | A |

TABLE 2-continued
| Antagonist Activity of Exemplary Compounds | | |
|---|---|---|
| Compound Number | Structure | $IC_{50}$ |
| 102 | 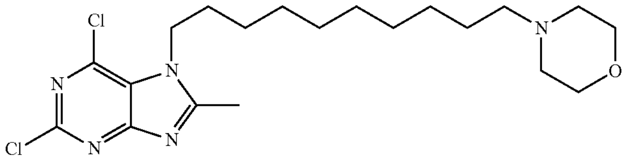 [SMILES: Cc1nc2nc(Cl)nc(Cl)c2n1CCCCCCCCCCN1CCOCC1] | A |
| 103 | 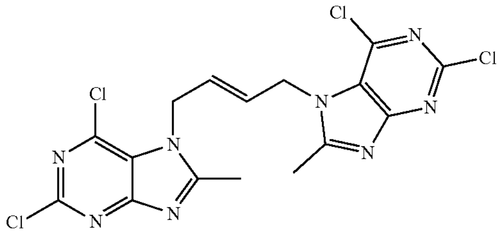 [SMILES: Cc1nc2nc(Cl)nc(Cl)c2n1C/C=C/Cn1c(C)nc2nc(Cl)nc(Cl)c21] | C |
| 104 | 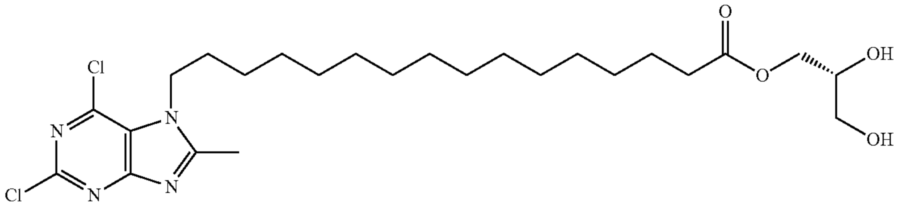 [SMILES: Cc1nc2nc(Cl)nc(Cl)c2n1CCCCCCCCCCCCCCCC(=O)OC[C@H](O)CO] | A |
| 105 | 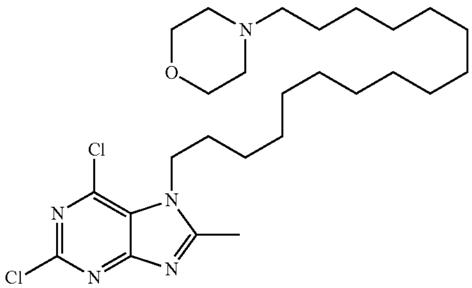 [SMILES: Cc1nc2nc(Cl)nc(Cl)c2n1CCCCCCCCCCCCCCCCN1CCOCC1] | A |
| 106 | 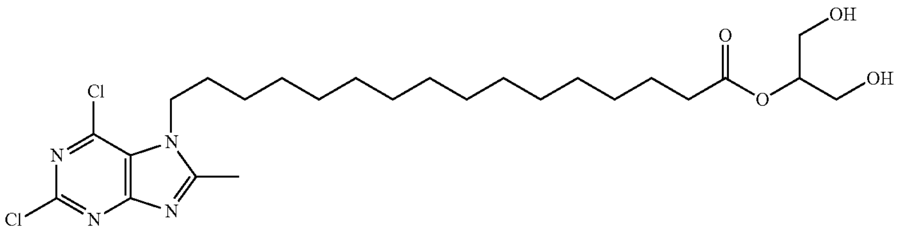 [SMILES: Cc1nc2nc(Cl)nc(Cl)c2n1CCCCCCCCCCCCCCCC(=O)OC(CO)CO] | B |
| 107 | 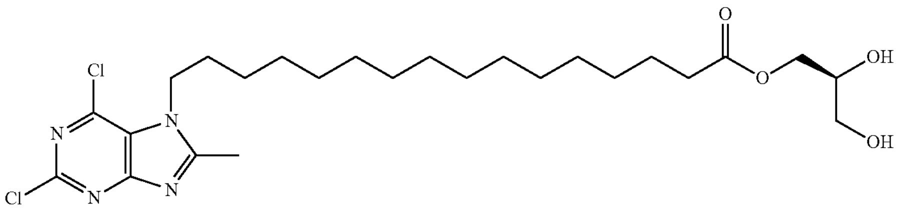 [SMILES: Cc1nc2nc(Cl)nc(Cl)c2n1CCCCCCCCCCCCCCCC(=O)OC[C@@H](O)CO] | B |

TABLE 2-continued
| Antagonist Activity of Exemplary Compounds | | |
|---|---|---|
| Compound Number | Structure | $IC_{50}$ |
| 108 | 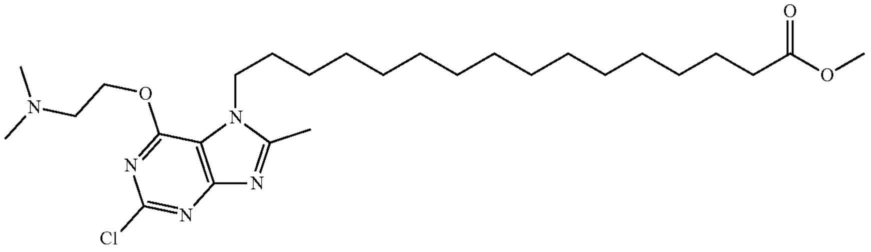 | B |
| 109 | 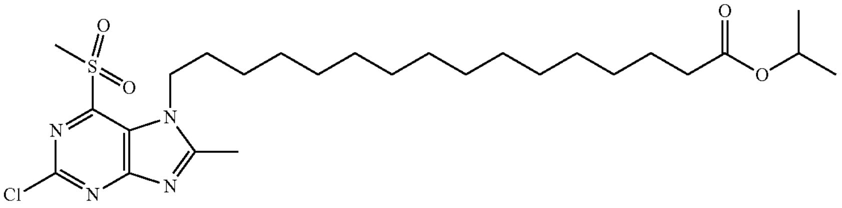 [SMILES: Cc1nc2nc(Cl)nc(S(C)(=O)=O)c2n1CCCCCCCCCCCCCCCC(=O)OC(C)C] | A |
| 110 | 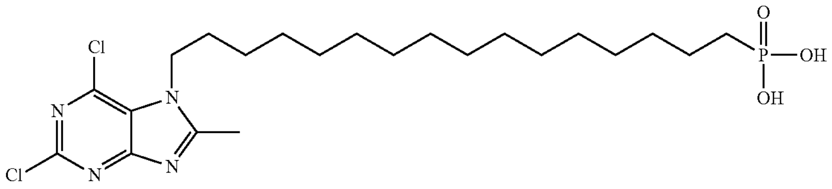 [SMILES: Cc1nc2nc(Cl)nc(Cl)c2n1CCCCCCCCCCCCCCCCP(=O)(O)O] | E |
| 111 | 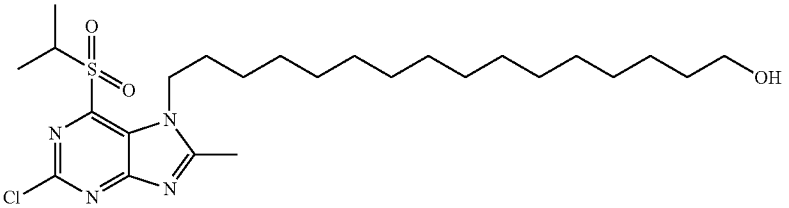 [SMILES: Cc1nc2nc(Cl)nc(S(=O)(=O)C(C)C)c2n1CCCCCCCCCCCCCCCCO] | A |
| 112 | 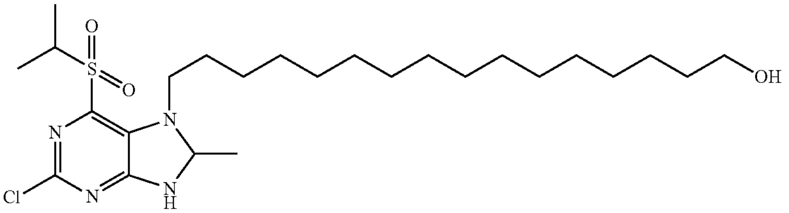 [SMILES: CC1Nc2nc(Cl)nc(S(=O)(=O)C(C)C)c2N1CCCCCCCCCCCCCCCCO] | B |
| 113 | 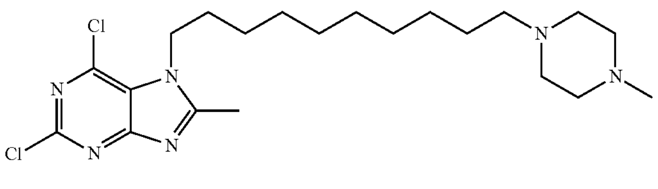 [SMILES: Cc1nc2nc(Cl)nc(Cl)c2n1CCCCCCCCCCN1CCN(C)CC1] | B |
| 114 | 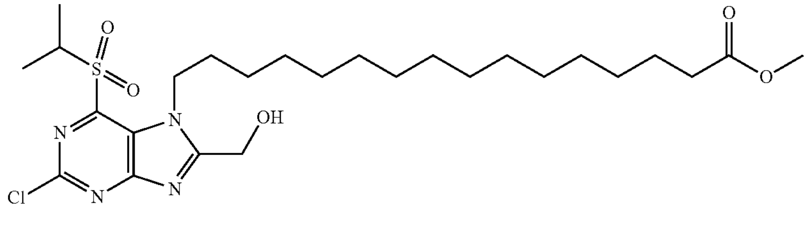 [SMILES: COC(=O)CCCCCCCCCCCCCCCn1c(CO)nc2nc(Cl)nc(S(=O)(=O)C(C)C)c21] | A |

TABLE 2-continued
| Antagonist Activity of Exemplary Compounds | | |
|---|---|---|
| Compound Number | Structure | $IC_{50}$ |
| 115 | 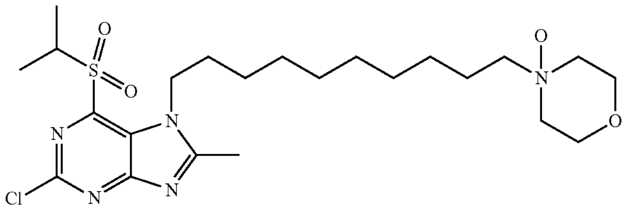 | E |
| 116 | 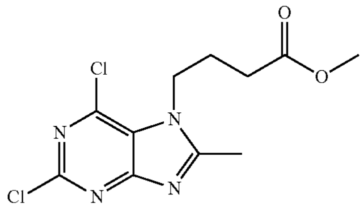 [SMILES: COC(=O)CCCn1c(C)nc2nc(Cl)nc(Cl)c21] | C |
| 117 | 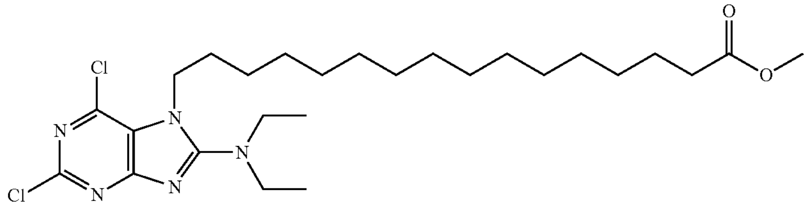 [SMILES: CCN(CC)c1nc2nc(Cl)nc(Cl)c2n1CCCCCCCCCCCCCCCC(=O)OC] | C |
| 118 | 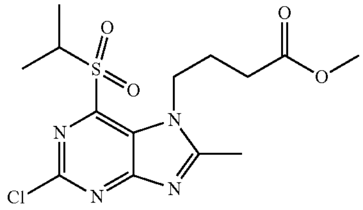 [SMILES: COC(=O)CCCn1c(C)nc2nc(Cl)nc(S(=O)(=O)C(C)C)c21] | B |
| 119 | 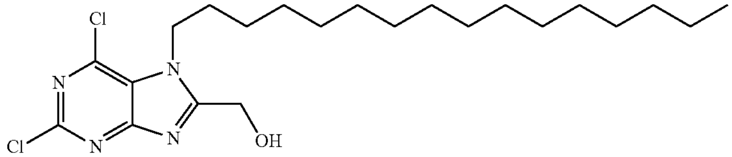 [SMILES: CCCCCCCCCCCCCCCCn1c(CO)nc2nc(Cl)nc(Cl)c21] | A |
| 120 | 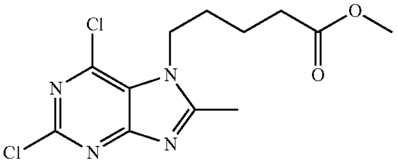 [SMILES: COC(=O)CCCCn1c(C)nc2nc(Cl)nc(Cl)c21] | C |
| 121 | 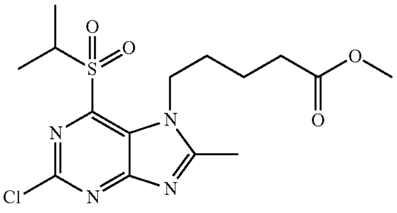 [SMILES: COC(=O)CCCCn1c(C)nc2nc(Cl)nc(S(=O)(=O)C(C)C)c21] | B |

TABLE 2-continued
Antagonist Activity of Exemplary Compounds
| Compound Number | Structure | $IC_{50}$ |
|---|---|---|
| 122 | 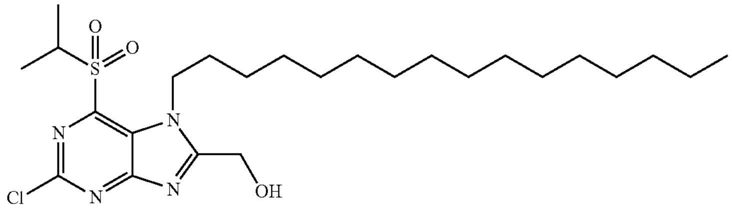 [SMILES: CCCCCCCCCCCCCCCCn1c(CO)nc2nc(Cl)nc(S(=O)(=O)C(C)C)c21] | A |
| 123 | 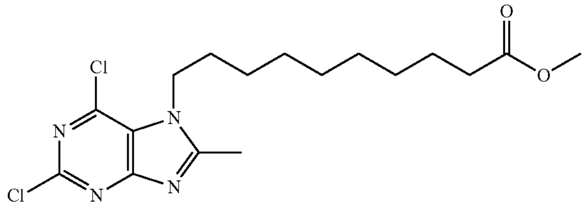 [SMILES: COC(=O)CCCCCCCCCn1c(C)nc2nc(Cl)nc(Cl)c21] | B |
| 124 | 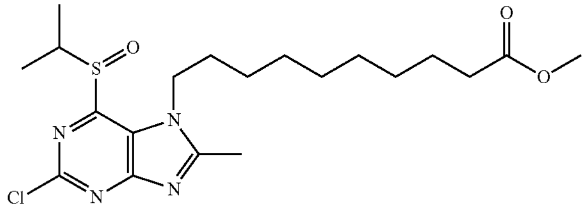 [SMILES: COC(=O)CCCCCCCCCn1c(C)nc2nc(Cl)nc(S(=O)C(C)C)c21] | A |
| 125 | 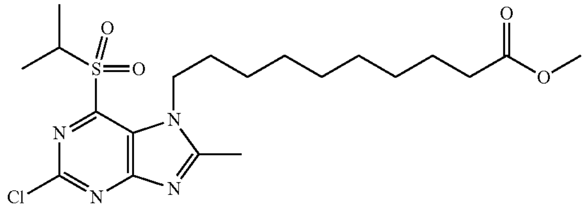 [SMILES: COC(=O)CCCCCCCCCn1c(C)nc2nc(Cl)nc(S(=O)(=O)C(C)C)c21] | B |
| 126 | 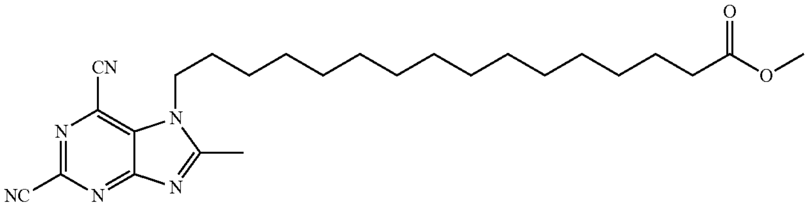 [SMILES: COC(=O)CCCCCCCCCCCCCCCn1c(C)nc2nc(C#N)nc(C#N)c21] | E |
| 127 | 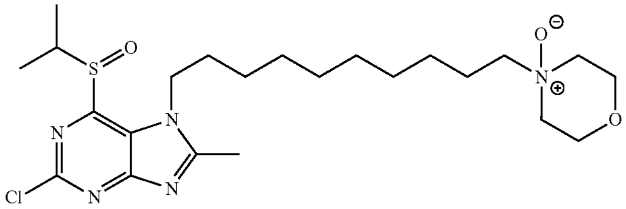 [SMILES: Cc1nc2nc(Cl)nc(S(=O)C(C)C)c2n1CCCCCCCCCC[N+]1([O-])CCOCC1] | E |
| 128 | 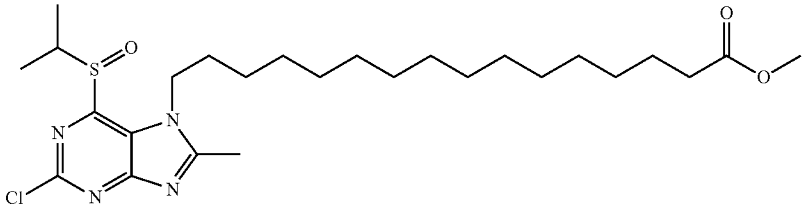 [SMILES: COC(=O)CCCCCCCCCCCCCCCn1c(C)nc2nc(Cl)nc(S(=O)C(C)C)c21] | A |

TABLE 2-continued
Antagonist Activity of Exemplary Compounds
| Compound Number | Structure | $IC_{50}$ |
|---|---|---|
| 129 | 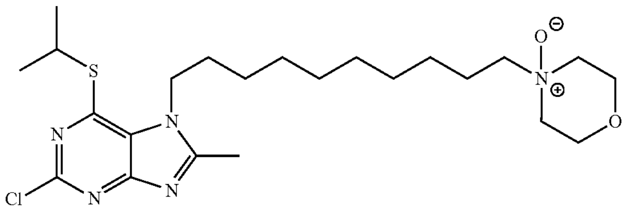 [SMILES: Cc1nc2nc(Cl)nc(SC(C)C)c2n1CCCCCCCCCC[N+]1([O-])CCOCC1] | E |
| 130 | 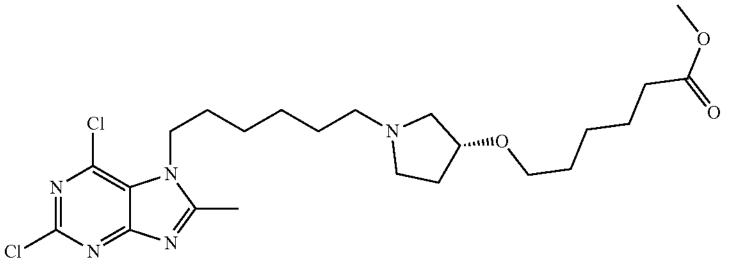 [SMILES: COC(=O)CCCCCO[C@@H]1CCN(CCCCCCn2c(C)nc3nc(Cl)nc(Cl)c32)C1] | A |
| 131 | 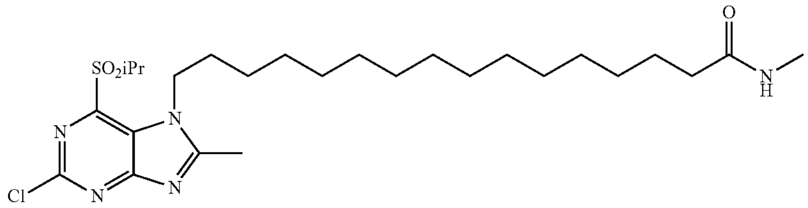 | A |
| 132 | 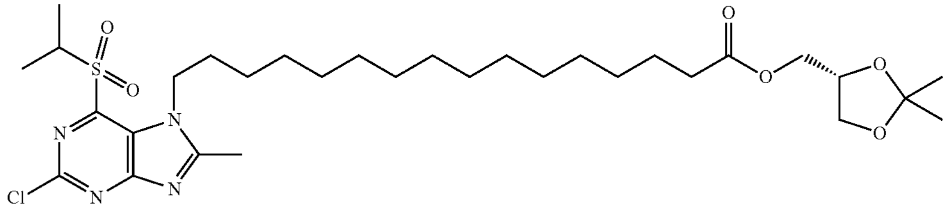 [SMILES: Cc1nc2nc(Cl)nc(S(=O)(=O)C(C)C)c2n1CCCCCCCCCCCCCCCC(=O)OC[C@H]1COC(C)(C)O1] | A |
| 133 | 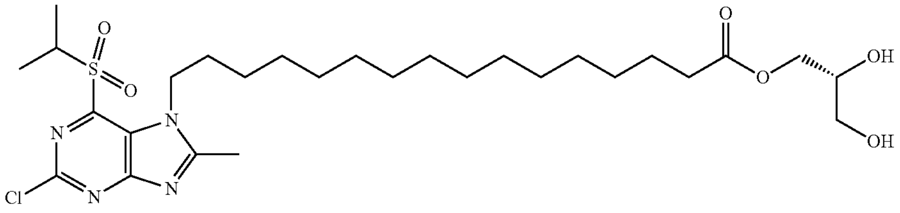 [SMILES: Cc1nc2nc(Cl)nc(S(=O)(=O)C(C)C)c2n1CCCCCCCCCCCCCCCC(=O)OC[C@H](O)CO] | B |
| 134 | 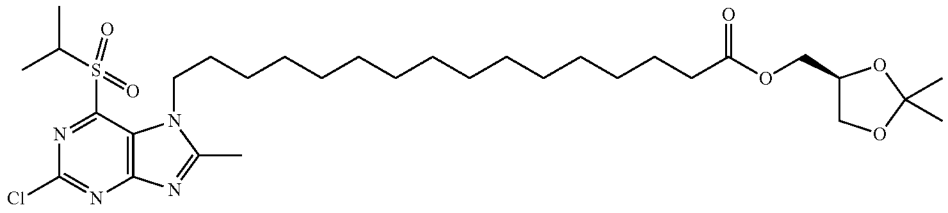 [SMILES: Cc1nc2nc(Cl)nc(S(=O)(=O)C(C)C)c2n1CCCCCCCCCCCCCCCC(=O)OC[C@@H]1COC(C)(C)O1] | A |

TABLE 2-continued
| Antagonist Activity of Exemplary Compounds | | |
|---|---|---|
| Compound Number | Structure | $IC_{50}$ |
| 135 | 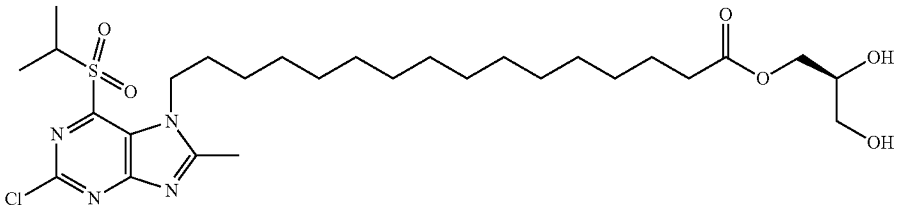 [SMILES: Cc1nc2nc(Cl)nc(S(=O)(=O)C(C)C)c2n1CCCCCCCCCCCCCCCC(=O)OC[C@@H](O)CO] | A |
| 136 | 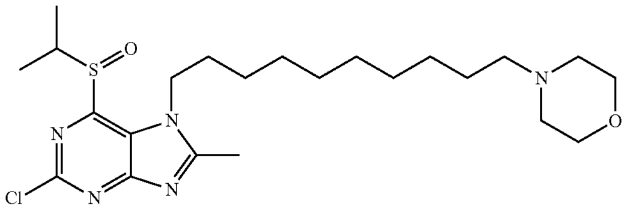 [SMILES: Cc1nc2nc(Cl)nc(S(=O)C(C)C)c2n1CCCCCCCCCCN1CCOCC1] | A |
| 137 | 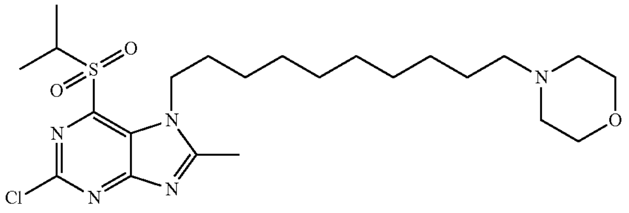 [SMILES: Cc1nc2nc(Cl)nc(S(=O)(=O)C(C)C)c2n1CCCCCCCCCCN1CCOCC1] | B |
| 138 | 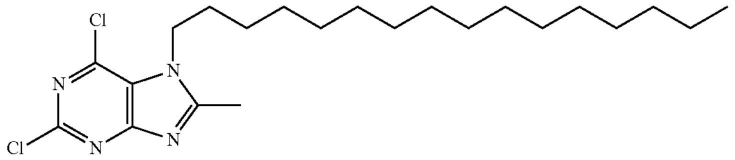 [SMILES: CCCCCCCCCCCCCCCCn1c(C)nc2nc(Cl)nc(Cl)c21] | A |
| 139 | 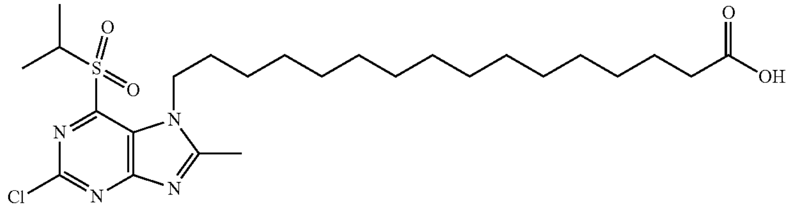 [SMILES: Cc1nc2nc(Cl)nc(S(=O)(=O)C(C)C)c2n1CCCCCCCCCCCCCCCC(=O)O] | A |
| 140 | 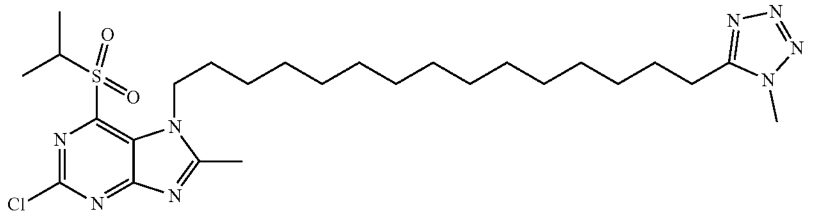 [SMILES: Cc1nc2nc(Cl)nc(S(=O)(=O)C(C)C)c2n1CCCCCCCCCCCCCCCc1nnnn1C] | A |
| 141 | 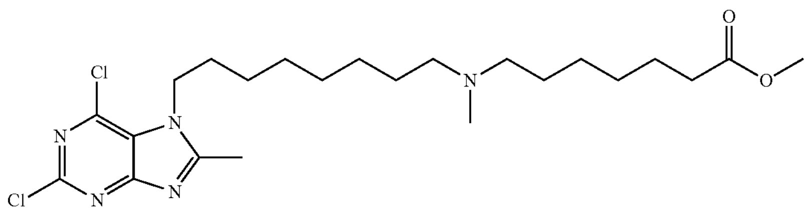 [SMILES: COC(=O)CCCCCCN(C)CCCCCCCCn1c(C)nc2nc(Cl)nc(Cl)c21] | A |

TABLE 2-continued
| Compound Number | Structure | $IC_{50}$ |
|---|---|---|
| Antagonist Activity of Exemplary Compounds | | |
| 142 | 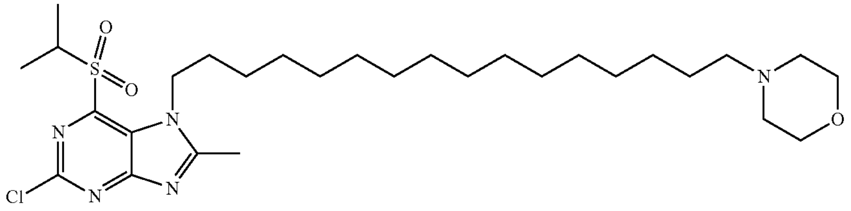 [SMILES: Cc1nc2nc(Cl)nc(S(=O)(=O)C(C)C)c2n1CCCCCCCCCCCCCCCCN1CCOCC1] | A |
| 143 | 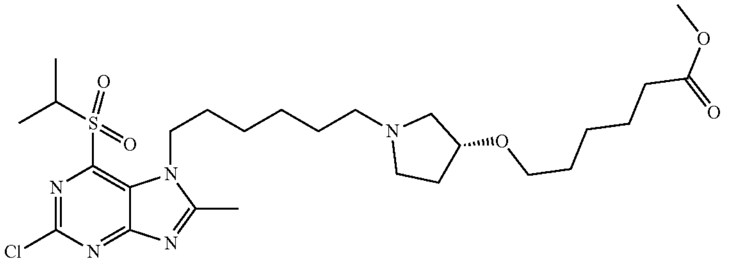 [SMILES: COC(=O)CCCCCO[C@@H]1CCN(CCCCCCn2c(C)nc3nc(Cl)nc(S(=O)(=O)C(C)C)c32)C1] | B |
| 144 | 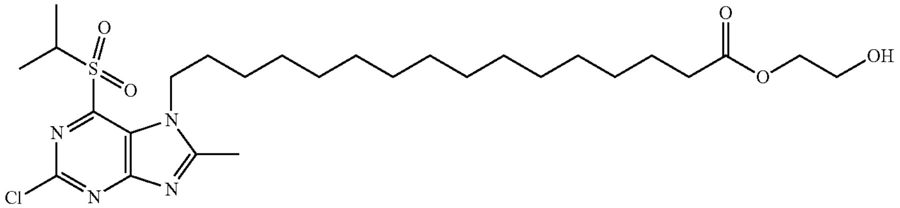 [SMILES: Cc1nc2nc(Cl)nc(S(=O)(=O)C(C)C)c2n1CCCCCCCCCCCCCCCC(=O)OCCO] | A |
| 145 | 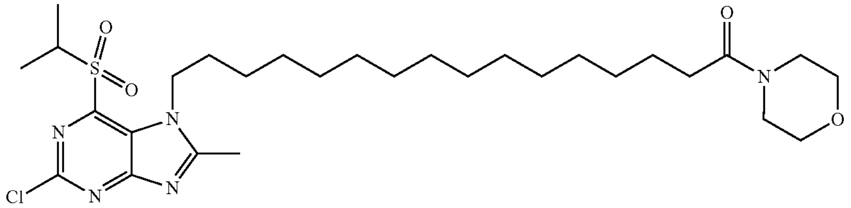 [SMILES: Cc1nc2nc(Cl)nc(S(=O)(=O)C(C)C)c2n1CCCCCCCCCCCCCCCC(=O)N1CCOCC1] | A |
| 146 | 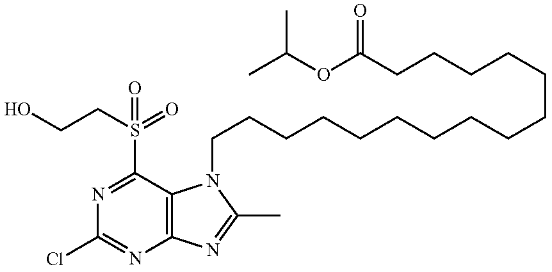 [SMILES: Cc1nc2nc(Cl)nc(S(=O)(=O)CCO)c2n1CCCCCCCCCCCCCCCC(=O)OC(C)C] | A |
| 147 | 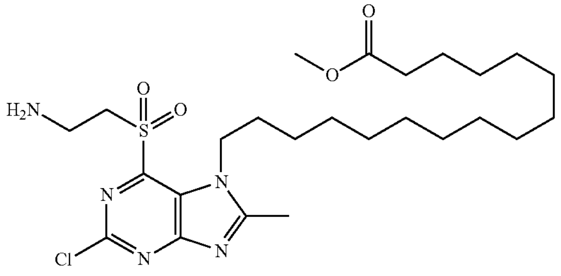 [SMILES: COC(=O)CCCCCCCCCCCCCCCn1c(C)nc2nc(Cl)nc(S(=O)(=O)CCN)c21] | B |

TABLE 2-continued
| Antagonist Activity of Exemplary Compounds | | |
|---|---|---|
| Compound Number | Structure | $IC_{50}$ |
| 148 | 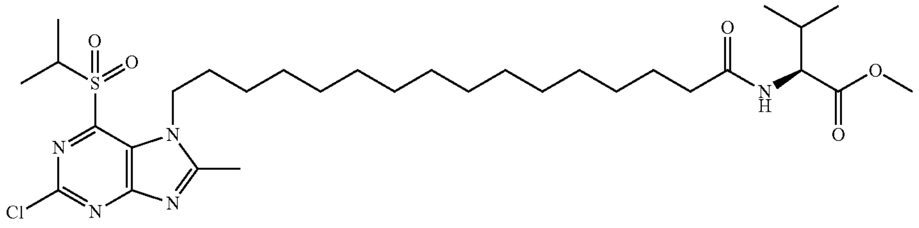 [SMILES: COC(=O)[C@@H](NC(=O)CCCCCCCCCCCCCCCn1c(C)nc2nc(Cl)nc(S(=O)(=O)C(C)C)c21)C(C)C] | A |
| 149 | 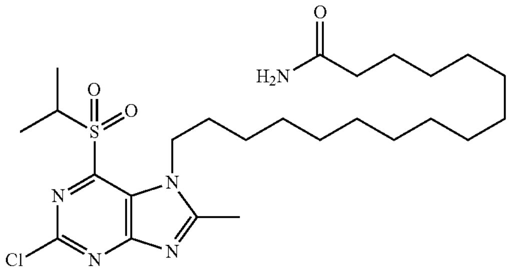 [SMILES: Cc1nc2nc(Cl)nc(S(=O)(=O)C(C)C)c2n1CCCCCCCCCCCCCCCC(N)=O] | A |
| 150 | 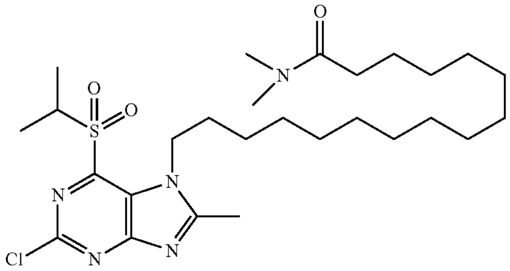 [SMILES: Cc1nc2nc(Cl)nc(S(=O)(=O)C(C)C)c2n1CCCCCCCCCCCCCCCC(=O)N(C)C] | A |
| 151 | 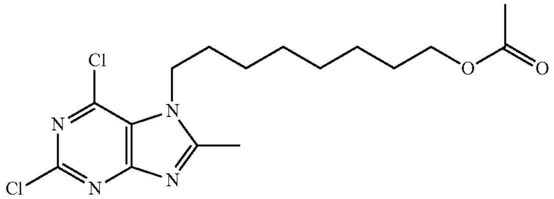 [SMILES: CC(=O)OCCCCCCCCn1c(C)nc2nc(Cl)nc(Cl)c21] | B |
| 152 | 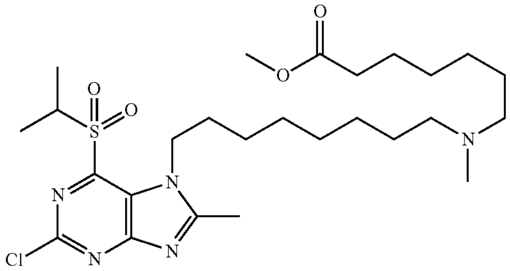 [SMILES: COC(=O)CCCCCCN(C)CCCCCCCCn1c(C)nc2nc(Cl)nc(S(=O)(=O)C(C)C)c21] | B |
| 153 | 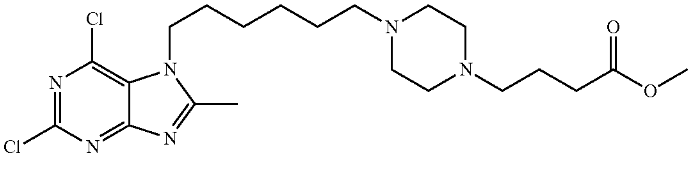 [SMILES: COC(=O)CCCN1CCN(CCCCCCn2c(C)nc3nc(Cl)nc(Cl)c32)CC1] | B |

TABLE 2-continued
| Antagonist Activity of Exemplary Compounds | | |
|---|---|---|
| Compound Number | Structure | $IC_{50}$ |
| 154 | 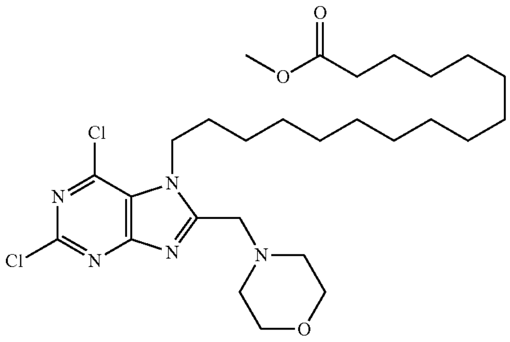 [SMILES: COC(=O)CCCCCCCCCCCCCCCn1c(CN2CCOCC2)nc2nc(Cl)nc(Cl)c21] | A |
| 155 | 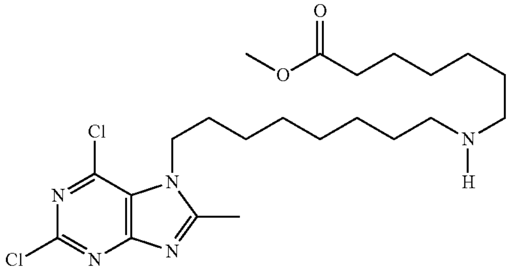 [SMILES: COC(=O)CCCCCCNCCCCCCCCn1c(C)nc2nc(Cl)nc(Cl)c21] | A |
| 156 | 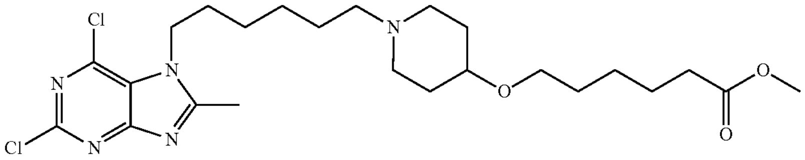 [SMILES: COC(=O)CCCCCOC1CCN(CCCCCCn2c(C)nc3nc(Cl)nc(Cl)c32)CC1] | B |
| 157 | 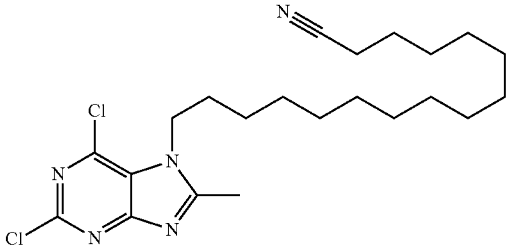 [SMILES: Cc1nc2nc(Cl)nc(Cl)c2n1CCCCCCCCCCCCCCCC#N] | A |
| 158 | 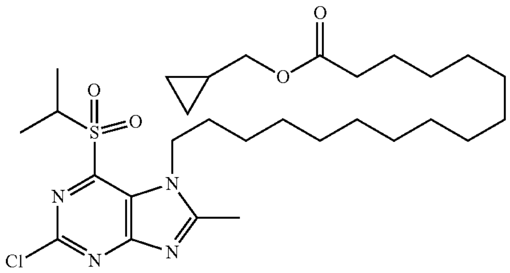 [SMILES: Cc1nc2nc(Cl)nc(S(=O)(=O)C(C)C)c2n1CCCCCCCCCCCCCCCC(=O)OCC1CC1] | A |

TABLE 2-continued
| Antagonist Activity of Exemplary Compounds | | |
|---|---|---|
| Compound Number | Structure | $IC_{50}$ |
| 159 | 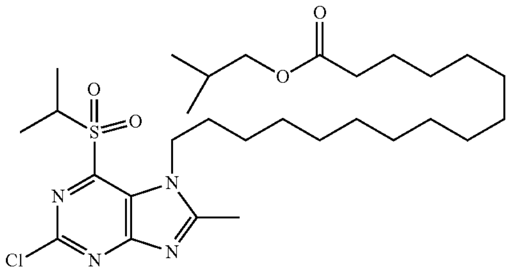 [SMILES: Cc1nc2nc(Cl)nc(S(=O)(=O)C(C)C)c2n1CCCCCCCCCCCCCCCC(=O)OCC(C)C] | B |
| 160 | 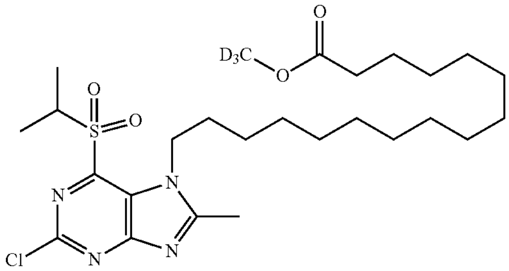 [SMILES: [2H]C([2H])([2H])OC(=O)CCCCCCCCCCCCCCCn1c(C)nc2nc(Cl)nc(S(=O)(=O)C(C)C)c21] | A |
| 161 | 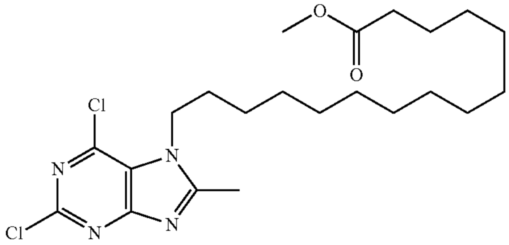 [SMILES: COC(=O)CCCCCCCCCCCCCCn1c(C)nc2nc(Cl)nc(Cl)c21] | A |
| 162 | 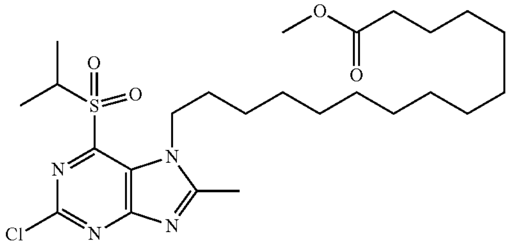 [SMILES: COC(=O)CCCCCCCCCCCCCCn1c(C)nc2nc(Cl)nc(S(=O)(=O)C(C)C)c21] | A |
| 163 | 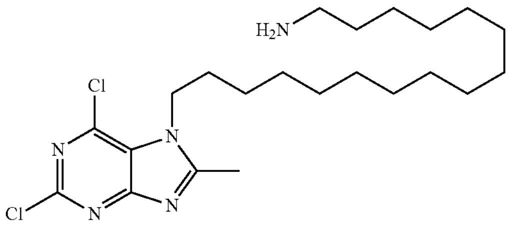 [SMILES: Cc1nc2nc(Cl)nc(Cl)c2n1CCCCCCCCCCCCCCCCN] | A |

TABLE 2-continued
| Antagonist Activity of Exemplary Compounds | | |
|---|---|---|
| Compound Number | Structure | $IC_{50}$ |
| 164 | 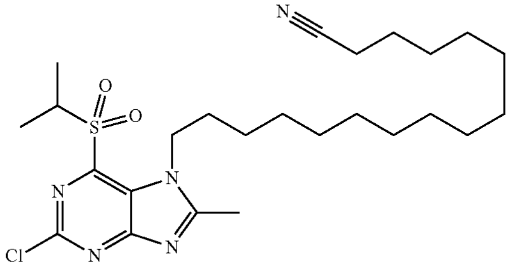 [SMILES: Cc1nc2nc(Cl)nc(S(=O)(=O)C(C)C)c2n1CCCCCCCCCCCCCCCC#N] | A |
| 165 | 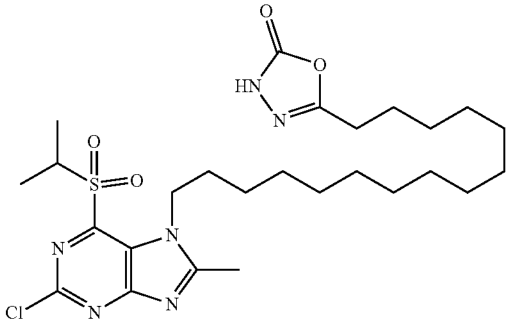 [SMILES: Cc1nc2nc(Cl)nc(S(=O)(=O)C(C)C)c2n1CCCCCCCCCCCCCCCc1n[nH]c(=O)o1] | A |
| 166 | 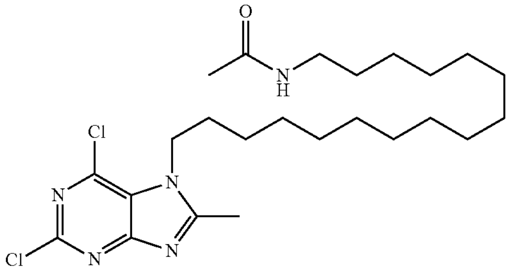 [SMILES: CC(=O)NCCCCCCCCCCCCCCCCn1c(C)nc2nc(Cl)nc(Cl)c21] | A |
| 167 | 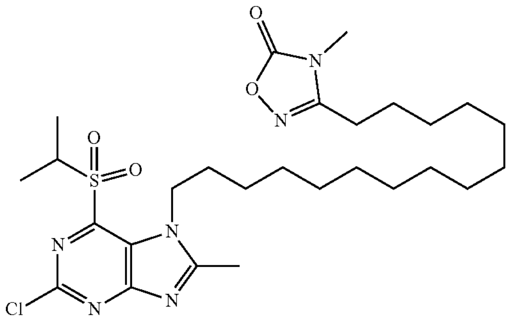 [SMILES: Cc1nc2nc(Cl)nc(S(=O)(=O)C(C)C)c2n1CCCCCCCCCCCCCCCc1noc(=O)n1C] | A |
| 168 | 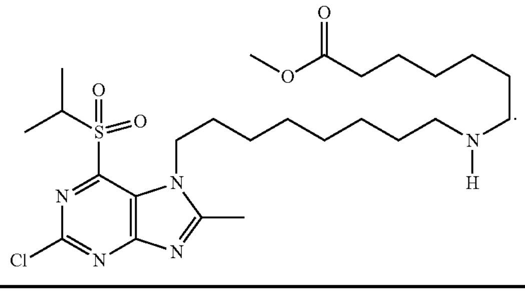 | A. |
Activity key: 1 nm-1 μM = A; 1 μM-5 μM = B; 5 μM-10 μM = C; 10 μM-20 μM = D; and >20 μM = E.

Example 3: Prophetic General Protocol to Evaluate Exemplary Compounds of the Disclosure in a Toxicity Study In vitro assessment: HEK293, and HEK293-derived SZ14, HEK293T, HEK293T expressing wild-type STING, HepG2, Huh7, HCT116, and A549 dual WT STING cells were seeded in 96-well plates and were treated with different concentration of the compounds for 19 hr. Cell survival rate was monitored using CellTiter-glo (Promega). $CC_{50}$ values were calculated using Xlfit.

Example 4: General Protocol to Evaluate Exemplary Compounds of the Disclosure in a Toxicity Study In vivo assessment: Group of 5 C57BL/6 mice (female, 12 weeks of age) were treated via i.p. injection with vehicle (90% saline/5% ethanol alcohol/5% cremophor) at 10 mg/kg, 5 mg/kg, and 1 mg/kg. Mouse body weight was recorded every other day for 5 days.

Figure 2:
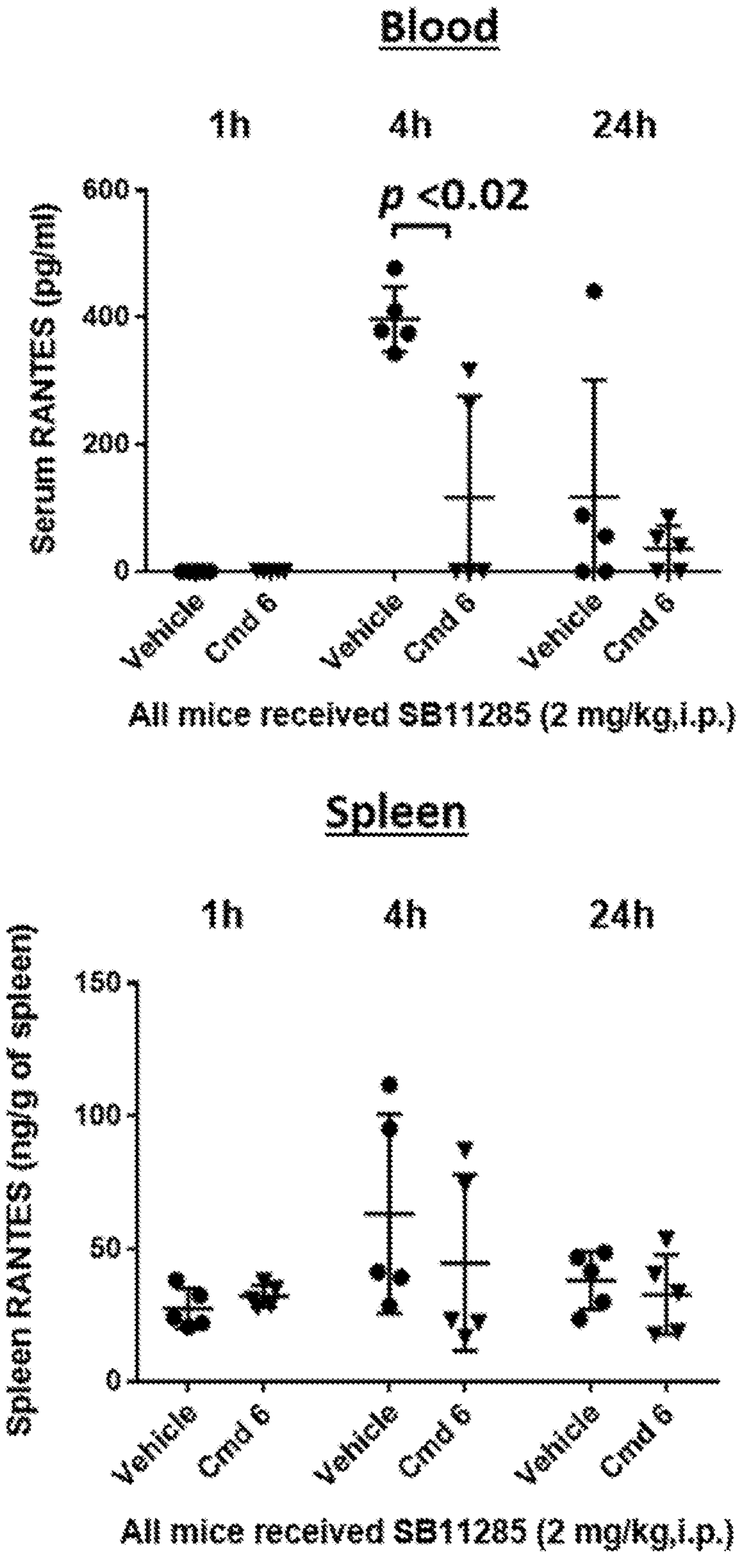
FIG. 2 shows the results of a study where mice treated with either vehicle or compound 6 (10 mg/kg) via i.p. injection for 1 hour followed by treatment with SB 11285 (2 mg/kg i.p.). Blood, spleen, and liver samples were collected at 1 hour, 4 hours, and 24 hours post treatment with SB 11285. The production of RANTES was monitored using ELISA. The basal level of RANTES in untreated mice (n=2) was undetectable in blood, 26.6 ng/g of spleen, and 6.17 ng/g of liver.
Figure 2:
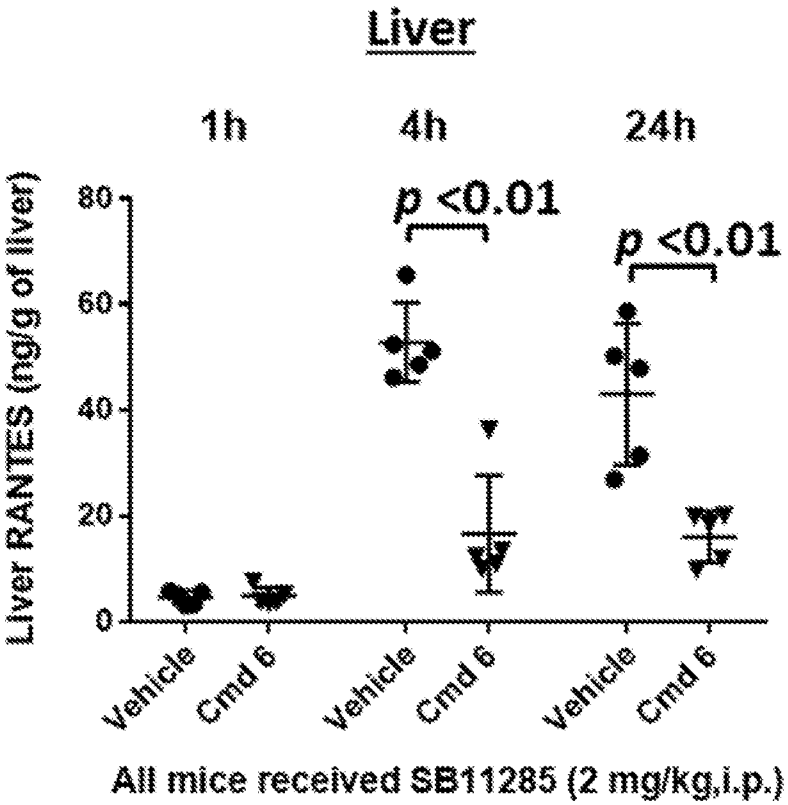
Figure 3:
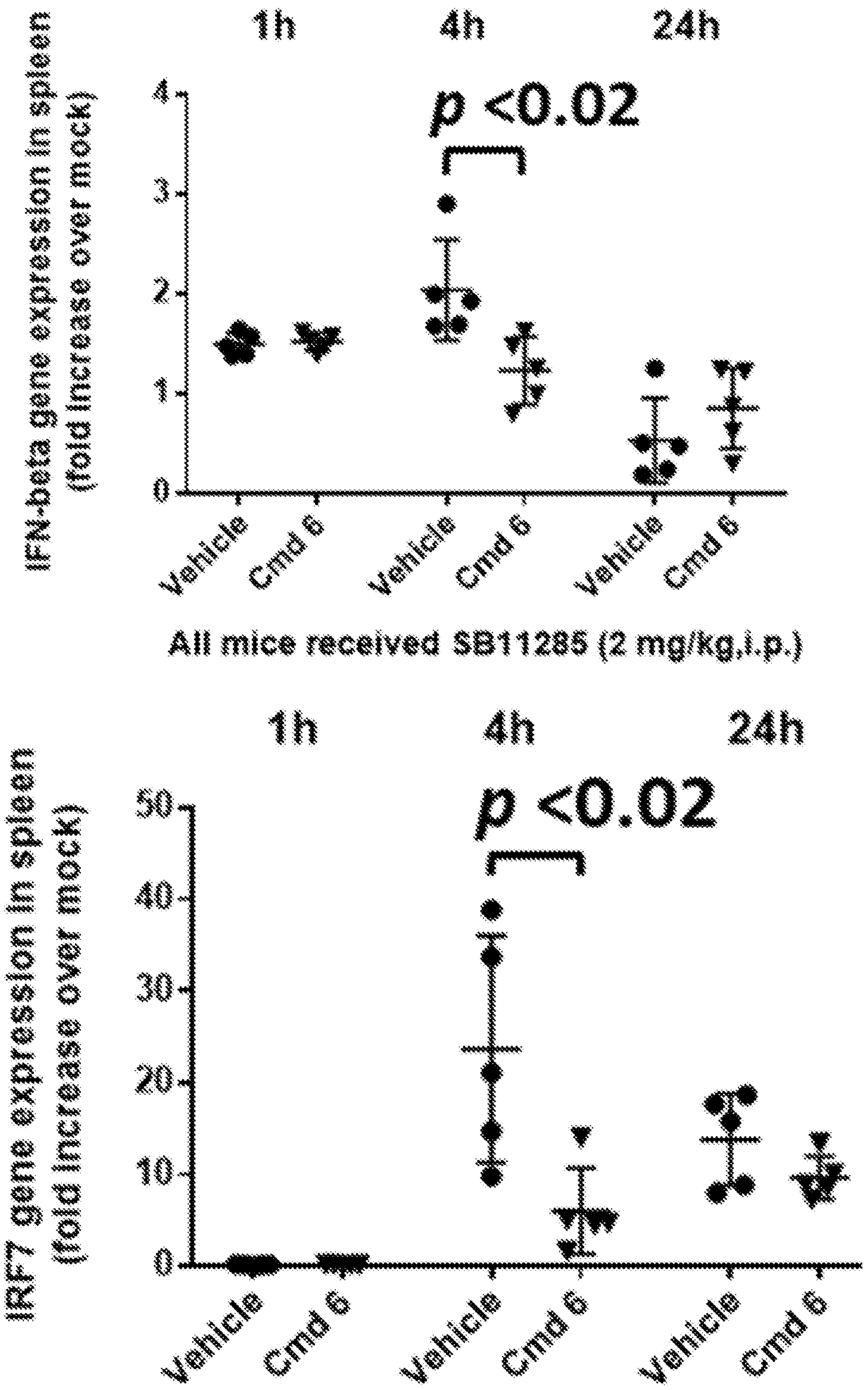
FIG. 3 shows the results of a study where mice treated with either vehicle or compound 6 (10 mg/kg) via i.p. injection for 1 hour followed by treatment with SB 11285 (2 mg/kg i.p.). Spleen samples were collected at 1 hour, 4 hours, and 24 hours post treatment with SB 11285. Total RNA was extraed using an RNeasy isolation kit and analyzed for IFN-β and IRF7 mRNA using RT-qPCR. All samples were normalized to GAPDH housekeeping gene expression. Results are shown as the fold increase over untreated mice.
Figure 3:
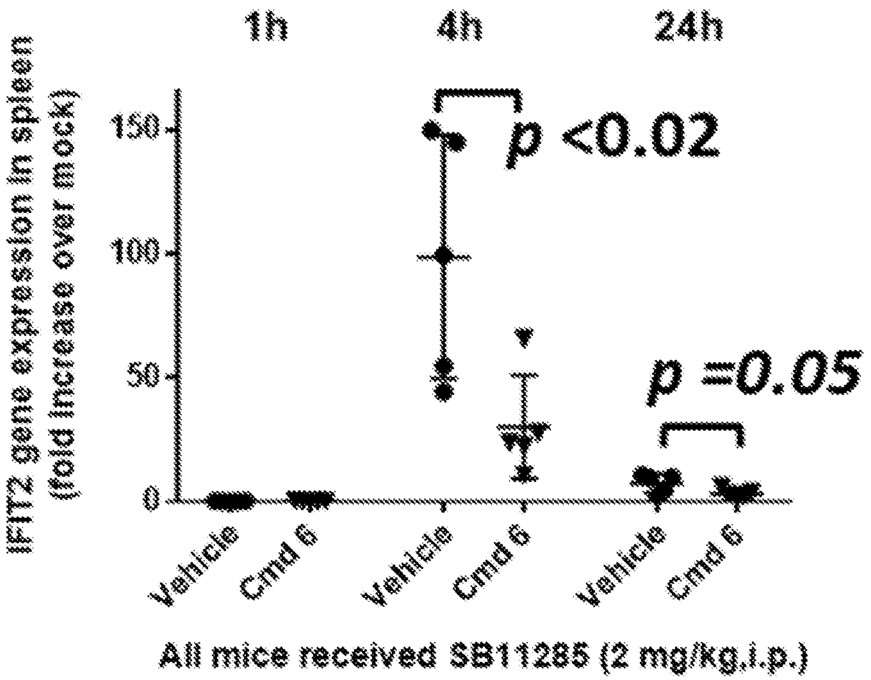
Figure 3:
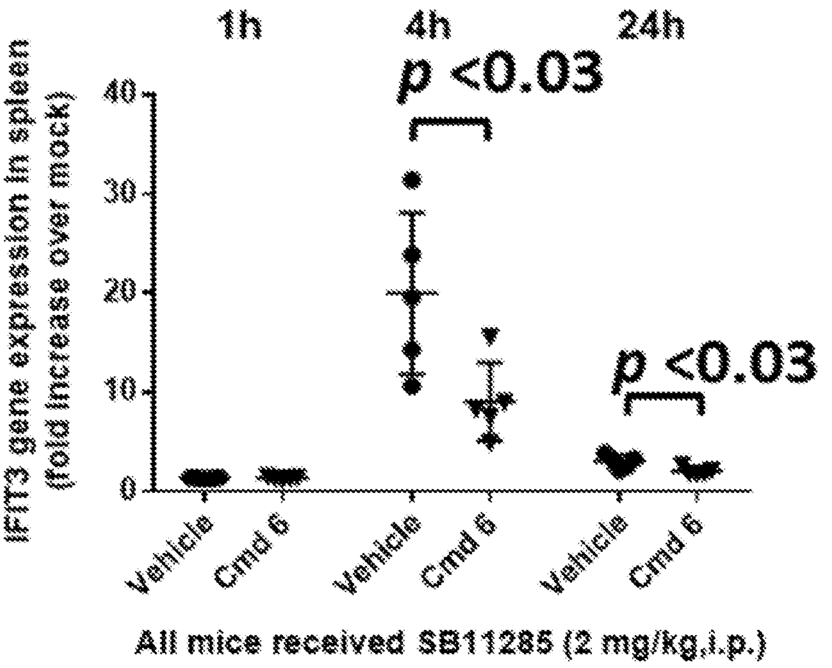
Figure 3:
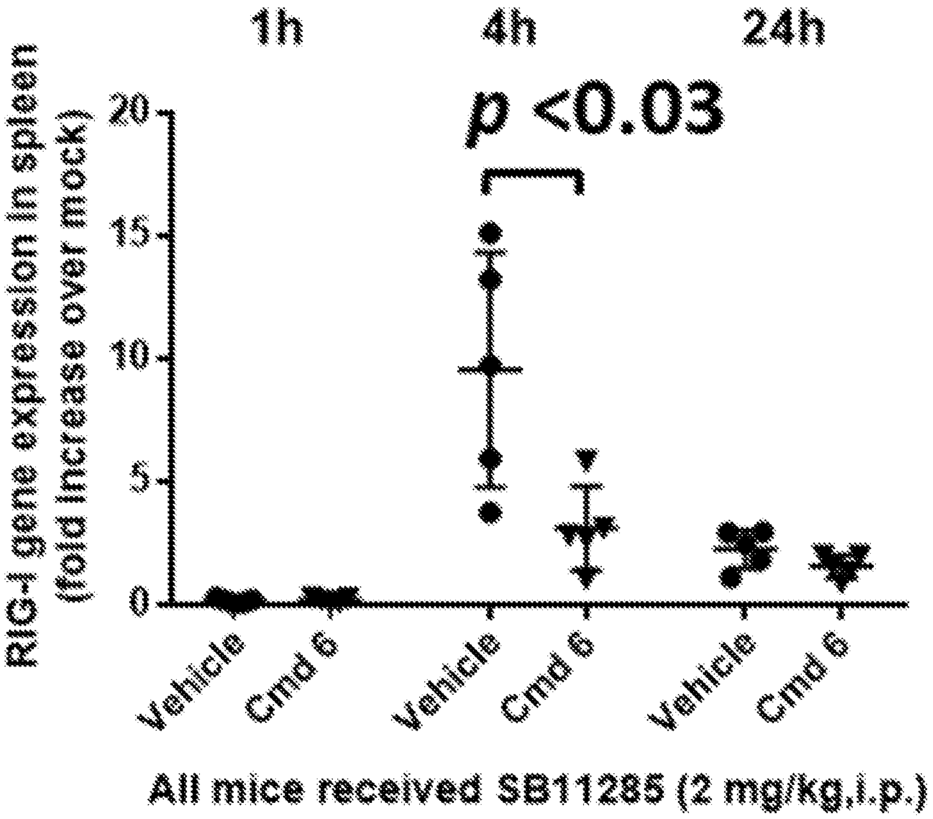

Example 5: General Protocol to Evaluate Exemplary Compounds of the Disclosure in their Ability to Antagonize Synthetic STING-Agonist-Induced Cytokine Activity in Mice Groups of mice were pretreated with vehicle or compound (10 mg/kg) via i.p. injection for 1 h, followed by treatment with synthetic STING antagonist (2 mg/kg. i.p.). Blood, spleen, and liver samples were collected at 1 h, 4 h, and 24 h post-agonist treatment. The production of IFN-β was monitored using ELISA. The basal level of IFN-β in untreated mice (n=2) was undetectable. The production of RANTES was monitored using ELISA. The basal level of RANTES in untreated mice (n=2), blood (undetectable), spleen (26.6 ng/g of spleen), liver (6.17 ng/g of liver). Results of these studies are depicted in FIGS. 1-3.

Figure 4:
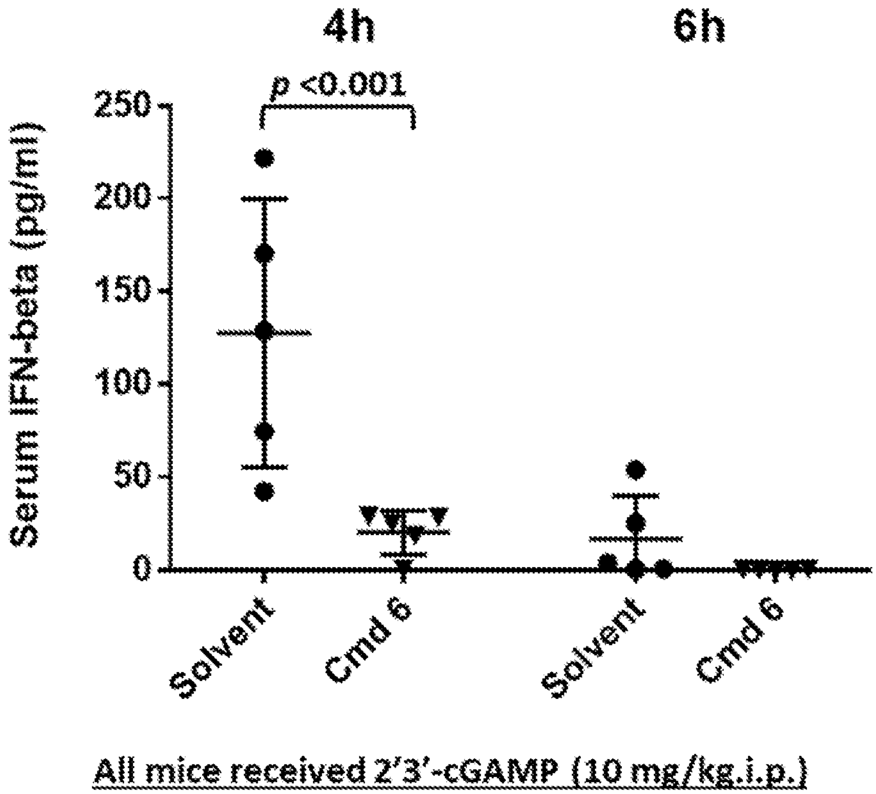
FIG. 4 shows the results of a study where mice treated with either vehicle or compound 6 (10 mg/kg) via i.p. injection for 1 hour followed by treatment with 2'3'-cGAMP (10 mg/kg i.p.). Blood samples were collected at 4 hours and 6 hours post-cGAMP treatment. The production of IFN-β was monitored using ELISA.

Example 6: General Protocol to Evaluate Exemplary Compounds of the Disclosure in their Ability to Antagonize 2',3'-cGAMP-Induced Cytokine Activity in Mice Groups of mice were pretreated with vehicle or compound (10 mg/kg) via i.p. injection for 1 h, followed by treatment with 2'3'-cGAMP (10 mg/kg. i.p.). Blood samples were collected at 4 h and 6 h post-cGAMP treatment. The production of IFN-β was monitored using ELISA. The results of this study are depicted in FIG. 4.

INCORPORATION BY REFERENCE

All US and PCT patent application publications and US patents mentioned herein are hereby incorporated by reference in their entirety, as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

We claim:

1. A compound of formula I:

I

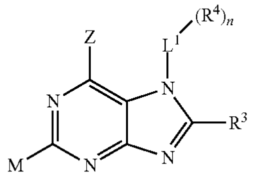

or a pharmaceutically acceptable salt thereof;

wherein

M is Cl or F;

Z is $SR^1$, $SO_2R^1$, or $N(R^1)(R^2)$ $R^1$ and $R^2$ are each independently H or alkyl;

$R^3$ is H, alkyl, methyl, haloalkyl, chloromethyl, alkyloxyalkyl, methoxymethyl, hydroxyalkyl, hydroxymethyl, aminoalkyl, diethylamino, aryl, phenyl, alkynyl, ethynyl, alkyne substituted with cycloalkyl, heterocyclylalkyl or morpholinylalkyl;

$L^1$ is $C_7$-$C_{15}$alkyl;

each $R^4$ is independently halo, CN, $SR^7$, $OR^7$, $NHCOR^7$, $NR^8CO_2R^7$, $N(R^7)(R^8)$, $COR^7$, $CO_2R^7$, $OC(O)R^7$, $CON(R^7)(R^8)$, heteroaryl, or heterocyclyl;

$R^7$ and $R^8$ are each independently selected from the group consisting of hydrogen, and alkyl; and n is an integer from 0-18.

2. The compound of claim 1, wherein M is Cl.

3. The compound of claim 1, wherein Z is $SO_2R^1$.

4. The compound of claim 1, wherein $R^1$ is methyl, ethyl, isopropyl, or hexyl.

5. The compound of claim 1, wherein $L^1$ is $C_7$alkylenyl, $C_9$alkylenyl, $C_{10}$alkylenyl, or $C_{15}$alkylenyl.

6. The compound of claim 1, wherein each $R^4$ is independently $CO_2R^7$, $COR^7$, heterocyclyl, $OR^7$, heteroaryl, or $CON(R^7)(R^8)$.

7. The compound of claim 1, wherein each $R^4$ is independently $CO_2R^7$, heterocyclyl, or $COR^7$.

8. The compound of claim 1, wherein n is 0, 1, or 2.

9. A compound selected from the group consisting of:

| Compound Number | Structure |
| --- | --- |
| 9 | 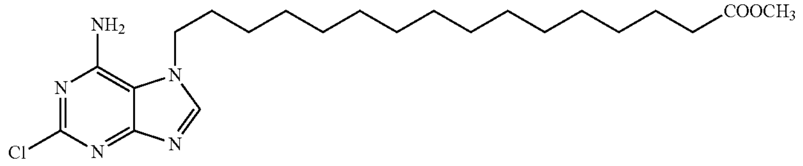 [SMILES: COC(=O)CCCCCCCCCCCCCCCn1cnc2nc(Cl)nc(N)c21] |

-continued
| Compound Number | Structure |
|---|---|
| 24 | 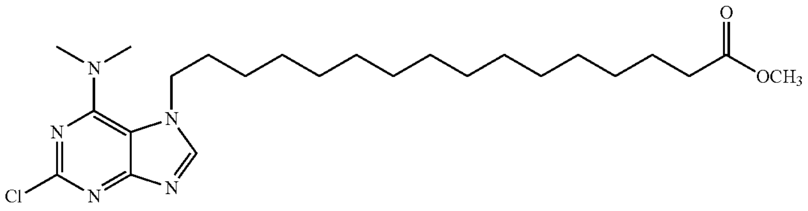 [SMILES: COC(=O)CCCCCCCCCCCCCCCn1cnc2nc(Cl)nc(N(C)C)c21] |
| 28 | 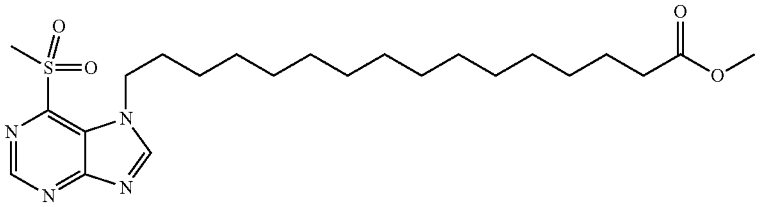 [SMILES: COC(=O)CCCCCCCCCCCCCCCn1cnc2ncnc(S(C)(=O)=O)c21] |
| 69 | 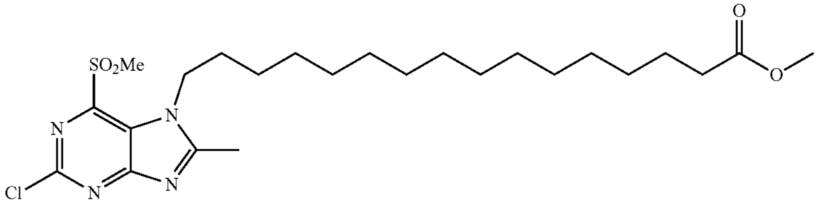 [SMILES: COC(=O)CCCCCCCCCCCCCCCn1c(C)nc2nc(Cl)nc(S(C)(=O)=O)c21] |
| 74 | 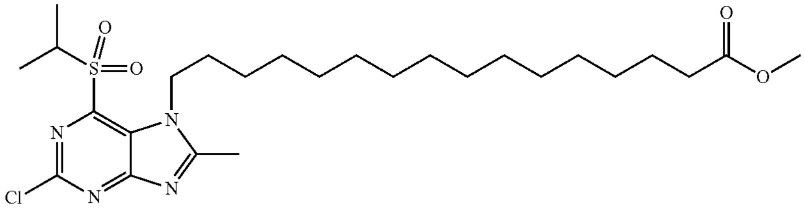 [SMILES: COC(=O)CCCCCCCCCCCCCCCn1c(C)nc2nc(Cl)nc(S(=O)(=O)C(C)C)c21] |
| 96 | 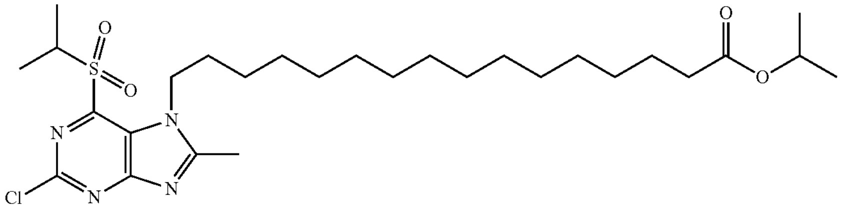 [SMILES: Cc1nc2nc(Cl)nc(S(=O)(=O)C(C)C)c2n1CCCCCCCCCCCCCCCC(=O)OC(C)C] |
| 97 | 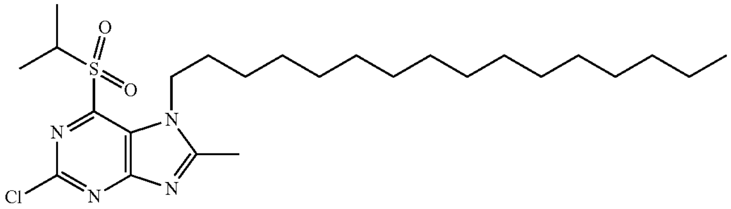 [SMILES: CCCCCCCCCCCCCCCCn1c(C)nc2nc(Cl)nc(S(=O)(=O)C(C)C)c21] |
| 109 | 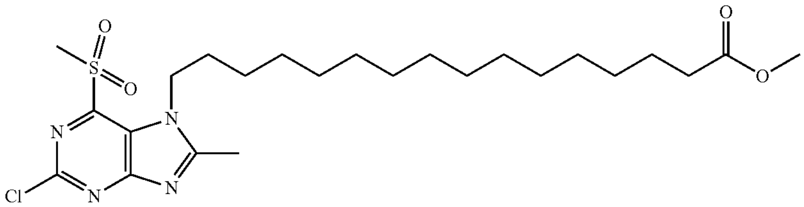 [SMILES: COC(=O)CCCCCCCCCCCCCCCn1c(C)nc2nc(Cl)nc(S(C)(=O)=O)c21] |

-continued
| Compound Number | Structure |
| --- | --- |
| 111 | 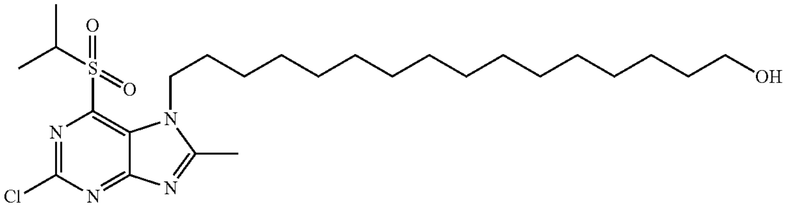 [SMILES: Cc1nc2nc(Cl)nc(S(=O)(=O)C(C)C)c2n1CCCCCCCCCCCCCCCCO] |
| 112 | 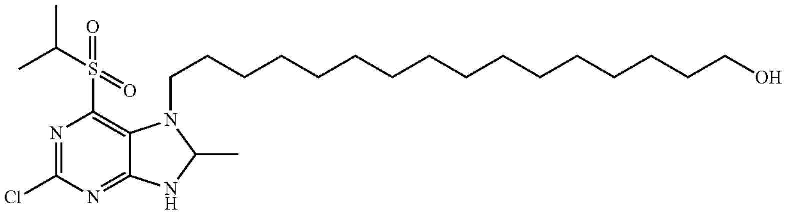 [SMILES: CC1Nc2nc(Cl)nc(S(=O)(=O)C(C)C)c2N1CCCCCCCCCCCCCCCCO] |
| 114 | 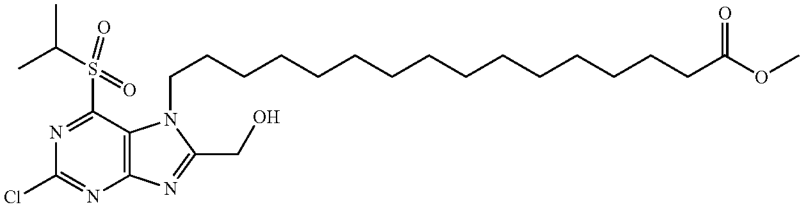 [SMILES: COC(=O)CCCCCCCCCCCCCCCn1c(CO)nc2nc(Cl)nc(S(=O)(=O)C(C)C)c21] |
| 118 | 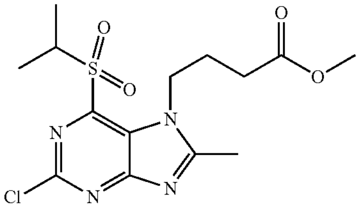 [SMILES: COC(=O)CCCn1c(C)nc2nc(Cl)nc(S(=O)(=O)C(C)C)c21] |
| 121 | 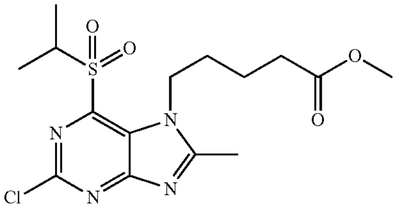 [SMILES: COC(=O)CCCCn1c(C)nc2nc(Cl)nc(S(=O)(=O)C(C)C)c21] |
| 122 | 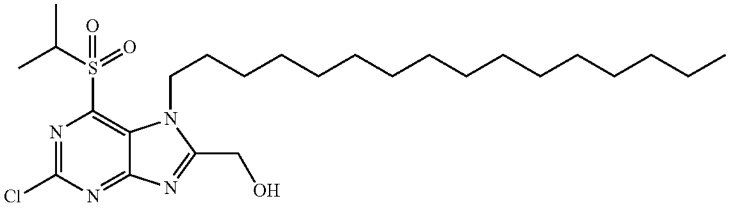 [SMILES: CCCCCCCCCCCCCCCCn1c(CO)nc2nc(Cl)nc(S(=O)(=O)C(C)C)c21] |
| 124 | 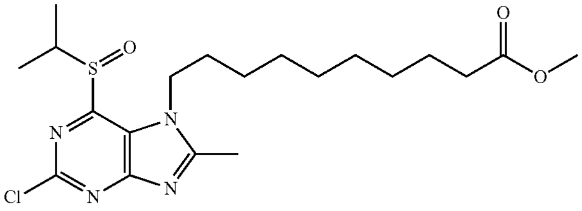 [SMILES: COC(=O)CCCCCCCCCn1c(C)nc2nc(Cl)nc(S(=O)C(C)C)c21] |

-continued
| Compound Number | Structure |
|---|---|
| 125 | 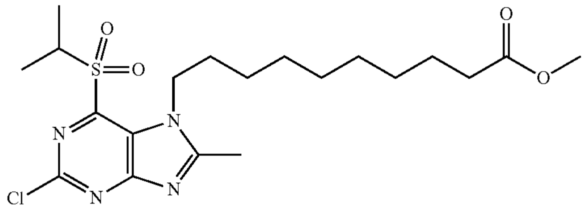 [SMILES: COC(=O)CCCCCCCCCn1c(C)nc2nc(Cl)nc(S(=O)(=O)C(C)C)c21] |
| 128 | 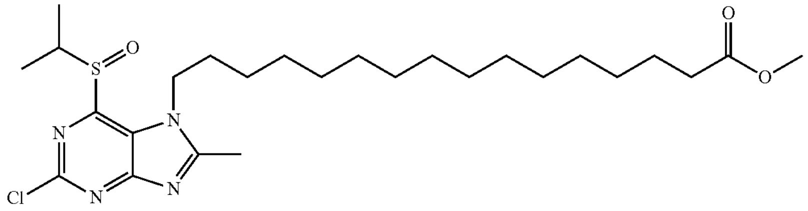 [SMILES: COC(=O)CCCCCCCCCCCCCCCn1c(C)nc2nc(Cl)nc(S(=O)C(C)C)c21] |
| 131 | 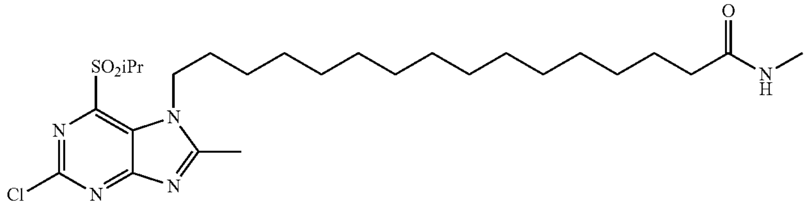 |
| 132 | 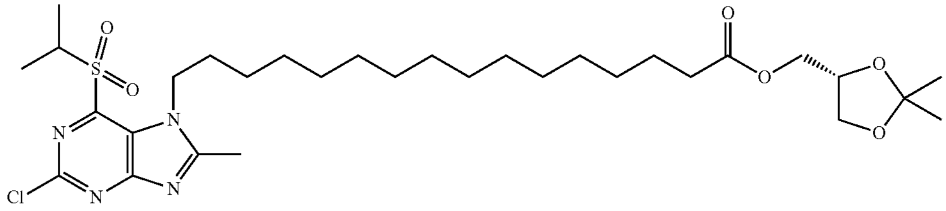 [SMILES: Cc1nc2nc(Cl)nc(S(=O)(=O)C(C)C)c2n1CCCCCCCCCCCCCCCC(=O)OC[C@H]1COC(C)(C)O1] |
| 133 | 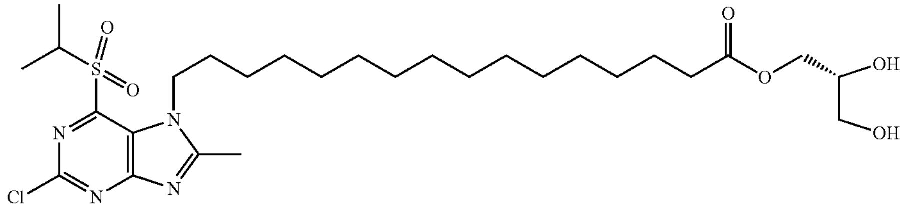 [SMILES: Cc1nc2nc(Cl)nc(S(=O)(=O)C(C)C)c2n1CCCCCCCCCCCCCCCC(=O)OC[C@H](O)CO] |
| 134 | 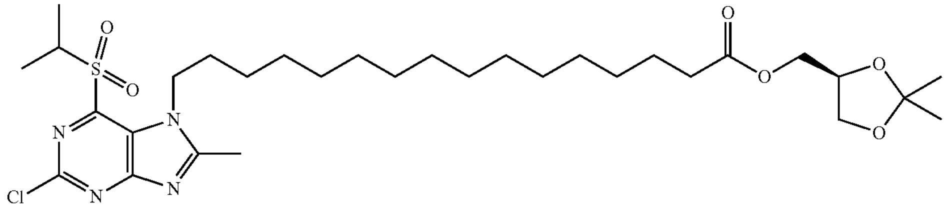 [SMILES: Cc1nc2nc(Cl)nc(S(=O)(=O)C(C)C)c2n1CCCCCCCCCCCCCCCC(=O)OC[C@@H]1COC(C)(C)O1] |
| 135 | 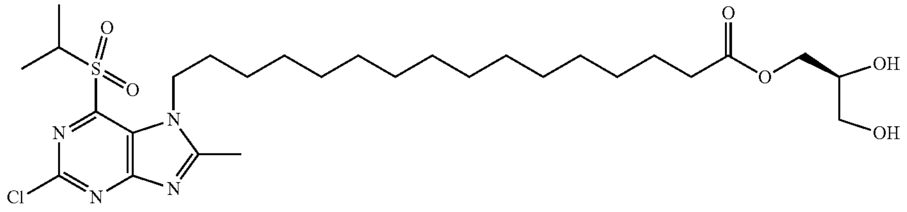 [SMILES: Cc1nc2nc(Cl)nc(S(=O)(=O)C(C)C)c2n1CCCCCCCCCCCCCCCC(=O)OC[C@@H](O)CO] |

-continued
| Compound Number | Structure |
| --- | --- |
| 136 | 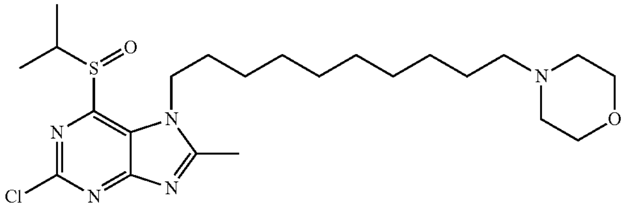 [SMILES: Cc1nc2nc(Cl)nc(S(=O)C(C)C)c2n1CCCCCCCCCCN1CCOCC1] |
| 137 | 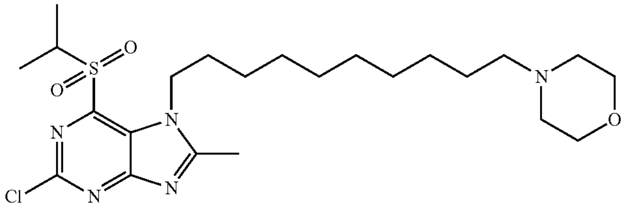 [SMILES: Cc1nc2nc(Cl)nc(S(=O)(=O)C(C)C)c2n1CCCCCCCCCCN1CCOCC1] |
| 138 | 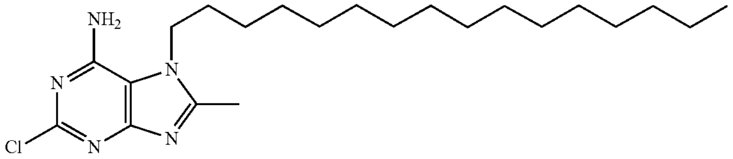 [SMILES: CCCCCCCCCCCCCCCCn1c(C)nc2nc(Cl)nc(N)c21] |
| 139 | 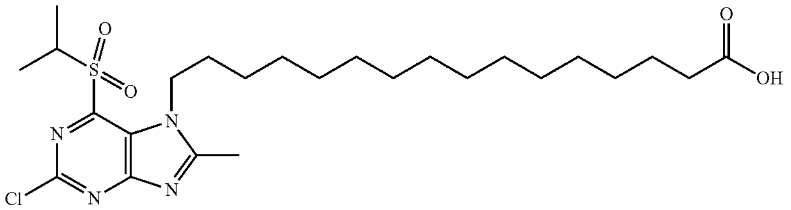 [SMILES: Cc1nc2nc(Cl)nc(S(=O)(=O)C(C)C)c2n1CCCCCCCCCCCCCCCC(=O)O] |
| 140 | 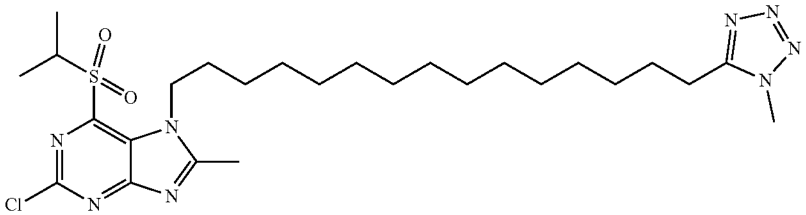 [SMILES: Cc1nc2nc(Cl)nc(S(=O)(=O)C(C)C)c2n1CCCCCCCCCCCCCCCc1nnnn1C] |
| 142 | 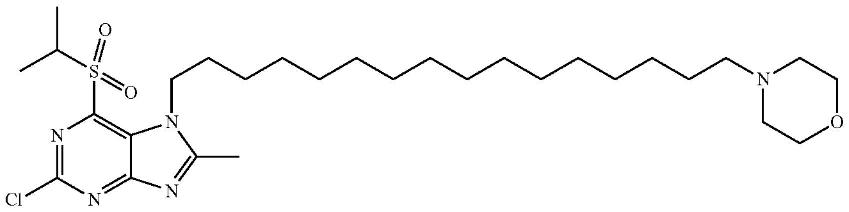 [SMILES: Cc1nc2nc(Cl)nc(S(=O)(=O)C(C)C)c2n1CCCCCCCCCCCCCCCCN1CCOCC1] |
| 143 | 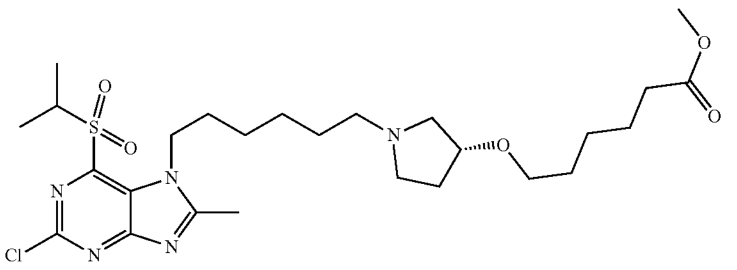 [SMILES: COC(=O)CCCCCO[C@@H]1CCN(CCCCCCn2c(C)nc3nc(Cl)nc(S(=O)(=O)C(C)C)c32)C1] |

-continued
| Compound Number | Structure |
|---|---|
| 144 | 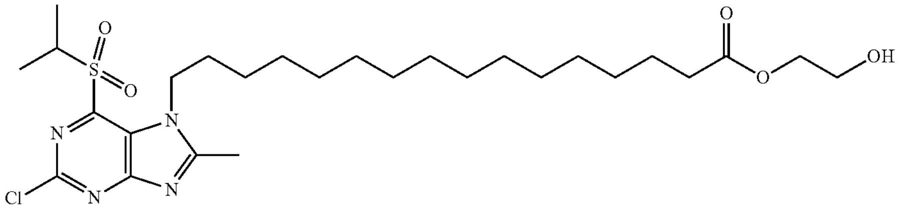 [SMILES: Cc1nc2nc(Cl)nc(S(=O)(=O)C(C)C)c2n1CCCCCCCCCCCCCCCC(=O)OCCO] |
| 145 | 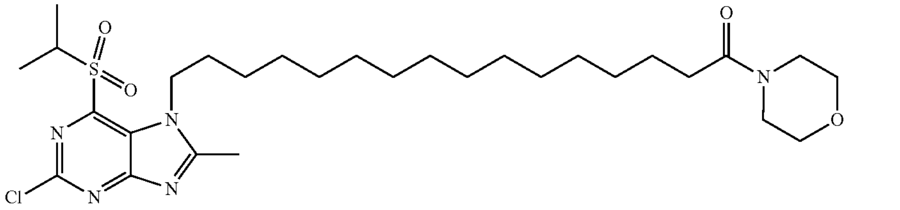 [SMILES: Cc1nc2nc(Cl)nc(S(=O)(=O)C(C)C)c2n1CCCCCCCCCCCCCCCC(=O)N1CCOCC1] |
| 146 | 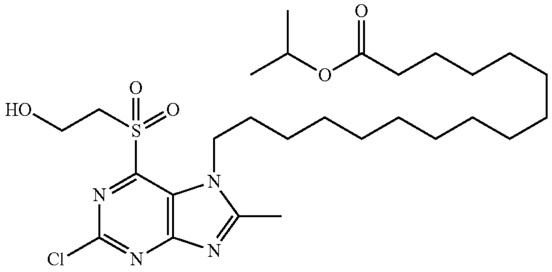 [SMILES: Cc1nc2nc(Cl)nc(S(=O)(=O)CCO)c2n1CCCCCCCCCCCCCCCC(=O)OC(C)C] |
| 147 | 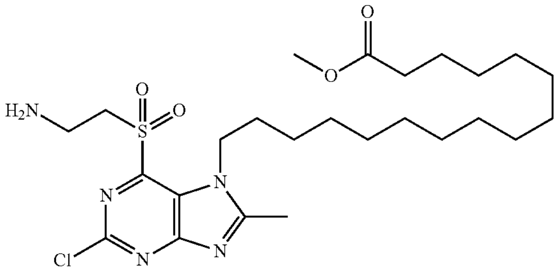 [SMILES: COC(=O)CCCCCCCCCCCCCCCn1c(C)nc2nc(Cl)nc(S(=O)(=O)CCN)c21] |
| 148 | 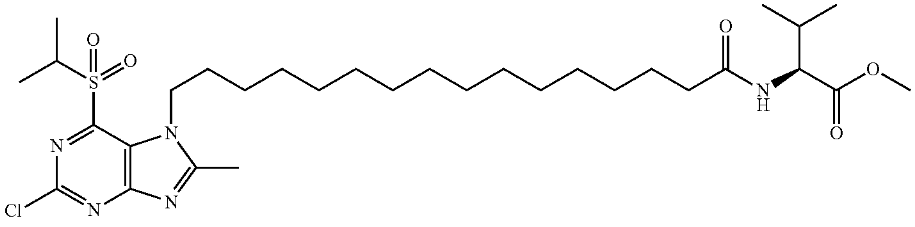 [SMILES: COC(=O)[C@@H](NC(=O)CCCCCCCCCCCCCCCn1c(C)nc2nc(Cl)nc(S(=O)(=O)C(C)C)c21)C(C)C] |
| 149 | 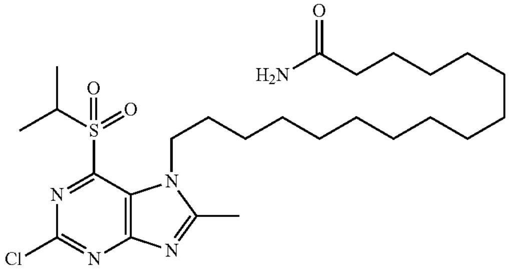 [SMILES: Cc1nc2nc(Cl)nc(S(=O)(=O)C(C)C)c2n1CCCCCCCCCCCCCCCC(N)=O] |

-continued
| Compound Number | Structure |
|---|---|
| 150 | 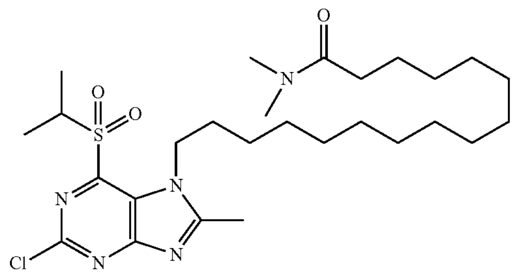 [SMILES: Cc1nc2nc(Cl)nc(S(=O)(=O)C(C)C)c2n1CCCCCCCCCCCCCCCC(=O)N(C)C] |
| 152 | 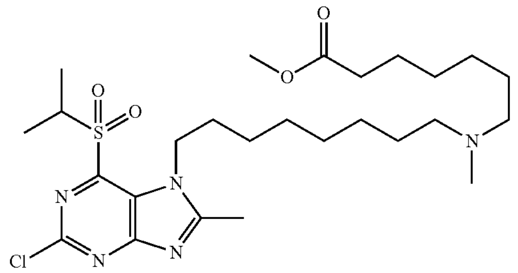 [SMILES: COC(=O)CCCCCCN(C)CCCCCCCCn1c(C)nc2nc(Cl)nc(S(=O)(=O)C(C)C)c21] |
| 158 | 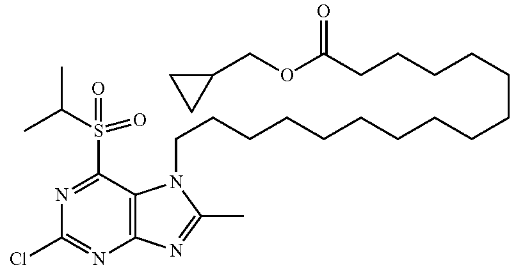 [SMILES: Cc1nc2nc(Cl)nc(S(=O)(=O)C(C)C)c2n1CCCCCCCCCCCCCCCC(=O)OCC1CC1] |
| 159 | 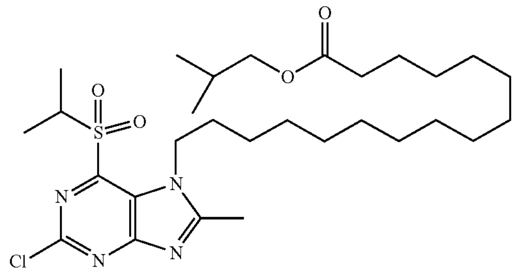 [SMILES: Cc1nc2nc(Cl)nc(S(=O)(=O)C(C)C)c2n1CCCCCCCCCCCCCCCC(=O)OCC(C)C] |
| 160 | 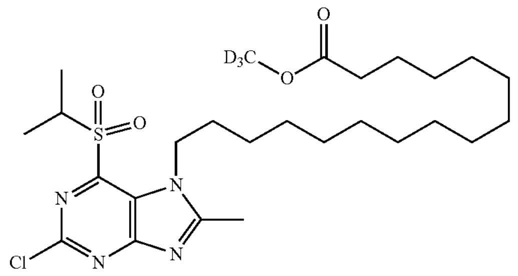 [SMILES: [2H]C([2H])([2H])OC(=O)CCCCCCCCCCCCCCCn1c(C)nc2nc(Cl)nc(S(=O)(=O)C(C)C)c21] |

-continued
| Compound Number | Structure |
|---|---|
| 162 | 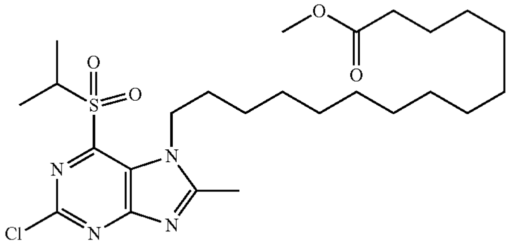 [SMILES: COC(=O)CCCCCCCCCCCCCCn1c(C)nc2nc(Cl)nc(S(=O)(=O)C(C)C)c21] |
| 164 | 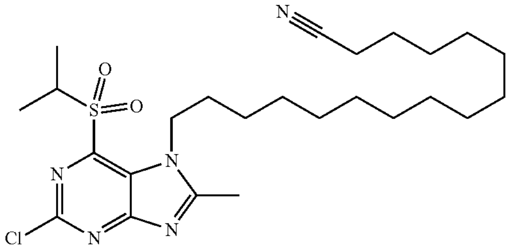 [SMILES: Cc1nc2nc(Cl)nc(S(=O)(=O)C(C)C)c2n1CCCCCCCCCCCCCCCC#N] |
| 165 | 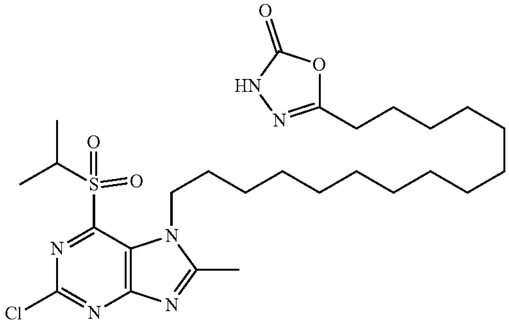 [SMILES: Cc1nc2nc(Cl)nc(S(=O)(=O)C(C)C)c2n1CCCCCCCCCCCCCCCc1n[nH]c(=O)o1] |
| 167 | 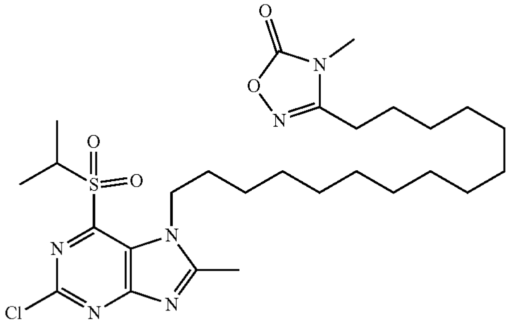 [SMILES: Cc1nc2nc(Cl)nc(S(=O)(=O)C(C)C)c2n1CCCCCCCCCCCCCCCc1noc(=O)n1C] |
| 168 | 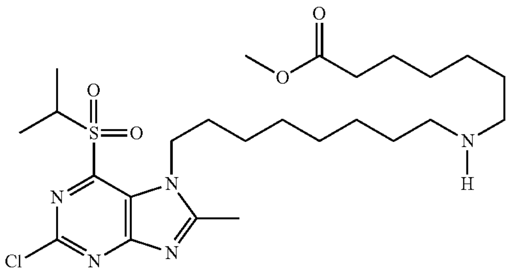 [SMILES: COC(=O)CCCCCCNCCCCCCCCn1c(C)nc2nc(Cl)nc(S(=O)(=O)C(C)C)c21] |

10. A pharmaceutical composition, comprising a compound of claim 1 and a pharmaceutically acceptable excipient.

11. A pharmaceutical composition, comprising a compound of claim 9 and a pharmaceutically acceptable excipient.

* * * * *